United States Patent
Nott et al.

(10) Patent No.: US 12,295,639 B2
(45) Date of Patent: May 13, 2025

(54) ESTIMATING STATE OF ULTRASONIC END EFFECTOR AND CONTROL SYSTEM THEREFOR

(71) Applicant: Cilag GmbH International, Zug (CH)

(72) Inventors: Cameron R. Nott, Fairfield, OH (US); Foster B. Stulen, Johns Island, SC (US); Fergus P. Quigley, Mason, OH (US); John E. Brady, Cincinnati, OH (US); Gregory A. Trees, Loveland, OH (US); Amrita Singh Sawhney, Pittsburgh, PA (US); Rafael J. Ruiz Ortiz, Mason, OH (US); Patrick J. Scoggins, Loveland, OH (US); Kristen G. Denzinger, Cincinnati, OH (US); Craig N. Faller, Batavia, OH (US); Madeleine C. Jayme, Cincinnati, OH (US); Alexander R. Cuti, Pittsburgh, PA (US); Matthew S. Schneider, Blue Ash, OH (US); Chad P. Boudreaux, Cincinnati, OH (US); Brian D. Black, Loveland, OH (US); Maxwell T. Rockman, Cincinnati, OH (US); Gregory D. Bishop, Hamilton, OH (US); Frederick E. Shelton, IV, Hillsboro, OH (US); David C. Yates, Morrow, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/647,890

(22) Filed: Apr. 26, 2024

(65) Prior Publication Data

US 2024/0358428 A1 Oct. 31, 2024

Related U.S. Application Data

(63) Continuation of application No. 17/962,901, filed on Oct. 10, 2022, now Pat. No. 12,042,207, which is a
(Continued)

(51) Int. Cl.
*A61B 18/12* (2006.01)
*A61B 8/00* (2006.01)
(Continued)

(52) U.S. Cl.
CPC ........ *A61B 18/1206* (2013.01); *A61B 8/4483* (2013.01); *A61B 17/320068* (2013.01);
(Continued)

(58) Field of Classification Search
None
See application file for complete search history.

(56) References Cited

U.S. PATENT DOCUMENTS

| 5,042,460 A | 8/1991 | Sakurai et al. |
| 7,982,776 B2 | 7/2011 | Dunki-Jacobs et al. |

(Continued)

FOREIGN PATENT DOCUMENTS

| CN | 206097107 U | 4/2017 |
| JP | 2003061975 A | 3/2003 |

OTHER PUBLICATIONS

IEEE Std No. 177, "Standard Definitions and Methods of Measurement for Piezoelectric Vibrators," published May 1966, The Institute of Electrical and Electronics Engineers, Inc., New York, N.Y.
(Continued)

*Primary Examiner* — Linda C Dvorak
*Assistant Examiner* — Nicholas S Borsch

(57) ABSTRACT

Various aspects of a generator, ultrasonic device, and method for estimating a state of an end effector of an
(Continued)

ultrasonic device are disclosed. The ultrasonic device includes an electromechanical ultrasonic system defined by a predetermined resonant frequency, including an ultrasonic transducer coupled to an ultrasonic blade. A control circuit measures a complex impedance of an ultrasonic transducer, wherein the complex impedance is defined as $Z_g(t)=V_g(t)/I_g(t)$. The control circuit receives a complex impedance measurement data point and compares the complex impedance measurement data point to a data point in a reference complex impedance characteristic pattern. The control circuit then classifies the complex impedance measurement data point based on a result of the comparison analysis and assigns a state or condition of the end effector based on the result of the comparison analysis.

19 Claims, 89 Drawing Sheets

Related U.S. Application Data continuation of application No. 16/115,214, filed on Aug. 28, 2018, now Pat. No. 11,464,559.

(60) Provisional application No. 62/721,999, filed on Aug. 23, 2018, provisional application No. 62/721,994, filed on Aug. 23, 2018, provisional application No. 62/721,995, filed on Aug. 23, 2018, provisional application No. 62/721,996, filed on Aug. 23, 2018, provisional application No. 62/721,998, filed on Aug. 23, 2018, provisional application No. 62/692,747, filed on Jun. 30, 2018, provisional application No. 62/692,748, filed on Jun. 30, 2018, provisional application No. 62/692,768, filed on Jun. 30, 2018, provisional application No. 62/650,882, filed on Mar. 30, 2018, provisional application No. 62/650,887, filed on Mar. 30, 2018, provisional application No. 62/650,877, filed on Mar. 30, 2018, provisional application No. 62/650,898, filed on Mar. 30, 2018, provisional application No. 62/640,415, filed on Mar. 8, 2018, provisional application No. 62/640,417, filed on Mar. 8, 2018, provisional application No. 62/611,339, filed on Dec. 28, 2017, provisional application No. 62/611,341, filed on Dec. 28, 2017, provisional application No. 62/611,340, filed on Dec. 28, 2017.

(51) Int. Cl.
| | | |
|---|---|---|
| *A61B 17/32* | (2006.01) | |
| *A61B 18/14* | (2006.01) | |
| *A61B 34/30* | (2016.01) | |
| *A61B 90/00* | (2016.01) | |
| *G06F 1/02* | (2006.01) | |
| *A61B 17/00* | (2006.01) | |
| *A61B 17/072* | (2006.01) | |
| *A61B 18/00* | (2006.01) | |

(52) U.S. Cl.
CPC ...... *A61B 17/320092* (2013.01); *A61B 18/12* (2013.01); *A61B 18/14* (2013.01); *A61B 34/30* (2016.02); *A61B 90/37* (2016.02); *G06F 1/022* (2013.01); *A61B 2017/00017* (2013.01); *A61B 2017/00022* (2013.01); *A61B 2017/00026* (2013.01); *A61B 2017/0003* (2013.01); *A61B 2017/00075* (2013.01); *A61B 2017/00084* (2013.01); *A61B 2017/00106* (2013.01); *A61B 2017/00115* (2013.01); *A61B 2017/00199* (2013.01); *A61B 2017/00221* (2013.01); *A61B 2017/00398* (2013.01); *A61B 2017/00464* (2013.01); *A61B 2017/07285* (2013.01); *A61B 2018/00994* (2013.01); *A61B 2090/064* (2016.02); *A61B 2090/066* (2016.02); *A61B 2090/0809* (2016.02); *A61B 2090/0811* (2016.02); *A61B 2217/005* (2013.01); *A61B 2217/007* (2013.01)

(56) References Cited

U.S. PATENT DOCUMENTS

| | | |
|---|---|---|
| 7,995,045 B2 | 8/2011 | Dunki-Jacobs |
| 8,512,365 B2 | 8/2013 | Wiener et al. |
| 9,017,326 B2 | 4/2015 | DiNardo et al. |
| 9,089,360 B2 | 7/2015 | Messerly et al. |
| 9,095,367 B2 | 8/2015 | Olson et al. |
| 9,241,731 B2 | 1/2016 | Boudreaux et al. |
| 9,345,481 B2 | 5/2016 | Hall et al. |
| 9,750,523 B2 | 9/2017 | Tsubuku |
| 9,757,142 B2 | 9/2017 | Shimizu |
| 9,788,851 B2 | 10/2017 | Dannaher et al. |
| 9,808,244 B2 | 11/2017 | Leimbach et al. |
| 9,808,246 B2 | 11/2017 | Shelton, IV et al. |
| 10,034,704 B2 | 7/2018 | Asher et al. |
| 10,098,527 B2 | 10/2018 | Weisenburgh, II et al. |
| 10,595,887 B2 | 3/2020 | Shelton, IV et al. |
| 10,610,286 B2 | 4/2020 | Wiener et al. |
| 10,624,691 B2 | 4/2020 | Wiener et al. |
| 10,677,764 B2 | 6/2020 | Ross et al. |
| 10,687,884 B2 | 6/2020 | Wiener et al. |
| 10,695,081 B2 | 6/2020 | Shelton, IV et al. |
| 10,743,872 B2 | 8/2020 | Leimbach et al. |
| 10,755,813 B2 | 8/2020 | Shelton, IV et al. |
| 10,765,470 B2 | 9/2020 | Yates et al. |
| 10,849,697 B2 | 12/2020 | Yates et al. |
| 10,881,399 B2 | 1/2021 | Shelton, IV et al. |
| 10,892,899 B2 | 1/2021 | Shelton, IV et al. |
| 10,898,256 B2 | 1/2021 | Yates et al. |
| 10,898,622 B2 | 1/2021 | Shelton, IV et al. |
| 10,912,580 B2 | 2/2021 | Green et al. |
| 10,932,772 B2 | 3/2021 | Shelton, IV et al. |
| 10,932,872 B2 | 3/2021 | Shelton, IV et al. |
| 10,944,728 B2 | 3/2021 | Wiener et al. |
| 10,966,791 B2 | 4/2021 | Harris et al. |
| 10,987,178 B2 | 4/2021 | Shelton, IV et al. |
| 11,013,563 B2 | 5/2021 | Shelton, IV et al. |
| 11,026,751 B2 | 6/2021 | Shelton, IV et al. |
| 11,045,591 B2 | 6/2021 | Shelton, IV et al. |
| 11,051,876 B2 | 7/2021 | Shelton, IV et al. |
| 11,058,498 B2 | 7/2021 | Shelton, IV et al. |
| 11,069,012 B2 | 7/2021 | Shelton, IV et al. |
| 11,076,921 B2 | 8/2021 | Shelton, IV et al. |
| 11,100,631 B2 | 8/2021 | Yates et al. |
| 11,114,195 B2 | 9/2021 | Shelton, IV et al. |
| 11,129,669 B2 | 9/2021 | Stulen et al. |
| 11,132,462 B2 | 9/2021 | Shelton, IV et al. |
| 11,147,607 B2 | 10/2021 | Yates et al. |
| 11,160,605 B2 | 11/2021 | Shelton, IV et al. |
| 11,166,772 B2 | 11/2021 | Shelton, IV et al. |
| 11,179,175 B2 | 11/2021 | Houser et al. |
| 11,179,208 B2 | 11/2021 | Yates et al. |
| 11,202,570 B2 | 12/2021 | Shelton, IV et al. |
| 11,213,359 B2 | 1/2022 | Shelton, IV et al. |
| 11,253,315 B2 | 2/2022 | Yates et al. |
| 11,266,468 B2 | 3/2022 | Shelton, IV et al. |
| 11,284,936 B2 | 3/2022 | Shelton, IV et al. |
| 11,291,495 B2 | 4/2022 | Yates et al. |
| 11,304,720 B2 | 4/2022 | Kimball et al. |
| 11,304,745 B2 | 4/2022 | Shelton, IV et al. |
| 11,311,306 B2 | 4/2022 | Shelton, IV et al. |
| 11,317,937 B2 | 5/2022 | Nott et al. |
| 11,364,075 B2 | 6/2022 | Yates et al. |
| 11,376,002 B2 | 7/2022 | Shelton, IV et al. |
| 11,410,259 B2 | 8/2022 | Harris et al. |
| 11,419,630 B2 | 8/2022 | Yates et al. |
| 11,432,885 B2 | 9/2022 | Shelton, IV et al. |

(56) References Cited

U.S. PATENT DOCUMENTS

| | | |
|---|---|---|
| 11,464,535 B2 | 10/2022 | Shelton, IV et al. |
| 11,464,559 B2 | 10/2022 | Nott et al. |
| 11,529,187 B2 | 12/2022 | Shelton, IV et al. |
| 11,540,855 B2 | 1/2023 | Messerly et al. |
| 11,559,308 B2 | 1/2023 | Yates et al. |
| 11,571,234 B2 | 2/2023 | Nott et al. |
| 11,602,393 B2 | 3/2023 | Shelton, IV et al. |
| 11,607,239 B2 | 3/2023 | Swensgard et al. |
| 11,612,408 B2 | 3/2023 | Yates et al. |
| 11,666,331 B2 | 6/2023 | Shelton, IV et al. |
| 11,672,605 B2 | 6/2023 | Messerly et al. |
| 11,678,881 B2 | 6/2023 | Yates et al. |
| 11,678,927 B2 * | 6/2023 | Brady ................. H03H 9/0004 606/169 |
| 11,696,760 B2 | 7/2023 | Shelton, IV et al. |
| 11,771,487 B2 | 10/2023 | Shelton, IV et al. |
| 11,786,245 B2 | 10/2023 | Shelton, IV |
| 11,844,545 B2 | 12/2023 | Scoggins et al. |
| 11,857,152 B2 | 1/2024 | Shelton, IV et al. |
| 11,864,728 B2 | 1/2024 | Shelton, IV et al. |
| 2002/0049551 A1 | 4/2002 | Friedman et al. |
| 2003/0130711 A1 | 7/2003 | Pearson et al. |
| 2009/0036794 A1 | 2/2009 | Stubhaug et al. |
| 2009/0259221 A1 | 10/2009 | Tahara et al. |
| 2011/0306840 A1 | 12/2011 | Allen et al. |
| 2013/0331873 A1 * | 12/2013 | Ross ..................... B06B 1/0207 606/169 |
| 2013/0331875 A1 | 12/2013 | Ross et al. |
| 2014/0081255 A1 | 3/2014 | Johnson et al. |
| 2014/0084949 A1 * | 3/2014 | Smith .................... A61B 8/429 324/693 |
| 2014/0263552 A1 | 9/2014 | Hall et al. |
| 2015/0328474 A1 | 11/2015 | Flyash et al. |
| 2016/0278841 A1 | 9/2016 | Panescu et al. |
| 2019/0069949 A1 | 3/2019 | Vrba et al. |
| 2019/0167296 A1 | 6/2019 | Tsubuku et al. |
| 2019/0200906 A1 | 7/2019 | Shelton, IV et al. |
| 2019/0200987 A1 | 7/2019 | Shelton, IV et al. |
| 2019/0201021 A1 | 7/2019 | Shelton, IV et al. |
| 2019/0201039 A1 | 7/2019 | Widenhouse et al. |
| 2019/0201042 A1 | 7/2019 | Nott et al. |
| 2019/0201087 A1 | 7/2019 | Shelton, IV et al. |
| 2019/0201090 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201115 A1 | 7/2019 | Shelton, IV et al. |
| 2019/0201118 A1 | 7/2019 | Shelton, IV et al. |
| 2019/0201139 A1 | 7/2019 | Shelton, IV et al. |
| 2019/0201140 A1 | 7/2019 | Yates et al. |
| 2019/0201142 A1 | 7/2019 | Shelton, IV et al. |
| 2019/0201146 A1 | 7/2019 | Shelton, IV et al. |
| 2019/0205567 A1 | 7/2019 | Shelton, IV et al. |
| 2019/0206555 A1 | 7/2019 | Morgan et al. |
| 2019/0206561 A1 | 7/2019 | Shelton, IV et al. |

OTHER PUBLICATIONS

CRC Press, "The Measurement, Instrumentation and Sensors Handbook," 1999, Section VII, Chapter 41, Peter O'Shea, "Phase Measurement," pp. 1303-1321, ISBN 0-8493-2145-X.

* cited by examiner

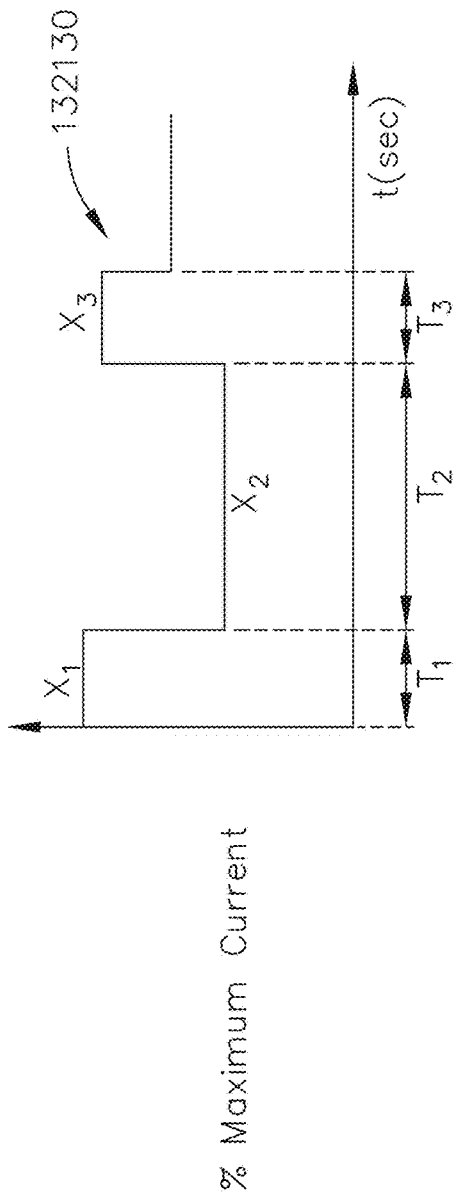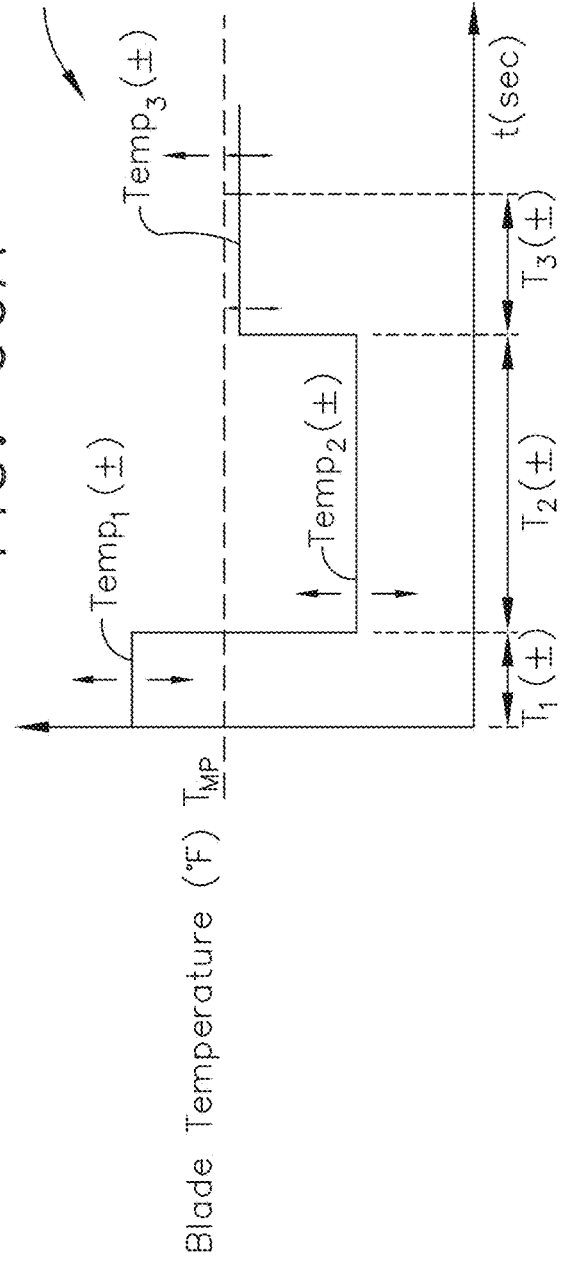

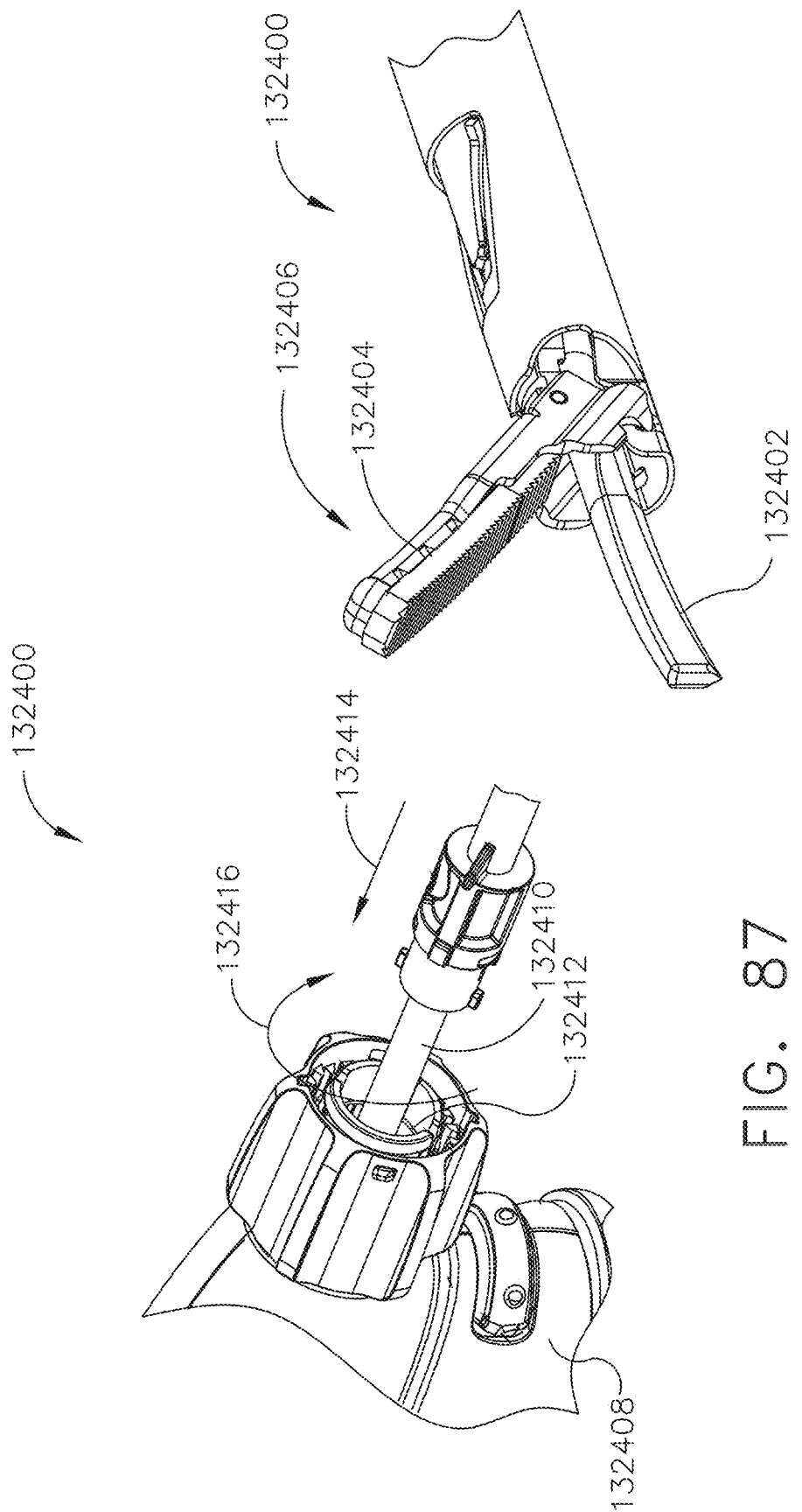

ESTIMATING STATE OF ULTRASONIC END EFFECTOR AND CONTROL SYSTEM THEREFOR

CROSS-REFERENCE TO RELATED APPLICATIONS

This application is a continuation application claiming priority under 35 U.S.C. § 120 to U.S. patent application Ser. No. 17/962,901, titled ESTIMATING STATE OF ULTRASONIC END EFFECTOR AND CONTROL SYSTEM THEREFOR, filed Oct. 10, 2022, which issued on Jul. 23, 2024 as U.S. Pat. No. 12,042,207, which is a continuation application claiming priority under 35 U.S.C. § 120 to U.S. patent application Ser. No. 16/115,214, titled ESTIMATING STATE OF ULTRASONIC END EFFECTOR AND CONTROL SYSTEM THEREFOR, filed Aug. 28, 2018, which issued on Oct. 11, 2022 as U.S. Pat. No. 11,464,559, which claims priority under 35 U.S.C. § 119(e) to U.S. Provisional Patent Application Ser. No. 62/721,995, titled CONTROLLING AN ULTRASONIC SURGICAL INSTRUMENT ACCORDING TO TISSUE LOCATION, filed on Aug. 23, 2018, the disclosure of each of which is herein incorporated by reference in its entirety.

This application is a continuation application claiming priority under 35 U.S.C. § 120 to U.S. patent application Ser. No. 17/962,901, titled ESTIMATING STATE OF ULTRASONIC END EFFECTOR AND CONTROL SYSTEM THEREFOR, filed Oct. 10, 2022, which issued on Jul. 23, 2024 as U.S. Pat. No. 12,042,207, which is a continuation application claiming priority under 35 U.S.C. § 120 to U.S. patent application Ser. No. 16/115,214, titled ESTIMATING STATE OF ULTRASONIC END EFFECTOR AND CONTROL SYSTEM THEREFOR, filed Aug. 28, 2018, which issued on Oct. 11, 2022 as U.S. Pat. No. 11,464,559, which also claims priority under 35 U.S.C. § 119(e) to U.S. Provisional Patent Application Ser. No. 62/721,998, titled SITUATIONAL AWARENESS OF ELECTROSURGICAL SYSTEMS, filed on Aug. 23, 2018, the disclosure of each of which is herein incorporated by reference in its entirety.

This application is a continuation application claiming priority under 35 U.S.C. § 120 to U.S. patent application Ser. No. 17/962,901, titled ESTIMATING STATE OF ULTRASONIC END EFFECTOR AND CONTROL SYSTEM THEREFOR, filed Oct. 10, 2022, which issued on Jul. 23, 2024 as U.S. Pat. No. 12,042,207, which is a continuation application claiming priority under 35 U.S.C. § 120 to U.S. patent application Ser. No. 16/115,214, titled ESTIMATING STATE OF ULTRASONIC END EFFECTOR AND CONTROL SYSTEM THEREFOR, filed Aug. 28, 2018, which issued on Oct. 11, 2022 as U.S. Pat. No. 11,464,559, which also claims priority under 35 U.S.C. § 119(e) to U.S. Provisional Patent Application Ser. No. 62/721,999, titled INTERRUPTION OF ENERGY DUE TO INADVERTENT CAPACITIVE COUPLING, filed on Aug. 23, 2018, the disclosure of each of which is herein incorporated by reference in its entirety.

This application is a continuation application claiming priority under 35 U.S.C. § 120 to U.S. patent application Ser. No. 17/962,901, titled ESTIMATING STATE OF ULTRASONIC END EFFECTOR AND CONTROL SYSTEM THEREFOR, filed Oct. 10, 2022, which issued on Jul. 23, 2024 as U.S. Pat. No. 12,042,207, which is a continuation application claiming priority under 35 U.S.C. § 120 to U.S. patent application Ser. No. 16/115,214, titled ESTIMATING STATE OF ULTRASONIC END EFFECTOR AND CONTROL SYSTEM THEREFOR, filed Aug. 28, 2018, which issued on Oct. 11, 2022 as U.S. Pat. No. 11,464,559, which also claims priority under 35 U.S.C. § 119(e) to U.S. Provisional Patent Application Ser. No. 62/721,994, titled BIPOLAR COMBINATION DEVICE THAT AUTOMATICALLY ADJUSTS PRESSURE BASED ON ENERGY MODALITY, filed on Aug. 23, 2018, the disclosure of each of which is herein incorporated by reference in its entirety.

This application is a continuation application claiming priority under 35 U.S.C. § 120 to U.S. patent application Ser. No. 17/962,901, titled ESTIMATING STATE OF ULTRASONIC END EFFECTOR AND CONTROL SYSTEM THEREFOR, filed Oct. 10, 2022, which issued on Jul. 23, 2024 as U.S. Pat. No. 12,042,207, which is a continuation application claiming priority under 35 U.S.C. § 120 to U.S. patent application Ser. No. 16/115,214, titled ESTIMATING STATE OF ULTRASONIC END EFFECTOR AND CONTROL SYSTEM THEREFOR, filed Aug. 28, 2018, which issued on Oct. 11, 2022 as U.S. Pat. No. 11,464,559, which also claims priority under 35 U.S.C. § 119(e) to U.S. Provisional Patent Application Ser. No. 62/721,996, titled RADIO FREQUENCY ENERGY DEVICE FOR DELIVERING COMBINED ELECTRICAL SIGNALS, filed on Aug. 23, 2018, the disclosure of each of which is herein incorporated by reference in its entirety.

This application is a continuation application claiming priority under 35 U.S.C. § 120 to U.S. patent application Ser. No. 17/962,901, titled ESTIMATING STATE OF ULTRASONIC END EFFECTOR AND CONTROL SYSTEM THEREFOR, filed Oct. 10, 2022, which issued on Jul. 23, 2024 as U.S. Pat. No. 12,042,207, which is a continuation application claiming priority under 35 U.S.C. § 120 to U.S. patent application Ser. No. 16/115,214, titled ESTIMATING STATE OF ULTRASONIC END EFFECTOR AND CONTROL SYSTEM THEREFOR, filed Aug. 28, 2018, which issued on Oct. 11, 2022 as U.S. Pat. No. 11,464,559, which also claims priority under 35 U.S.C. § 119(e) to U.S. Provisional Patent Application Ser. No. 62/692,747, titled SMART ACTIVATION OF AN ENERGY DEVICE BY ANOTHER DEVICE, filed on Jun. 30, 2018, to U.S. Provisional Patent Application Ser. No. 62/692,748, titled SMART ENERGY ARCHITECTURE, filed on Jun. 30, 2018, and to U.S. Provisional Patent Application Ser. No. 62/692,768, titled SMART ENERGY DEVICES, filed on Jun. 30, 2018, the disclosure of each of which is herein incorporated by reference in its entirety.

This application is a continuation application claiming priority under 35 U.S.C. § 120 to U.S. patent application Ser. No. 17/962,901, titled ESTIMATING STATE OF ULTRASONIC END EFFECTOR AND CONTROL SYSTEM THEREFOR, filed Oct. 10, 2022, which issued on Jul. 23, 2024 as U.S. Pat. No. 12,042,207, which is a continuation application claiming priority under 35 U.S.C. § 120 to U.S. patent application Ser. No. 16/115,214, titled ESTIMATING STATE OF ULTRASONIC END EFFECTOR AND CONTROL SYSTEM THEREFOR, filed Aug. 28, 2018, which issued on Oct. 11, 2022 as U.S. Pat. No. 11,464,559, which also claims the benefit of priority under 35 U.S.C. § 119(e) to U.S. Provisional Patent Application Ser. No. 62/640,417, titled TEMPERATURE CONTROL IN ULTRASONIC DEVICE AND CONTROL SYSTEM THEREFOR, filed Mar. 8, 2018, and to U.S. Provisional Patent Application Ser. No. 62/640,415, titled ESTIMATING STATE OF ULTRASONIC END EFFECTOR AND CONTROL SYSTEM THEREFOR, filed Mar. 8, 2018, the disclosure of each of which is herein incorporated by reference in its entirety.

This application is a continuation application claiming priority under 35 U.S.C. § 120 to U.S. patent application Ser.

No. 17/962,901, titled ESTIMATING STATE OF ULTRASONIC END EFFECTOR AND CONTROL SYSTEM THEREFOR, filed Oct. 10, 2022, which issued on Jul. 23, 2024 as U.S. Pat. No. 12,042,207, which is a continuation application claiming priority under 35 U.S.C. § 120 to U.S. patent application Ser. No. 16/115,214, titled ESTIMATING STATE OF ULTRASONIC END EFFECTOR AND CONTROL SYSTEM THEREFOR, filed Aug. 28, 2018, which issued on Oct. 11, 2022 as U.S. Pat. No. 11,464,559, which also claims the benefit of priority under 35 U.S.C. § 119(e) to U.S. Provisional Patent Application Ser. No. 62/650,898 filed on Mar. 30, 2018, titled CAPACITIVE COUPLED RETURN PATH PAD WITH SEPARABLE ARRAY ELEMENTS, to U.S. Provisional Patent Application Ser. No. 62/650,887, titled SURGICAL SYSTEMS WITH OPTIMIZED SENSING CAPABILITIES, filed Mar. 30, 2018, to U.S. Provisional Patent Application Ser. No. 62/650,882, titled SMOKE EVACUATION MODULE FOR INTERACTIVE SURGICAL PLATFORM, filed Mar. 30, 2018, and to U.S. Provisional Patent Application Ser. No. 62/650,877, titled SURGICAL SMOKE EVACUATION SENSING AND CONTROLS, filed Mar. 30, 2018, the disclosure of each of which is herein incorporated by reference in its entirety.

This application is a continuation application claiming priority under 35 U.S.C. § 120 to U.S. patent application Ser. No. 17/962,901, titled ESTIMATING STATE OF ULTRASONIC END EFFECTOR AND CONTROL SYSTEM THEREFOR, filed Oct. 10, 2022, which issued on Jul. 23, 2024 as U.S. Pat. No. 12,042,207, which is a continuation application claiming priority under 35 U.S.C. § 120 to U.S. patent application Ser. No. 16/115,214, titled ESTIMATING STATE OF ULTRASONIC END EFFECTOR AND CONTROL SYSTEM THEREFOR, filed Aug. 28, 2018, which issued on Oct. 11, 2022 as U.S. Pat. No. 11,464,559, which also claims the benefit of priority under 35 U.S.C. § 119(e) to U.S. Provisional Patent Application Ser. No. 62/611,341, titled INTERACTIVE SURGICAL PLATFORM, filed Dec. 28, 2017, to U.S. Provisional Patent Application Ser. No. 62/611,340, titled CLOUD-BASED MEDICAL ANALYTICS, filed Dec. 28, 2017, and to U.S. Provisional Patent Application Ser. No. 62/611,339, titled ROBOT ASSISTED SURGICAL PLATFORM, filed Dec. 28, 2017, the disclosure of each of which is herein incorporated by reference in its entirety.

BACKGROUND

In a surgical environment, smart energy devices may be needed in a smart energy architecture environment. Ultrasonic surgical devices, such as ultrasonic scalpels, are finding increasingly widespread applications in surgical procedures by virtue of their unique performance characteristics. Depending upon specific device configurations and operational parameters, ultrasonic surgical devices can provide substantially simultaneous transection of tissue and homeostasis by coagulation, desirably minimizing patient trauma. An ultrasonic surgical device may comprise a handpiece containing an ultrasonic transducer, and an instrument coupled to the ultrasonic transducer having a distally-mounted end effector (e.g., a blade tip) to cut and seal tissue. In some cases, the instrument may be permanently affixed to the handpiece. In other cases, the instrument may be detachable from the handpiece, as in the case of a disposable instrument or an interchangeable instrument. The end effector transmits ultrasonic energy to tissue brought into contact with the end effector to realize cutting and sealing action. Ultrasonic surgical devices of this nature can be configured for open surgical use, laparoscopic, or endoscopic surgical procedures including robotic-assisted procedures.

Ultrasonic energy cuts and coagulates tissue using temperatures lower than those used in electrosurgical procedures and can be transmitted to the end effector by an ultrasonic generator in communication with the handpiece. Vibrating at high frequencies (e.g., 55,500 cycles per second), the ultrasonic blade denatures protein in the tissue to form a sticky coagulum. Pressure exerted on tissue by the blade surface collapses blood vessels and allows the coagulum to form a hemostatic seal. A surgeon can control the cutting speed and coagulation by the force applied to the tissue by the end effector, the time over which the force is applied, and the selected excursion level of the end effector.

The ultrasonic transducer may be modeled as an equivalent circuit comprising a first branch having a static capacitance and a second "motional" branch having a serially connected inductance, resistance and capacitance that define the electromechanical properties of a resonator. Known ultrasonic generators may include a tuning inductor for tuning out the static capacitance at a resonant frequency so that substantially all of a generator's drive signal current flows into the motional branch. Accordingly, by using a tuning inductor, the generator's drive signal current represents the motional branch current, and the generator is thus able to control its drive signal to maintain the ultrasonic transducer's resonant frequency. The tuning inductor may also transform the phase impedance plot of the ultrasonic transducer to improve the generator's frequency lock capabilities. However, the tuning inductor must be matched with the specific static capacitance of an ultrasonic transducer at the operational resonant frequency. In other words, a different ultrasonic transducer having a different static capacitance requires a different tuning inductor.

Additionally, in some ultrasonic generator architectures, the generator's drive signal exhibits asymmetrical harmonic distortion that complicates impedance magnitude and phase measurements. For example, the accuracy of impedance phase measurements may be reduced due to harmonic distortion in the current and voltage signals.

Moreover, electromagnetic interference in noisy environments decreases the ability of the generator to maintain lock on the ultrasonic transducer's resonant frequency, increasing the likelihood of invalid control algorithm inputs.

Electrosurgical devices for applying electrical energy to tissue in order to treat and/or destroy the tissue are also finding increasingly widespread applications in surgical procedures. An electrosurgical device may comprise a handpiece and an instrument having a distally-mounted end effector (e.g., one or more electrodes). The end effector can be positioned against the tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flowing through the tissue may form hemostatic seals within the tissue and/or between tissues and thus may be particularly useful for sealing blood vessels, for example. The end effector of an electrosurgical device may also comprise a cutting member that is movable relative to the tissue and the electrodes to transect the tissue.

Electrical energy applied by an electrosurgical device can be transmitted to the instrument by a generator in communication with the handpiece. The electrical energy may be in the form of radio frequency (RF) energy. RF energy is a form of electrical energy that may be in the frequency range of 300 kHz to 1 MHz, as described in EN60601-2-2:2009+A11:2011, Definition 201.3.218—HIGH FREQUENCY. For example, the frequencies in monopolar RF applications are typically restricted to less than 5 MHz. However, in bipolar RF applications, the frequency can be almost any value. Frequencies above 200 kHz are typically used for monopolar applications in order to avoid the unwanted stimulation of nerves and muscles which would result from the use of low frequency current. Lower frequencies may be used for bipolar techniques if a risk analysis shows the possibility of neuromuscular stimulation has been mitigated to an acceptable level. Normally, frequencies above 5 MHz are not used in order to minimize the problems associated with high frequency leakage currents. It is generally recognized that 10 mA is the lower threshold of thermal effects on tissue.

During its operation, an electrosurgical device can transmit low frequency RF energy through tissue, which causes ionic agitation, or friction, in effect resistive heating, thereby increasing the temperature of the tissue. Because a sharp boundary may be created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy may work particularly well on connective tissue, which is primarily comprised of collagen and shrinks when contacted by heat.

Due to their unique drive signal, sensing and feedback needs, ultrasonic and electrosurgical devices have generally required different generators. Additionally, in cases where the instrument is disposable or interchangeable with a handpiece, ultrasonic and electrosurgical generators are limited in their ability to recognize the particular instrument configuration being used and to optimize control and diagnostic processes accordingly. Moreover, capacitive coupling between the non-isolated and patient-isolated circuits of the generator, especially in cases where higher voltages and frequencies are used, may result in exposure of a patient to unacceptable levels of leakage current.

Furthermore, due to their unique drive signal, sensing and feedback needs, ultrasonic and electrosurgical devices have generally required different user interfaces for the different generators. In such conventional ultrasonic and electrosurgical devices, one user interface is configured for use with an ultrasonic instrument whereas a different user interface may be configured for use with an electrosurgical instrument. Such user interfaces include hand and/or foot activated user interfaces such as hand activated switches and/or foot activated switches. As various aspects of combined generators for use with both ultrasonic and electrosurgical instruments are contemplated in the subsequent disclosure, additional user interfaces that are configured to operate with both ultrasonic and/or electrosurgical instrument generators also are contemplated.

Additional user interfaces for providing feedback, whether to the user or other machine, are contemplated within the subsequent disclosure to provide feedback indicating an operating mode or status of either an ultrasonic and/or electrosurgical instrument. Providing user and/or machine feedback for operating a combination ultrasonic and/or electrosurgical instrument will require providing sensory feedback to a user and electrical/mechanical/electromechanical feedback to a machine. Feedback devices that incorporate visual feedback devices (e.g., an LCD display screen, LED indicators), audio feedback devices (e.g., a speaker, a buzzer) or tactile feedback devices (e.g., haptic actuators) for use in combined ultrasonic and/or electrosurgical instruments are contemplated in the subsequent disclosure.

Other electrical surgical instruments include, without limitation, irreversible and/or reversible electroporation, and/or microwave technologies, among others. Accordingly, the techniques disclosed herein are applicable to ultrasonic, bipolar or monopolar RF (electrosurgical), irreversible and/or reversible electroporation, and/or microwave based surgical instruments, among others.

SUMMARY

In one general aspect, a method of estimating a state of an end effector of an ultrasonic device is provided. The ultrasonic device including an electromechanical ultrasonic system defined by a predetermined resonant frequency, the electromechanical ultrasonic system including an ultrasonic transducer coupled to an ultrasonic blade. The method comprising: measuring, by a control circuit, a complex impedance of an ultrasonic transducer, wherein the complex impedance is defined as $$Z_g(t) = \frac{V_g(t)}{I_g(t)};$$

receiving, by the control circuit, a complex impedance measurement data point; comparing, by the control circuit, the complex impedance measurement data point to a data point in a reference complex impedance characteristic pattern; classifying, by the control circuit, the complex impedance measurement data point based on a result of the comparison analysis; and assigning, by the control circuit, a state or condition of the end effector based on the result of the comparison analysis.

In another aspect, a generator for estimating a state of an end effector of an ultrasonic device is provided. The ultrasonic device including an electromechanical ultrasonic system defined by a predetermined resonant frequency, the electromechanical ultrasonic system including an ultrasonic transducer coupled to an ultrasonic blade, the generator comprising: a control circuit coupled to a memory, the control circuit configured to: measure a complex impedance of an ultrasonic transducer, wherein the complex impedance is defined $$Z_g(t) = \frac{V_g(t)}{I_g(t)};$$

receive a complex impedance measurement data point; compare the complex impedance measurement data point to a data point in a reference complex impedance characteristic pattern; classify the complex impedance measurement data point based on a result of the comparison analysis; and assign a state or condition of the end effector based on the result of the comparison analysis.

In yet another aspect, an ultrasonic device for estimating a state of an end effector thereof is provided. The ultrasonic device comprising: an electromechanical ultrasonic system defined by a predetermined resonant frequency, the electromechanical ultrasonic system comprising an ultrasonic transducer coupled to an ultrasonic blade; a control circuit coupled to a memory, the control circuit configured to: measure a complex impedance of the ultrasonic transducer, wherein the complex impedance is defined as $$Z_g(t) = \frac{V_g(t)}{I_g(t)};$$

receive a complex impedance measurement data point; compare the complex impedance measurement data point to a data point in a reference complex impedance characteristic pattern; classify the complex impedance measurement data point based on a result of the comparison analysis; and assign a state or condition of the end effector based on the result of the comparison analysis.

In yet another aspect, a method of estimating a state of an end effector of an ultrasonic device is provided. The ultrasonic device including an electromechanical ultrasonic system defined by a predetermined resonant frequency, the electromechanical ultrasonic system including an ultrasonic transducer coupled to an ultrasonic blade. The method comprising: applying, by a drive circuit, a drive signal to an ultrasonic transducer, wherein the drive signal is a periodic signal defined by a magnitude and frequency; sweeping, by a processor or control circuit, the frequency of the drive signal from below resonance to above resonance of the electromagnetic ultrasonic system; measuring and recording, by the processor or control circuit, impedance/admittance circle variables $R_e$, $G_e$, $X_e$, $B_e$; comparing, by the processor or control circuit, measured impedance/admittance circle variables $R_e$, $G_e$, $X_e$, $B_e$ to reference impedance/admittance circle variables $R_{ref}$, $G_{ref}$, $X_{ref}$, $B_{ref}$; and determining, by the processor or control circuit, a state or condition of the end effector based on the result of the comparison analysis.

FIGURES

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

FIGS. 66A-66B are graphical representations of an ultrasonic transducer current hemostasis algorithm, where FIG. 66A is a graphical representation of percent of maximum current into an ultrasonic transducer as a function of time and FIG. 66B is a graphical representation of ultrasonic blade temperature as a function of time and tissue type, in accordance with at least one aspect of the present disclosure.

Figure 67:
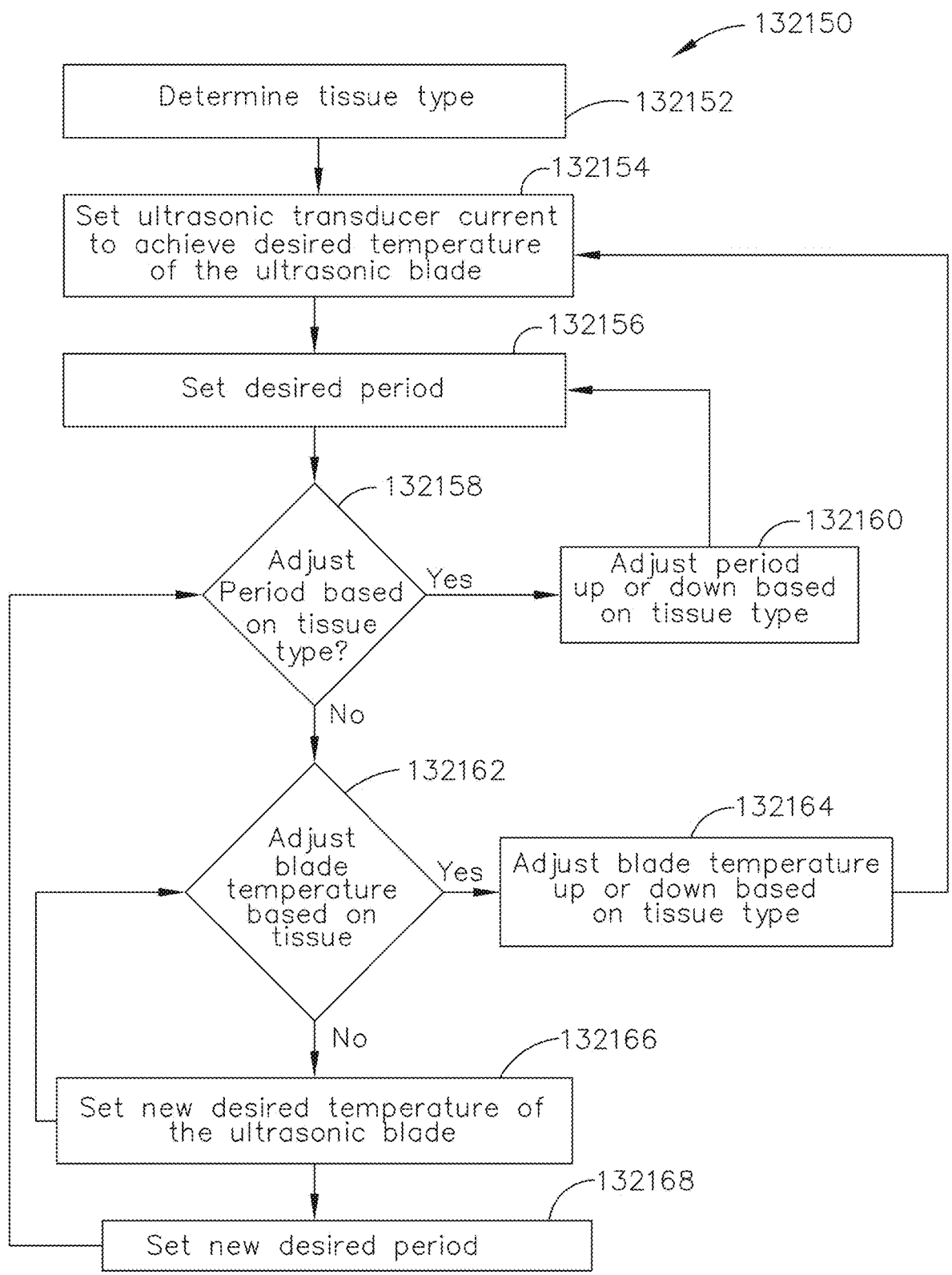

FIG. 67 is a logic flow diagram of a process depicting a control program or a logic configuration to control the temperature of an ultrasonic blade based on tissue type, in accordance with at least one aspect of the present disclosure.

Figure 68:
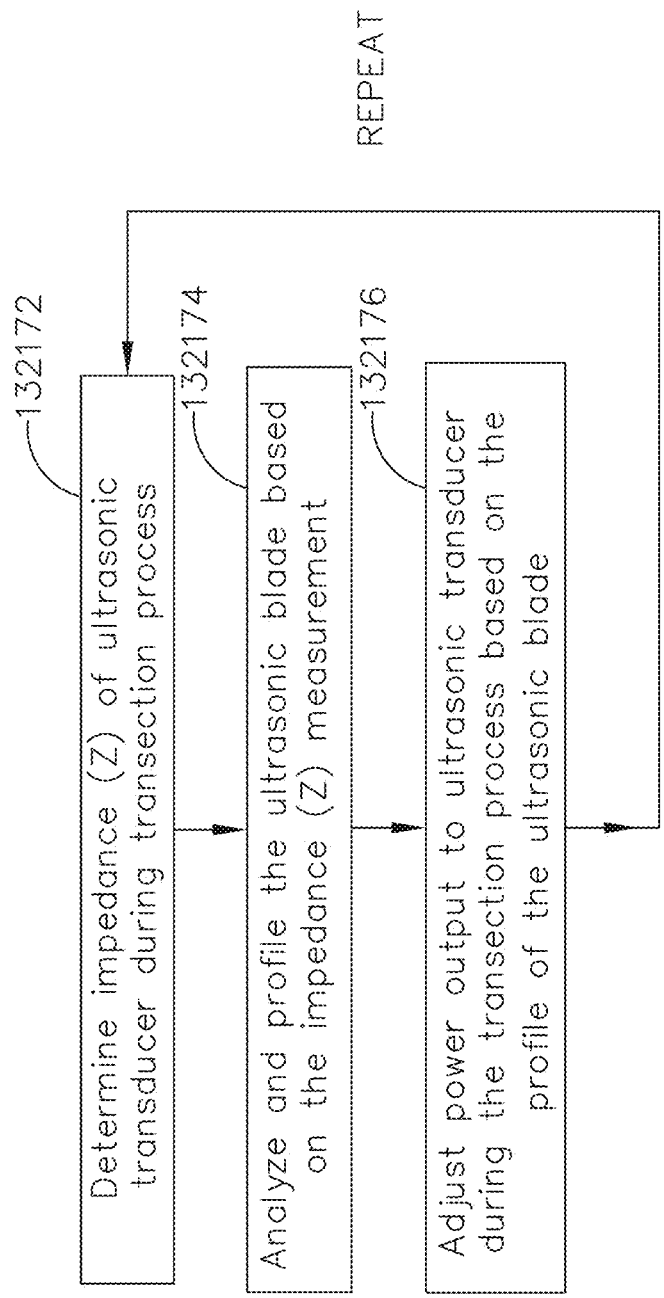

FIG. 68 is a logic flow diagram of a process depicting a control program or a logic configuration to monitor the impedance of an ultrasonic transducer to profile an ultrasonic blade and deliver power to the ultrasonic blade on the profile according to one aspect of the resent disclosure.

Figure 69A:
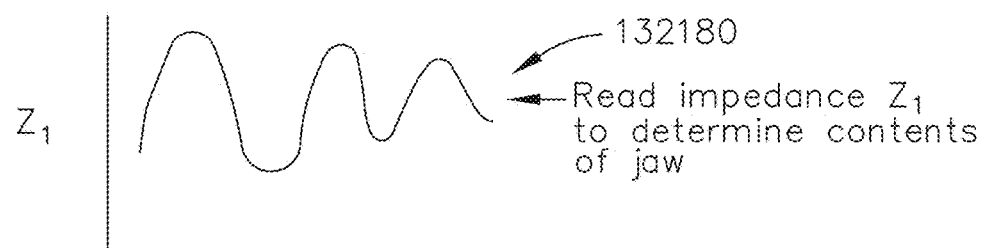
Figure 69B:
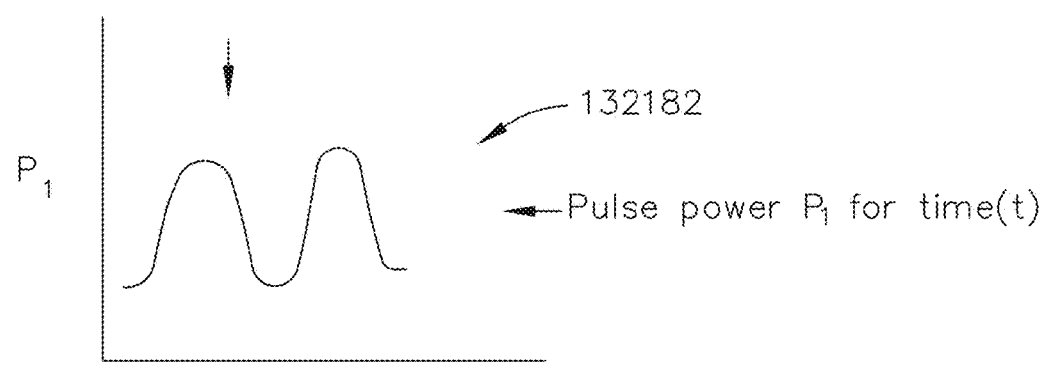
Figure 69C:
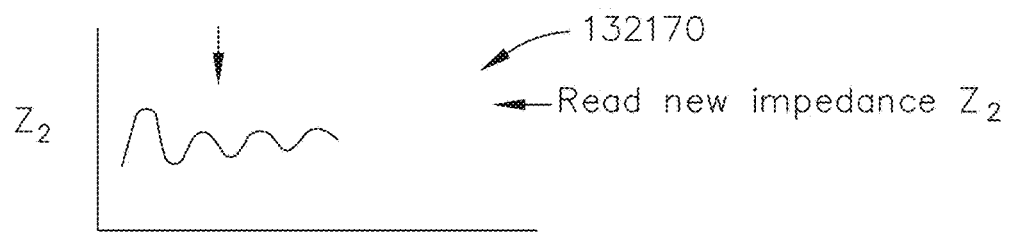
Figure 69D:
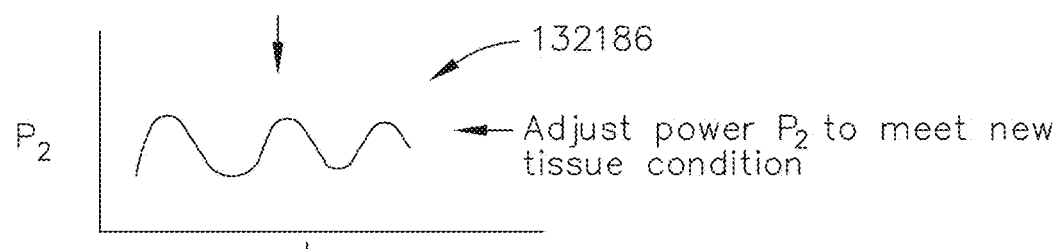

FIGS. 69A-69D is a series of graphical representations monitoring the impedance of an ultrasonic transducer to profile an ultrasonic blade and deliver power to the ultrasonic blade on the profile according to one aspect of the resent disclosure, where FIG. 69A is a graphical representation of the initial impedance of the ultrasonic transducer as a function of time, FIG. 69B is a graphical representation of power delivered to the ultrasonic blade as a function of time based on the initial impedance, FIG. 69C is a graphical representation of a new impedance of the ultrasonic transducer as a function of time, and FIG. 69D is a graphical representation of adjusted power delivered to the ultrasonic blade based on the new impedance.

Figure 70:
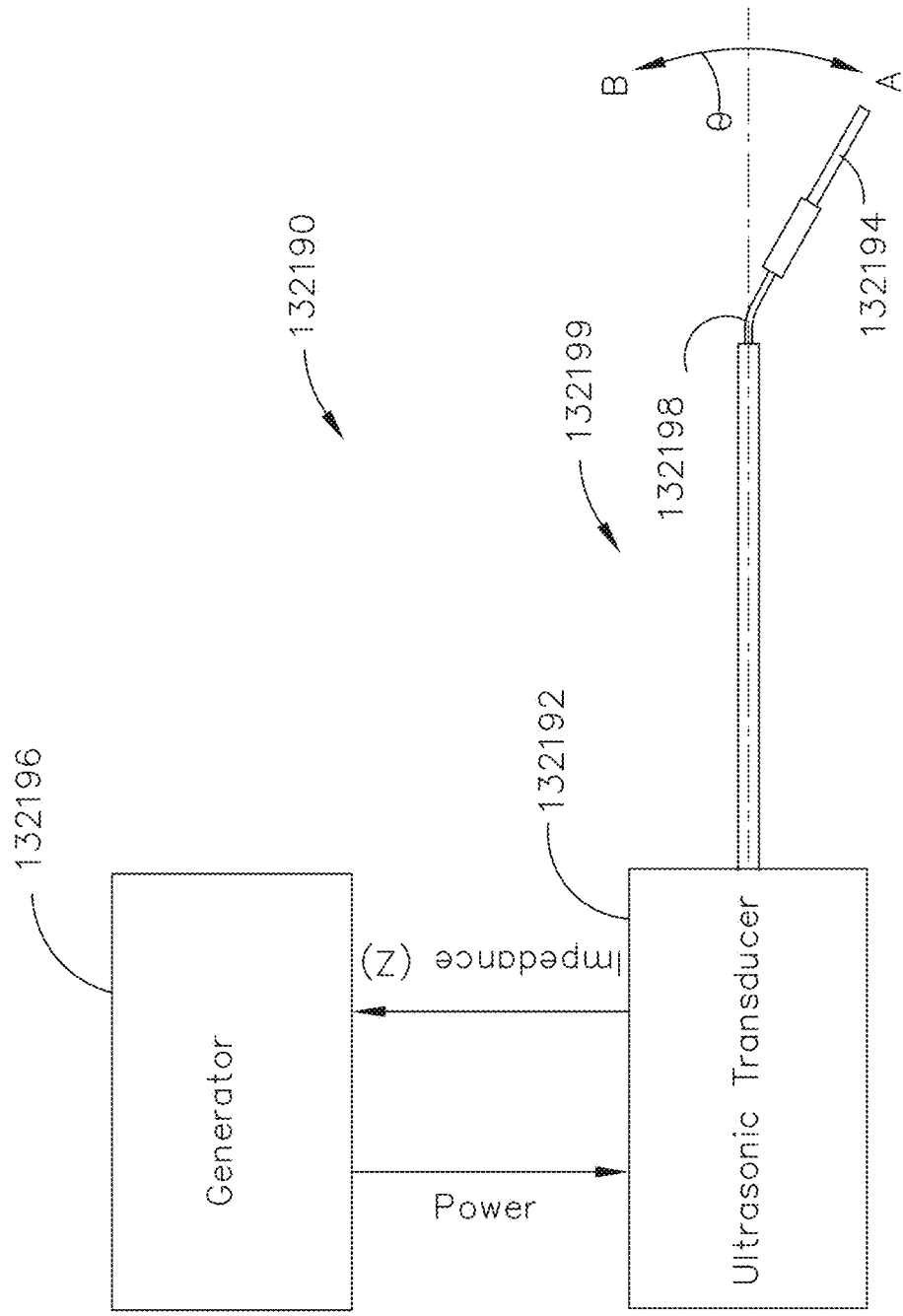

FIG. 70 is a system for adjusting complex impedance of the ultrasonic transducer to compensate for power lost when the ultrasonic blade is articulated, in accordance with at least one aspect of the present disclosure.

Figure 71:
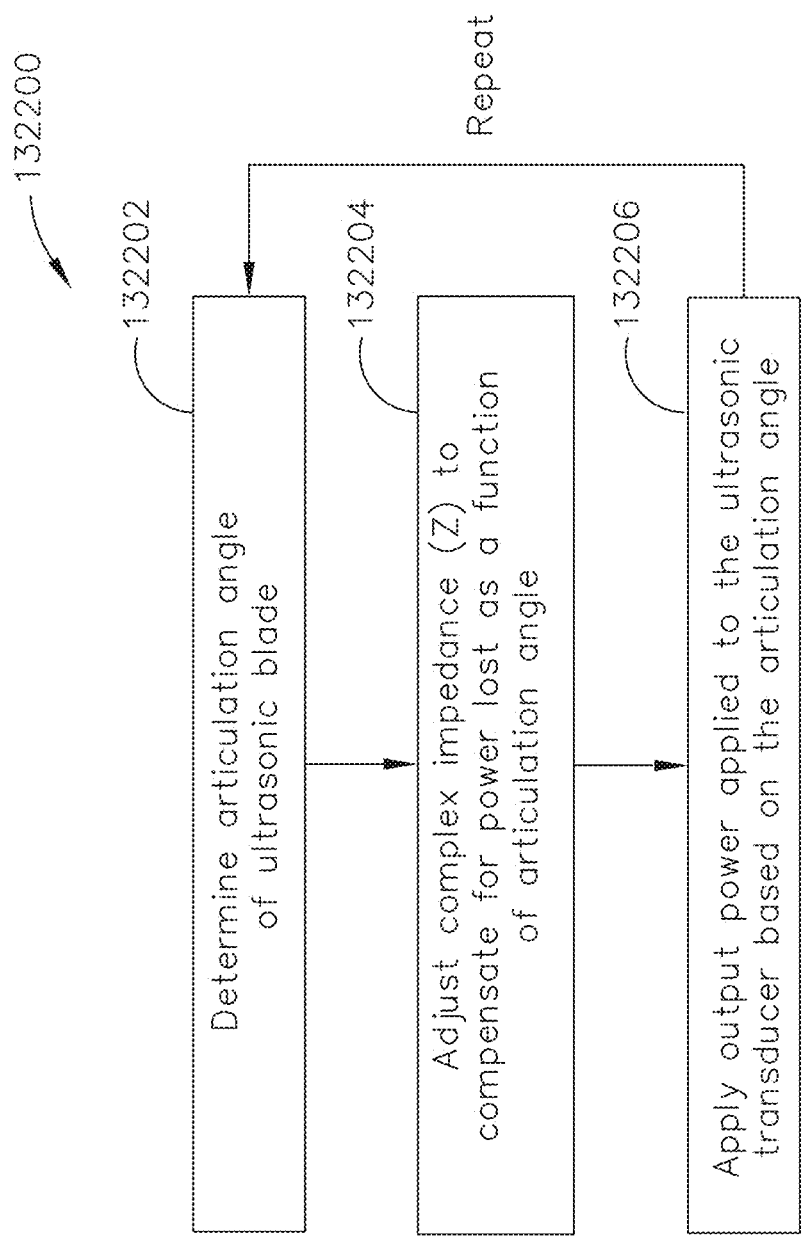

FIG. 71 is a logic flow diagram of a process depicting a control program or a logic configuration to compensate output power as a function of articulation angle, in accordance with at least one aspect of the present disclosure.

Figure 72:
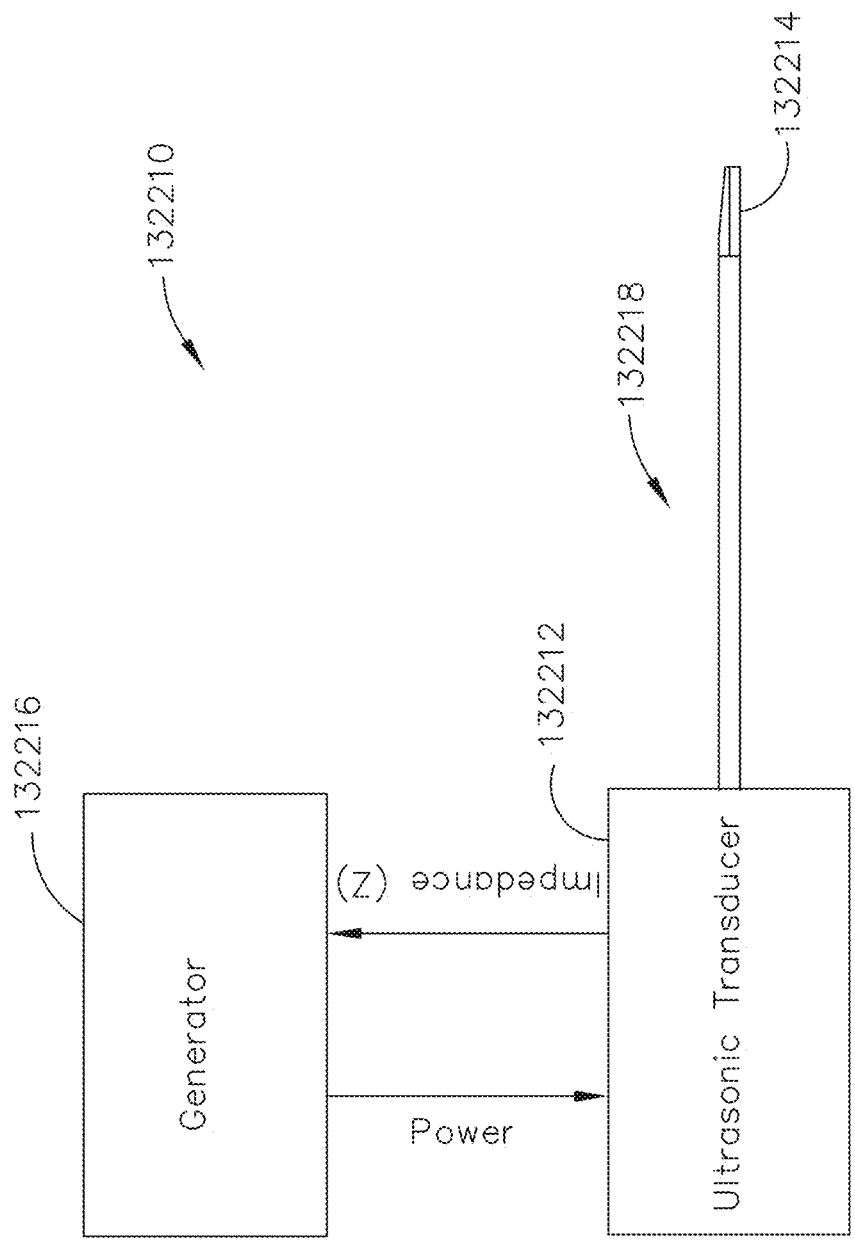

FIG. 72 is system for measuring complex impedance of an ultrasonic transducer in real time to determine action being performed by an ultrasonic blade, in accordance with at least one aspect of the present disclosure.

Figure 73:
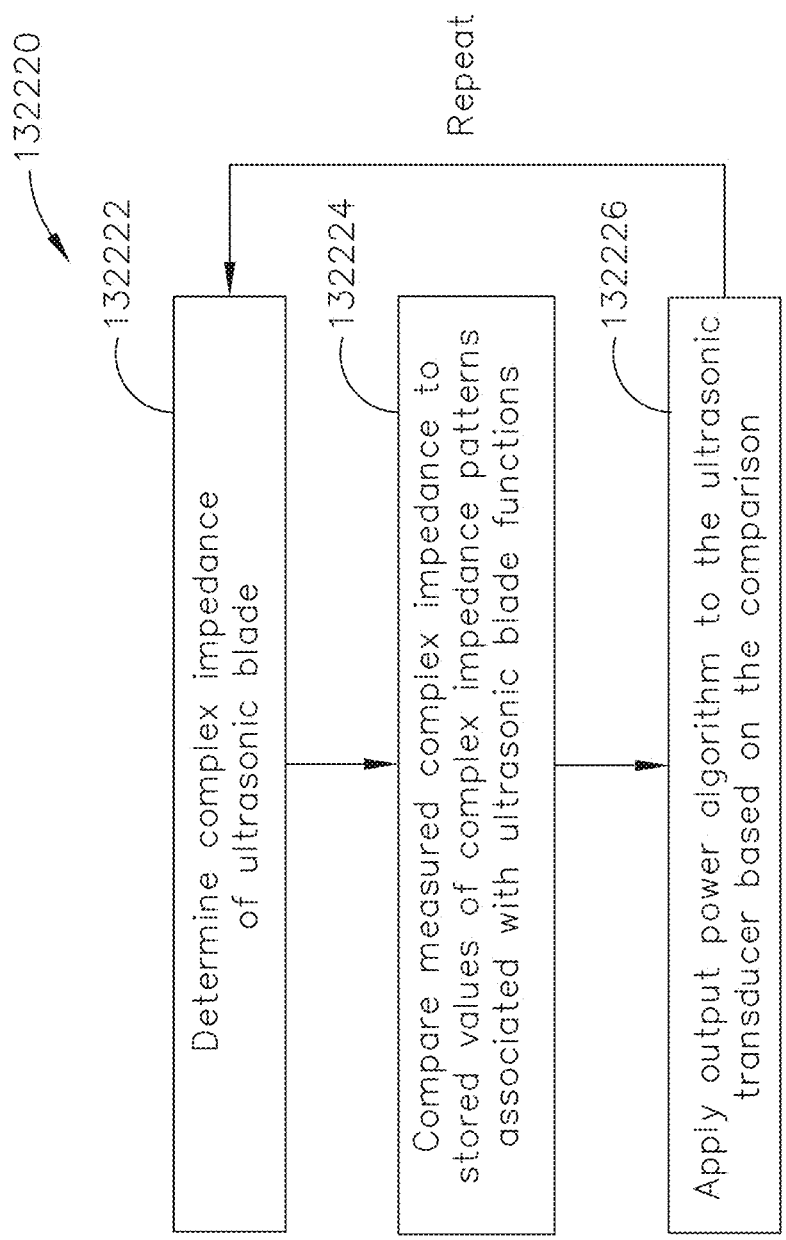

FIG. 73 is a logic flow diagram of a process depicting a control program or a logic configuration to determine action being performed by the ultrasonic blade based on the complex impedance pattern, in accordance with at least one aspect of the present disclosure.

Figure 74:
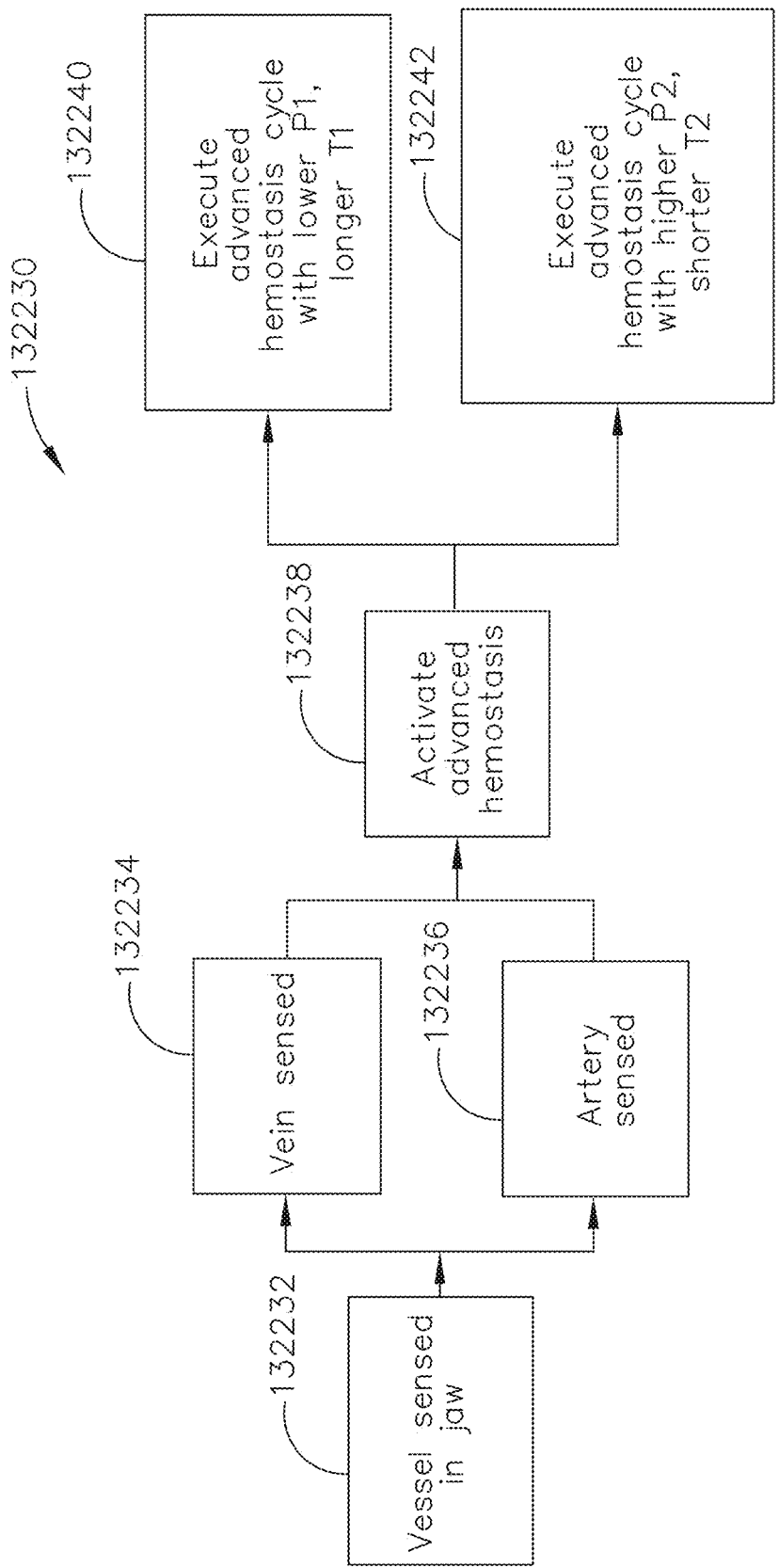

FIG. 74 is a logic flow diagram depicting a control program or a logic configuration of an adaptive process for identifying a hemostasis vessel, in accordance with at least one aspect of the present disclosure.

Figure 75:
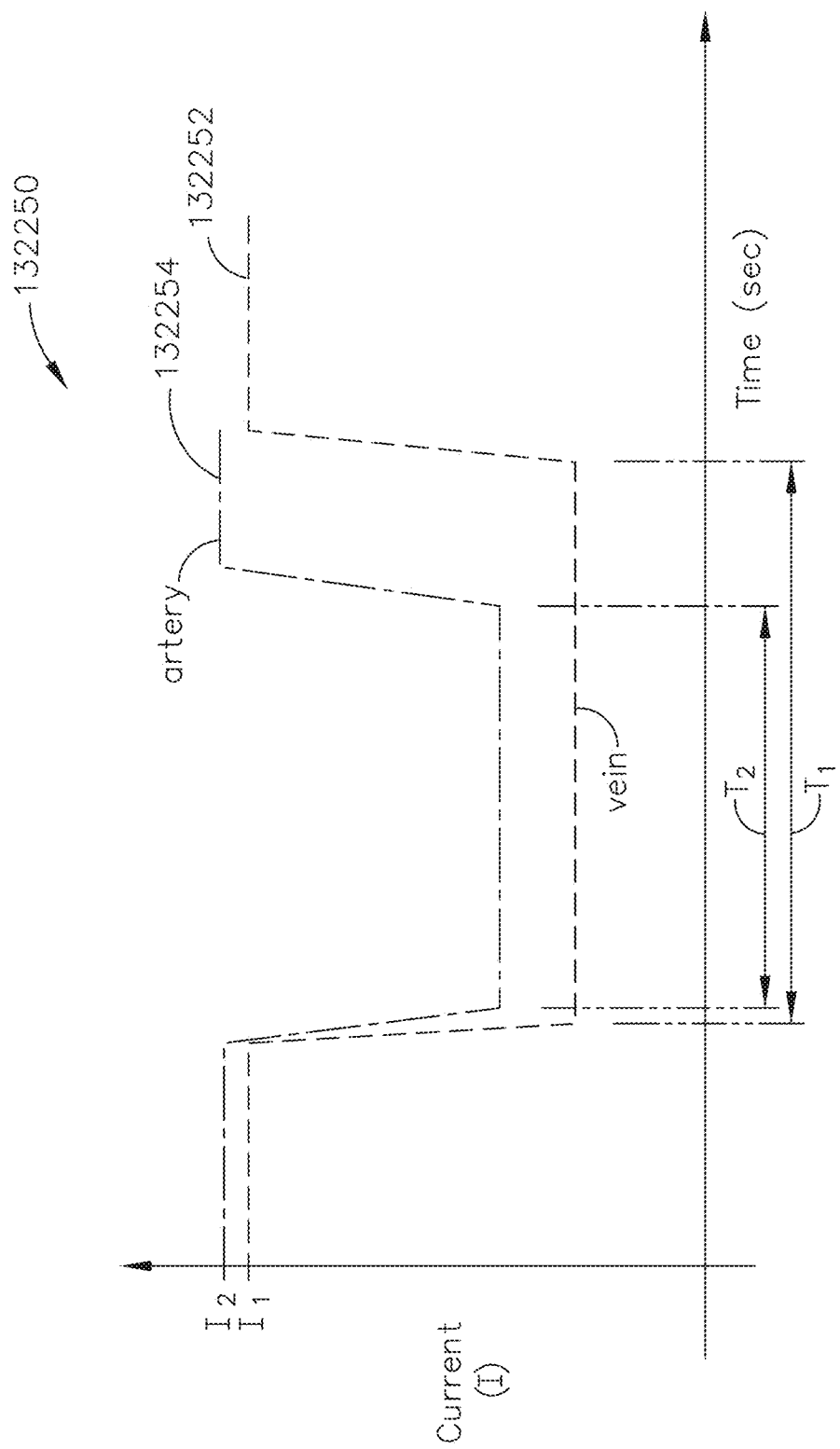

FIG. 75 is a graphical representation of ultrasonic transducer current profiles as a function of time for vein and artery vessel types, in accordance with at least one aspect of the present disclosure.

Figure 76:
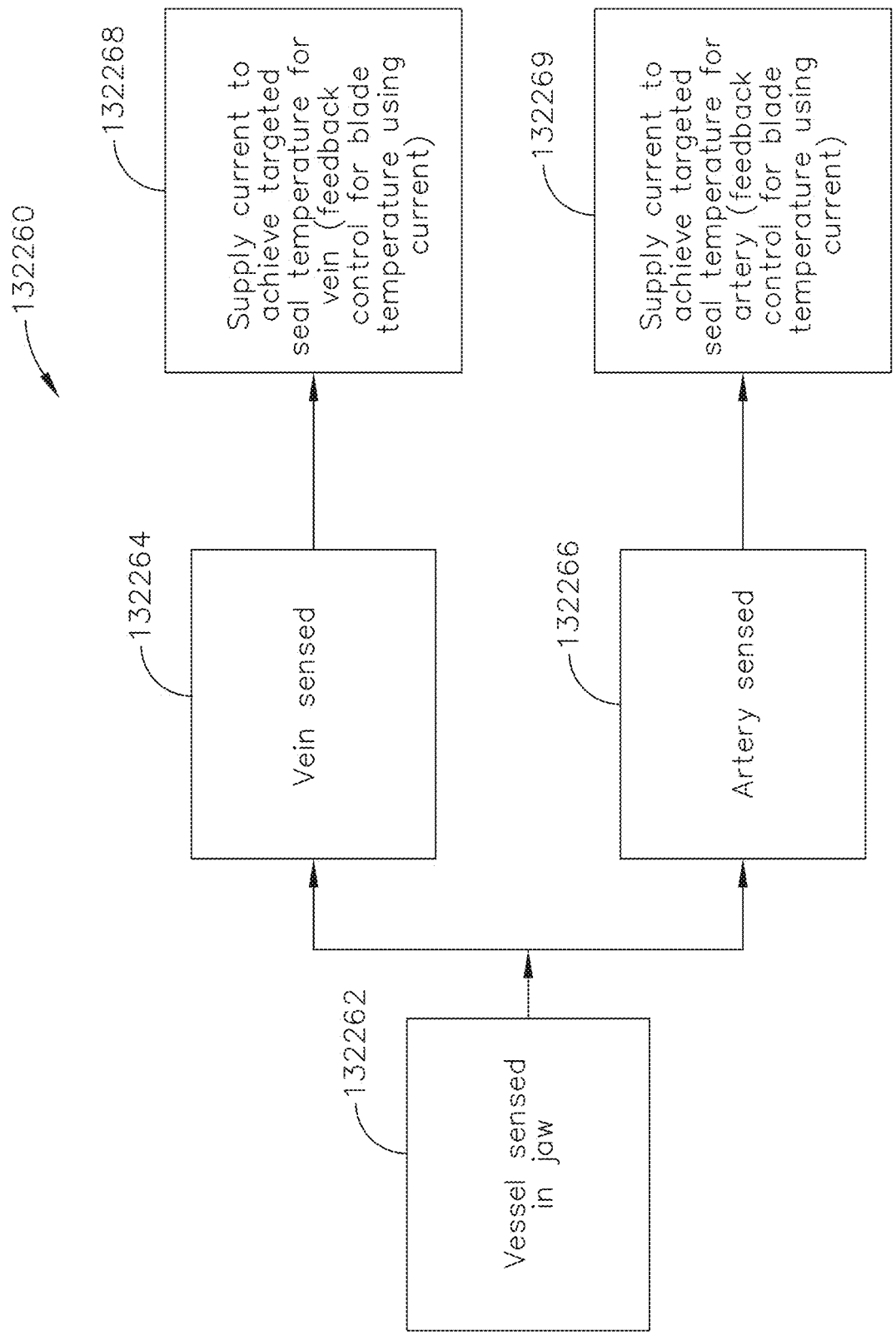

FIG. 76 is a logic flow diagram depicting a control program or a logic configuration of an adaptive process for identifying a hemostasis vessel, in accordance with at least one aspect of the present disclosure.

Figure 77:
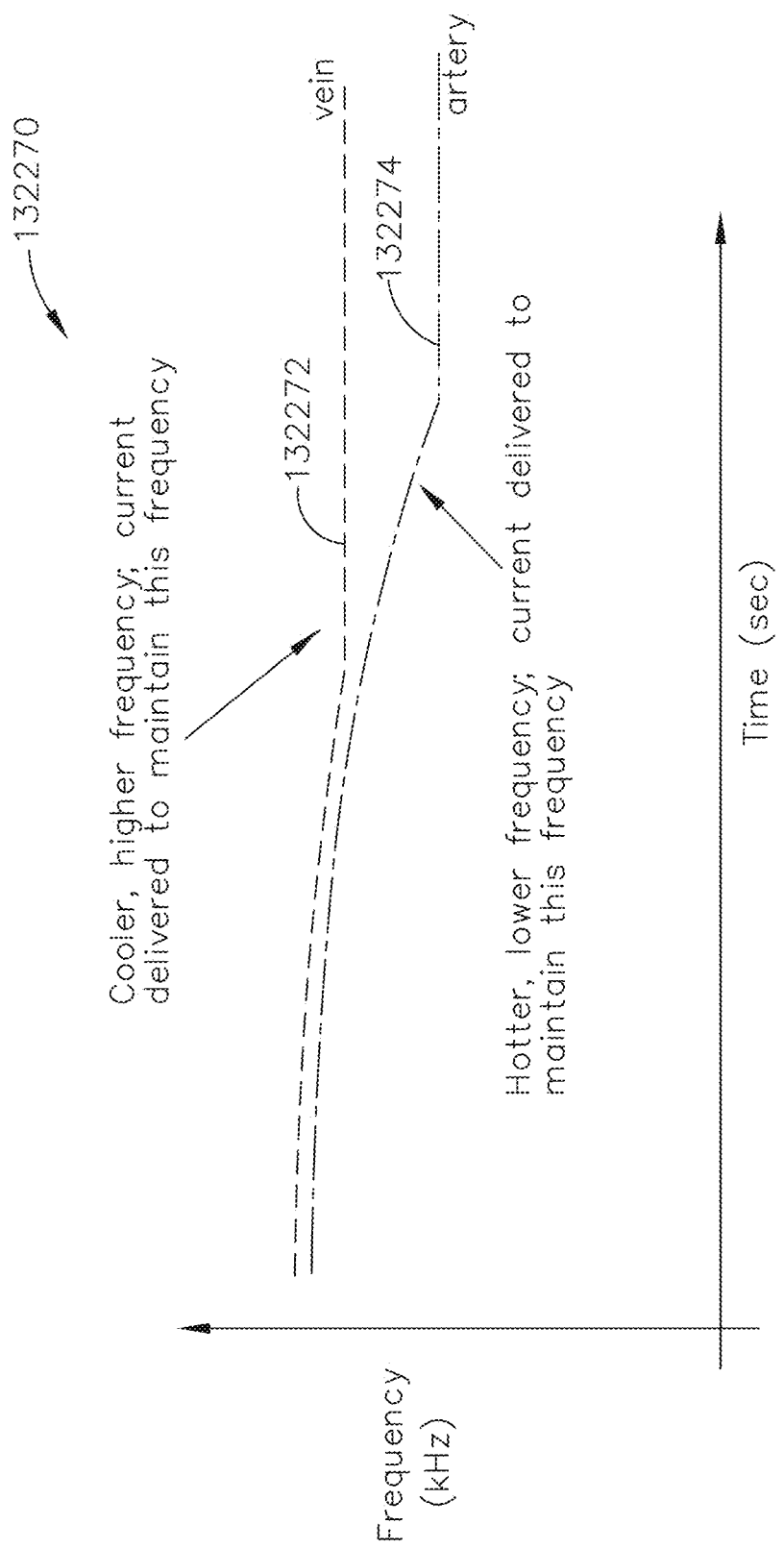

FIG. 77 is a graphical representation of ultrasonic transducer frequency profiles as a function of time for vein and artery vessel types, in accordance with at least one aspect of the present disclosure.

Figure 78:
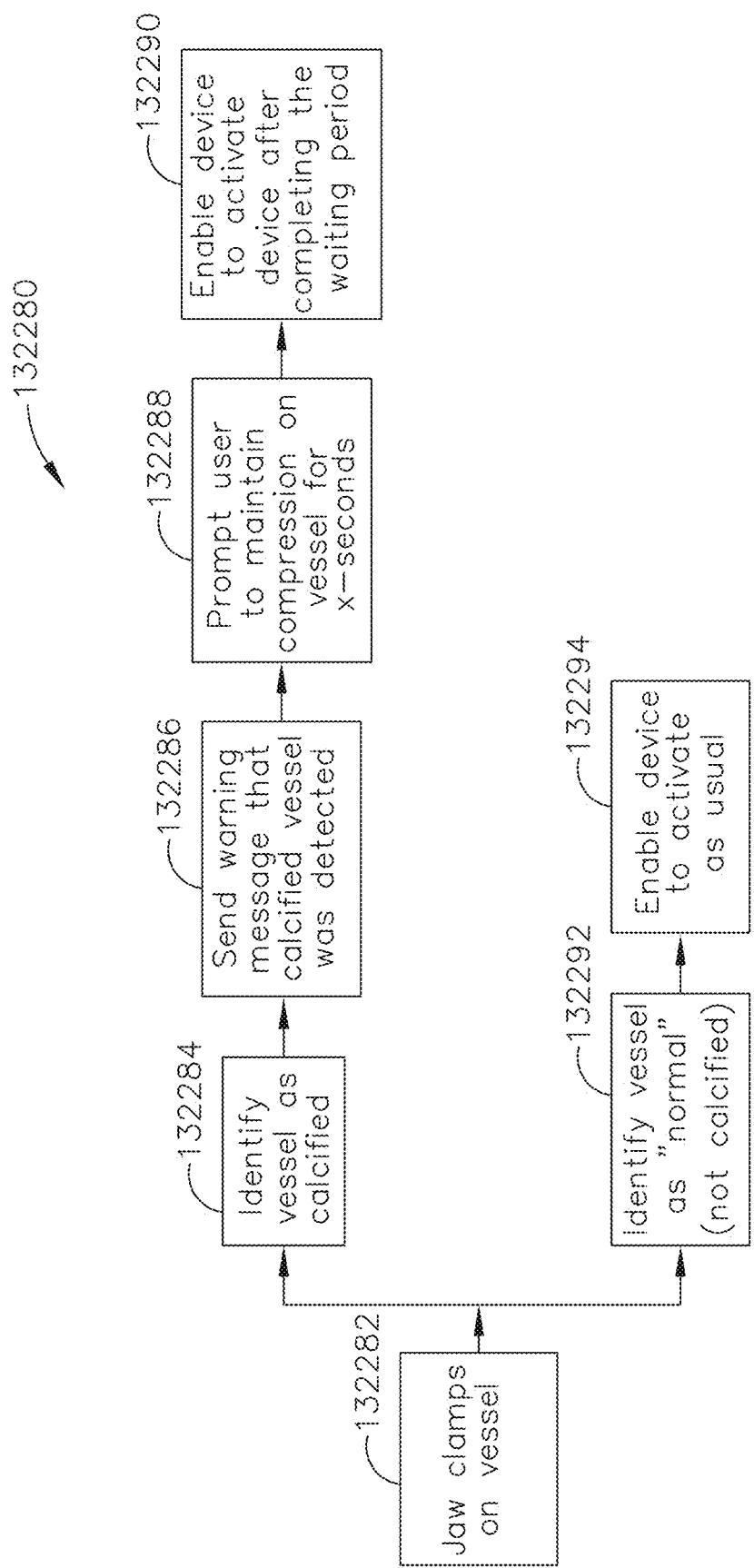

FIG. 78 is a logic flow diagram depicting a control program or a logic configuration of a process for identifying a calcified vessel, in accordance with at least one aspect of the present disclosure.

Figure 79:
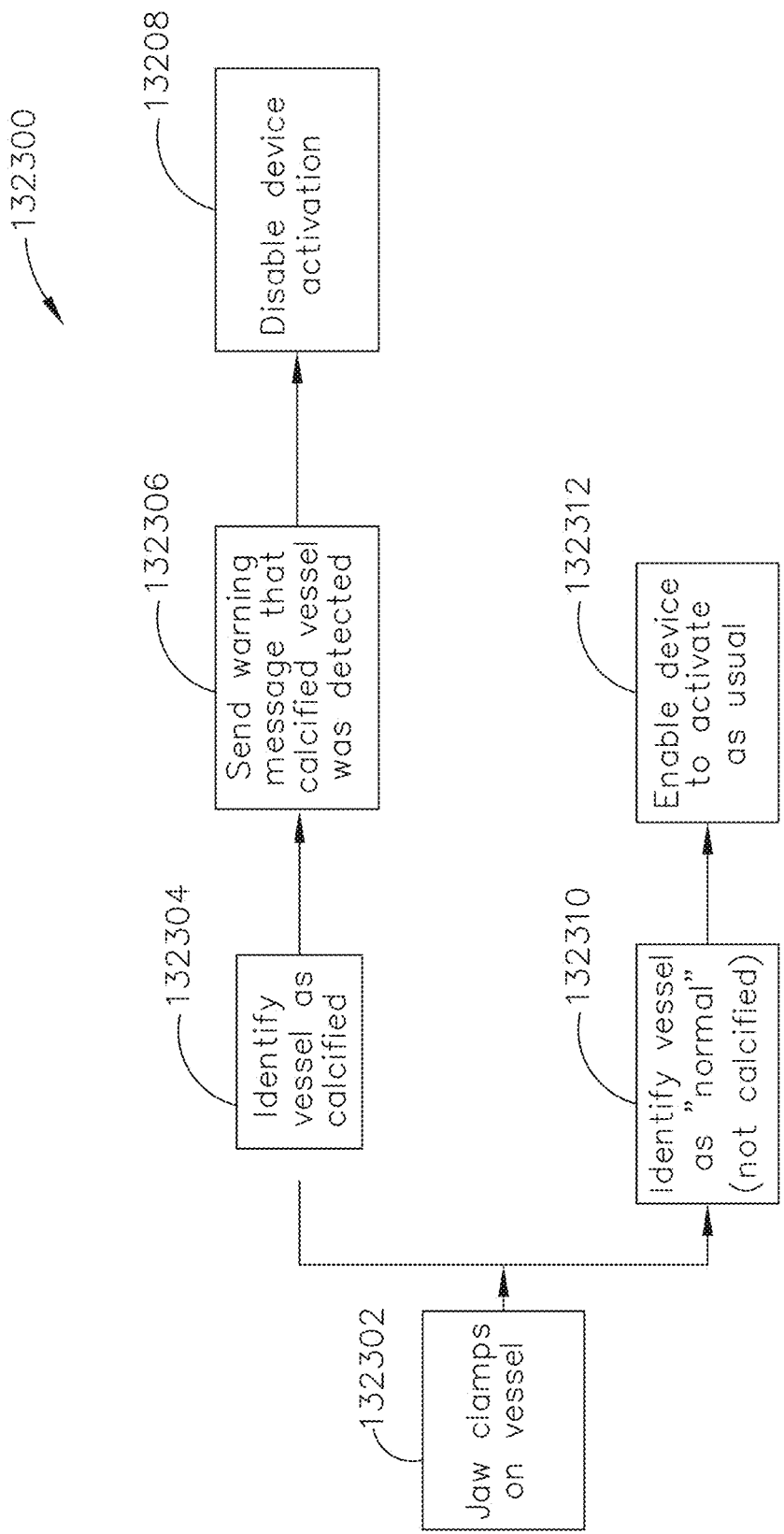

FIG. 79 is a logic flow diagram depicting a control program or a logic configuration of a process for identifying a calcified vessel, in accordance with at least one aspect of the present disclosure.

Figure 80:
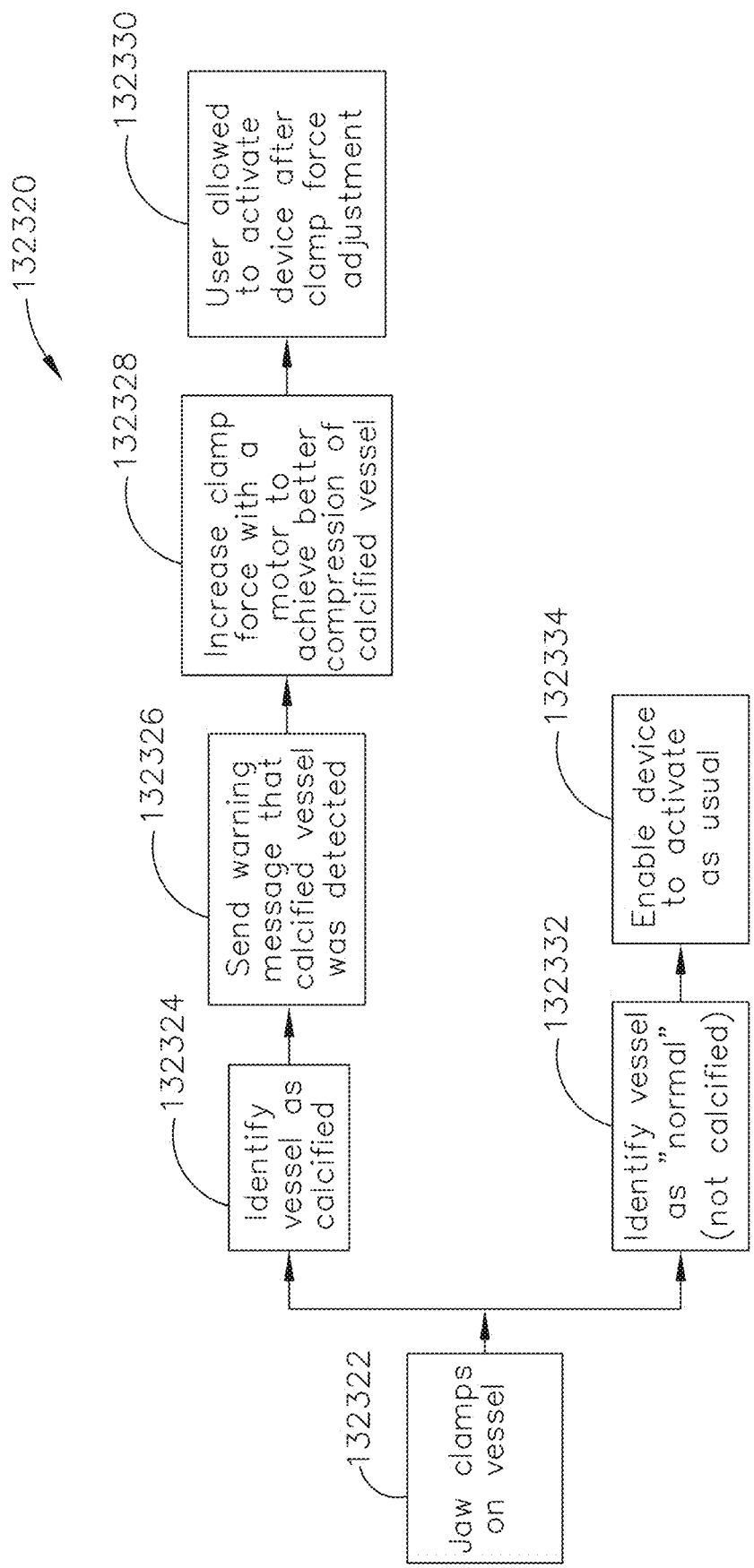

FIG. 80 is a logic flow diagram depicting a control program or a logic configuration of a process for identifying a calcified vessel, in accordance with at least one aspect of the present disclosure.

Figure 81:
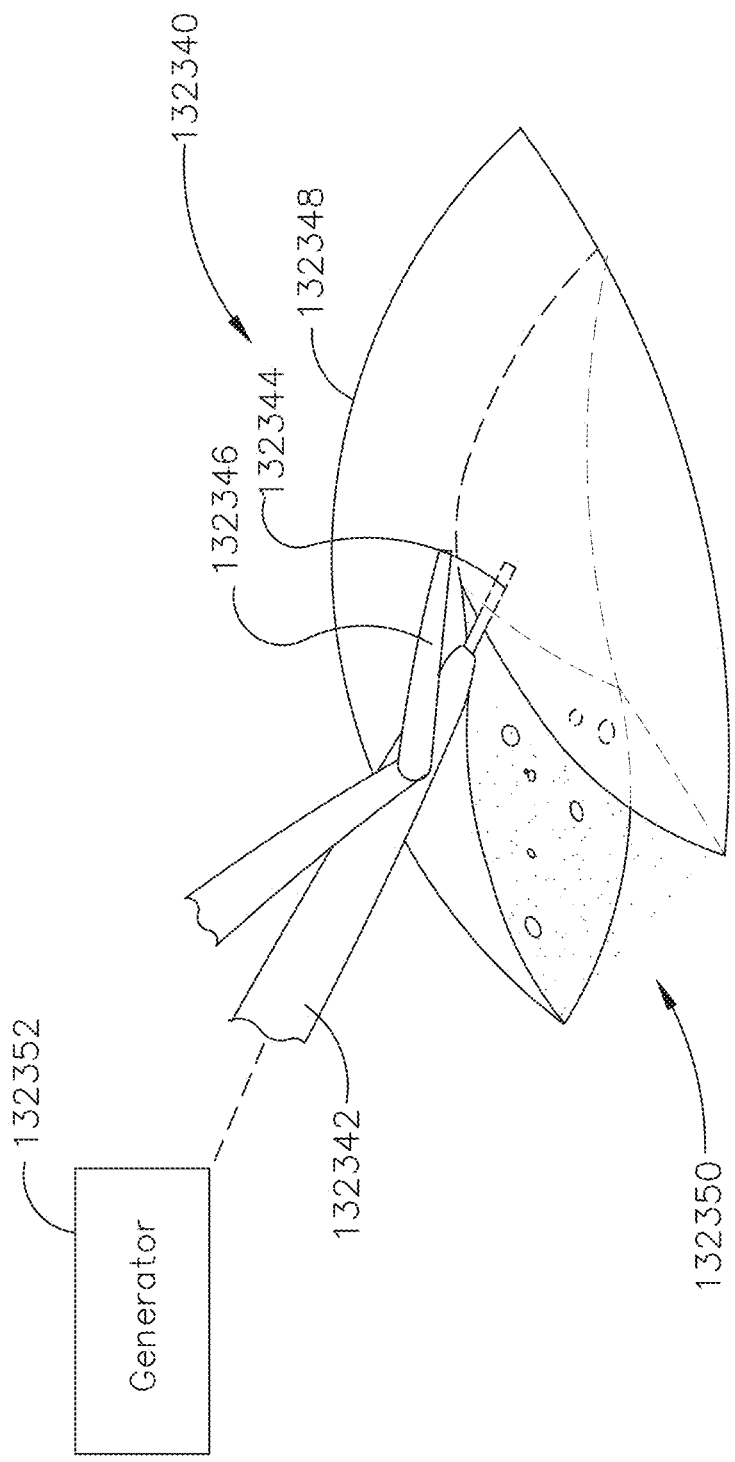

FIG. 81 is a diagram of a liver resection with vessels embedded in parenchymal tissue, in accordance with at least one aspect of the present disclosure.

Figure 82:
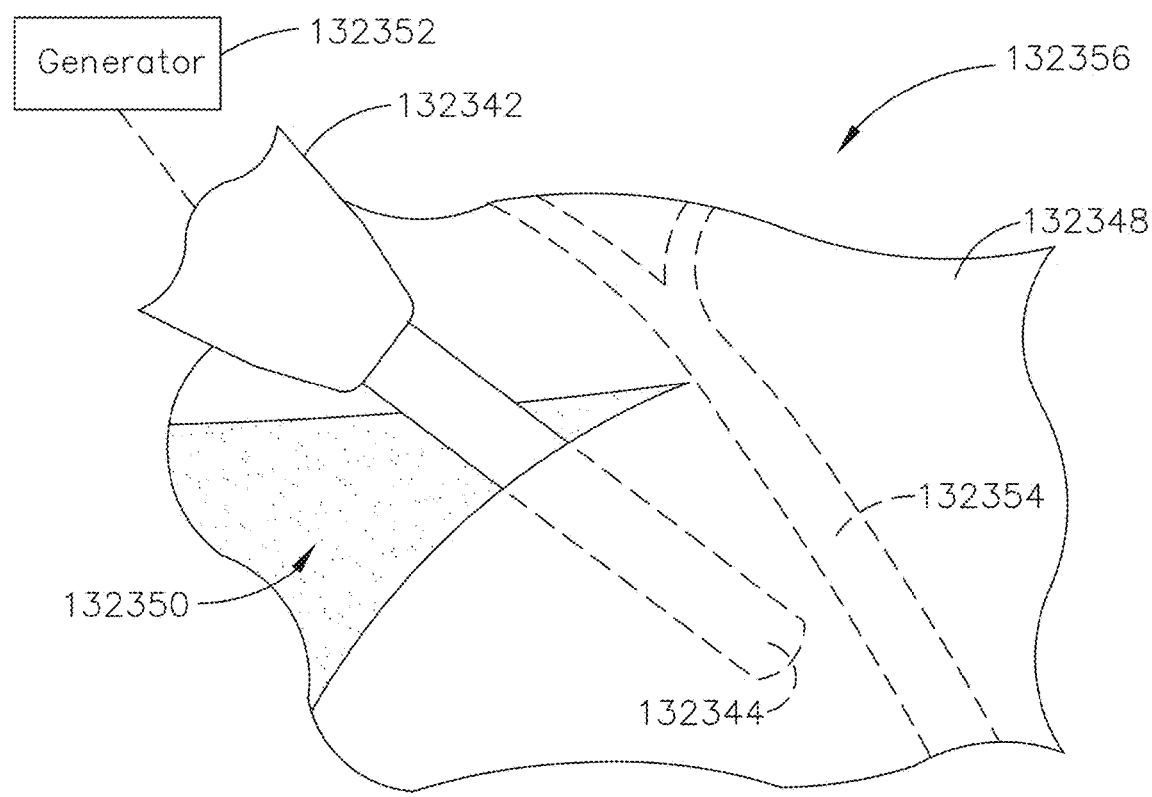

FIG. 82 is a diagram of an ultrasonic blade in parenchyma but not contacting a vessel, in accordance with at least one aspect of the present disclosure.

Figure 83A:
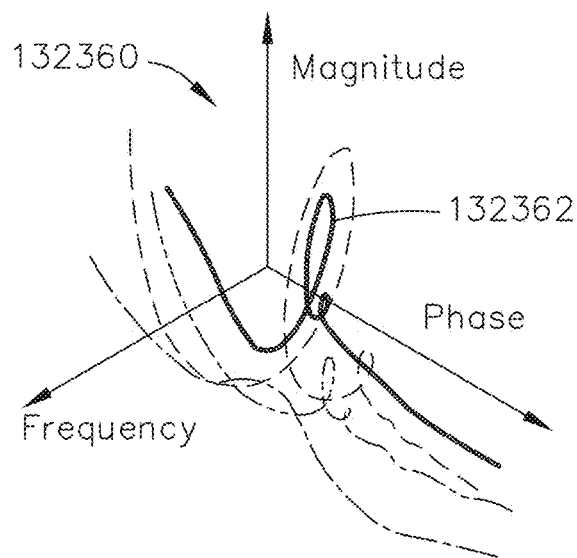
Figure 83B:
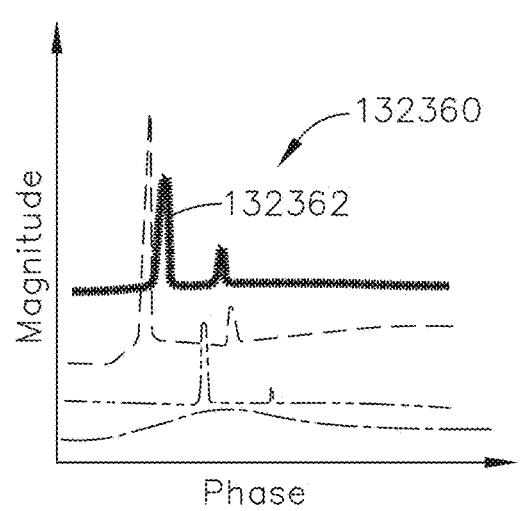

FIGS. 83A-83B are ultrasonic transducer impedance magnitude/phase plots with curves for parenchyma shown in red, in accordance with at least one aspect of the present disclosure.

Figure 84:
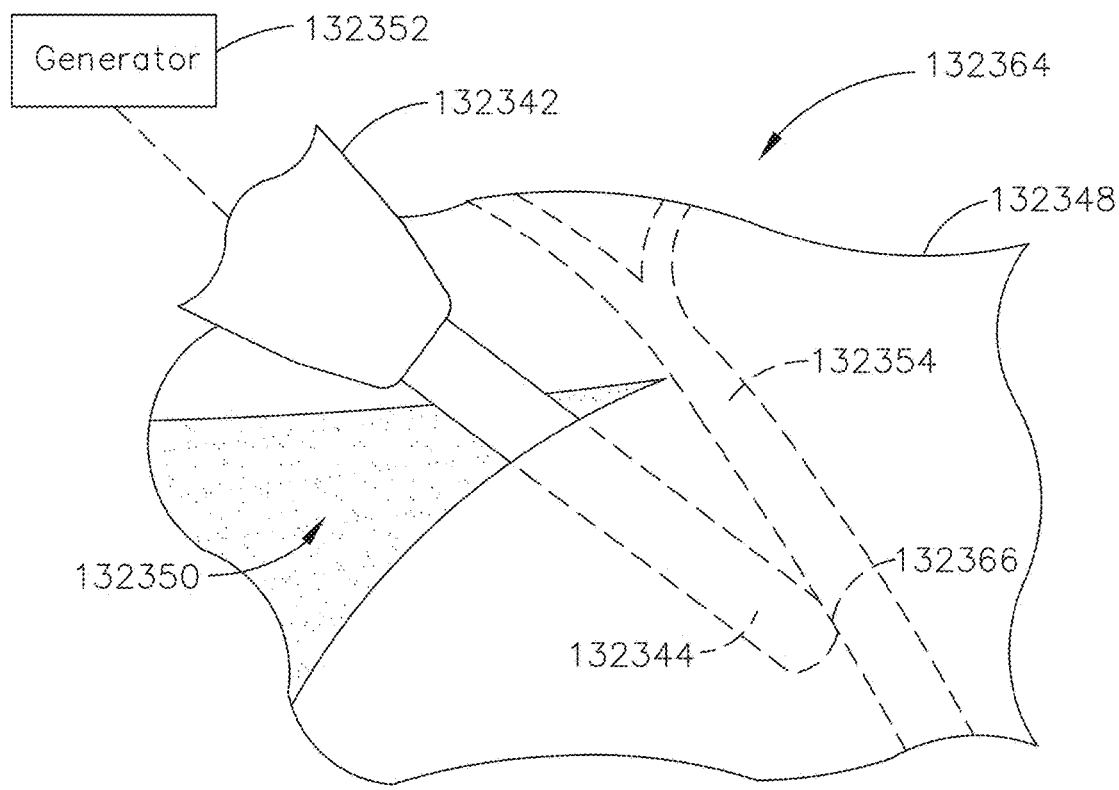

FIG. 84 is a diagram of an ultrasonic blade in parenchyma and contacting a large vessel.

Figure 85A:
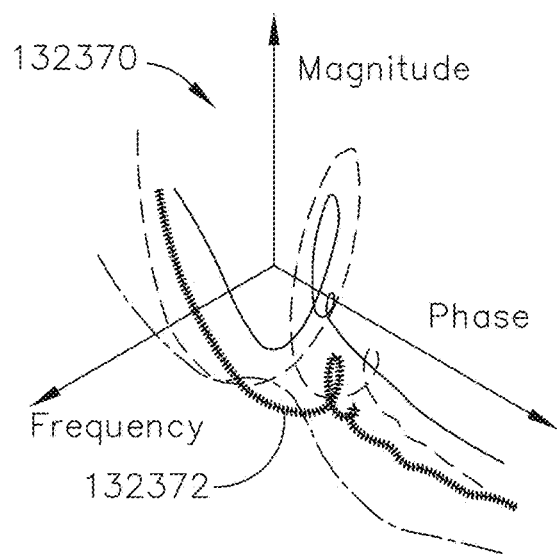
Figure 85B:
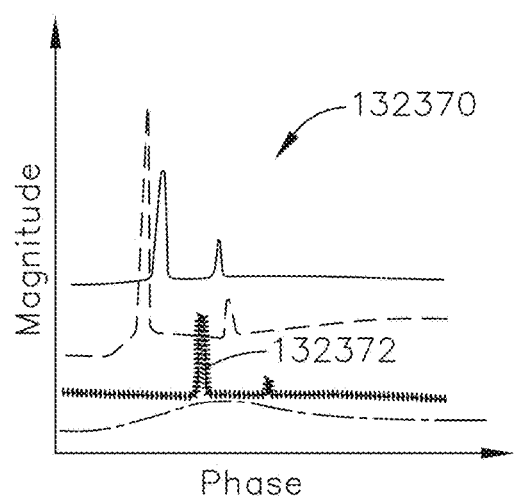

FIGS. 85A-85B are ultrasonic transducer impedance magnitude/phase plots with curves for a large vessel, in accordance with at least one aspect of the present disclosure.

Figure 86:
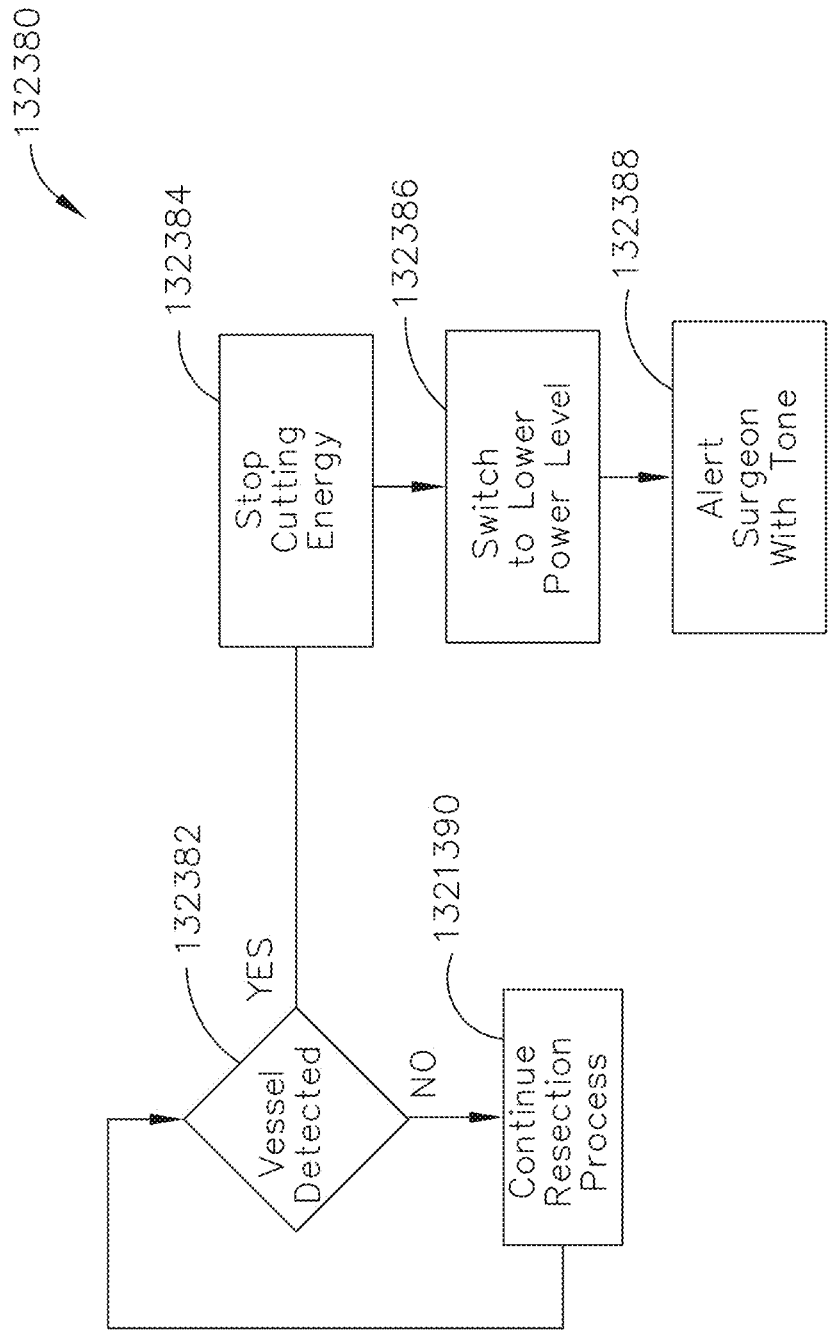

FIG. 86 is a logic flow diagram depicting a control program or a logic configuration of a process for treating tissue in parenchyma when a vessel is detected, in accordance with at least one aspect of the present disclosure.

FIG. 87 is an ultrasonic device configured to identify the status of the ultrasonic blade and determine the clocked clamp arm status to determine whether a disposable portion of a reusable and disposable ultrasonic device has been installed correctly, in accordance with at least one aspect of the present disclosure.

FIG. 88 is an end effector portion of the ultrasonic device shown in FIG. 87.

Figure 89:
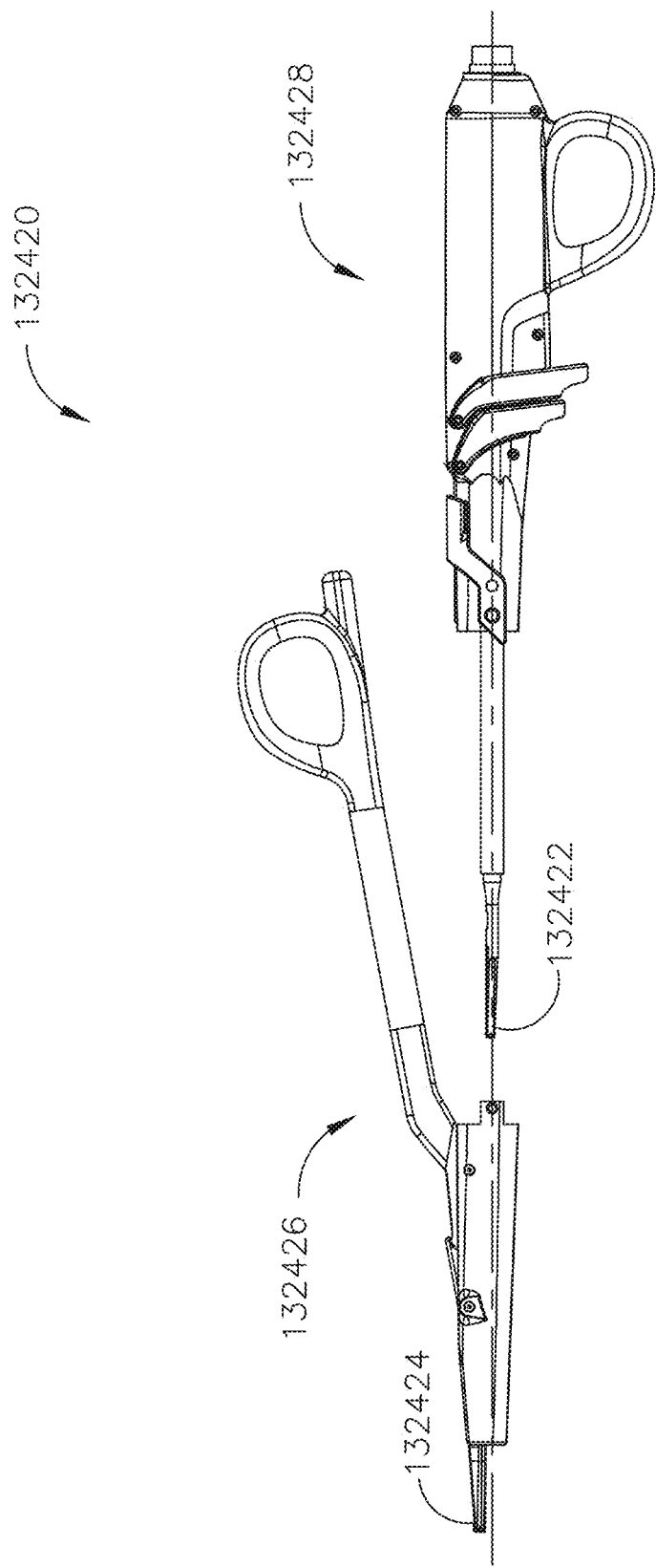

FIG. 89 is an ultrasonic device configured to identify the status of the ultrasonic blade and determine whether the clamp arm is not completely distal to determine whether a disposable portion of a reusable and disposable ultrasonic device has been installed correctly, in accordance with at least one aspect of the present disclosure.

Figure 90:
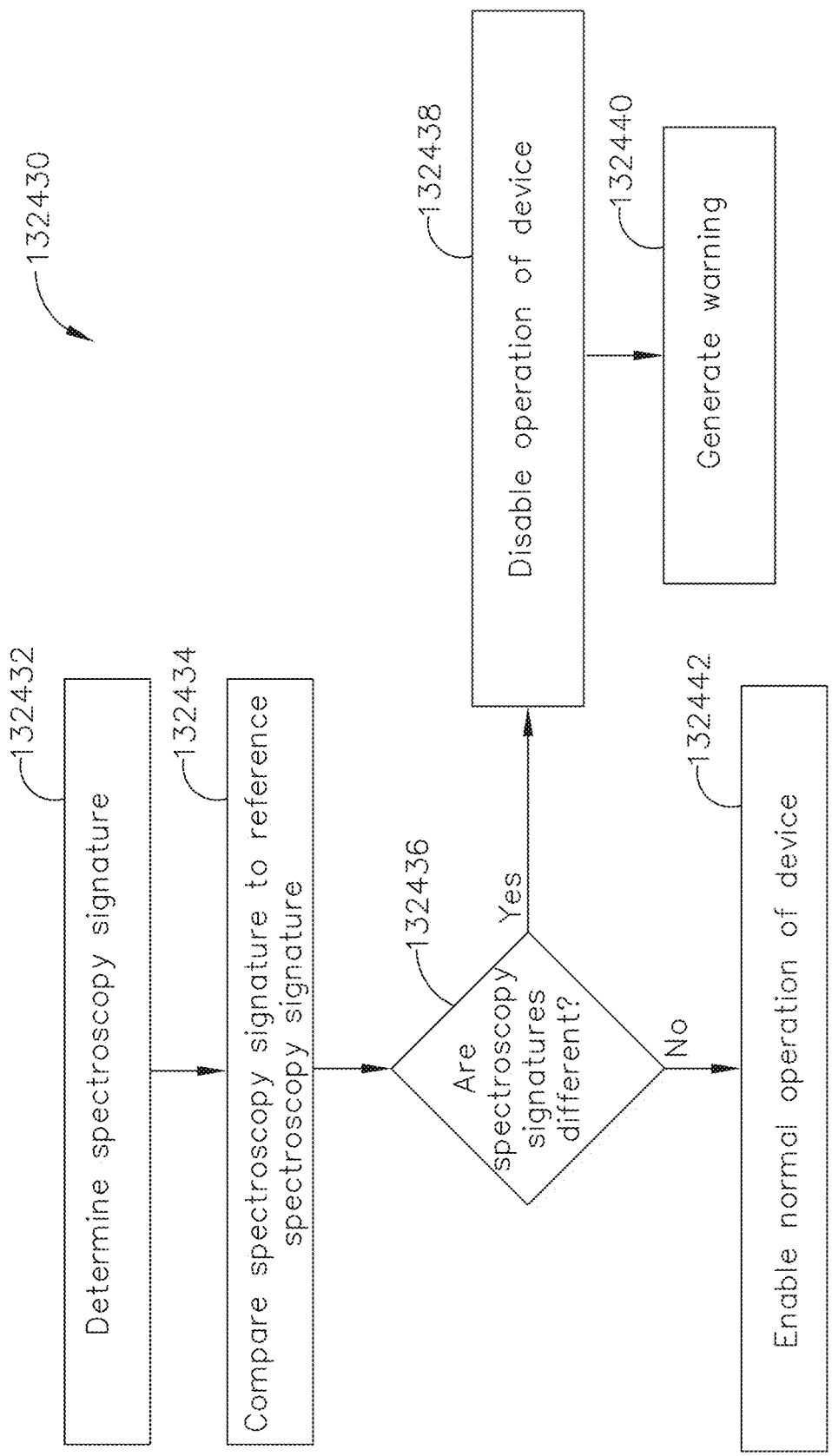

FIG. 90 is a logic flow diagram depicting a control program or a logic configuration to identify the status of components of reusable and disposable devices, in accordance with at least one aspect of the present disclosure.

Figure 91:
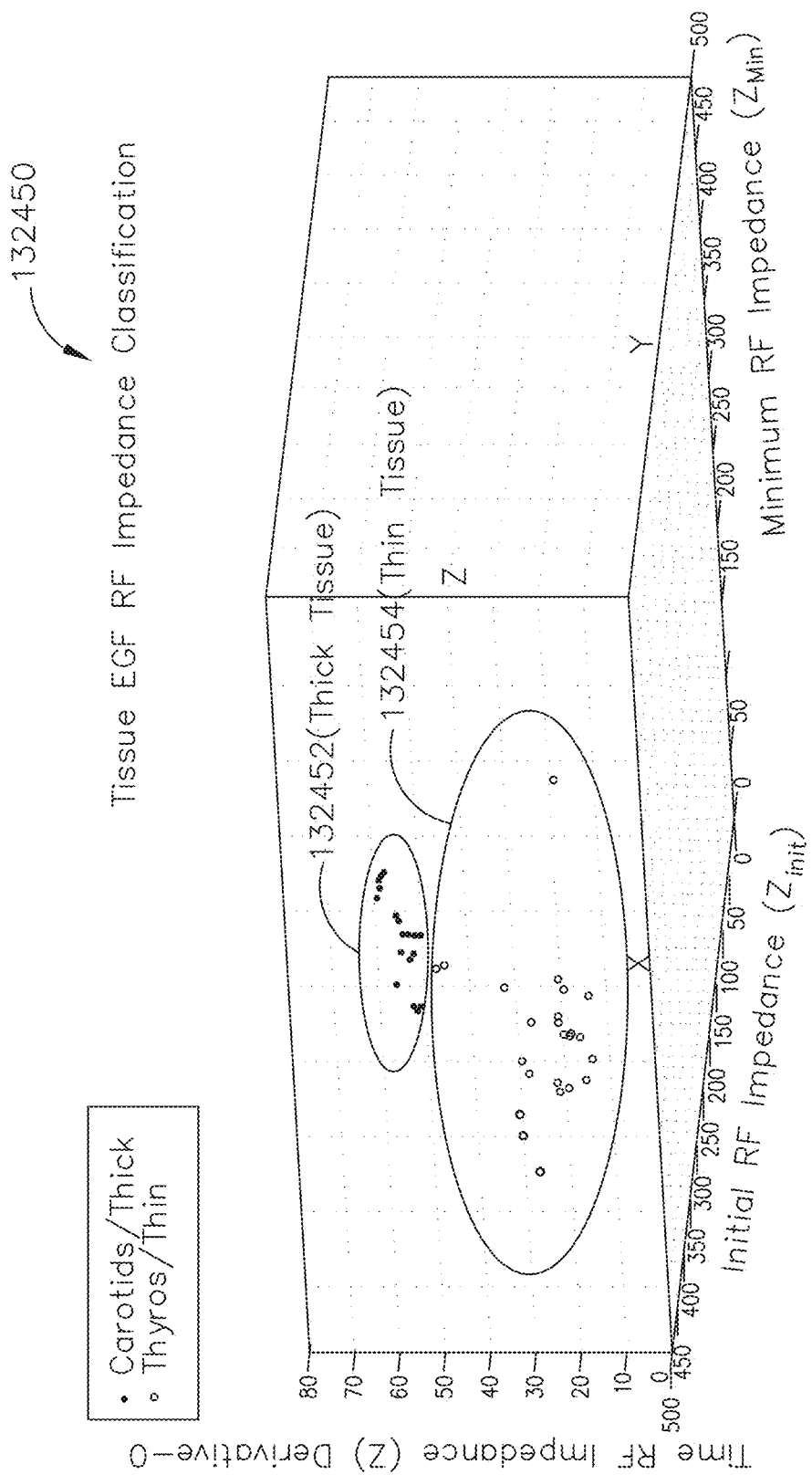

FIG. 91 is a three-dimensional graphical representation of tissue radio frequency (RF) impedance classification, in accordance with at least one aspect of the present disclosure.

Figure 92:
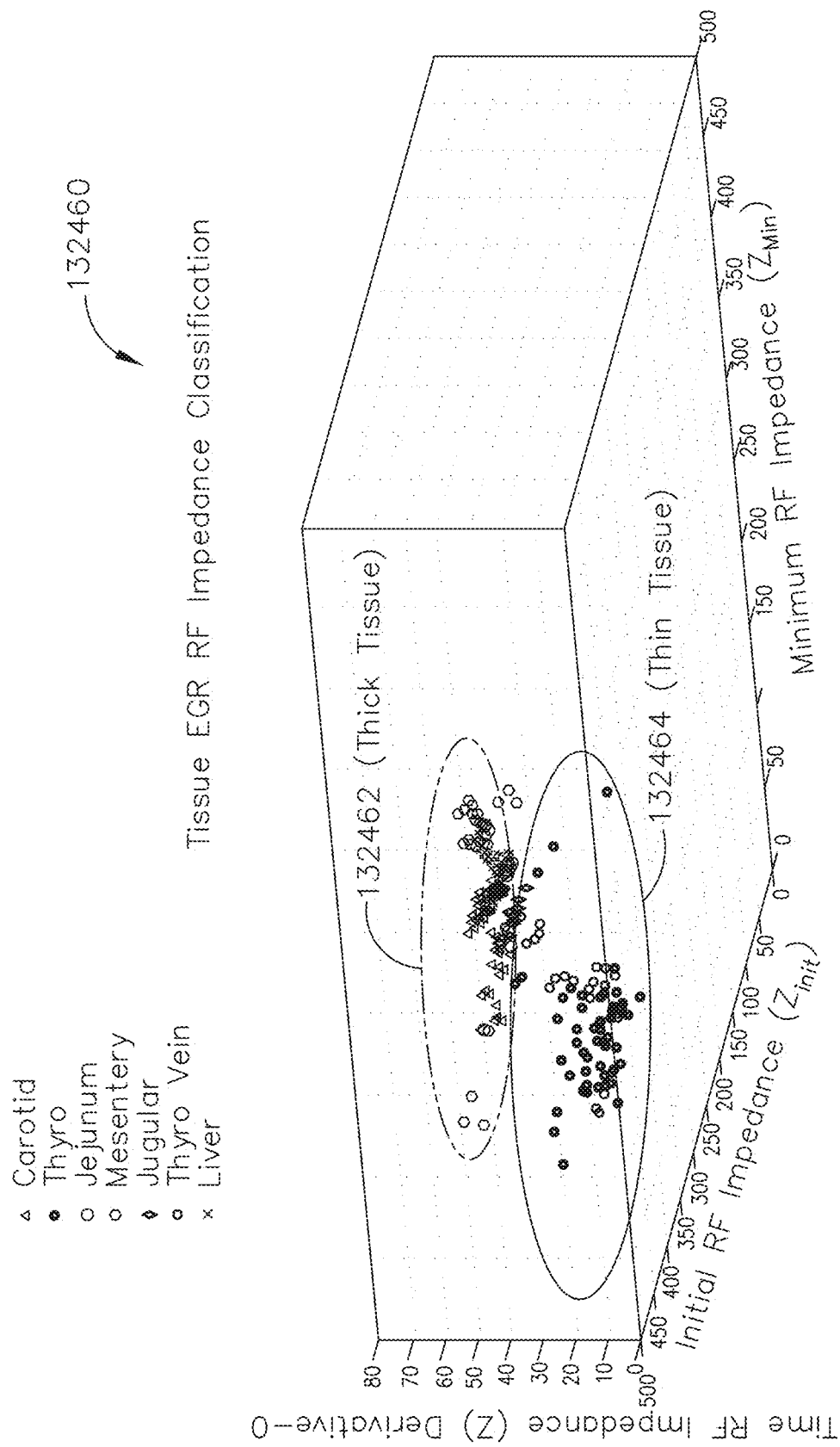

FIG. 92 is a three-dimensional graphical representation of tissue radio frequency (RF) impedance analysis, in accordance with at least one aspect of the present disclosure.

Figure 93:
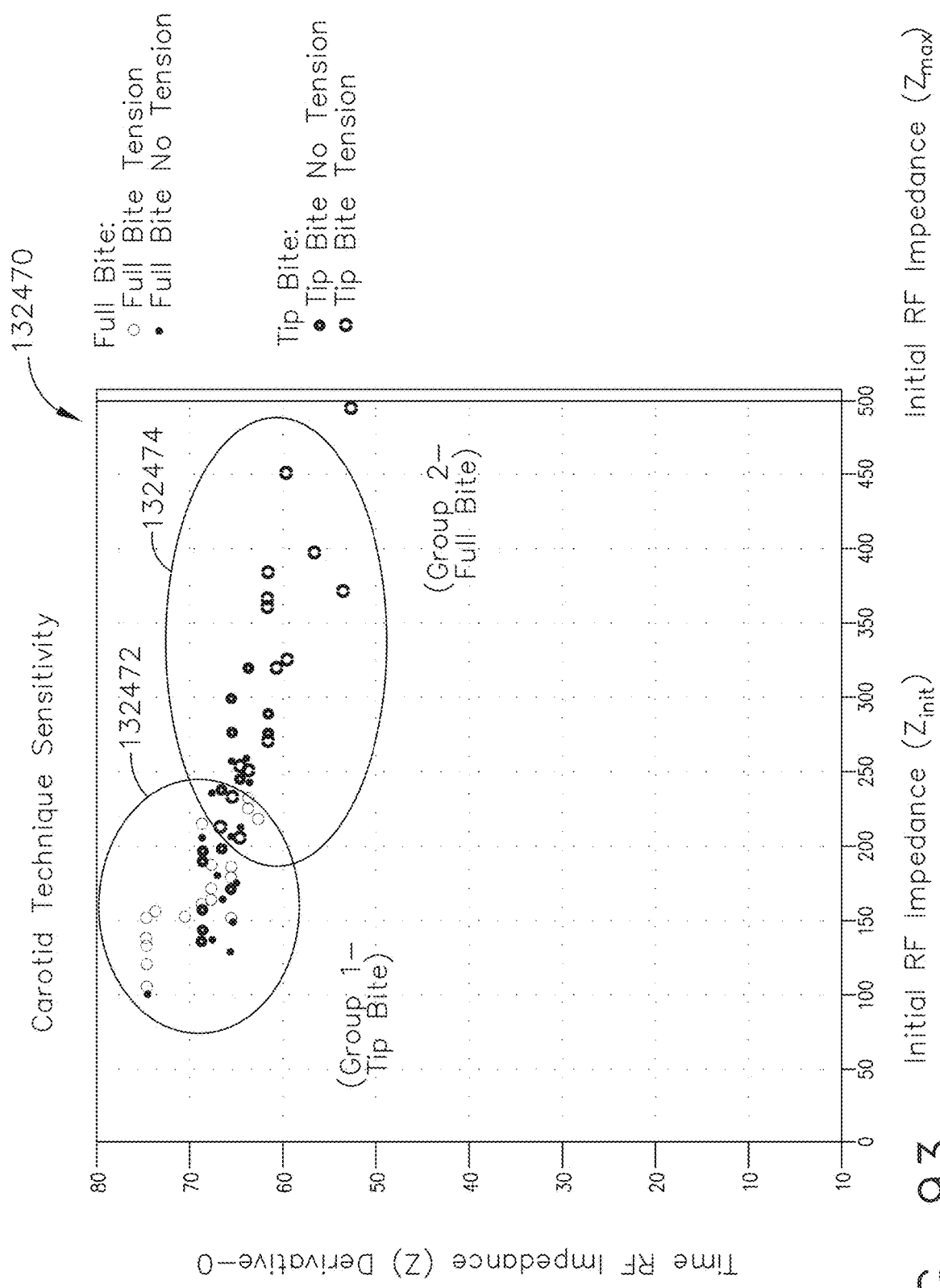

FIG. 93 is a graphical representation of carotid technique sensitivity where the time impedance (Z) derivative is plotted as a function of initial radio frequency (RF) impedance, in accordance with at least one aspect of the present disclosure.

Figure 94:
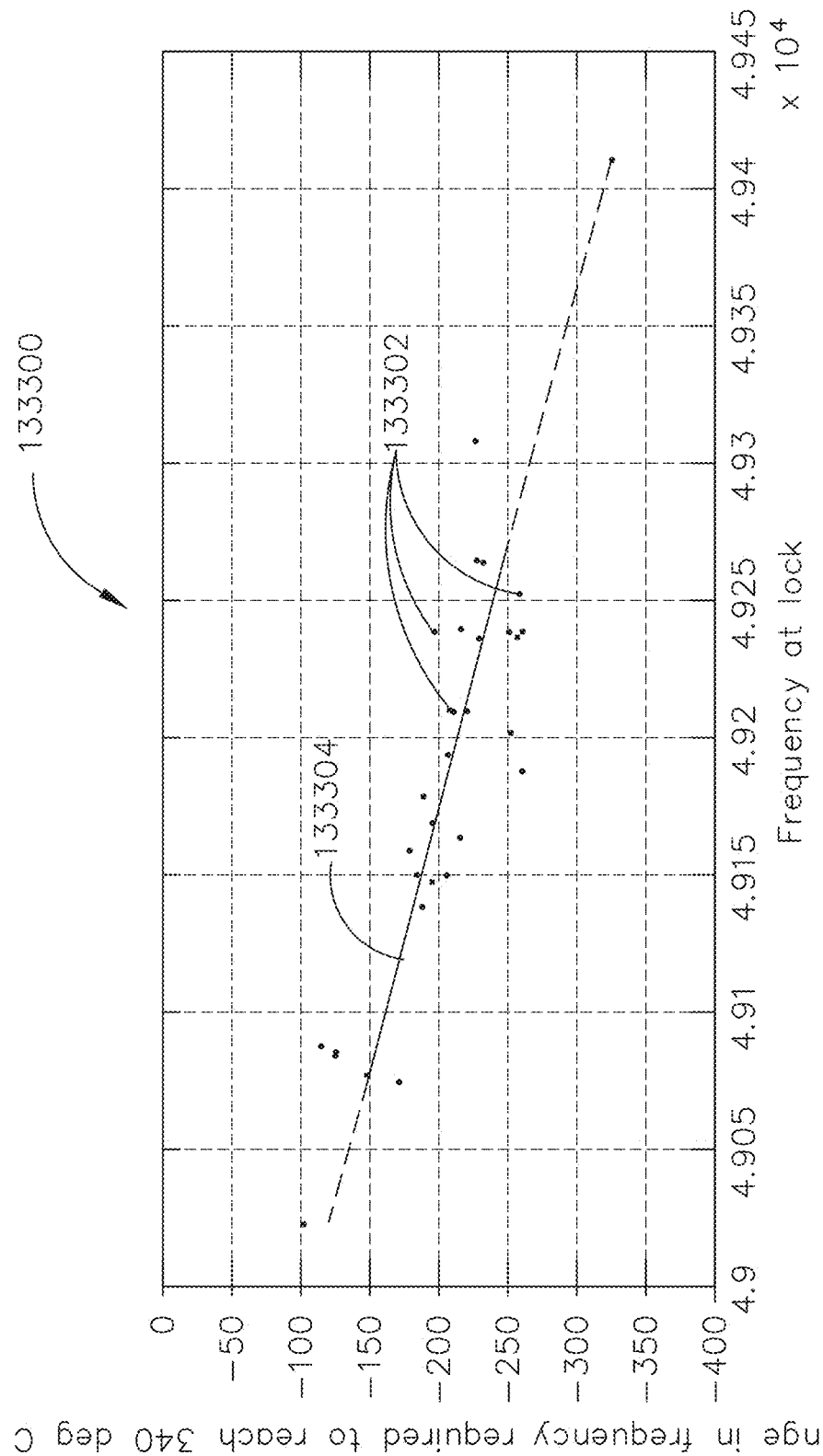

FIG. 94 is a graphical representation of the relationship between initial frequency and the change in frequency required to achieve a temperature of approximately 340° C., in accordance with at least one aspect of the present disclosure.

Figure 95:
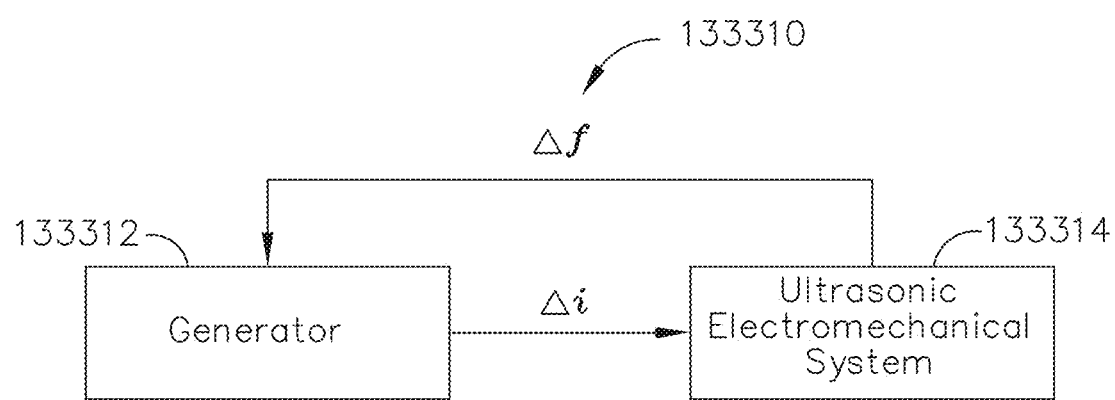

FIG. 95 illustrates a feedback control system comprising an ultrasonic generator to regulate the electrical current (i) set point applied to an ultrasonic transducer of an ultrasonic electromechanical system to prevent the frequency (f) of the ultrasonic transducer from decreasing lower than a predetermined threshold, in accordance with at least one aspect of the present disclosure.

Figure 96:
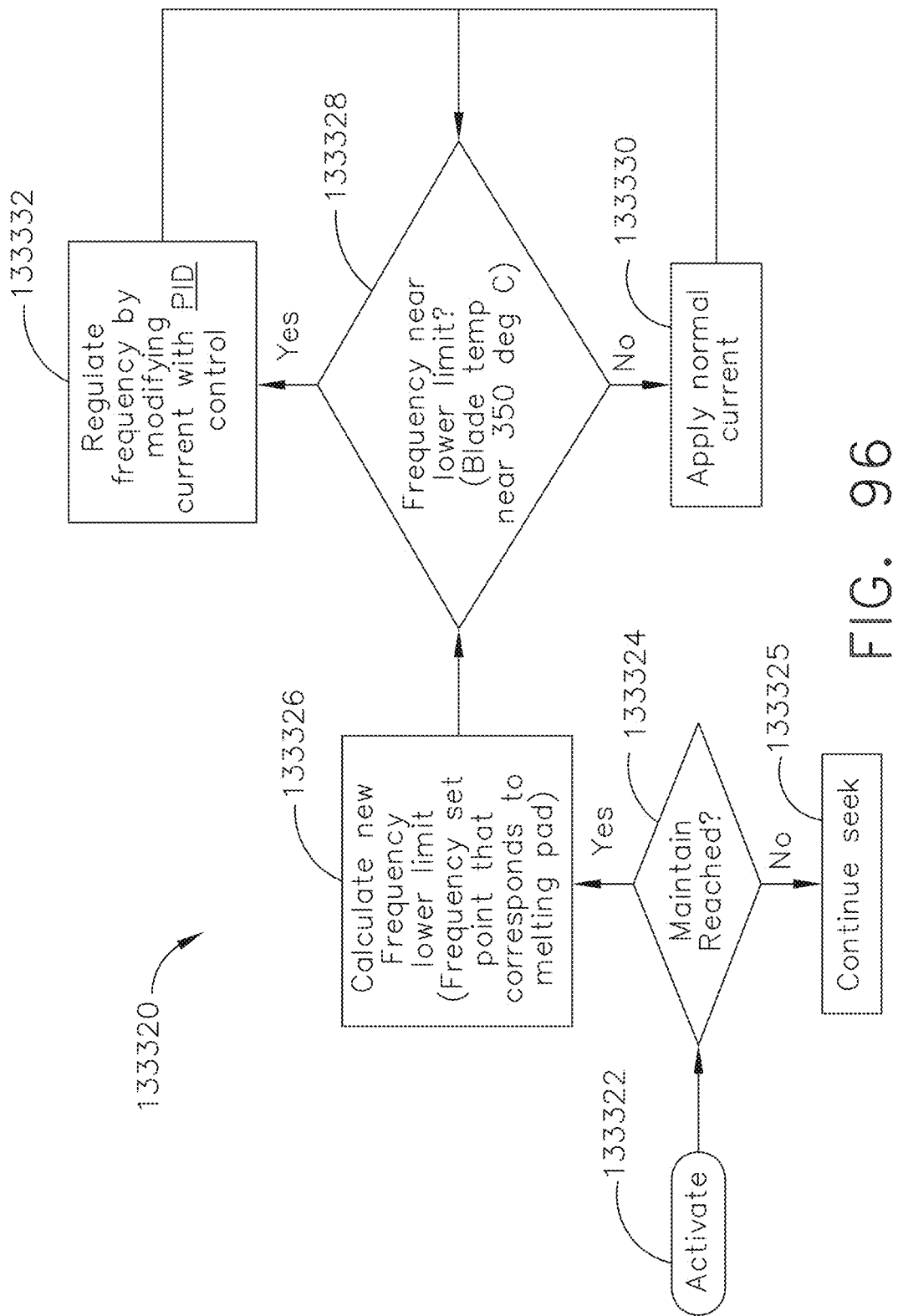

FIG. 96 is a logic flow diagram of a process depicting a control program or a logic configuration of a controlled thermal management process to protect an end effector pad, in accordance with at least one aspect of the present disclosure.

Figure 97:
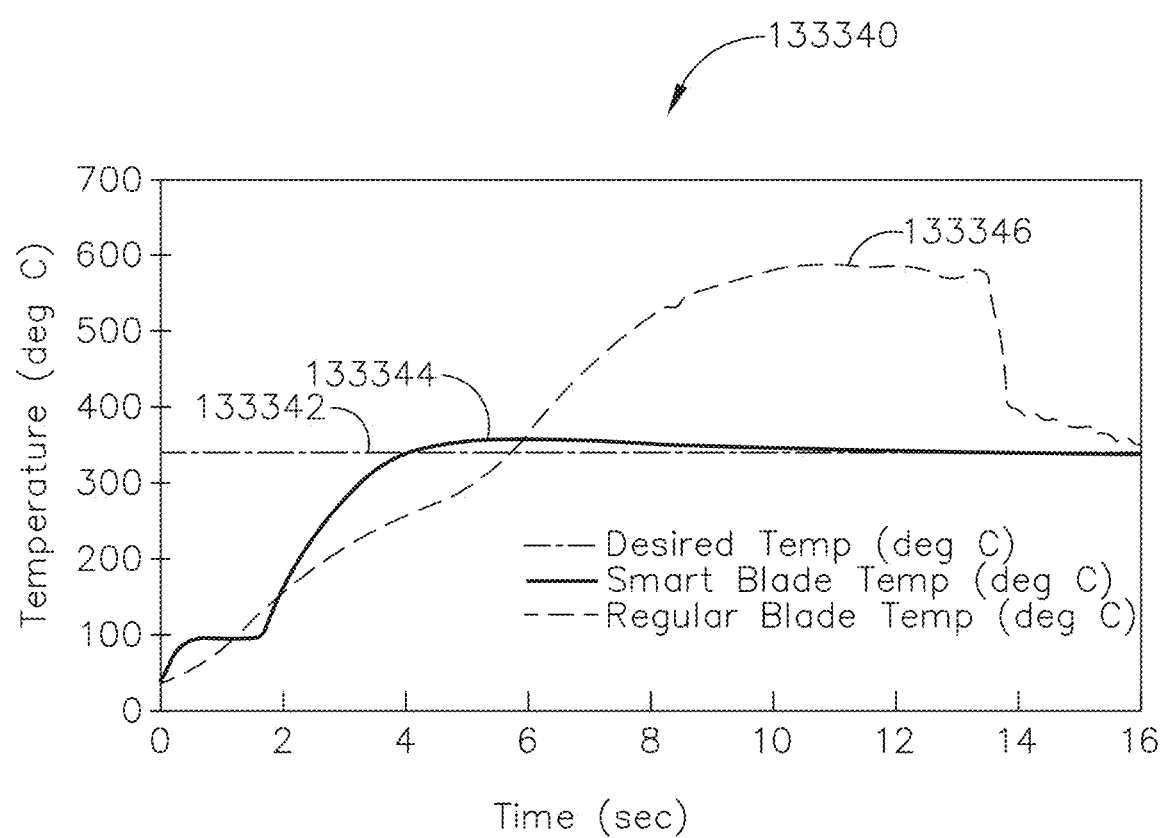

FIG. 97 is a graphical representation of temperature versus time comparing the desired temperature of an ultrasonic blade with a smart ultrasonic blade and a conventional ultrasonic blade, in accordance with at least one aspect of the present disclosure.

Figure 98:
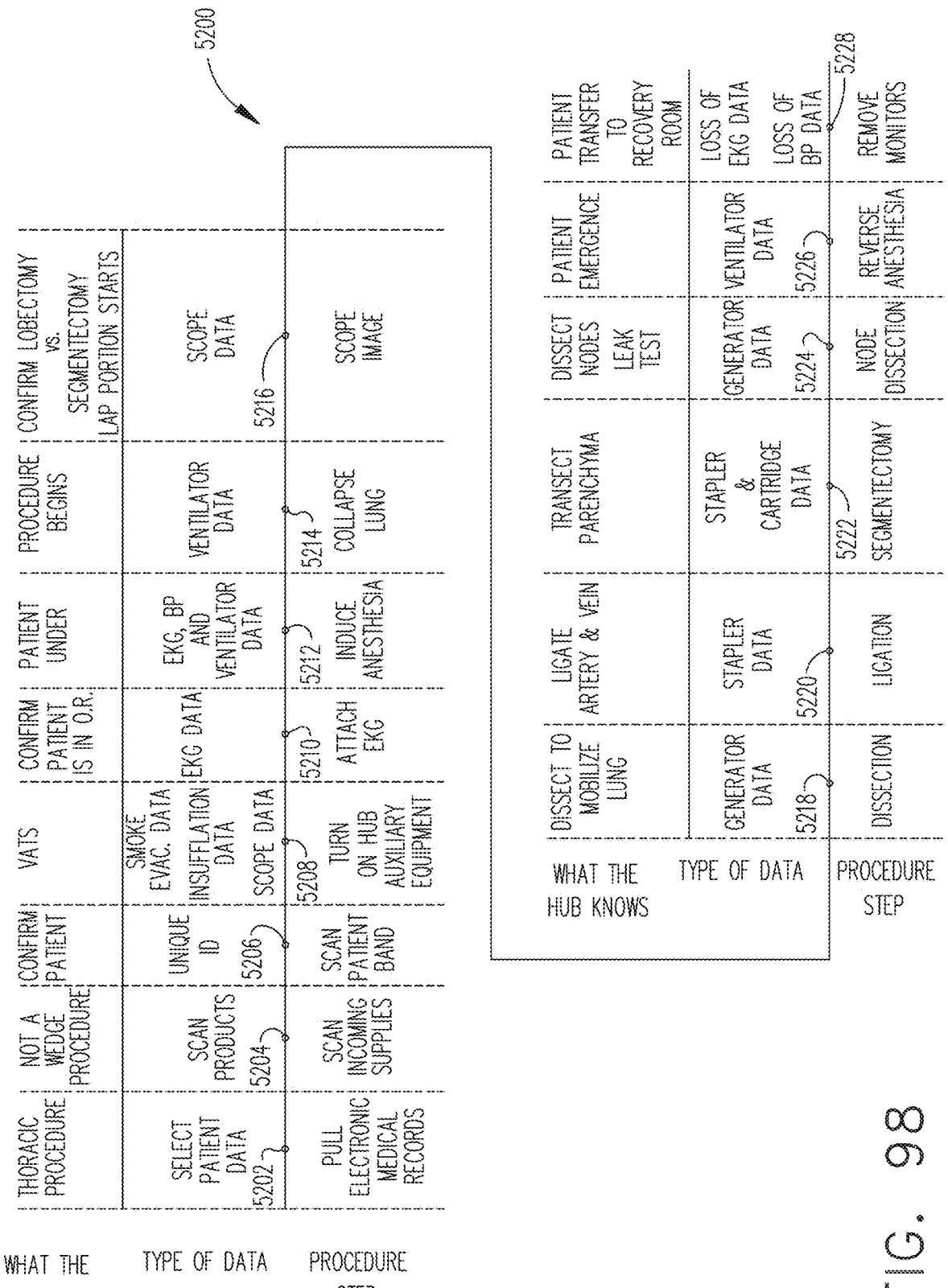

FIG. 98 is a timeline depicting situational awareness of a surgical hub, in accordance with at least one aspect of the present disclosure.

DESCRIPTION

Applicant of the present application owns the following U.S. patent applications, filed on Aug. 28, 2018, the disclosure of each of which is herein incorporated by reference in its entirety:

U.S. patent application Ser. No. 16/115,205, titled TEMPERATURE CONTROL OF ULTRASONIC END EFFECTOR AND CONTROL SYSTEM THEREFOR, now U.S. Patent Application Publication No. 2019/0201036;

U.S. patent application Ser. No. 16/115,233, titled RADIO FREQUENCY ENERGY DEVICE FOR DELIVERING COMBINED ELECTRICAL SIGNALS, now U.S. Pat. No. 11,364,075;

U.S. patent application Ser. No. 16/115,208, titled CONTROLLING AN ULTRASONIC SURGICAL INSTRUMENT ACCORDING TO TISSUE LOCATION, now U.S. Pat. No. 11,179,175;

U.S. patent application Ser. No. 16/115,220, titled CONTROLLING ACTIVATION OF AN ULTRASONIC SURGICAL INSTRUMENT ACCORDING TO THE PRESENCE OF TISSUE, now U.S. Patent Application Publication No. 2019/0201040;

U.S. patent application Ser. No. 16/115,232, titled DETERMINING TISSUE COMPOSITION VIA AN ULTRASONIC SYSTEM, now U.S. Patent Application Publication No. 2019/0201038;

U.S. patent application Ser. No. 16/115,239, titled DETERMINING THE STATE OF AN ULTRASONIC ELECTROMECHANICAL SYSTEM ACCORDING TO FREQUENCY SHIFT, now U.S. Patent Application Publication No. 2019/0201042;

U.S. patent application Ser. No. 16/115,247, titled DETERMINING THE STATE OF AN ULTRASONIC END EFFECTOR, now U.S. Pat. No. 11,317,937;

U.S. patent application Ser. No. 16/115,211, titled SITUATIONAL AWARENESS OF ELECTROSURGICAL SYSTEMS, now U.S. Patent Application Publication No. 2019/0201039;

U.S. patent application Ser. No. 16/115,226, titled MECHANISMS FOR CONTROLLING DIFFERENT ELECTROMECHANICAL SYSTEMS OF AN ELECTROSURGICAL INSTRUMENT, now U.S. Patent Application Publication No. 2019/0201075;

U.S. patent application Ser. No. 16/115,240, titled DETECTION OF END EFFECTOR IMMERSION IN LIQUID, now U.S. Patent Application Publication No. 2019/0201043;

U.S. patent application Ser. No. 16/115,249, titled INTERRUPTION OF ENERGY DUE TO INADVERTENT CAPACITIVE COUPLING, now U.S. Pat. No. 11,291,495;

U.S. patent application Ser. No. 16/115,256, titled INCREASING RADIO FREQUENCY TO CREATE PAD-LESS MONOPOLAR LOOP, now U.S. Pat. No. 11,253,315;

U.S. patent application Ser. No. 16/115,223, titled BIPOLAR COMBINATION DEVICE THAT AUTOMATICALLY ADJUSTS PRESSURE BASED ON ENERGY MODALITY, now U.S. Pat. No. 11,147,607; and U.S. patent application Ser. No. 16/115,238, titled ACTIVATION OF ENERGY DEVICES, now U.S. Pat. No. 11,304,720.

Applicant of the present application owns the following U.S. patent applications, filed on Aug. 23, 2018, the disclosure of each of which is herein incorporated by reference in its entirety:

U.S. Provisional Patent Application Ser. No. 62/721,995, titled CONTROLLING AN ULTRASONIC SURGICAL INSTRUMENT ACCORDING TO TISSUE LOCATION;

U.S. Provisional Patent Application Ser. No. 62/721,998, titled SITUATIONAL AWARENESS OF ELECTROSURGICAL SYSTEMS;

U.S. Provisional Patent Application Ser. No. 62/721,999, titled INTERRUPTION OF ENERGY DUE TO INADVERTENT CAPACITIVE COUPLING;

U.S. Provisional Patent Application Ser. No. 62/721,994, titled BIPOLAR COMBINATION DEVICE THAT AUTOMATICALLY ADJUSTS PRESSURE BASED ON ENERGY MODALITY; and U.S. Provisional Patent Application Ser. No. 62/721,996, titled RADIO FREQUENCY ENERGY DEVICE FOR DELIVERING COMBINED ELECTRICAL SIGNALS.

Applicant of the present application owns the following U.S. patent applications, filed on Jun. 30, 2018, the disclosure of each of which is herein incorporated by reference in its entirety:

- U.S. Provisional Patent Application Ser. No. 62/692,747, titled SMART ACTIVATION OF AN ENERGY DEVICE BY ANOTHER DEVICE;
- U.S. Provisional Patent Application Ser. No. 62/692,748, titled SMART ENERGY ARCHITECTURE; and
- U.S. Provisional Patent Application Ser. No. 62/692,768, titled SMART ENERGY DEVICES.

Applicant of the present application owns the following U.S. patent applications, filed on Jun. 29, 2018, the disclosure of each of which is herein incorporated by reference in its entirety:

- U.S. patent application Ser. No. 16/024,090, titled CAPACITIVE COUPLED RETURN PATH PAD WITH SEPARABLE ARRAY ELEMENTS;
- U.S. patent application Ser. No. 16/024,057, titled CONTROLLING A SURGICAL INSTRUMENT ACCORDING TO SENSED CLOSURE PARAMETERS;
- U.S. patent application Ser. No. 16/024,067, titled SYSTEMS FOR ADJUSTING END EFFECTOR PARAMETERS BASED ON PERIOPERATIVE INFORMATION;
- U.S. patent application Ser. No. 16/024,075, titled SAFETY SYSTEMS FOR SMART POWERED SURGICAL STAPLING;
- U.S. patent application Ser. No. 16/024,083, titled SAFETY SYSTEMS FOR SMART POWERED SURGICAL STAPLING;
- U.S. patent application Ser. No. 16/024,094, titled SURGICAL SYSTEMS FOR DETECTING END EFFECTOR TISSUE DISTRIBUTION IRREGULARITIES;
- U.S. patent application Ser. No. 16/024,138, titled SYSTEMS FOR DETECTING PROXIMITY OF SURGICAL END EFFECTOR TO CANCEROUS TISSUE;
- U.S. patent application Ser. No. 16/024,150, titled SURGICAL INSTRUMENT CARTRIDGE SENSOR ASSEMBLIES;
- U.S. patent application Ser. No. 16/024,160, titled VARIABLE OUTPUT CARTRIDGE SENSOR ASSEMBLY;
- U.S. patent application Ser. No. 16/024,124, titled SURGICAL INSTRUMENT HAVING A FLEXIBLE ELECTRODE;
- U.S. patent application Ser. No. 16/024,132, titled SURGICAL INSTRUMENT HAVING A FLEXIBLE CIRCUIT;
- U.S. patent application Ser. No. 16/024,141, titled SURGICAL INSTRUMENT WITH A TISSUE MARKING ASSEMBLY;
- U.S. patent application Ser. No. 16/024,162, titled SURGICAL SYSTEMS WITH PRIORITIZED DATA TRANSMISSION CAPABILITIES;
- U.S. patent application Ser. No. 16/024,066, titled SURGICAL EVACUATION SENSING AND MOTOR CONTROL;
- U.S. patent application Ser. No. 16/024,096, titled SURGICAL EVACUATION SENSOR ARRANGEMENTS;
- U.S. patent application Ser. No. 16/024,116, titled SURGICAL EVACUATION FLOW PATHS;
- U.S. patent application Ser. No. 16/024,149, titled SURGICAL EVACUATION SENSING AND GENERATOR CONTROL;
- U.S. patent application Ser. No. 16/024,180, titled SURGICAL EVACUATION SENSING AND DISPLAY;
- U.S. patent application Ser. No. 16/024,245, titled COMMUNICATION OF SMOKE EVACUATION SYSTEM PARAMETERS TO HUB OR CLOUD IN SMOKE EVACUATION MODULE FOR INTERACTIVE SURGICAL PLATFORM;
- U.S. patent application Ser. No. 16/024,258, titled SMOKE EVACUATION SYSTEM INCLUDING A SEGMENTED CONTROL CIRCUIT FOR INTERACTIVE SURGICAL PLATFORM;
- U.S. patent application Ser. No. 16/024,265, titled SURGICAL EVACUATION SYSTEM WITH A COMMUNICATION CIRCUIT FOR COMMUNICATION BETWEEN A FILTER AND A SMOKE EVACUATION DEVICE; and
- U.S. patent application Ser. No. 16/024,273, titled DUAL IN-SERIES LARGE AND SMALL DROPLET FILTERS.

Applicant of the present application owns the following U.S. Provisional Patent Applications, filed on Jun. 28, 2018, the disclosure of each of which is herein incorporated by reference in its entirety:

- U.S. Provisional Patent Application Ser. No. 62/691,228, titled A METHOD OF USING REINFORCED FLEX CIRCUITS WITH MULTIPLE SENSORS WITH ELECTROSURGICAL DEVICES;
- U.S. Provisional Patent Application Ser. No. 62/691,227, titled CONTROLLING A SURGICAL INSTRUMENT ACCORDING TO SENSED CLOSURE PARAMETERS;
- U.S. Provisional Patent Application Ser. No. 62/691,230, titled SURGICAL INSTRUMENT HAVING A FLEXIBLE ELECTRODE;
- U.S. Provisional Patent Application Ser. No. 62/691,219, titled SURGICAL EVACUATION SENSING AND MOTOR CONTROL;
- U.S. Provisional Patent Application Ser. No. 62/691,257, titled COMMUNICATION OF SMOKE EVACUATION SYSTEM PARAMETERS TO HUB OR CLOUD IN SMOKE EVACUATION MODULE FOR INTERACTIVE SURGICAL PLATFORM;
- U.S. Provisional Patent Application Ser. No. 62/691,262, titled SURGICAL EVACUATION SYSTEM WITH A COMMUNICATION CIRCUIT FOR COMMUNICATION BETWEEN A FILTER AND A SMOKE EVACUATION DEVICE; and
- U.S. Provisional Patent Application Ser. No. 62/691,251, titled DUAL IN-SERIES LARGE AND SMALL DROPLET FILTERS.

Applicant of the present application owns the following U.S. Provisional Patent Application, filed on Apr. 19, 2018, the disclosure of each of which is herein incorporated by reference in its entirety:

- U.S. Provisional Patent Application Ser. No. 62/659,900, titled METHOD OF HUB COMMUNICATION.

Applicant of the present application owns the following U.S. Provisional Patent Applications, filed on Mar. 30, 2018, the disclosure of each of which is herein incorporated by reference in its entirety:

- U.S. Provisional Patent Application Ser. No. 62/650,898 filed on Mar. 30, 2018, titled CAPACITIVE COUPLED RETURN PATH PAD WITH SEPARABLE ARRAY ELEMENTS;
- U.S. Provisional Patent Application Ser. No. 62/650,887, titled SURGICAL SYSTEMS WITH OPTIMIZED SENSING CAPABILITIES;

U.S. Provisional Patent Application Ser. No. 62/650,882, titled SMOKE EVACUATION MODULE FOR INTERACTIVE SURGICAL PLATFORM; and U.S. Provisional Patent Application Ser. No. 62/650,877, titled SURGICAL SMOKE EVACUATION SENSING AND CONTROLS Applicant of the present application owns the following U.S. patent applications, filed on Mar. 29, 2018, the disclosure of each of which is herein incorporated by reference in its entirety:

- U.S. patent application Ser. No. 15/940,641, titled INTERACTIVE SURGICAL SYSTEMS WITH ENCRYPTED COMMUNICATION CAPABILITIES;
- U.S. patent application Ser. No. 15/940,648, titled INTERACTIVE SURGICAL SYSTEMS WITH CONDITION HANDLING OF DEVICES AND DATA CAPABILITIES;
- U.S. patent application Ser. No. 15/940,656, titled SURGICAL HUB COORDINATION OF CONTROL AND COMMUNICATION OF OPERATING ROOM DEVICES;
- U.S. patent application Ser. No. 15/940,666, titled SPATIAL AWARENESS OF SURGICAL HUBS IN OPERATING ROOMS;
- U.S. patent application Ser. No. 15/940,670, titled COOPERATIVE UTILIZATION OF DATA DERIVED FROM SECONDARY SOURCES BY INTELLIGENT SURGICAL HUBS;
- U.S. patent application Ser. No. 15/940,677, titled SURGICAL HUB CONTROL ARRANGEMENTS;
- U.S. patent application Ser. No. 15/940,632, titled DATA STRIPPING METHOD TO INTERROGATE PATIENT RECORDS AND CREATE ANONYMIZED RECORD;
- U.S. patent application Ser. No. 15/940,640, titled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;
- U.S. patent application Ser. No. 15/940,645, titled SELF DESCRIBING DATA PACKETS GENERATED AT AN ISSUING INSTRUMENT;
- U.S. patent application Ser. No. 15/940,649, titled DATA PAIRING TO INTERCONNECT A DEVICE MEASURED PARAMETER WITH AN OUTCOME;
- U.S. patent application Ser. No. 15/940,654, titled SURGICAL HUB SITUATIONAL AWARENESS;
- U.S. patent application Ser. No. 15/940,663, titled SURGICAL SYSTEM DISTRIBUTED PROCESSING;
- U.S. patent application Ser. No. 15/940,668, titled AGGREGATION AND REPORTING OF SURGICAL HUB DATA;
- U.S. patent application Ser. No. 15/940,671, titled SURGICAL HUB SPATIAL AWARENESS TO DETERMINE DEVICES IN OPERATING THEATER;
- U.S. patent application Ser. No. 15/940,686, titled DISPLAY OF ALIGNMENT OF STAPLE CARTRIDGE TO PRIOR LINEAR STAPLE LINE;
- U.S. patent application Ser. No. 15/940,700, titled STERILE FIELD INTERACTIVE CONTROL DISPLAYS;
- U.S. patent application Ser. No. 15/940,629, titled COMPUTER IMPLEMENTED INTERACTIVE SURGICAL SYSTEMS;
- U.S. patent application Ser. No. 15/940,704, titled USE OF LASER LIGHT AND RED-GREEN-BLUE COLORATION TO DETERMINE PROPERTIES OF BACK SCATTERED LIGHT;
- U.S. patent application Ser. No. 15/940,722, titled CHARACTERIZATION OF TISSUE IRREGULARITIES THROUGH THE USE OF MONO-CHROMATIC LIGHT REFRACTIVITY; and
- U.S. patent application Ser. No. 15/940,742, titled DUAL CMOS ARRAY IMAGING.
- U.S. patent application Ser. No. 15/940,636, titled ADAPTIVE CONTROL PROGRAM UPDATES FOR SURGICAL DEVICES;
- U.S. patent application Ser. No. 15/940,653, titled ADAPTIVE CONTROL PROGRAM UPDATES FOR SURGICAL HUBS;
- U.S. patent application Ser. No. 15/940,660, titled CLOUD-BASED MEDICAL ANALYTICS FOR CUSTOMIZATION AND RECOMMENDATIONS TO A USER;
- U.S. patent application Ser. No. 15/940,679, titled CLOUD-BASED MEDICAL ANALYTICS FOR LINKING OF LOCAL USAGE TRENDS WITH THE RESOURCE ACQUISITION BEHAVIORS OF LARGER DATA SET;
- U.S. patent application Ser. No. 15/940,694, titled CLOUD-BASED MEDICAL ANALYTICS FOR MEDICAL FACILITY SEGMENTED INDIVIDUALIZATION OF INSTRUMENT FUNCTION;
- U.S. patent application Ser. No. 15/940,634, titled CLOUD-BASED MEDICAL ANALYTICS FOR SECURITY AND AUTHENTICATION TRENDS AND REACTIVE MEASURES;
- U.S. patent application Ser. No. 15/940,706, titled DATA HANDLING AND PRIORITIZATION IN A CLOUD ANALYTICS NETWORK; and
- U.S. patent application Ser. No. 15/940,675, titled CLOUD INTERFACE FOR COUPLED SURGICAL DEVICES.
- U.S. patent application Ser. No. 15/940,627, titled DRIVE ARRANGEMENTS FOR ROBOT-ASSISTED SURGICAL PLATFORMS;
- U.S. patent application Ser. No. 15/940,637, titled COMMUNICATION ARRANGEMENTS FOR ROBOT-ASSISTED SURGICAL PLATFORMS;
- U.S. patent application Ser. No. 15/940,642, titled CONTROLS FOR ROBOT-ASSISTED SURGICAL PLATFORMS;
- U.S. patent application Ser. No. 15/940,676, titled AUTOMATIC TOOL ADJUSTMENTS FOR ROBOT-ASSISTED SURGICAL PLATFORMS;
- U.S. patent application Ser. No. 15/940,680, titled CONTROLLERS FOR ROBOT-ASSISTED SURGICAL PLATFORMS;
- U.S. patent application Ser. No. 15/940,683, titled COOPERATIVE SURGICAL ACTIONS FOR ROBOT-ASSISTED SURGICAL PLATFORMS;
- U.S. patent application Ser. No. 15/940,690, titled DISPLAY ARRANGEMENTS FOR ROBOT-ASSISTED SURGICAL PLATFORMS; and
- U.S. patent application Ser. No. 15/940,711, titled SENSING ARRANGEMENTS FOR ROBOT-ASSISTED SURGICAL PLATFORMS.

Applicant of the present application owns the following U.S. Provisional Patent Applications, filed on Mar. 28, 2018, the disclosure of each of which is herein incorporated by reference in its entirety:

- U.S. Provisional Patent Application Ser. No. 62/649,302, titled INTERACTIVE SURGICAL SYSTEMS WITH ENCRYPTED COMMUNICATION CAPABILITIES;

U.S. Provisional Patent Application Ser. No. 62/649,294, titled DATA STRIPPING METHOD TO INTERROGATE PATIENT RECORDS AND CREATE ANONYMIZED RECORD;

U.S. Provisional Patent Application Ser. No. 62/649,300, titled SURGICAL HUB SITUATIONAL AWARENESS;

U.S. Provisional Patent Application Ser. No. 62/649,309, titled SURGICAL HUB SPATIAL AWARENESS TO DETERMINE DEVICES IN OPERATING THEATER;

U.S. Provisional Patent Application Ser. No. 62/649,310, titled COMPUTER IMPLEMENTED INTERACTIVE SURGICAL SYSTEMS;

U.S. Provisional Patent Application Ser. No. 62/649,291, titled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, titled ADAPTIVE CONTROL PROGRAM UPDATES FOR SURGICAL DEVICES;

U.S. Provisional Patent Application Ser. No. 62/649,333, titled CLOUD-BASED MEDICAL ANALYTICS FOR CUSTOMIZATION AND RECOMMENDATIONS TO A USER;

U.S. Provisional Patent Application Ser. No. 62/649,327, titled CLOUD-BASED MEDICAL ANALYTICS FOR SECURITY AND AUTHENTICATION TRENDS AND REACTIVE MEASURES;

U.S. Provisional Patent Application Ser. No. 62/649,315, titled DATA HANDLING AND PRIORITIZATION IN A CLOUD ANALYTICS NETWORK;

U.S. Provisional Patent Application Ser. No. 62/649,313, titled CLOUD INTERFACE FOR COUPLED SURGICAL DEVICES;

U.S. Provisional Patent Application Ser. No. 62/649,320, titled DRIVE ARRANGEMENTS FOR ROBOT-ASSISTED SURGICAL PLATFORMS;

U.S. Provisional Patent Application Ser. No. 62/649,307, titled AUTOMATIC TOOL ADJUSTMENTS FOR ROBOT-ASSISTED SURGICAL PLATFORMS; and U.S. Provisional Patent Application Ser. No. 62/649,323, titled SENSING ARRANGEMENTS FOR ROBOT-ASSISTED SURGICAL PLATFORMS.

Applicant of the present application owns the following U.S. Provisional Patent Applications, filed on Mar. 8, 2018, the disclosure of each of which is herein incorporated by reference in its entirety:

U.S. Provisional Patent Application Ser. No. 62/640,417, titled TEMPERATURE CONTROL IN ULTRASONIC DEVICE AND CONTROL SYSTEM THEREFOR; and U.S. Provisional Patent Application Ser. No. 62/640,415, titled ESTIMATING STATE OF ULTRASONIC END EFFECTOR AND CONTROL SYSTEM THEREFOR.

Applicant of the present application owns the following U.S. Provisional Patent Applications, filed on Dec. 28, 2017, the disclosure of each of which is herein incorporated by reference in its entirety:

U.S. Provisional Patent Application Serial No. U.S. Provisional Patent Application Ser. No. 62/611,341, titled INTERACTIVE SURGICAL PLATFORM;

U.S. Provisional Patent Application Ser. No. 62/611,340, titled CLOUD-BASED MEDICAL ANALYTICS; and U.S. Provisional Patent Application Ser. No. 62/611,339, titled ROBOT ASSISTED SURGICAL PLATFORM.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to improved ultrasonic surgical devices, electrosurgical devices and generators for use therewith. Aspects of the ultrasonic surgical devices can be configured for transecting and/or coagulating tissue during surgical procedures, for example. Aspects of the electrosurgical devices can be configured for transecting, coagulating, scaling, welding and/or desiccating tissue during surgical procedures, for example.

Figure 1:
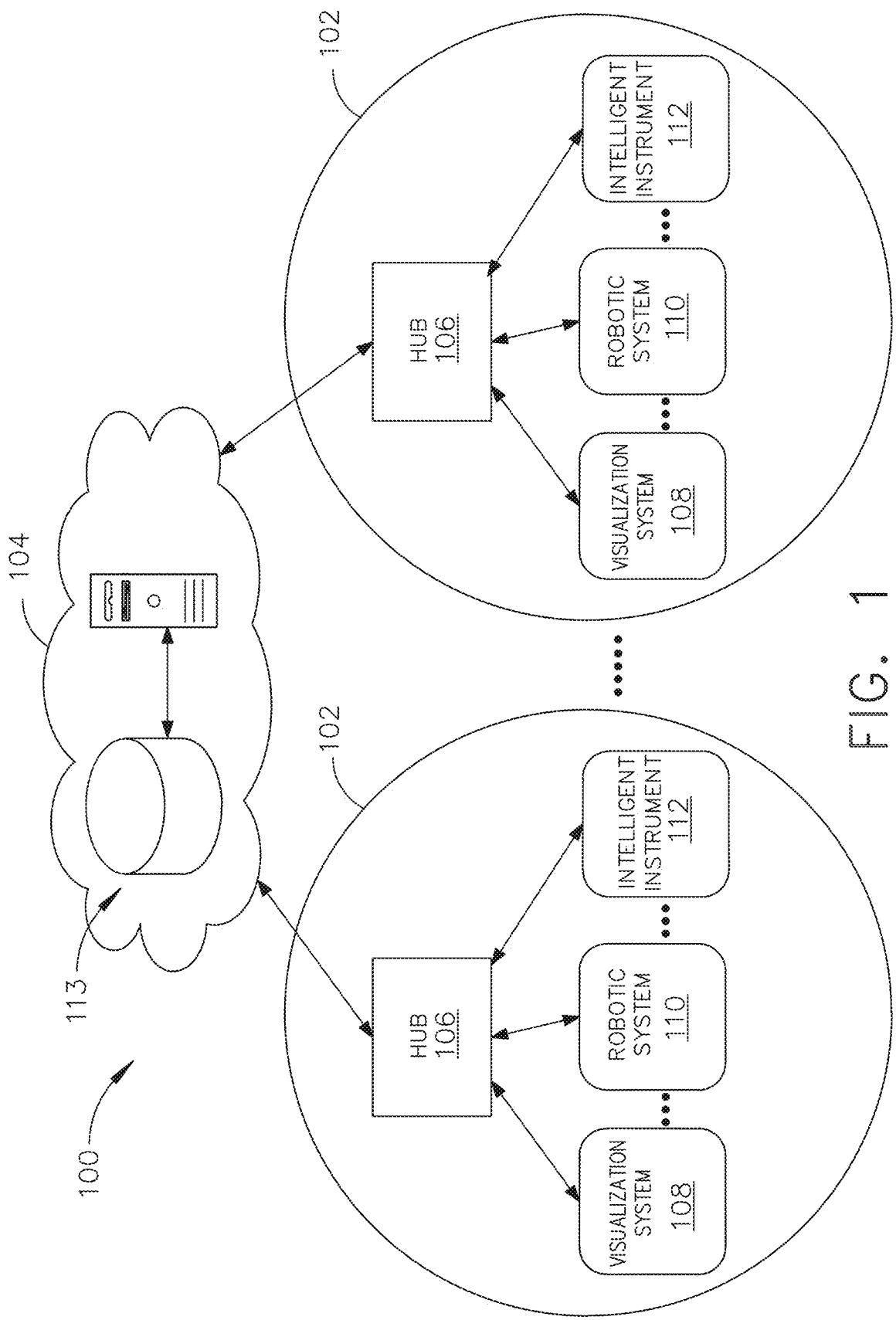
FIG. 1 is a block diagram of a computer-implemented interactive surgical system, in accordance with at least one aspect of the present disclosure.

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 3:
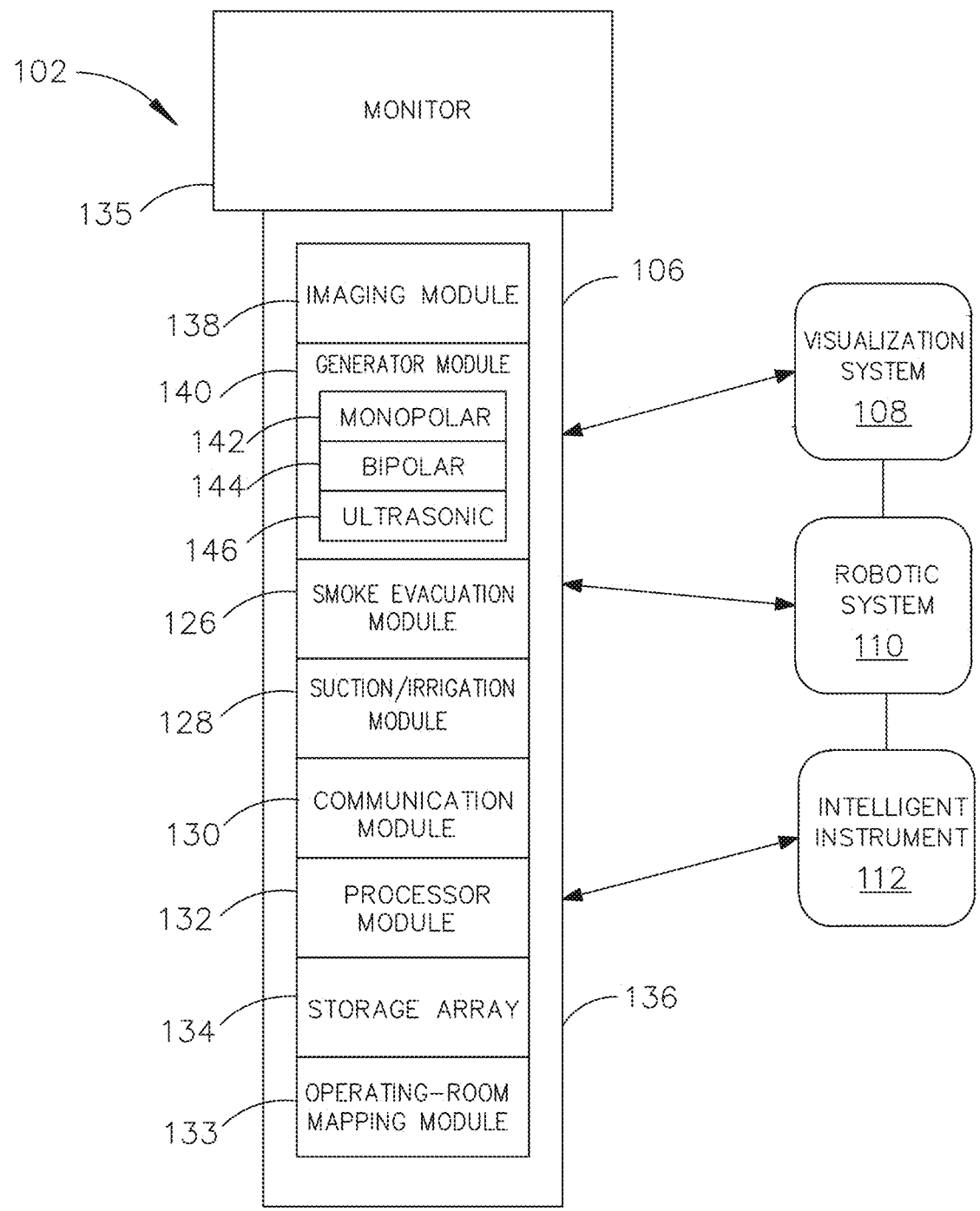
FIG. 3 is a surgical hub paired with a visualization system, a robotic system, and an intelligent instrument, in accordance with at least one aspect of the present disclosure.

FIG. 3 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 2:
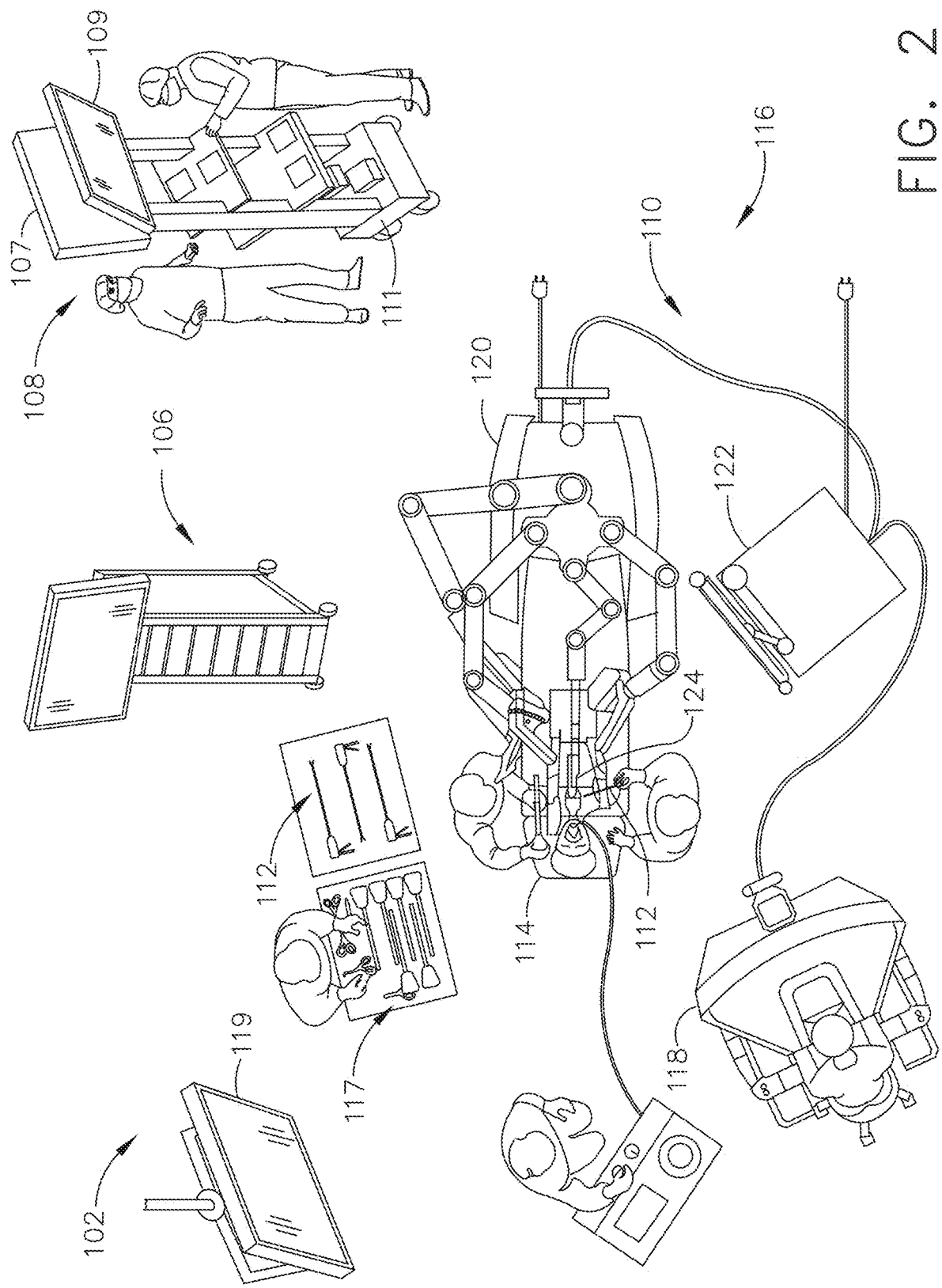
FIG. 2 is a surgical system being used to perform a surgical procedure in an operating room, in accordance with at least one aspect of the present disclosure.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Referring now to FIG. 3, a hub 106 is depicted in communication with a visualization system 108, a robotic system 110, and a handheld intelligent surgical instrument 112. The hub 106 includes: an operating room mapping module 133, a hub display 135, an imaging module 138, a generator module 140 with integrated monopolar 146, bipolar 147, and ultrasonic 148 components, a communication module 130, a processor module 132, and a storage array 134. In certain aspects, as illustrated in FIG. 3, the hub 106 further includes a smoke evacuation module 126 and/or a suction/irrigation module 128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts, Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 5:
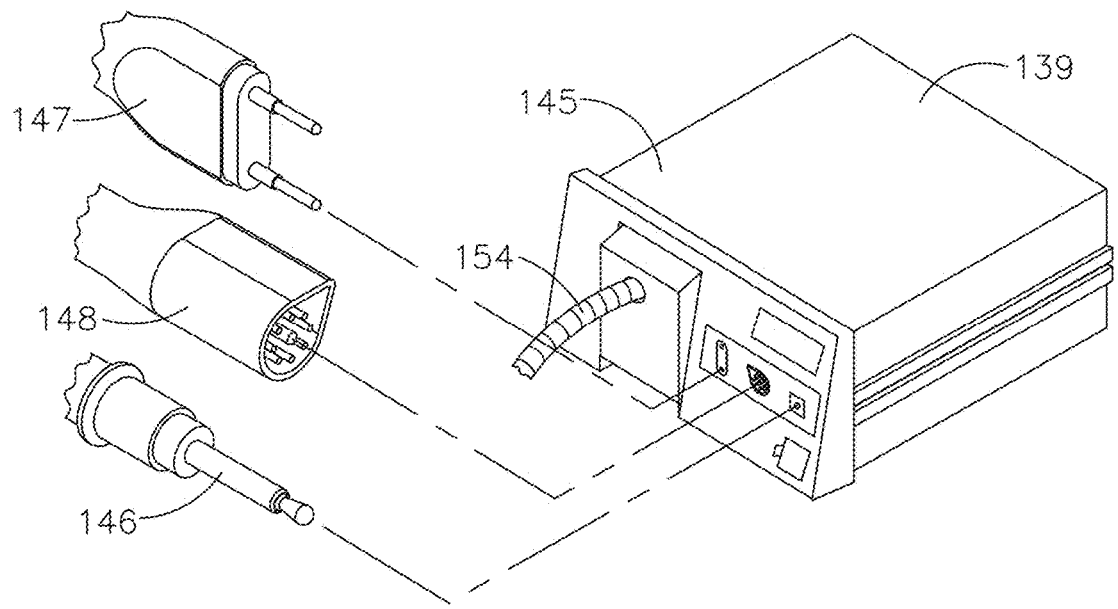
FIG. 5 is a perspective view of a combo generator module with bipolar, ultrasonic, and monopolar contacts and a smoke evacuation component, in accordance with at least one aspect of the present disclosure.

Referring to FIGS. 3-7, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. As illustrated in FIG. 5, the generator module 140 can be a generator module with integrated monopolar, bipolar, and ultrasonic components supported in a single housing unit 139 slidably insertable into the hub modular enclosure 136. As illustrated in FIG. 5, the generator module 140 can be configured to connect to a monopolar device 146, a bipolar device 147, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128 and interactive communication therebetween.

Figure 4:
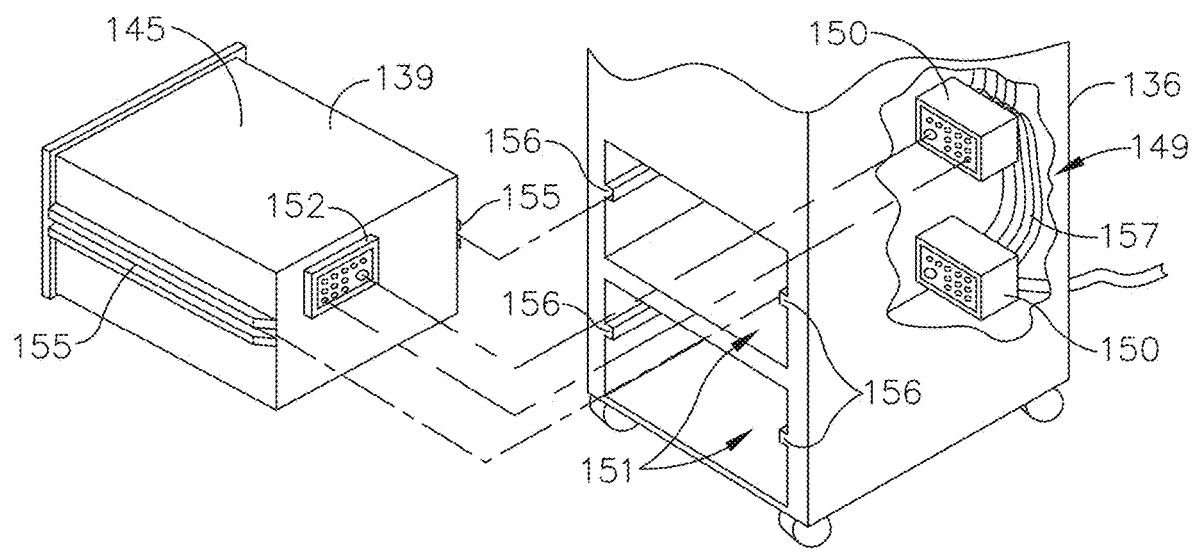
FIG. 4 is a partial perspective view of a surgical hub enclosure, and of a combo generator module slidably receivable in a drawer of the surgical hub enclosure, in accordance with at least one aspect of the present disclosure.

In one aspect, the hub modular enclosure 136 includes docking stations, or drawers, 151, herein also referred to as drawers, which are configured to slidably receive the modules 140, 126, 128. FIG. 4 illustrates a partial perspective view of a surgical hub enclosure 136, and a combo generator module 145 slidably receivable in a docking station 151 of the surgical hub enclosure 136. A docking port 152 with power and data contacts on a rear side of the combo generator module 145 is configured to engage a corresponding docking port 150 with power and data contacts of a corresponding docking station 151 of the hub modular enclosure 136 as the combo generator module 145 is slid into position within the corresponding docking station 151 of the hub module enclosure 136. In one aspect, the combo generator module 145 includes a bipolar, ultrasonic, and monopolar module and a smoke evacuation module integrated together into a single housing unit 139, as illustrated in FIG. 5.

In various aspects, the smoke evacuation module 126 includes a fluid line 154 that conveys captured/collected smoke and/or fluid away from a surgical site and to, for example, the smoke evacuation module 126. Vacuum suction originating from the smoke evacuation module 126 can draw the smoke into an opening of a utility conduit at the surgical site. The utility conduit, coupled to the fluid line, can be in the form of a flexible tube terminating at the smoke evacuation module 126. The utility conduit and the fluid line define a fluid path extending toward the smoke evacuation module 126 that is received in the hub enclosure 136.

In various aspects, the suction/irrigation module 128 is coupled to a surgical tool comprising an aspiration fluid line and a suction fluid line. In one example, the aspiration and suction fluid lines are in the form of flexible tubes extending from the surgical site toward the suction/irrigation module 128. One or more drive systems can be configured to cause irrigation and aspiration of fluids to and from the surgical site.

In one aspect, the surgical tool includes a shaft having an end effector at a distal end thereof and at least one energy treatment associated with the end effector, an aspiration tube, and an irrigation tube. The aspiration tube can have an inlet port at a distal end thereof and the aspiration tube extends through the shaft. Similarly, an irrigation tube can extend through the shaft and can have an inlet port in proximity to the energy deliver implement. The energy deliver implement is configured to deliver ultrasonic and/or RF energy to the surgical site and is coupled to the generator module 140 by a cable extending initially through the shaft.

The irrigation tube can be in fluid communication with a fluid source, and the aspiration tube can be in fluid communication with a vacuum source. The fluid source and/or the vacuum source can be housed in the suction/irrigation module 128. In one example, the fluid source and/or the vacuum source can be housed in the hub enclosure 136 separately from the suction/irrigation module 128. In such example, a fluid interface can be configured to connect the suction/irrigation module 128 to the fluid source and/or the vacuum source.

In one aspect, the modules 140, 126, 128 and/or their corresponding docking stations on the hub modular enclosure 136 may include alignment features that are configured to align the docking ports of the modules into engagement with their counterparts in the docking stations of the hub modular enclosure 136. For example, as illustrated in FIG. 4, the combo generator module 145 includes side brackets 155 that are configured to slidably engage with corresponding brackets 156 of the corresponding docking station 151 of the hub modular enclosure 136. The brackets cooperate to guide the docking port contacts of the combo generator module 145 into an electrical engagement with the docking port contacts of the hub modular enclosure 136.

In some aspects, the drawers 151 of the hub modular enclosure 136 are the same, or substantially the same size, and the modules are adjusted in size to be received in the drawers 151. For example, the side brackets 155 and/or 156 can be larger or smaller depending on the size of the module. In other aspects, the drawers 151 are different in size and are each designed to accommodate a particular module.

Furthermore, the contacts of a particular module can be keyed for engagement with the contacts of a particular drawer to avoid inserting a module into a drawer with mismatching contacts.

As illustrated in FIG. 4, the docking port 150 of one drawer 151 can be coupled to the docking port 150 of another drawer 151 through a communications link 157 to facilitate an interactive communication between the modules housed in the hub modular enclosure 136. The docking ports 150 of the hub modular enclosure 136 may alternatively, or additionally, facilitate a wireless interactive communication between the modules housed in the hub modular enclosure 136. Any suitable wireless communication can be employed, such as for example Air Titan-Bluetooth.

Figure 6:
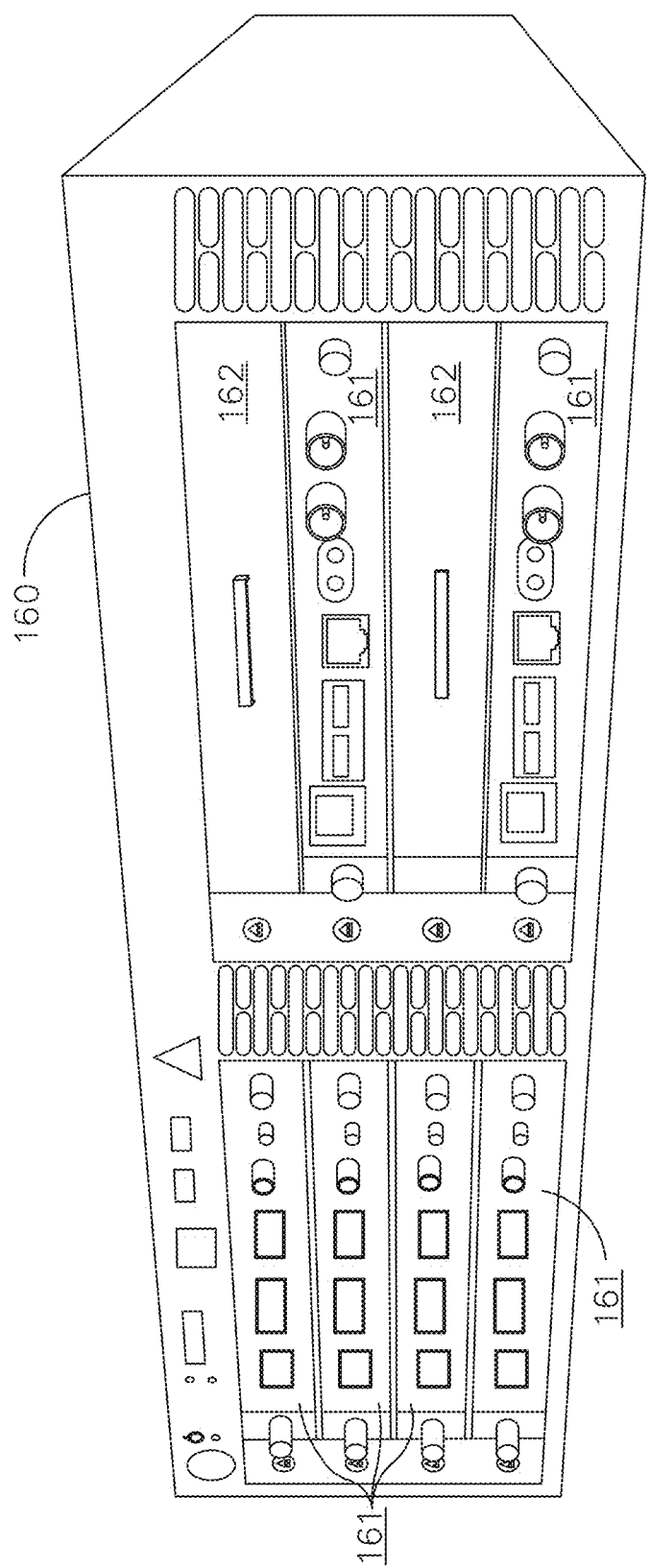
FIG. 6 illustrates individual power bus attachments for a plurality of lateral docking ports of a lateral modular housing configured to receive a plurality of modules, in accordance with at least one aspect of the present disclosure.

FIG. 6 illustrates individual power bus attachments for a plurality of lateral docking ports of a lateral modular housing 160 configured to receive a plurality of modules of a surgical hub 206. The lateral modular housing 160 is configured to laterally receive and interconnect the modules 161. The modules 161 are slidably inserted into docking stations 162 of lateral modular housing 160, which includes a backplane for interconnecting the modules 161. As illustrated in FIG. 6, the modules 161 are arranged laterally in the lateral modular housing 160. Alternatively, the modules 161 may be arranged vertically in a lateral modular housing.

Figure 7:
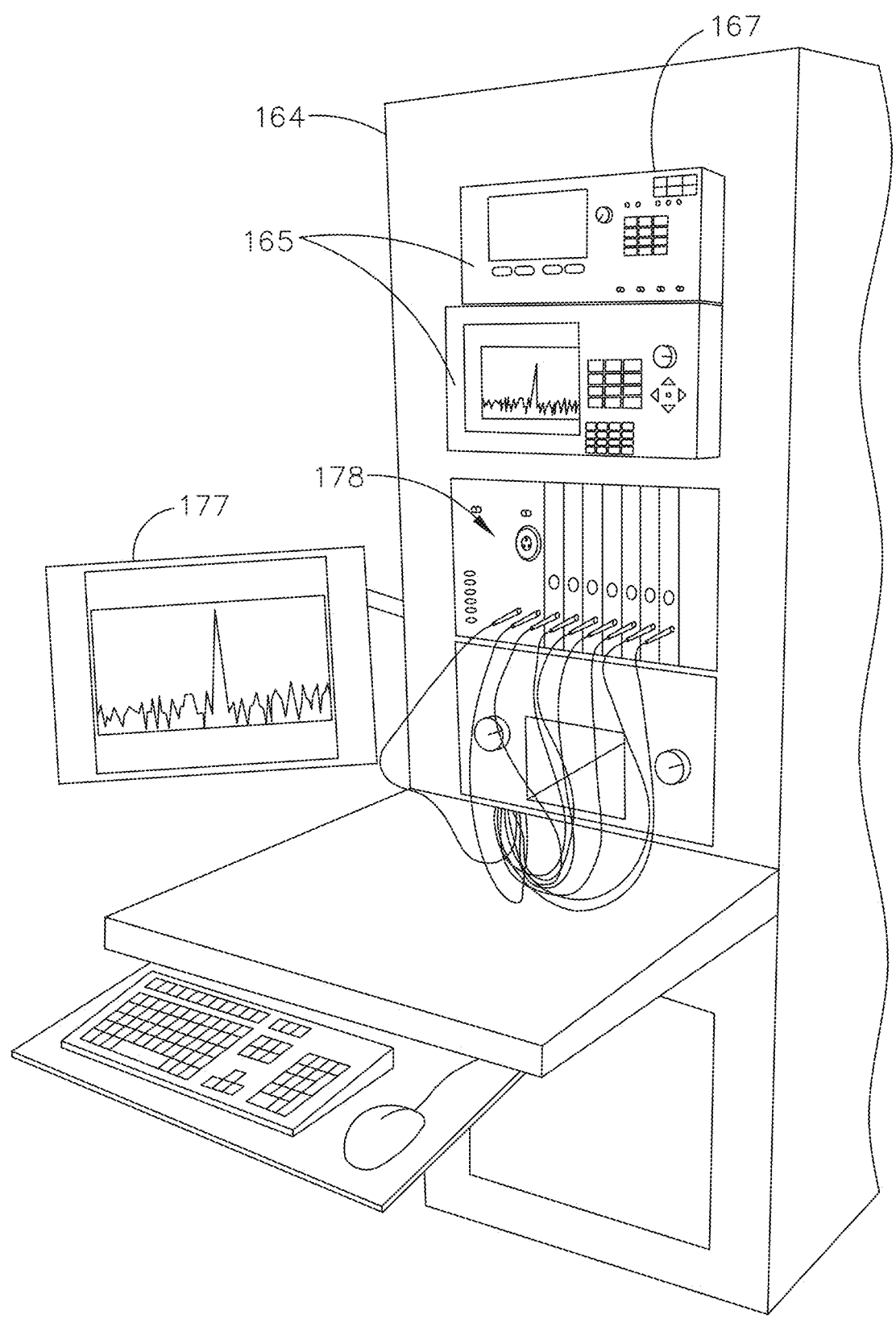
FIG. 7 illustrates a vertical modular housing configured to receive a plurality of modules, in accordance with at least one aspect of the present disclosure.

FIG. 7 illustrates a vertical modular housing 164 configured to receive a plurality of modules 165 of the surgical hub 106. The modules 165 are slidably inserted into docking stations, or drawers, 167 of vertical modular housing 164, which includes a backplane for interconnecting the modules 165. Although the drawers 167 of the vertical modular housing 164 are arranged vertically, in certain instances, a vertical modular housing 164 may include drawers that are arranged laterally. Furthermore, the modules 165 may interact with one another through the docking ports of the vertical modular housing 164. In the example of FIG. 7, a display 177 is provided for displaying data relevant to the operation of the modules 165. In addition, the vertical modular housing 164 includes a master module 178 housing a plurality of sub-modules that are slidably received in the master module 178.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, each of which is herein incorporated by reference in its entirety.

Figure 8:
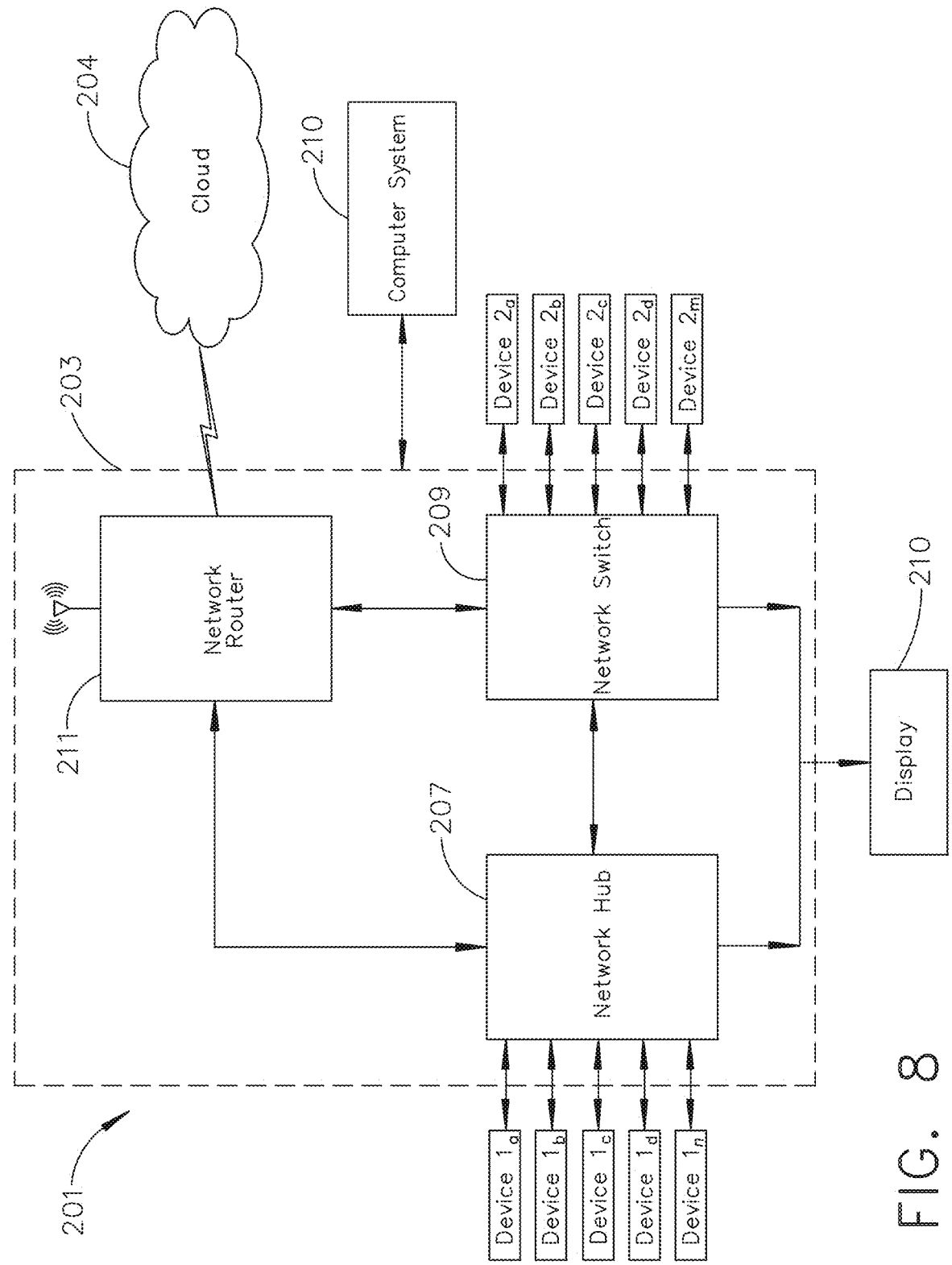
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half duplex mode. The network hub 207 does not store any media access control/Internet Protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2a-2m may be connected to a network switch 209 over a wired channel or a wireless channel. The network switch 209 works in the data link layer of the OSI model. The network switch 209 is a multicast device for connecting the devices 2a-2m located in the same operating theater to the network. The network switch 209 sends data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and handles a data type known as frames. Frames carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1a-1n/2a-2m.

Figure 9:
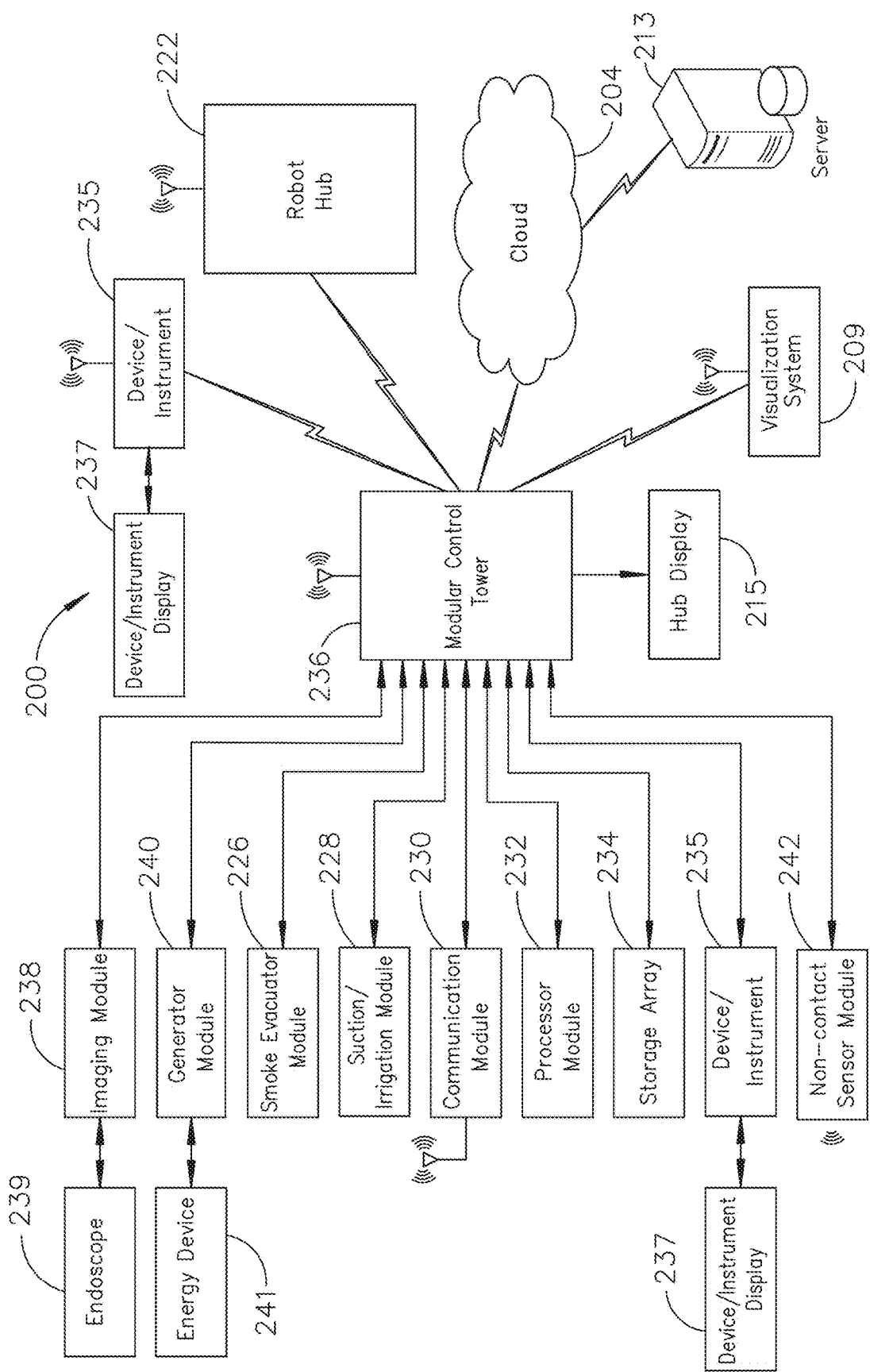
FIG. 9 illustrates a computer-implemented interactive surgical system, in accordance with at least one aspect of the present disclosure.
Figure 10:
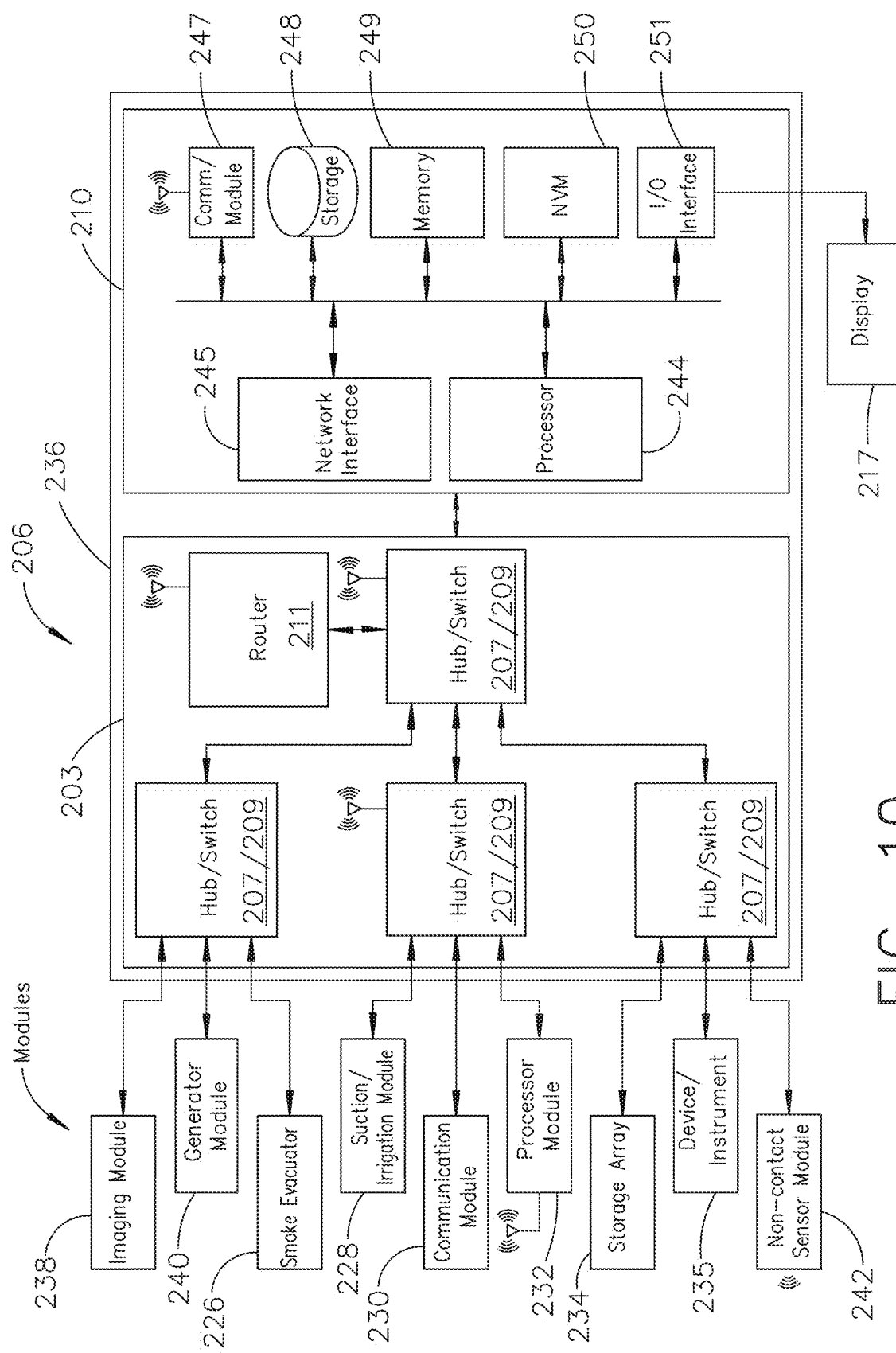
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charnel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9-10, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

Figure 11:
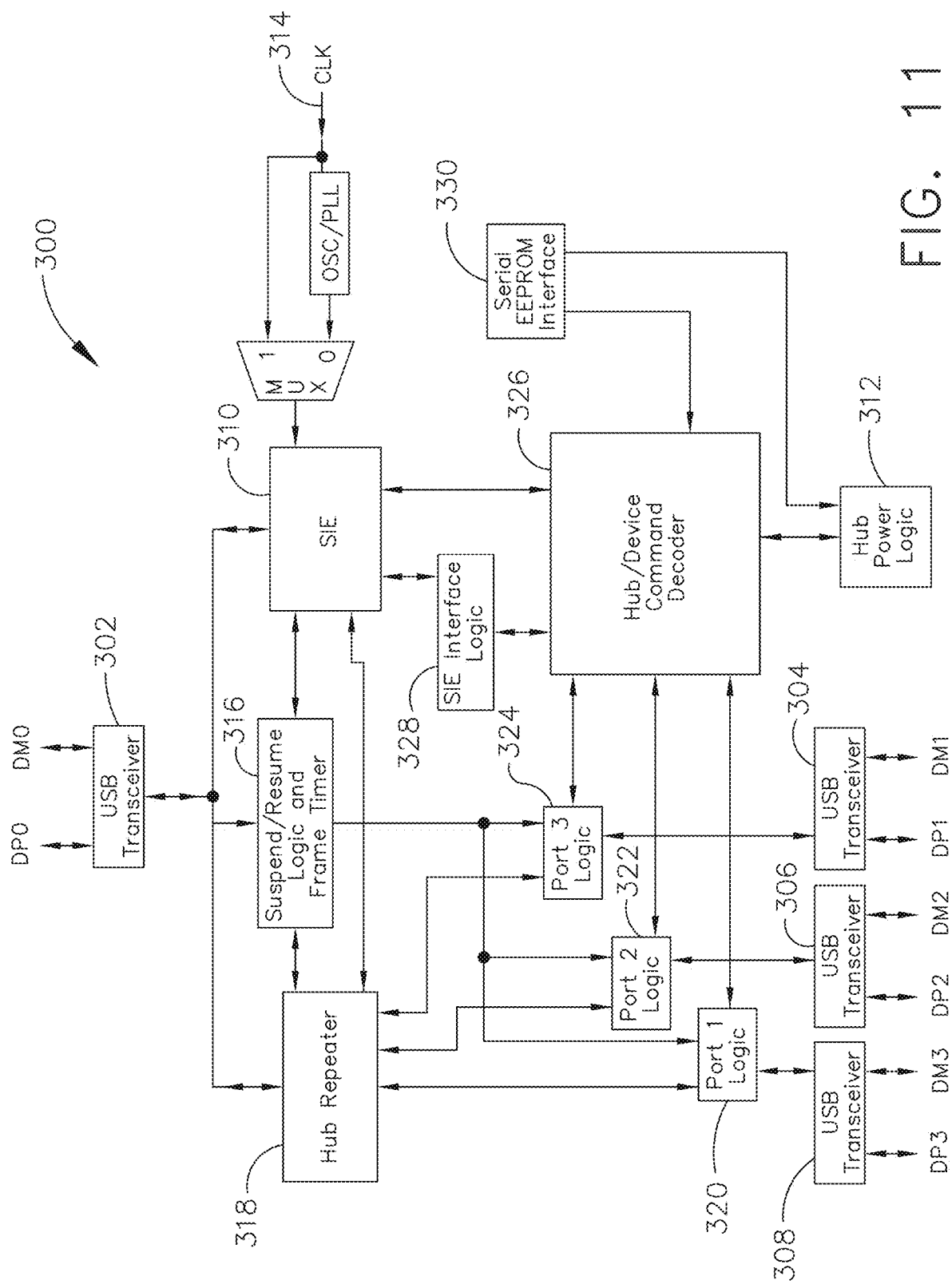
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, in accordance with at least one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Surgical Instrument Hardware

Figure 12:
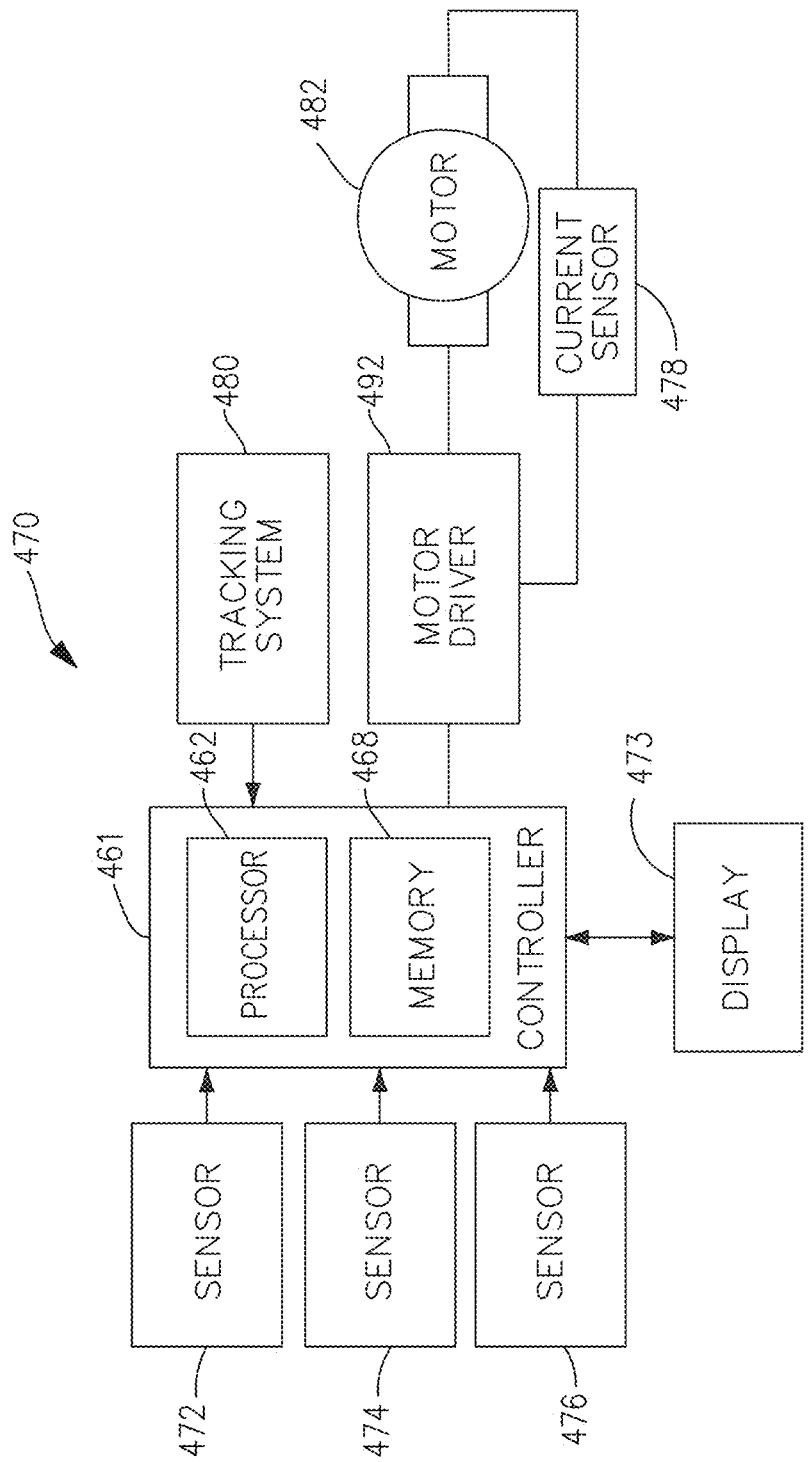
FIG. 12 illustrates a logic diagram of a control system of a surgical instrument or tool, in accordance with at least one aspect of the present disclosure.

FIG. 12 illustrates a logic diagram of a control system 470 of a surgical instrument or tool in accordance with one or more aspects of the present disclosure. The system 470 comprises a control circuit. The control circuit includes a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive a clamp arm closure member. A tracking system 480 is configured to determine the position of the longitudinally movable displacement member. The position information is provided to the processor 462, which can be programmed or configured to determine the position of the longitudinally movable drive member as well as the position of the closure member. Additional motors may be provided at the tool driver interface to control closure tube travel, shaft rotation, articulation, or clamp arm closure, or a combination of the above. A display 473 displays a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife, articulation systems, clamp arm, or a combination of the above. In one aspect, the microcontroller 461 includes a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In other arrangements, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable battery cells. In at least one example, the battery cells can be lithium-ion batteries which can be couplable to and separable from the power assembly.

The motor driver 492 may be an A3941 available from Allegro Microsystems, Inc. The A3941 492 is a full-bridge controller for use with external N-channel power metal-oxide semiconductor field-effect transistors (MOSFETs) specifically designed for inductive loads, such as brush DC motors. The driver 492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the low-side FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 comprises a controlled motor drive circuit arrangement comprising a position sensor 472 according to one aspect of this disclosure. The position sensor 472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a longitudinal displacement member to open and close a clamp arm, which can be adapted and configured to include a rack of drive teeth. In other aspects, the displacement member represents a clamp arm closure member configured to close and to open a clamp arm of a stapler, ultrasonic, or electrosurgical device, or combinations of the above. Accordingly, as used herein, the term displacement member is used generically to refer to any movable member of the surgical instrument or tool such as the drive member, the clamp arm, or any element that can be displaced. Accordingly, the absolute positioning system can, in effect, track the displacement of the clamp arm by tracking the linear displacement of the longitudinally movable drive member.

In other aspects, the absolute positioning system can be configured to track the position of a clamp arm in the process of closing or opening. In various other aspects, the displacement member may be coupled to any position sensor 472 suitable for measuring linear displacement. Thus, the longitudinally movable drive member, or clamp arm, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member to open and close a clamp arm.

A single revolution of the sensor element associated with the position sensor 472 is equivalent to a longitudinal linear displacement $d_1$ of the of the displacement member, where $d_1$ is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches are fed back to the microcontroller 461 that applies logic to determine a unique position signal corresponding to the longitudinal linear displacement $d_1+d_2+ \ldots d_n$ of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system comprises a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 is a low-voltage and low-power component and includes four Hall-effect elements in an area of the position sensor 472 that is located above a magnet. A high-resolution ADC and a smart power management controller are also provided on the chip. A coordinate rotation digital computer (CORDIC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the microcontroller 461. The position sensor 472 provides 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system takes into account properties like mass, inertia, viscous friction, inductance resistance, etc., to predict what the states and outputs of the physical system will be by knowing the input.

The absolute positioning system provides an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, is configured to measure one or more parameters of the end effector, such as, for example, the amplitude of the strain exerted on the anvil during a clamping operation, which can be indicative of the closure forces applied to the anvil. The measured strain is converted to a digital signal and provided to the processor 462. Alternatively, or in addition to the sensor 474, a sensor 476, such as, for example, a load sensor, can measure the closure force applied by the closure drive system to the anvil in a stapler or a clamp arm in an ultrasonic or electrosurgical instrument. The sensor 476, such as, for example, a load sensor, can measure the firing force applied to a closure member coupled to a clamp arm of the surgical instrument or tool or the force applied by a clamp arm to tissue located in the jaws of an ultrasonic or electrosurgical instrument. Alternatively, a current sensor 478 can be employed to measure the current drawn by the motor 482. The displacement member also may be configured to engage a clamp arm to open or close the clamp arm. The force sensor may be configured to measure the clamping force on tissue. The force required to advance the displacement member can correspond to the current drawn by the motor 482, for example. The measured force is converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 474, such as, for example, a micro-strain gauge, that is configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain is converted to a digital signal and provided to a processor 462 of the microcontroller 461. A load sensor 476 can measure the force used to operate the knife element, for example, to cut the tissue captured between the anvil and the staple cartridge. A load sensor 476 can measure the force used to operate the clamp arm element, for example, to capture tissue between the clamp arm and an ultrasonic blade or to capture tissue between the clamp arm and a jaw of an electrosurgical instrument. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub as shown in FIGS. 8-11.

Figure 13:
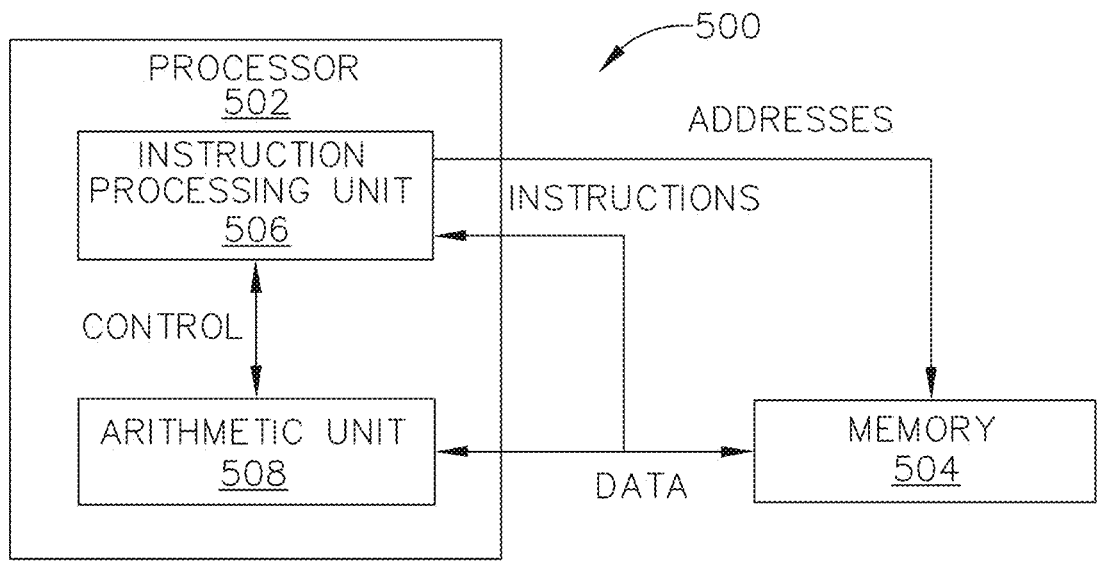
FIG. 13 illustrates a control circuit configured to control aspects of the surgical instrument or tool, in accordance with at least one aspect of the present disclosure.

FIG. 13 illustrates a control circuit 500 configured to control aspects of the surgical instrument or tool according to one aspect of this disclosure. The control circuit 500 can be configured to implement various processes described herein. The control circuit 500 may comprise a microcontroller comprising one or more processors 502 (e.g., microprocessor, microcontroller) coupled to at least one memory circuit 504. The memory circuit 504 stores machine-executable instructions that, when executed by the processor 502, cause the processor 502 to execute machine instructions to implement various processes described herein. The processor 502 may be any one of a number of single-core or multicore processors known in the art. The memory circuit 504 may comprise volatile and non-volatile storage media. The processor 502 may include an instruction processing unit 506 and an arithmetic unit 508. The instruction processing unit may be configured to receive instructions from the memory circuit 504 of this disclosure.

Figure 14:
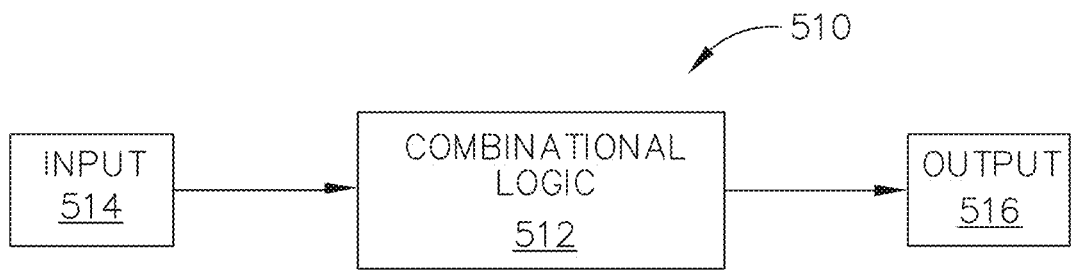
FIG. 14 illustrates a combinational logic circuit configured to control aspects of the surgical instrument or tool, in accordance with at least one aspect of the present disclosure.

FIG. 14 illustrates a combinational logic circuit 510 configured to control aspects of the surgical instrument or tool according to one aspect of this disclosure. The combinational logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 15:
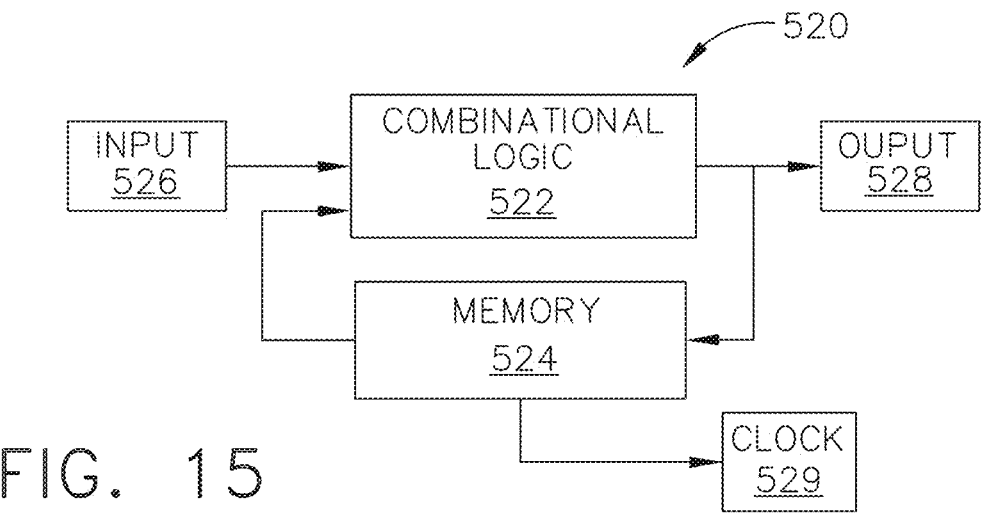
FIG. 15 illustrates a sequential logic circuit configured to control aspects of the surgical instrument or tool, in accordance with at least one aspect of the present disclosure.

FIG. 15 illustrates a sequential logic circuit 520 configured to control aspects of the surgical instrument or tool according to one aspect of this disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 13) and a finite state machine to implement various processes herein. In other aspects, the finite state machine may comprise a combination of a combinational logic circuit (e.g., combinational logic circuit 510, FIG. 14) and the sequential logic circuit 520.

Figure 16:
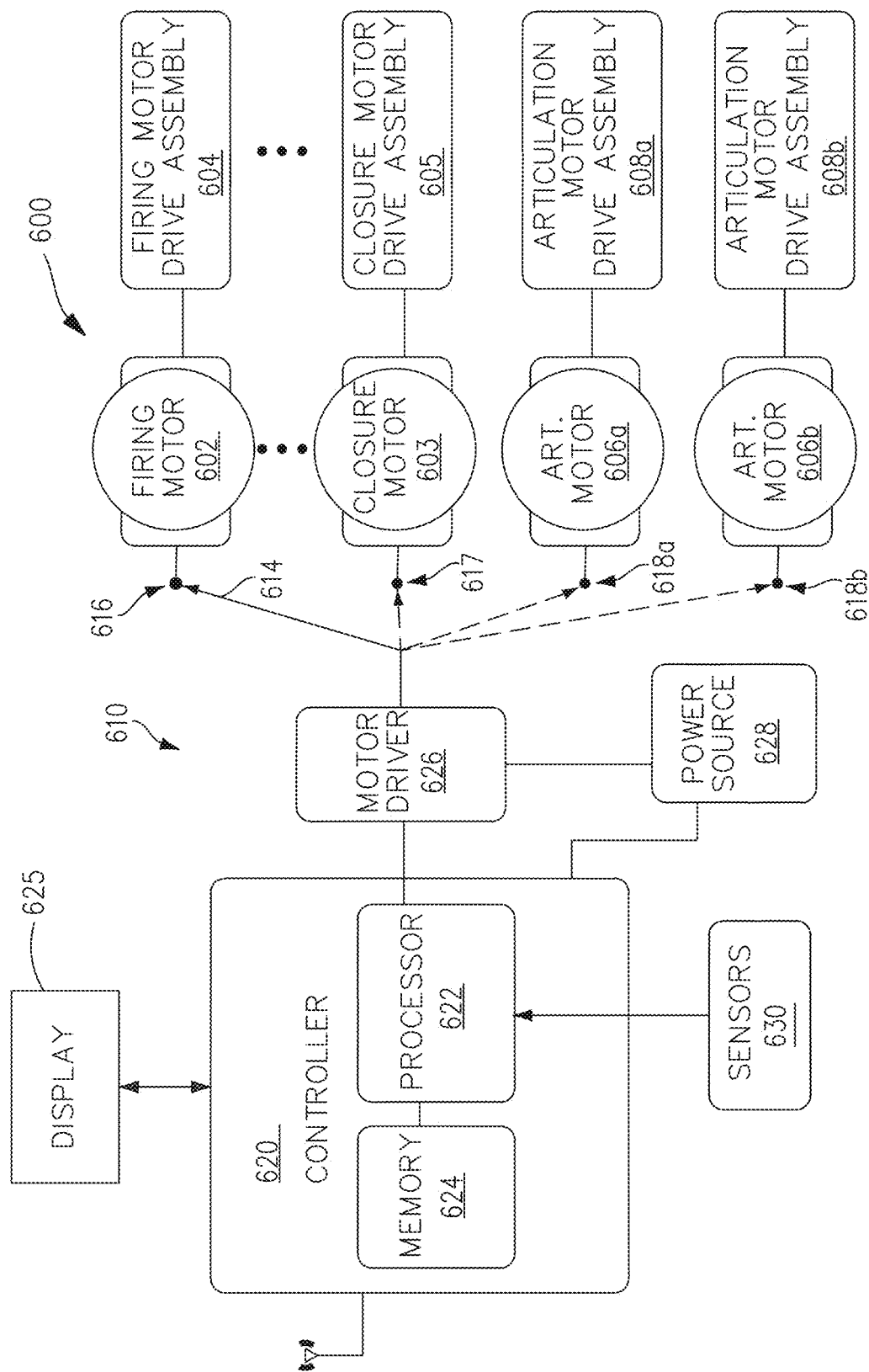
FIG. 16 illustrates a surgical instrument or tool comprising a plurality of motors which can be activated to perform various functions, in accordance with at least one aspect of the present disclosure.

FIG. 16 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the clamp arm closure member. The closure member may be retracted by reversing the direction of the motor 602, which also causes the clamp arm to open.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motor 603 may be operably coupled to a closure motor drive assembly 605 which can be configured to transmit closure motions, generated by the motor 603 to the end effector, in particular to displace a closure tube to close the clamp arm and compress tissue between the clamp arm and either an ultrasonic blade or jaw member of an electrosurgical device. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described above, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube or closure member to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 16, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 16, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In certain instances, the microcontroller 620 may include a microprocessor 622 (the "processor") and one or more non-transitory computer-readable mediums or memory units 624 (the "memory"). The microcontroller 620 is coupled to a display 625. In certain instances, the memory 624 may store various program instructions, which when executed may cause the processor 622 to perform a plurality of functions and/or calculations described herein. In certain instances, one or more of the memory units 624 may be coupled to the processor 622, for example. In various aspects, the microcontroller 620 may communicate over a wired or wireless channel, or combinations thereof.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor 622 is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the closure member coupled to the clamp arm of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

Figure 17:
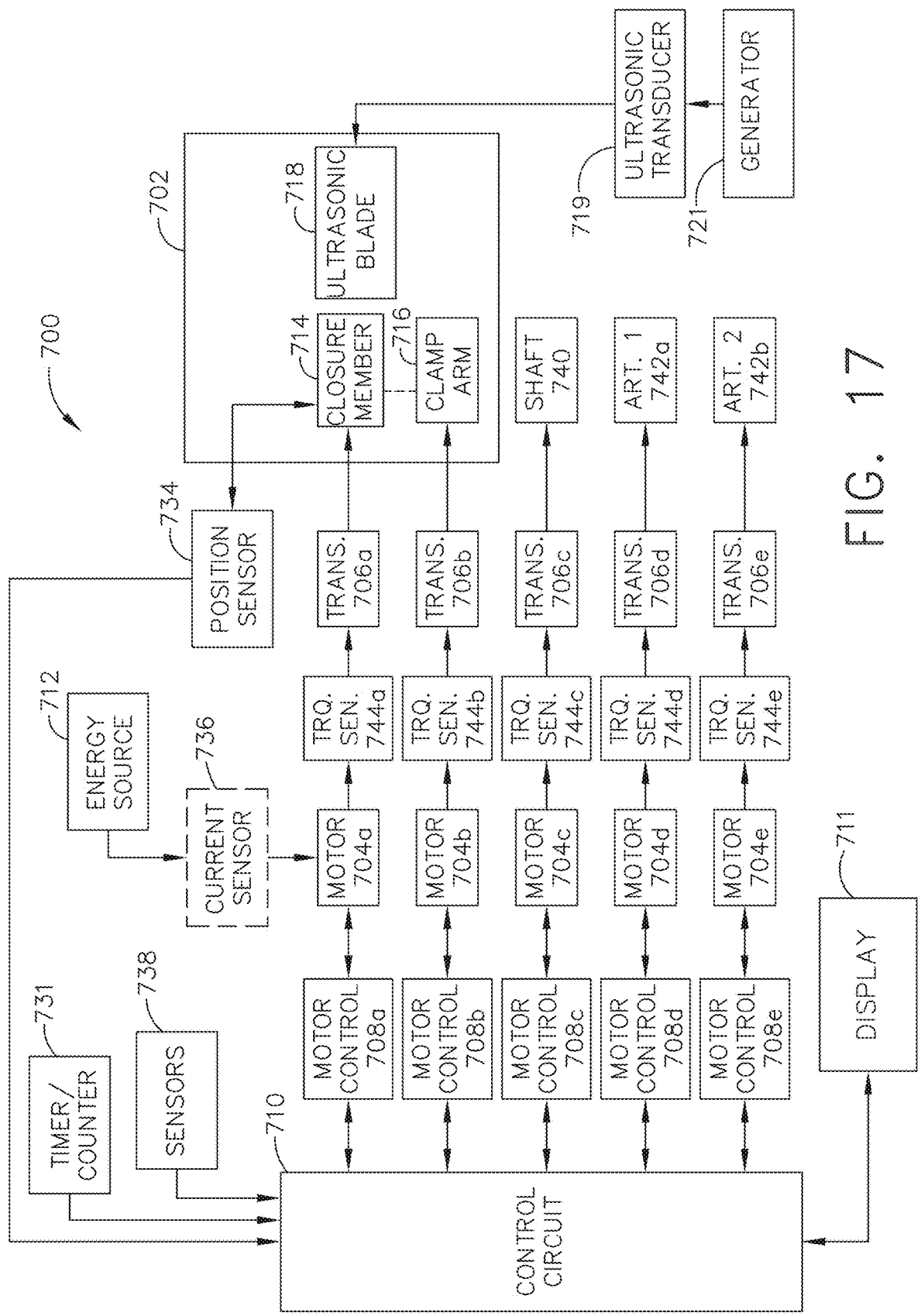
FIG. 17 is a schematic diagram of a robotic surgical instrument configured to operate a surgical tool described herein, in accordance with at least one aspect of the present disclosure.

FIG. 17 is a schematic diagram of a robotic surgical instrument 700 configured to operate a surgical tool described herein according to one aspect of this disclosure. The robotic surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, or one or more articulation members, or combinations thereof. The surgical instrument 700 comprises a control circuit 710 configured to control motor-driven firing members, closure members, shaft members, or one or more articulation members, or combinations thereof.

In one aspect, the robotic surgical instrument 700 comprises a control circuit 710 configured to control a clamp arm 716 and a closure member 714 portion of an end effector 702, an ultrasonic blade 718 coupled to an ultrasonic transducer 719 excited by an ultrasonic generator 721, a shaft 740, and one or more articulation members 742a, 742b via a plurality of motors 704a-704e. A position sensor 734 may be configured to provide position feedback of the closure member 714 to the control circuit 710. Other sensors 738 may be configured to provide feedback to the control circuit 710. A timer/counter 731 provides timing and counting information to the control circuit 710. An energy source 712 may be provided to operate the motors 704a-704e, and a current sensor 736 provides motor current feedback to the control circuit 710. The motors 704a-704e can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the closure member 714 as determined by the position sensor 734 with the output of the timer/counter 731 such that the control circuit 710 can determine the position of the closure member 714 at a specific time (t) relative to a starting position or the time (t) when the closure member 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the clamp arm 716. Other control programs control the rotation of the shaft 740 and the articulation members 742a, 742b.

In one aspect, the control circuit 710 may generate motor set point signals. The motor set point signals may be provided to various motor controllers 708a-708e. The motor controllers 708a-708e may comprise one or more circuits configured to provide motor drive signals to the motors 704a-704e to drive the motors 704a-704e as described herein. In some examples, the motors 704a-704e may be brushed DC electric motors. For example, the velocity of the motors 704a-704e may be proportional to the respective motor drive signals. In some examples, the motors 704a-704e may be brushless DC electric motors, and the respective motor drive signals may comprise a PWM signal provided to one or more stator windings of the motors 704a-704e. Also, in some examples, the motor controllers 708a-708e may be omitted and the control circuit 710 may generate the motor drive signals directly.

In one aspect, the control circuit 710 may initially operate each of the motors 704a-704e in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704a-704e during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704a-704e based on translation data describing a position of the displacement member in a closed-loop manner to translate the displacement member at a constant velocity.

In one aspect, the motors 704a-704e may receive power from an energy source 712. The energy source 712 may be a DC power supply driven by a main alternating current power source, a battery, a super capacitor, or any other suitable energy source. The motors 704a-704e may be mechanically coupled to individual movable mechanical elements such as the closure member 714, clamp arm 716, shaft 740, articulation 742a, and articulation 742b via respective transmissions 706a-706e. The transmissions 706a-706e may include one or more gears or other linkage components to couple the motors 704a-704e to movable mechanical elements. A position sensor 734 may sense a position of the closure member 714. The position sensor 734 may be or include any type of sensor that is capable of generating position data that indicate a position of the closure member 714. In some examples, the position sensor 734 may include an encoder configured to provide a series of pulses to the control circuit 710 as the closure member 714 translates distally and proximally. The control circuit 710 may track the pulses to determine the position of the closure member 714. Other suitable position sensors may be used, including, for example, a proximity sensor. Other types of position sensors may provide other signals indicating motion of the closure member 714. Also, in some examples, the position sensor 734 may be omitted. Where any of the motors 704a-704e is a stepper motor, the control circuit 710 may track the position of the closure member 714 by aggregating the number and direction of steps that the motor 704 has been instructed to execute. The position sensor 734 may be located in the end effector 702 or at any other portion of the instrument. The outputs of each of the motors 704a-704e include a torque sensor 744a-744e to sense force and have an encoder to sense rotation of the drive shaft.

In one aspect, the control circuit 710 is configured to drive a firing member such as the closure member 714 portion of the end effector 702. The control circuit 710 provides a motor set point to a motor control 708a, which provides a drive signal to the motor 704a. The output shaft of the motor 704a is coupled to a torque sensor 744a. The torque sensor 744a is coupled to a transmission 706a which is coupled to the closure member 714. The transmission 706a comprises movable mechanical elements such as rotating elements and a firing member to control the movement of the closure member 714 distally and proximally along a longitudinal axis of the end effector 702. In one aspect, the motor 704a may be coupled to the knife gear assembly, which includes a knife gear reduction set that includes a first knife drive gear and a second knife drive gear. A torque sensor 744a provides a firing force feedback signal to the control circuit 710. The firing force signal represents the force required to fire or displace the closure member 714. A position sensor 734 may be configured to provide the position of the closure member 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708a. In response to the firing signal, the motor 704a may drive the firing member distally along the longitudinal axis of the end effector 702 from a proximal stroke start position to a stroke end position distal to the stroke start position. As the closure member 714 translates distally, the clamp arm 716 closes towards the ultrasonic blade 718.

In one aspect, the control circuit 710 is configured to drive a closure member such as the clamp arm 716 portion of the end effector 702. The control circuit 710 provides a motor set point to a motor control 708b, which provides a drive signal to the motor 704b. The output shaft of the motor 704b is coupled to a torque sensor 744b. The torque sensor 744b is coupled to a transmission 706b which is coupled to the clamp arm 716. The transmission 706b comprises movable mechanical elements such as rotating elements and a closure member to control the movement of the clamp arm 716 from the open and closed positions. In one aspect, the motor 704*b* is coupled to a closure gear assembly, which includes a closure reduction gear set that is supported in meshing engagement with the closure spur gear. The torque sensor 744*b* provides a closure force feedback signal to the control circuit 710. The closure force feedback signal represents the closure force applied to the clamp arm 716. The position sensor 734 may be configured to provide the position of the closure member as a feedback signal to the control circuit 710. Additional sensors 738 in the end effector 702 may provide the closure force feedback signal to the control circuit 710. The pivotable clamp arm 716 is positioned opposite the ultrasonic blade 718. When ready to use, the control circuit 710 may provide a closure signal to the motor control 708*b*. In response to the closure signal, the motor 704*b* advances a closure member to grasp tissue between the clamp arm 716 and the ultrasonic blade 718.

In one aspect, the control circuit 710 is configured to rotate a shaft member such as the shaft 740 to rotate the end effector 702. The control circuit 710 provides a motor set point to a motor control 708*c*, which provides a drive signal to the motor 704*c*. The output shaft of the motor 704*c* is coupled to a torque sensor 744*c*. The torque sensor 744*c* is coupled to a transmission 706*c* which is coupled to the shaft 740. The transmission 706*c* comprises movable mechanical elements such as rotating elements to control the rotation of the shaft 740 clockwise or counterclockwise up to and over 360°. In one aspect, the motor 704*c* is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744*c* provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In one aspect, the control circuit 710 is configured to articulate the end effector 702. The control circuit 710 provides a motor set point to a motor control 708*d*, which provides a drive signal to the motor 704*d*. The output shaft of the motor 704*d* is coupled to a torque sensor 744*d*. The torque sensor 744*d* is coupled to a transmission 706*d* which is coupled to an articulation member 742*a*. The transmission 706*d* comprises movable mechanical elements such as articulation elements to control the articulation of the end effector 702 ±65°. In one aspect, the motor 704*d* is coupled to an articulation nut, which is rotatably journaled on the proximal end portion of the distal spine portion and is rotatably driven thereon by an articulation gear assembly. The torque sensor 744*d* provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742*a*, 742*b*. These articulation members 742*a*, 742*b* are driven by separate disks on the robot interface (the rack) which are driven by the two motors 708*d*, 708*e*. When the separate firing motor 704*a* is provided, each of articulation links 742*a*, 742*b* can be antagonistically driven with respect to the other link in order to provide a resistive holding motion and a load to the head when it is not moving and to provide an articulation motion as the head is articulated. The articulation members 742*a*, 742*b* attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704*a*-704*e* may comprise a brushed DC motor with a gearbox and mechanical links to a firing member, closure member, or articulation member. Another example includes electric motors 704*a*-704*e* that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704*a*-704*e*. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the robotic surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the clamp arm 716 to determine tissue location using segmented electrodes. The torque sensors 744*a*-744*e* may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the ultrasonic blade 718 has tissue on it, and (4) the load and position on both articulation rods.

In one aspect, the one or more sensors 738 may comprise a strain gauge, such as a micro-strain gauge, configured to measure the magnitude of the strain in the clamp arm 716 during a clamped condition. The strain gauge provides an electrical signal whose amplitude varies with the magnitude of the strain. The sensors 738 may comprise a pressure sensor configured to detect a pressure generated by the presence of compressed tissue between the clamp arm 716 and the ultrasonic blade 718. The sensors 738 may be configured to detect impedance of a tissue section located between the clamp arm 716 and the ultrasonic blade 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the clamp arm 716 by the closure drive system. For example, one or more sensors 738 can be at an interaction point between the closure tube and the clamp arm 716 to detect the closure forces applied by the closure tube to the clamp arm 716. The forces exerted on the clamp arm 716 can be representative of the tissue compression experienced by the tissue section captured between the clamp arm 716 and the ultrasonic blade 718. The one or more sensors 738 can be positioned at various interaction points along the closure drive system to detect the closure forces applied to the clamp arm 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the clamp arm 716.

In one aspect, a current sensor 736 can be employed to measure the current drawn by each of the motors 704a-704e. The force required to advance any of the movable mechanical elements such as the closure member 714 corresponds to the current drawn by one of the motors 704a-704e. The force is converted to a digital signal and provided to the control circuit 710. The control circuit 710 can be configured to simulate the response of the actual system of the instrument in the software of the controller. A displacement member can be actuated to move the closure member 714 in the end effector 702 at or near a target velocity. The robotic surgical instrument 700 can include a feedback controller, which can be one of any feedback controllers, including, but not limited to a PID, a state feedback, a linear-quadratic (LQR), and/or an adaptive controller, for example. The robotic surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, which is herein incorporated by reference in its entirety.

Figure 18:
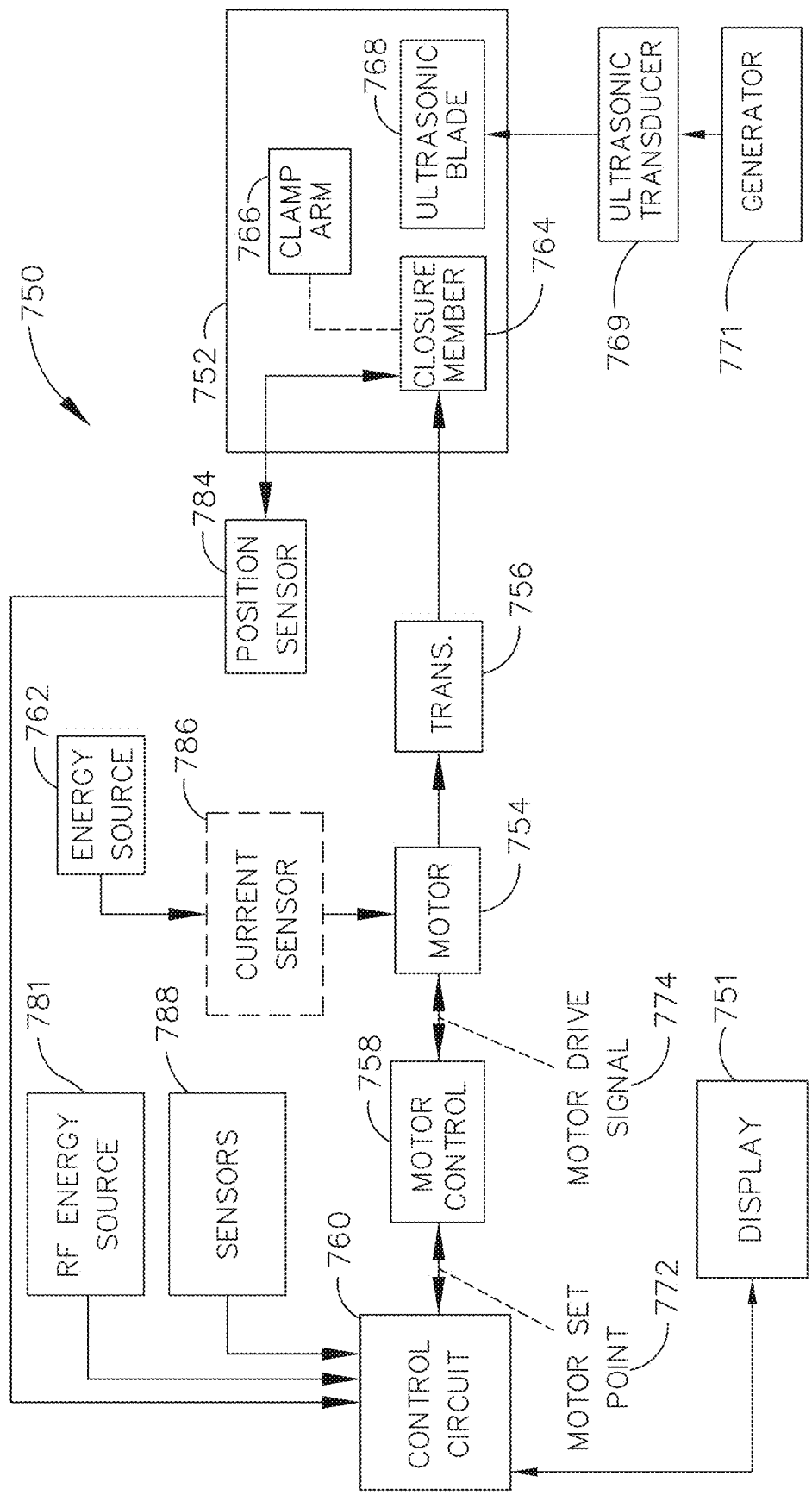
FIG. 18 illustrates a block diagram of a surgical instrument programmed to control the distal translation of a displacement member, in accordance with at least one aspect of the present disclosure.

FIG. 18 illustrates a schematic diagram of a surgical instrument 750 configured to control the distal translation of a displacement member according to one aspect of this disclosure. In one aspect, the surgical instrument 750 is programmed to control the distal translation of a displacement member such as the closure member 764. The surgical instrument 750 comprises an end effector 752 that may comprise a clamp arm 766, a closure member 764, and an ultrasonic blade 768 coupled to an ultrasonic transducer 769 driven by an ultrasonic generator 771.

The position, movement, displacement, and/or translation of a linear displacement member, such as the closure member 764, can be measured by an absolute positioning system, sensor arrangement, and position sensor 784. Because the closure member 764 is coupled to a longitudinally movable drive member, the position of the closure member 764 can be determined by measuring the position of the longitudinally movable drive member employing the position sensor 784. Accordingly, in the following description, the position, displacement, and/or translation of the closure member 764 can be achieved by the position sensor 784 as described herein. A control circuit 760 may be programmed to control the translation of the displacement member, such as the closure member 764. The control circuit 760, in some examples, may comprise one or more microcontrollers, microprocessors, or other suitable processors for executing instructions that cause the processor or processors to control the displacement member, e.g., the closure member 764, in the manner described. In one aspect, a timer/counter 781 provides an output signal, such as the elapsed time or a digital count, to the control circuit 760 to correlate the position of the closure member 764 as determined by the position sensor 784 with the output of the timer/counter 781 such that the control circuit 760 can determine the position of the closure member 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the closure member 764 via a transmission 756. The transmission 756 may include one or more gears or other linkage components to couple the motor 754 to the closure member 764. A position sensor 784 may sense a position of the closure member 764. The position sensor 784 may be or include any type of sensor that is capable of generating position data that indicate a position of the closure member 764. In some examples, the position sensor 784 may include an encoder configured to provide a series of pulses to the control circuit 760 as the closure member 764 translates distally and proximally. The control circuit 760 may track the pulses to determine the position of the closure member 764. Other suitable position sensors may be used, including, for example, a proximity sensor. Other types of position sensors may provide other signals indicating motion of the closure member 764. Also, in some examples, the position sensor 784 may be omitted. Where the motor 754 is a stepper motor, the control circuit 760 may track the position of the closure member 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the clamp arm 766 during a clamped condition. The strain gauge provides an electrical signal whose amplitude varies with the magnitude of the strain. The sensors 788 may comprise a pressure sensor configured to detect a pressure generated by the presence of compressed tissue between the clamp arm 766 and the ultrasonic blade 768. The sensors 788 may be configured to detect impedance of a tissue section located between the clamp arm 766 and the ultrasonic blade 768 that is indicative of the thickness and/or fullness of tissue located therebetween.

The sensors 788 may be is configured to measure forces exerted on the clamp arm 766 by a closure drive system. For example, one or more sensors 788 can be at an interaction point between a closure tube and the clamp arm 766 to detect the closure forces applied by a closure tube to the clamp arm 766. The forces exerted on the clamp arm 766 can be representative of the tissue compression experienced by the tissue section captured between the clamp arm 766 and the ultrasonic blade 768. The one or more sensors 788 can be positioned at various interaction points along the closure drive system to detect the closure forces applied to the clamp arm 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the clamp arm 766.

A current sensor 786 can be employed to measure the current drawn by the motor 754. The force required to advance the closure member 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move a closure member 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or closure member 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical sealing and cutting implements. For example, a motor 754 may drive a displacement member distally and proximally along a longitudinal axis of the end effector 752. The end effector 752 may comprise a pivotable clamp arm 766 and, when configured for use, an ultrasonic blade 768 positioned opposite the clamp arm 766. A clinician may grasp tissue between the clamp arm 766 and the ultrasonic blade 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, the closure member 764 with a cutting element positioned at a distal end, may cut the tissue between the ultrasonic blade 768 and the clamp arm 766.

In various examples, the surgical instrument 750 may comprise a control circuit 760 programmed to control the distal translation of the displacement member, such as the closure member 764, for example, based on one or more tissue conditions. The control circuit 760 may be programmed to sense tissue conditions, such as thickness, either directly or indirectly, as described herein. The control circuit 760 may be programmed to select a control program based on tissue conditions. A control program may describe the distal motion of the displacement member. Different control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

Figure 19:
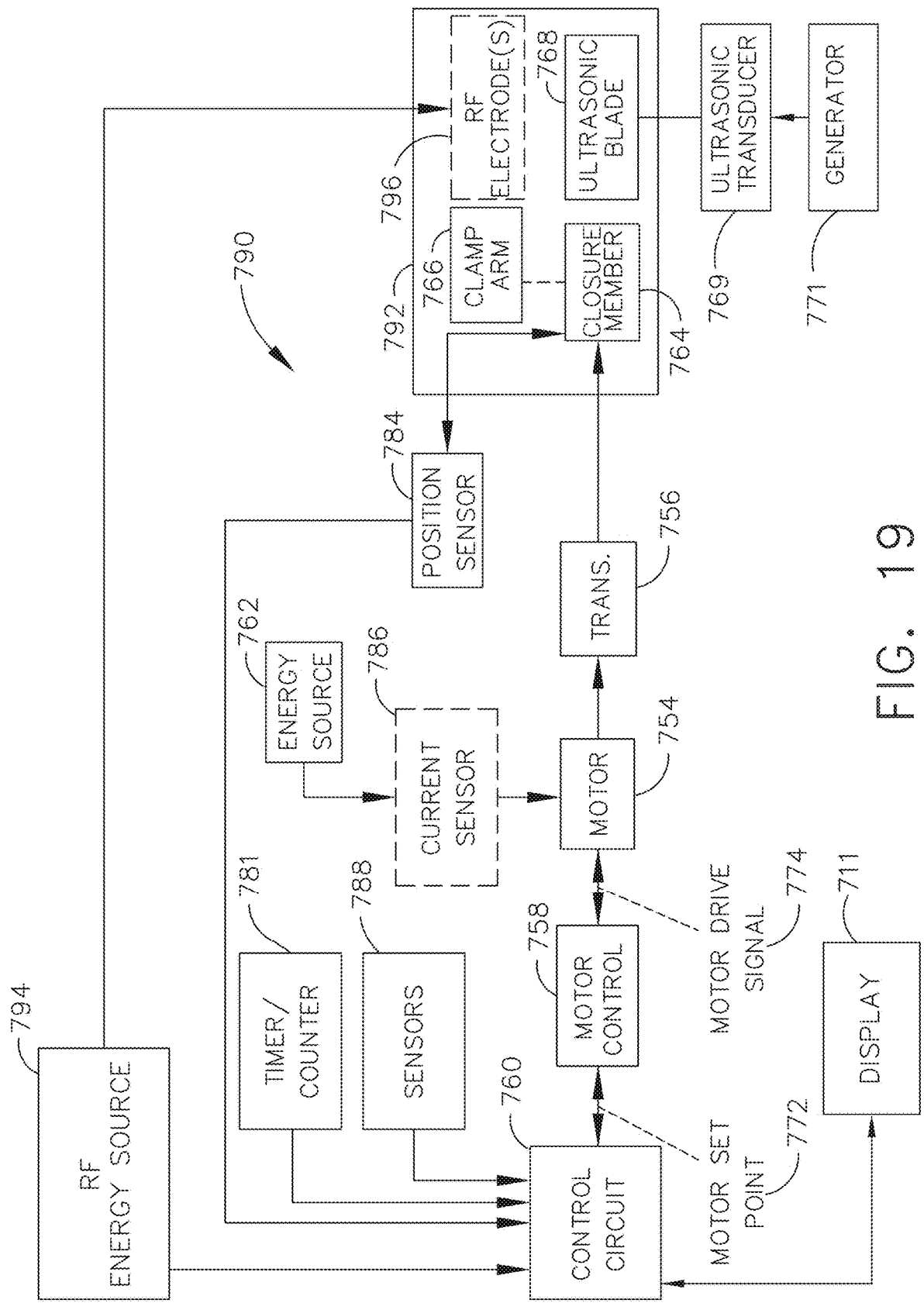
FIG. 19 is a schematic diagram of a surgical instrument configured to control various functions, in accordance with at least one aspect of the present disclosure.

FIG. 19 is a schematic diagram of a surgical instrument 790 configured to control various functions according to one aspect of this disclosure. In one aspect, the surgical instrument 790 is programmed to control distal translation of a displacement member such as the closure member 764. The surgical instrument 790 comprises an end effector 792 that may comprise a clamp arm 766, a closure member 764, and an ultrasonic blade 768 which may be interchanged with or work in conjunction with one or more RF electrodes 796 (shown in dashed line). The surgical instrument 790 further comprises a control circuit 760 that may be coupled to the display 711. The ultrasonic blade 768 is coupled to an ultrasonic transducer 769 driven by an ultrasonic generator 771.

In one aspect, sensors 788 may be implemented as a limit switch, electromechanical device, solid-state switches, Hall-effect devices, MR devices, GMR devices, magnetometers, among others. In other implementations, the sensors 638 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 788 may include electrical conductorless switches, ultrasonic switches, accelerometers, and inertial sensors, among others.

In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In some examples, the position sensor 784 may be omitted. Where the motor 754 is a stepper motor, the control circuit 760 may track the position of the closure member 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 792. The sensors 788 may include one or more sensors.

An RF energy source 794 is coupled to the end effector 792 and is applied to the RF electrode 796 when the RF electrode 796 is provided in the end effector 792 in place of the ultrasonic blade 768 or to work in conjunction with the ultrasonic blade 768. For example, the ultrasonic blade is made of electrically conductive metal and may be employed as the return path for electrosurgical RF current. The control circuit 760 controls the delivery of the RF energy to the RF electrode 796.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

Generator Hardware

Adaptive Ultrasonic Blade Control Algorithms

In various aspects smart ultrasonic energy devices may comprise adaptive algorithms to control the operation of the ultrasonic blade. In one aspect, the ultrasonic blade adaptive control algorithms are configured to identify tissue type and adjust device parameters. In one aspect, the ultrasonic blade control algorithms are configured to parameterize tissue type. An algorithm to detect the collagen/elastic ratio of tissue to tune the amplitude of the distal tip of the ultrasonic blade is described in the following section of the present disclosure. Various aspects of smart ultrasonic energy devices are described herein in connection with FIGS. 1-94, for example. Accordingly, the following description of adaptive ultrasonic blade control algorithms should be read in conjunction with FIGS. 1-94 and the description associated therewith.

Tissue Type Identification and Device Parameter Adjustments

In certain surgical procedures it would be desirable to employ adaptive ultrasonic blade control algorithms. In one aspect, adaptive ultrasonic blade control algorithms may be employed to adjust the parameters of the ultrasonic device based on the type of tissue in contact with the ultrasonic blade. In one aspect, the parameters of the ultrasonic device may be adjusted based on the location of the tissue within the jaws of the ultrasonic end effector, for example, the location of the tissue between the clamp arm and the ultrasonic blade. The impedance of the ultrasonic transducer may be employed to differentiate what percentage of the tissue is located in the distal or proximal end of the end effector. The reactions of the ultrasonic device may be based on the tissue type or compressibility of the tissue. In another aspect, the parameters of the ultrasonic device may be adjusted based on the identified tissue type or parameterization. For example, the mechanical displacement amplitude of the distal tip of the ultrasonic blade may be tuned based on the ration of collagen to elastin tissue detected during the tissue identification procedure. The ratio of collagen to elastin tissue may be detected used a variety of techniques including infrared (IR) surface reflectance and emissivity. The force applied to the tissue by the clamp arm and/or the stroke of the clamp arm to produce gap and compression. Electrical continuity across a jaw equipped with electrodes may be employed to determine what percentage of the jaw is covered with tissue.

Figure 20:
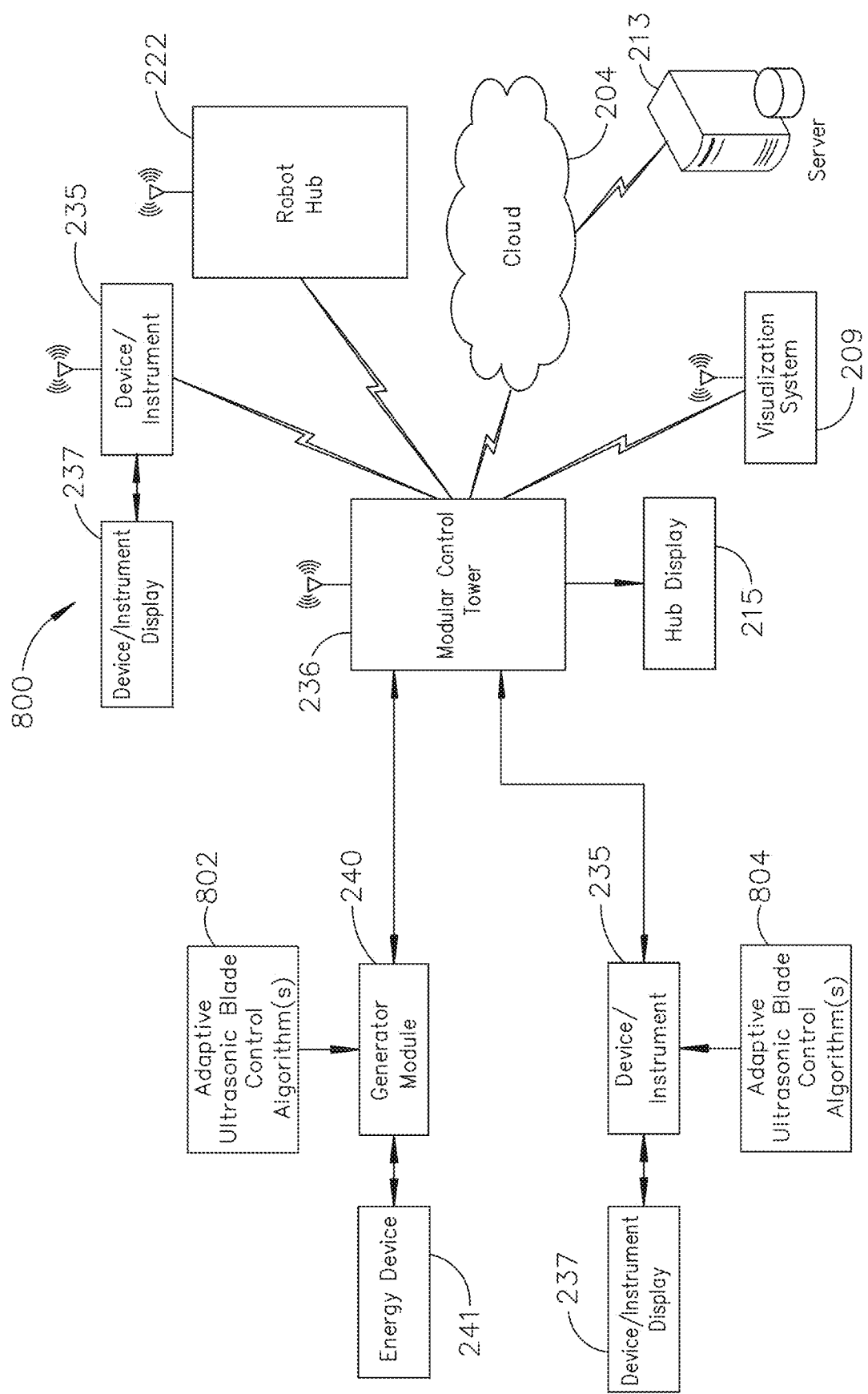
FIG. 20 is a system configured to execute adaptive ultrasonic blade control algorithms in a surgical data network comprising a modular communication hub, in accordance with at least one aspect of the present disclosure.

FIG. 20 is a system 800 configured to execute adaptive ultrasonic blade control algorithms in a surgical data network comprising a modular communication hub, in accordance with at least one aspect of the present disclosure. In one aspect, the generator module 240 is configured to execute the adaptive ultrasonic blade control algorithm(s) 802 as described herein with reference to FIGS. 53-105. In another aspect, the device/instrument 235 is configured to execute the adaptive ultrasonic blade control algorithm(s) 804 as described herein with reference to FIGS. 53-105. In another aspect, both the device/instrument 235 and the device/instrument 235 are configured to execute the adaptive ultrasonic blade control algorithms 802, 804 as described herein with reference to FIGS. 53-105.

The generator module 240 may comprise a patient isolated stage in communication with a non-isolated stage via a power transformer. A secondary winding of the power transformer is contained in the isolated stage and may comprise a tapped configuration (e.g., a center-tapped or a non-center-tapped configuration) to define drive signal outputs for delivering drive signals to different surgical instruments, such as, for example, an ultrasonic surgical instrument, an RF electrosurgical instrument, and a multifunction surgical instrument which includes ultrasonic and RF energy modes that can be delivered alone or simultaneously. In particular, the drive signal outputs may output an ultrasonic drive signal (e.g., a 420V root-mean-square (RMS) drive signal) to an ultrasonic surgical instrument 241, and the drive signal outputs may output an RF electrosurgical drive signal (e.g., a 100V RMS drive signal) to an RF electrosurgical instrument 241. Aspects of the generator module 240 are described herein with reference to FIGS. 21-28B.

The generator module 240 or the device/instrument 235 or both are coupled to the modular control tower 236 connected to multiple operating theater devices such as, for example, intelligent surgical instruments, robots, and other computerized devices located in the operating theater, as described with reference to FIGS. 8-11, for example.

Figure 21:
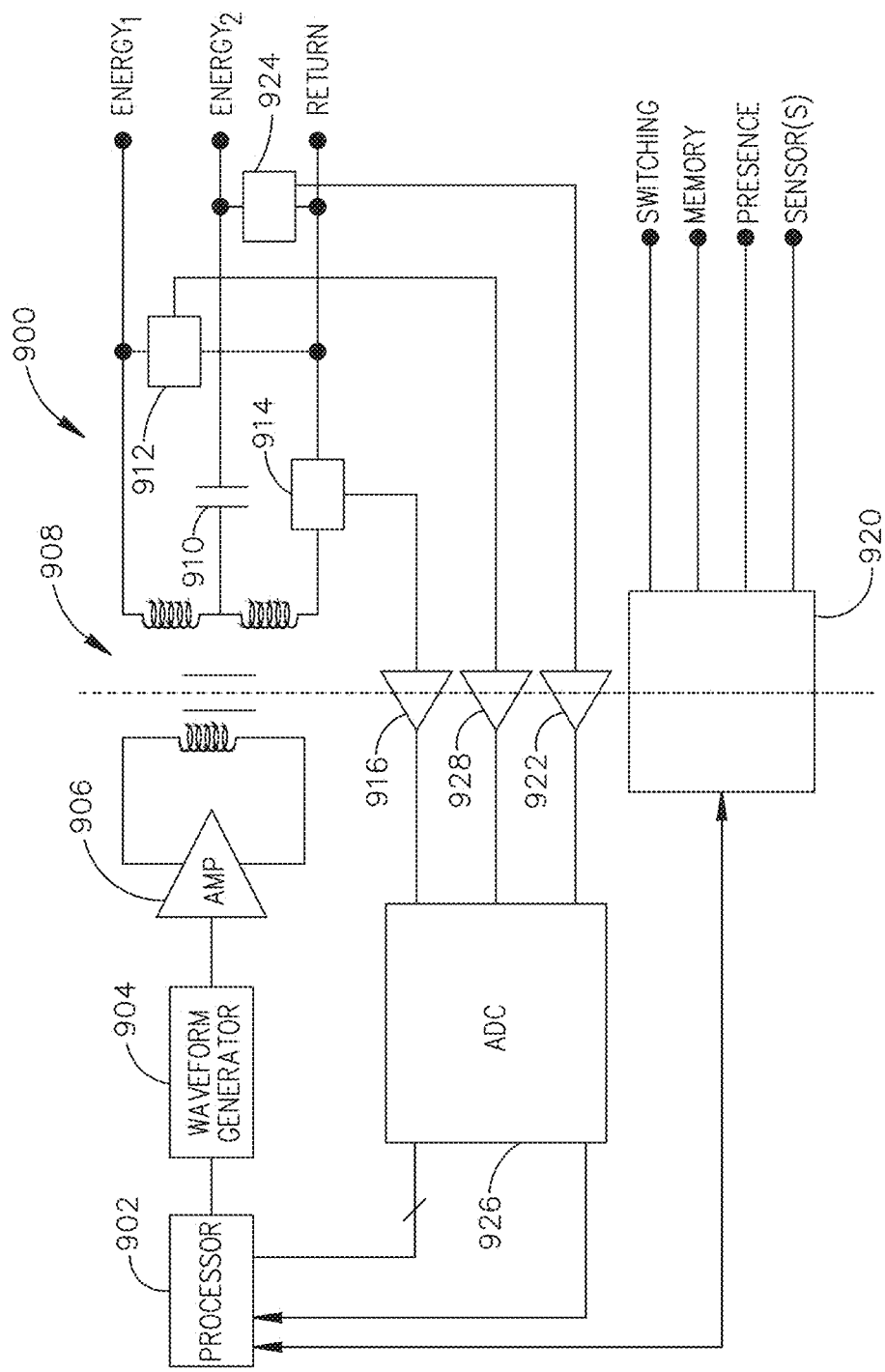
FIG. 21 illustrates an example of a generator, in accordance with at least one aspect of the present disclosure.

FIG. 21 illustrates an example of a generator 900, which is one form of a generator configured to couple to an ultrasonic instrument and further configured to execute adaptive ultrasonic blade control algorithms in a surgical data network comprising a modular communication hub as shown in FIG. 20. The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue. The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 1106 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled ENERGY$_1$ and RETURN. A second signal of a second energy modality is coupled across a capacitor 910 and is provided to the surgical instrument between the terminals labeled ENERGY$_2$ and RETURN. It will be appreciated that more than two energy modalities may be output and thus the subscript "n" may be used to designate that up to n ENERGY$_n$ terminals may be provided, where n is a positive integer greater than 1. It also will be appreciated that up to "n" return paths RETURN$_n$ may be provided without departing from the scope of the present disclosure.

A first voltage sensing circuit 912 is coupled across the terminals labeled ENERGY, and the RETURN path to measure the output voltage therebetween. A second voltage sensing circuit 924 is coupled across the terminals labeled ENERGY$_2$ and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 916, 922 and the output of the current sensing circuit 914 is provided to another isolation transformer 918. The outputs of the isolation transformers 916, 928, 922 in the on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled ENERGY$_1$/RETURN or the second voltage sensing circuit 924 coupled across the terminals labeled ENERGY$_2$/RETURN by the output of the current sensing circuit 914 disposed in series with the RETURN leg of the secondary side of the power transformer 908. The outputs of the first and second voltage sensing circuits 912, 924 are provided to separate isolations transformers 916, 922 and the output of the current sensing circuit 914 is provided to another isolation transformer 916. The digitized voltage and current sensing measurements from the ADC circuit 926 are provided the processor 902 for computing impedance. As an example, the first energy modality ENERGY$_1$ may be ultrasonic energy and the second energy modality ENERGY$_2$ may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 21 shows a single return path RETURN may be provided for two or more energy modalities, in other aspects, multiple return paths RETURN$_n$ may be provided for each energy modality ENERGY$_n$. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 21, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled $ENERGY_1$ and RETURN as shown in FIG. 21. In one example, a connection of RF bipolar electrodes to the generator 900 output would be preferably located between the output labeled $ENERGY_2$ and RETURN. In the case of monopolar output, the preferred connections would be active electrode (e.g., pencil or other probe) to the $ENERGY_2$ output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions-all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; an SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIGS. 3 and 9, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Figure 22:
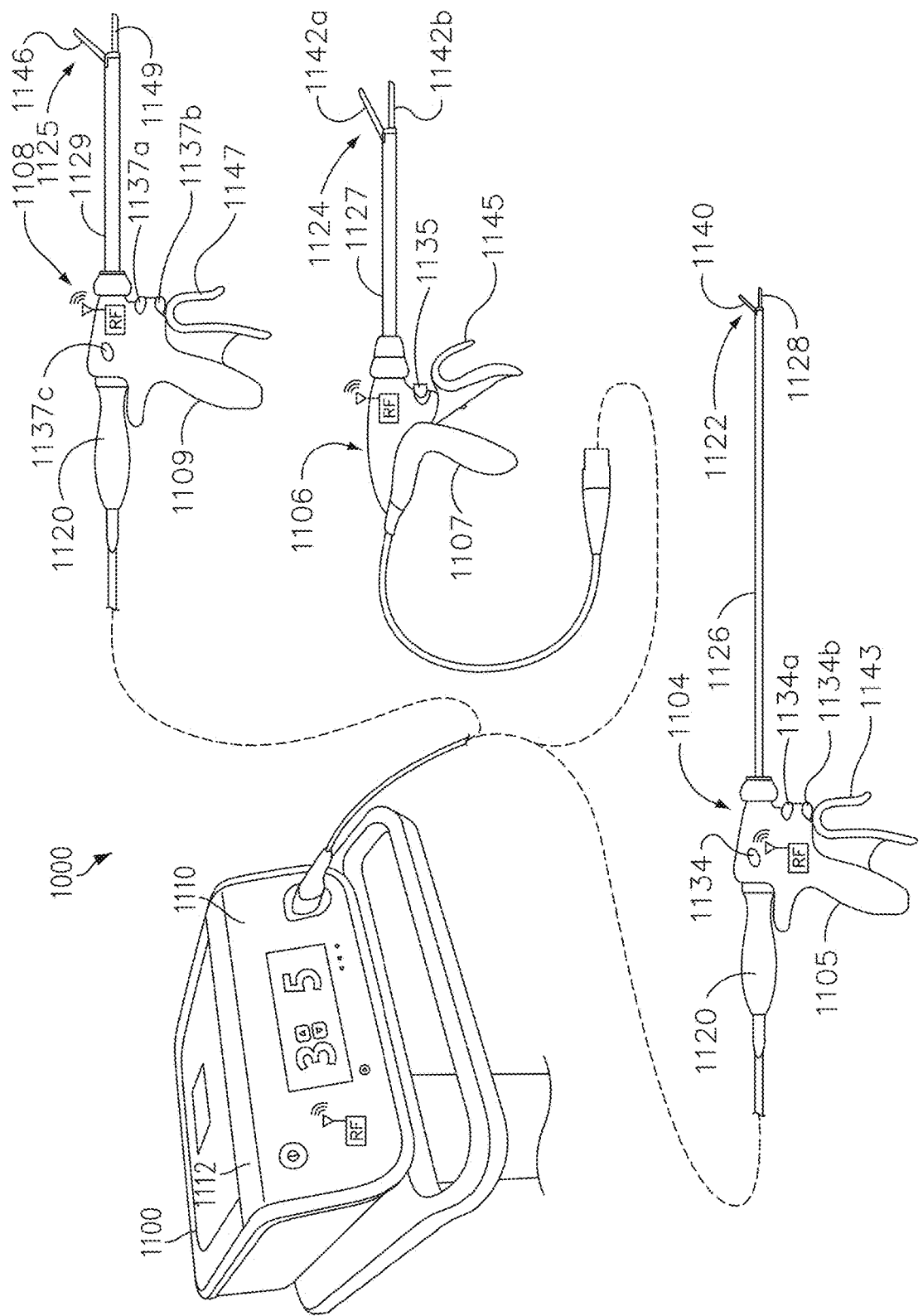
FIG. 22 is a surgical system comprising a generator and various surgical instruments usable therewith, in accordance with at least one aspect of the present disclosure.

FIG. 22 illustrates one form of a surgical system 1000 comprising a generator 1100 and various surgical instruments 1104, 1106, 1108 usable therewith, where the surgical instrument 1104 is an ultrasonic surgical instrument, the surgical instrument 1106 is an RF electrosurgical instrument, and the multifunction surgical instrument 1108 is a combination ultrasonic/RF electrosurgical instrument. The generator 1100 is configurable for use with a variety of surgical instruments. According to various forms, the generator 1100 may be configurable for use with different surgical instruments of different types including, for example, ultrasonic surgical instruments 1104, RF electrosurgical instruments 1106, and multifunction surgical instruments 1108 that integrate RF and ultrasonic energies delivered simultaneously from the generator 1100. Although in the form of FIG. 22 the generator 1100 is shown separate from the surgical instruments 1104, 1106, 1108 in one form, the generator 1100 may be formed integrally with any of the surgical instruments 1104, 1106, 1108 to form a unitary surgical system. The generator 1100 comprises an input device 1110 located on a front panel of the generator 1100 console. The input device 1110 may comprise any suitable device that generates signals suitable for programming the operation of the generator 1100. The generator 1100 may be configured for wired or wireless communication.

The generator 1100 is configured to drive multiple surgical instruments 1104, 1106, 1108. The first surgical instrument is an ultrasonic surgical instrument 1104 and comprises a handpiece 1105 (HP), an ultrasonic transducer 1120, a shaft 1126, and an end effector 1122. The end effector 1122 comprises an ultrasonic blade 1128 acoustically coupled to the ultrasonic transducer 1120 and a clamp arm 1140. The handpiece 1105 comprises a trigger 1143 to operate the clamp arm 1140 and a combination of the toggle buttons 1134a, 1134b, 1134c to energize and drive the ultrasonic blade 1128 or other function. The toggle buttons 1134a, 1134b, 1134c can be configured to energize the ultrasonic transducer 1120 with the generator 1100.

The generator 1100 also is configured to drive a second surgical instrument 1106. The second surgical instrument 1106 is an RF electrosurgical instrument and comprises a handpiece 1107 (HP), a shaft 1127, and an end effector 1124. The end effector 1124 comprises electrodes in clamp arms 1142a, 1142b and return through an electrical conductor portion of the shaft 1127. The electrodes are coupled to and energized by a bipolar energy source within the generator 1100. The handpiece 1107 comprises a trigger 1145 to operate the clamp arms 1142a, 1142b and an energy button 1135 to actuate an energy switch to energize the electrodes in the end effector 1124.

The generator 1100 also is configured to drive a multifunction surgical instrument 1108. The multifunction surgical instrument 1108 comprises a handpiece 1109 (HP), a shaft 1129, and an end effector 1125. The end effector 1125 comprises an ultrasonic blade 1149 and a clamp arm 1146. The ultrasonic blade 1149 is acoustically coupled to the ultrasonic transducer 1120. The handpiece 1109 comprises a trigger 1147 to operate the clamp arm 1146 and a combination of the toggle buttons 1137a, 1137b, 1137c to energize and drive the ultrasonic blade 1149 or other function. The toggle buttons 1137a, 1137b, 1137c can be configured to energize the ultrasonic transducer 1120 with the generator 1100 and energize the ultrasonic blade 1149 with a bipolar energy source also contained within the generator 1100.

The generator 1100 is configurable for use with a variety of surgical instruments. According to various forms, the generator 1100 may be configurable for use with different surgical instruments of different types including, for example, the ultrasonic surgical instrument 1104, the RF electrosurgical instrument 1106, and the multifunction surgical instrument 1108 that integrates RF and ultrasonic energies delivered simultaneously from the generator 1100. Although in the form of FIG. 22 the generator 1100 is shown separate from the surgical instruments 1104, 1106, 1108, in another form the generator 1100 may be formed integrally with any one of the surgical instruments 1104, 1106, 1108 to form a unitary surgical system. As discussed above, the generator 1100 comprises an input device 1110 located on a front panel of the generator 1100 console. The input device 1110 may comprise any suitable device that generates signals suitable for programming the operation of the generator 1100. The generator 1100 also may comprise one or more output devices 1112. Further aspects of generators for digitally generating electrical signal waveforms and surgical instruments are described in U.S. patent publication US-2017-0086914-A1, which is herein incorporated by reference in its entirety.

Figure 23:
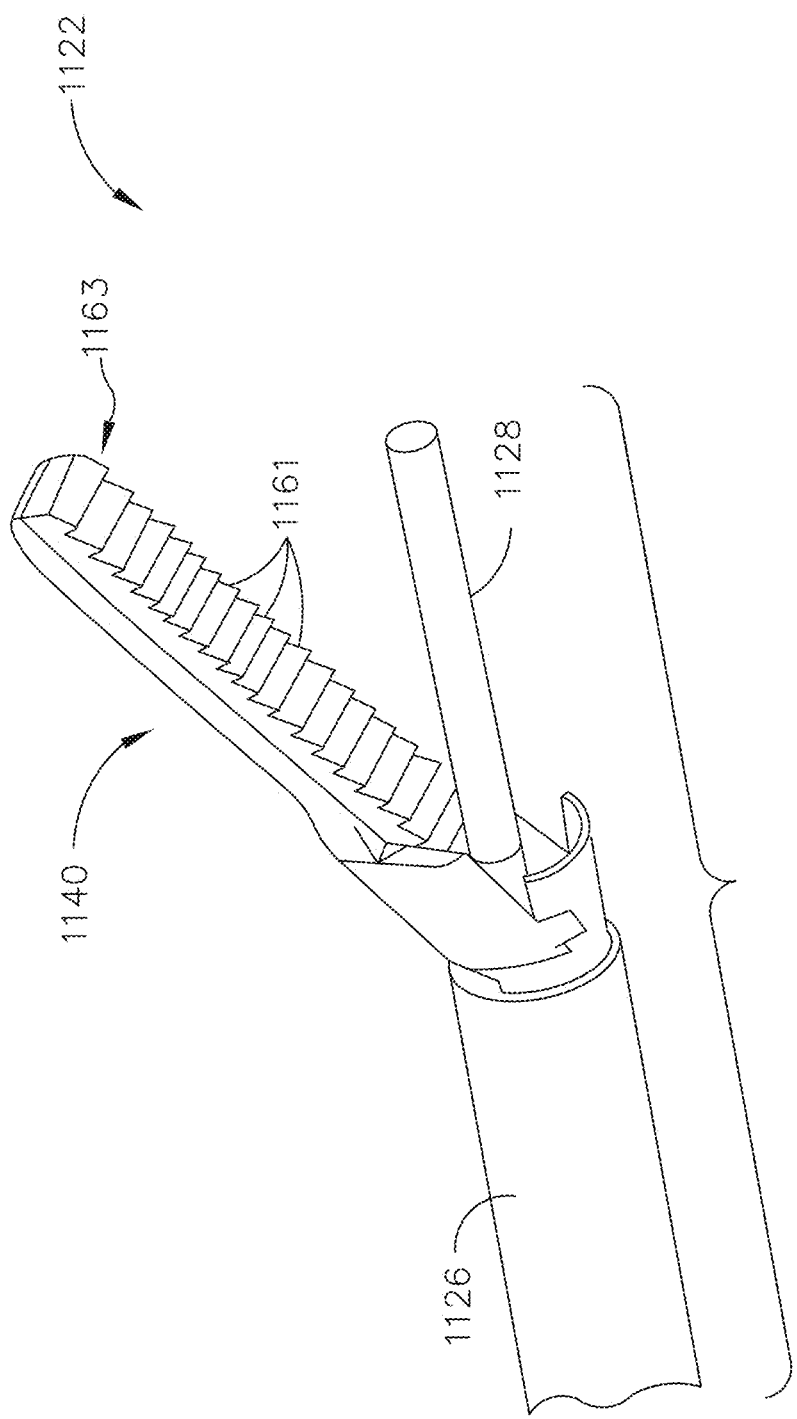
FIG. 23 is an end effector, in accordance with at least one aspect of the present disclosure.

FIG. 23 is an end effector 1122 of the example ultrasonic device 1104, in accordance with at least one aspect of the present disclosure. The end effector 1122 may comprise a blade 1128 that may be coupled to the ultrasonic transducer 1120 via a wave guide. When driven by the ultrasonic transducer 1120, the blade 1128 may vibrate and, when brought into contact with tissue, may cut and/or coagulate the tissue, as described herein. According to various aspects, and as illustrated in FIG. 23, the end effector 1122 may also comprise a clamp arm 1140 that may be configured for cooperative action with the blade 1128 of the end effector 1122. With the blade 1128, the clamp arm 1140 may comprise a set of jaws. The clamp arm 1140 may be pivotally connected at a distal end of a shaft 1126 of the instrument portion 1104. The clamp arm 1140 may include a clamp arm tissue pad 1163, which may be formed from TEFLON® or other suitable low-friction material. The pad 1163 may be mounted for cooperation with the blade 1128, with pivotal movement of the clamp arm 1140 positioning the clamp pad 1163 in substantially parallel relationship to, and in contact with, the blade 1128. By this construction, a tissue bite to be clamped may be grasped between the tissue pad 1163 and the blade 1128. The tissue pad 1163 may be provided with a sawtooth-like configuration including a plurality of axially spaced, proximally extending gripping teeth 1161 to enhance the gripping of tissue in cooperation with the blade 1128. The clamp arm 1140 may transition from the open position shown in FIG. 23 to a closed position (with the clamp arm 1140 in contact with or proximity to the blade 1128) in any suitable manner. For example, the handpiece 1105 may comprise a jaw closure trigger. When actuated by a clinician, the jaw closure trigger may pivot the clamp arm 1140 in any suitable manner.

The generator 1100 may be activated to provide the drive signal to the ultrasonic transducer 1120 in any suitable manner. For example, the generator 1100 may comprise a foot switch 1430 (FIG. 24) coupled to the generator 1100 via a footswitch cable 1432. A clinician may activate the ultrasonic transducer 1120, and thereby the ultrasonic transducer 1120 and blade 1128, by depressing the foot switch 1430. In addition, or instead of the foot switch 1430, some aspects of the device 1104 may utilize one or more switches positioned on the handpiece 1105 that, when activated, may cause the generator 1100 to activate the ultrasonic transducer 1120. In one aspect, for example, the one or more switches may comprise a pair of toggle buttons 1134a, 1134b, 1134c (FIG. 22), for example, to determine an operating mode of the device 1104. When the toggle button 1134a is depressed, for example, the ultrasonic generator 1100 may provide a maximum drive signal to the ultrasonic transducer 1120, causing it to produce maximum ultrasonic energy output. Depressing toggle button 1134b may cause the ultrasonic generator 1100 to provide a user-selectable drive signal to the ultrasonic transducer 1120, causing it to produce less than the maximum ultrasonic energy output. The device 1104 additionally or alternatively may comprise a second switch to, for example, indicate a position of a jaw closure trigger for operating the jaws via the clamp arm 1140 of the end effector 1122. Also, in some aspects, the ultrasonic generator 1100 may be activated based on the position of the jaw closure trigger, (e.g., as the clinician depresses the jaw closure trigger to close the jaws via the clamp arm 1140, ultrasonic energy may be applied).

Additionally or alternatively, the one or more switches may comprise a toggle button 1134c that, when depressed, causes the generator 1100 to provide a pulsed output (FIG. 22). The pulses may be provided at any suitable frequency and grouping, for example. In certain aspects, the power level of the pulses may be the power levels associated with toggle buttons 1134a, 1134b (maximum, less than maximum), for example.

It will be appreciated that a device 1104 may comprise any combination of the toggle buttons 1134a, 1134b, 1134c (FIG. 22). For example, the device 1104 could be configured to have only two toggle buttons: a toggle button 1134a for producing maximum ultrasonic energy output and a toggle button 1134c for producing a pulsed output at either the maximum or less than maximum power level per. In this way, the drive signal output configuration of the generator 1100 could be five continuous signals, or any discrete number of individual pulsed signals (1, 2, 3, 4, or 5). In certain aspects, the specific drive signal configuration may be controlled based upon, for example, EEPROM settings in the generator 1100 and/or user power level selection(s).

In certain aspects, a two-position switch may be provided as an alternative to a toggle button 1134c (FIG. 22). For example, a device 1104 may include a toggle button 1134a for producing a continuous output at a maximum power level and a two-position toggle button 1134b. In a first detented position, toggle button 1134b may produce a continuous output at a less than maximum power level, and in a second detented position the toggle button 1134b may produce a pulsed output (e.g., at either a maximum or less than maximum power level, depending upon the EEPROM settings).

In some aspects, the RF electrosurgical end effector 1124, 1125 (FIG. 22) may also comprise a pair of electrodes. The electrodes may be in communication with the generator 1100, for example, via a cable. The electrodes may be used, for example, to measure an impedance of a tissue bite present between the clamp arm 1142a, 1146 and the blade 1142b, 1149. The generator 1100 may provide a signal (e.g., a non-therapeutic signal) to the electrodes. The impedance of the tissue bite may be found, for example, by monitoring the current, voltage, etc. of the signal.

Figure 24:
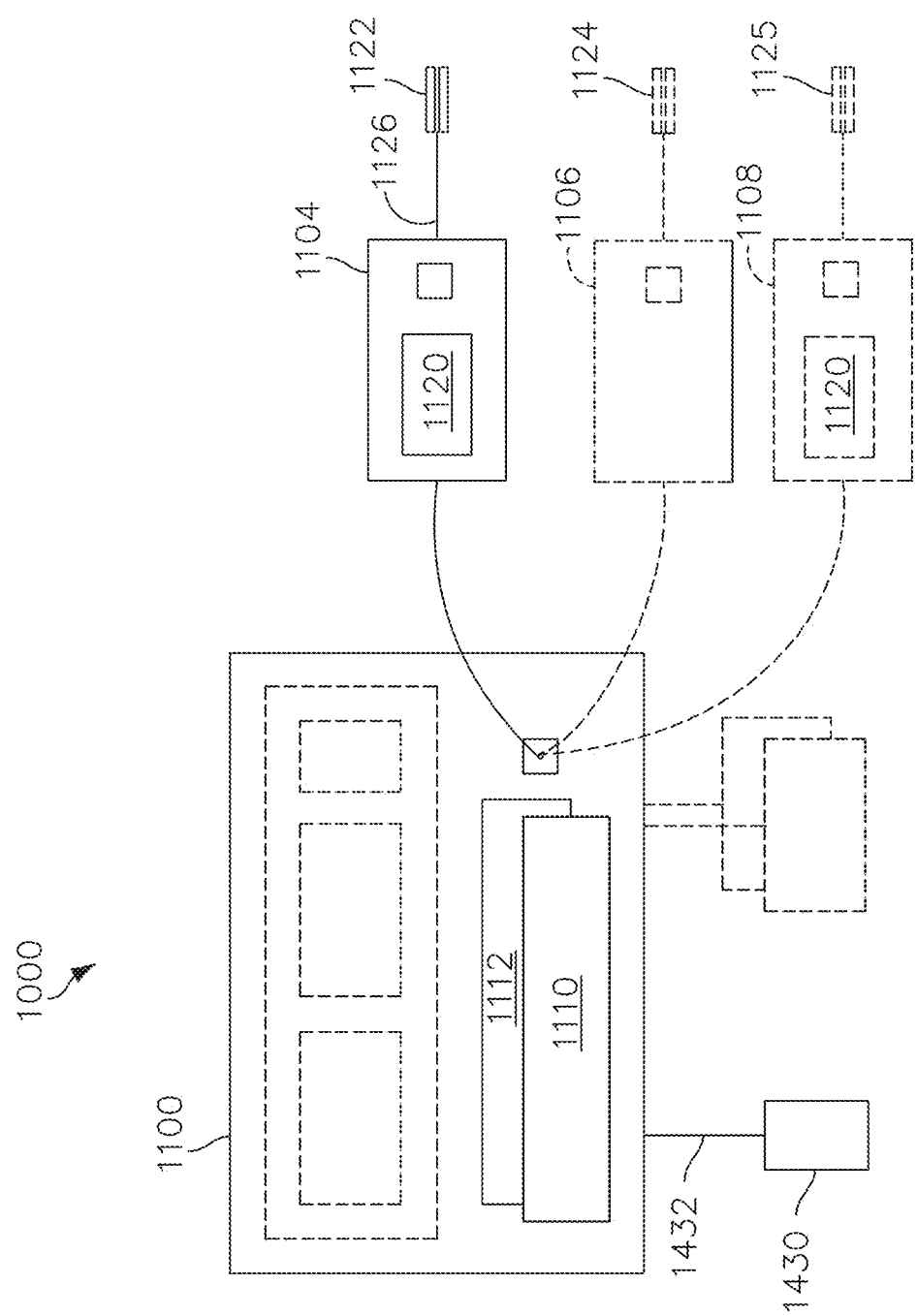
FIG. 24 is a diagram of the surgical system of FIG. 22, in accordance with at least one aspect of the present disclosure.

In various aspects, the generator 1100 may comprise several separate functional elements, such as modules and/or blocks, as shown in FIG. 24, a diagram of the surgical system 1000 of FIG. 22. Different functional elements or modules may be configured for driving the different kinds of surgical devices 1104, 1106, 1108. For example an ultrasonic generator module may drive an ultrasonic device, such as the ultrasonic device 1104. An electrosurgery/RF generator module may drive the electrosurgical device 1106. The modules may generate respective drive signals for driving the surgical devices 1104, 1106, 1108. In various aspects, the ultrasonic generator module and/or the electrosurgery/RF generator module each may be formed integrally with the generator 1100. Alternatively, one or more of the modules may be provided as a separate circuit module electrically coupled to the generator 1100. (The modules are shown in phantom to illustrate this option.) Also, in some aspects, the electrosurgery/RF generator module may be formed integrally with the ultrasonic generator module, or vice versa.

In accordance with the described aspects, the ultrasonic generator module may produce a drive signal or signals of particular voltages, currents, and frequencies (e.g. 55,500 cycles per second, or Hz). The drive signal or signals may be provided to the ultrasonic device 1104, and specifically to the transducer 1120, which may operate, for example, as described above. In one aspect, the generator 1100 may be configured to produce a drive signal of a particular voltage, current, and/or frequency output signal that can be stepped with high resolution, accuracy, and repeatability.

In accordance with the described aspects, the electrosurgery/RF generator module may generate a drive signal or signals with output power sufficient to perform bipolar electrosurgery using radio frequency (RF) energy. In bipolar electrosurgery applications, the drive signal may be provided, for example, to the electrodes of the electrosurgical device 1106, for example, as described above. Accordingly, the generator 1100 may be configured for therapeutic purposes by applying electrical energy to the tissue sufficient for treating the tissue (e.g., coagulation, cauterization, tissue welding, etc.).

The generator 1100 may comprise an input device 2150 (FIG. 27B) located, for example, on a front panel of the generator 1100 console. The input device 2150 may comprise any suitable device that generates signals suitable for programming the operation of the generator 1100. In operation, the user can program or otherwise control operation of the generator 1100 using the input device 2150. The input device 2150 may comprise any suitable device that generates signals that can be used by the generator (e.g., by one or more processors contained in the generator) to control the operation of the generator 1100 (e.g., operation of the ultrasonic generator module and/or electrosurgery/RF generator module). In various aspects, the input device 2150 includes one or more of: buttons, switches, thumbwheels, keyboard, keypad, touch screen monitor, pointing device, remote connection to a general purpose or dedicated computer. In other aspects, the input device 2150 may comprise a suitable user interface, such as one or more user interface screens displayed on a touch screen monitor, for example. Accordingly, by way of the input device 2150, the user can set or program various operating parameters of the generator, such as, for example, current (I), voltage (V), frequency (f), and/or period (T) of a drive signal or signals generated by the ultrasonic generator module and/or electrosurgery/RF generator module.

The generator 1100 may also comprise an output device 2140 (FIG. 27B) located, for example, on a front panel of the generator 1100 console. The output device 2140 includes one or more devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators).

Although certain modules and/or blocks of the generator 1100 may be described by way of example, it can be appreciated that a greater or lesser number of modules and/or blocks may be used and still fall within the scope of the aspects. Further, although various aspects may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In one aspect, the ultrasonic generator drive module and electrosurgery/RF drive module 1110 (FIG. 22) may comprise one or more embedded applications implemented as firmware, software, hardware, or any combination thereof. The modules may comprise various executable modules such as software, programs, data, drivers, application program interfaces (APIs), and so forth. The firmware may be stored in nonvolatile memory (NVM), such as in bit-masked read-only memory (ROM) or flash memory. In various implementations, storing the firmware in ROM may preserve flash memory. The NVM may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

In one aspect, the modules comprise a hardware component implemented as a processor for executing program instructions for monitoring various measurable characteristics of the devices 1104, 1106, 1108 and generating a corresponding output drive signal or signals for operating the devices 1104, 1106, 1108. In aspects in which the generator 1100 is used in conjunction with the device 1104, the drive signal may drive the ultrasonic transducer 1120 in cutting and/or coagulation operating modes. Electrical characteristics of the device 1104 and/or tissue may be measured and used to control operational aspects of the generator 1100 and/or provided as feedback to the user. In aspects in which the generator 1100 is used in conjunction with the device 1106, the drive signal may supply electrical energy (e.g., RF energy) to the end effector 1124 in cutting, coagulation and/or desiccation modes. Electrical characteristics of the device 1106 and/or tissue may be measured and used to control operational aspects of the generator 1100 and/or provided as feedback to the user. In various aspects, as previously discussed, the hardware components may be implemented as DSP, PLD, ASIC, circuits, and/or registers. In one aspect, the processor may be configured to store and execute computer software program instructions to generate the step function output signals for driving various components of the devices 1104, 1106, 1108, such as the ultrasonic transducer 1120 and the end effectors 1122, 1124, 1125.

An electromechanical ultrasonic system includes an ultrasonic transducer, a waveguide, and an ultrasonic blade. The electromechanical ultrasonic system has an initial resonant frequency defined by the physical properties of the ultrasonic transducer, the waveguide, and the ultrasonic blade. The ultrasonic transducer is excited by an alternating voltage $V_g(t)$ and current $I_g(t)$ signal equal to the resonant frequency of the electromechanical ultrasonic system. When the electromechanical ultrasonic system is at resonance, the phase difference between the voltage $V_g(t)$ and current $I_g(t)$ signals is zero. Stated another way, at resonance the inductive impedance is equal to the capacitive impedance. As the ultrasonic blade heats up, the compliance of the ultrasonic blade (modeled as an equivalent capacitance) causes the resonant frequency of the electromechanical ultrasonic system to shift. Thus, the inductive impedance is no longer equal to the capacitive impedance causing a mismatch between the drive frequency and the resonant frequency of the electromechanical ultrasonic system. The system is now operating "off-resonance." The mismatch between the drive frequency and the resonant frequency is manifested as a phase difference between the voltage $V_g(t)$ and current $I_g(t)$ signals applied to the ultrasonic transducer. The generator electronics can easily monitor the phase difference between the voltage $V_g(t)$ and current $I_g(t)$ signals and can continuously adjust the drive frequency until the phase difference is once again zero. At this point, the new drive frequency is equal to the new resonant frequency of the electromechanical ultrasonic system. The change in phase and/or frequency can be used as an indirect measurement of the ultrasonic blade temperature.

Figure 25:
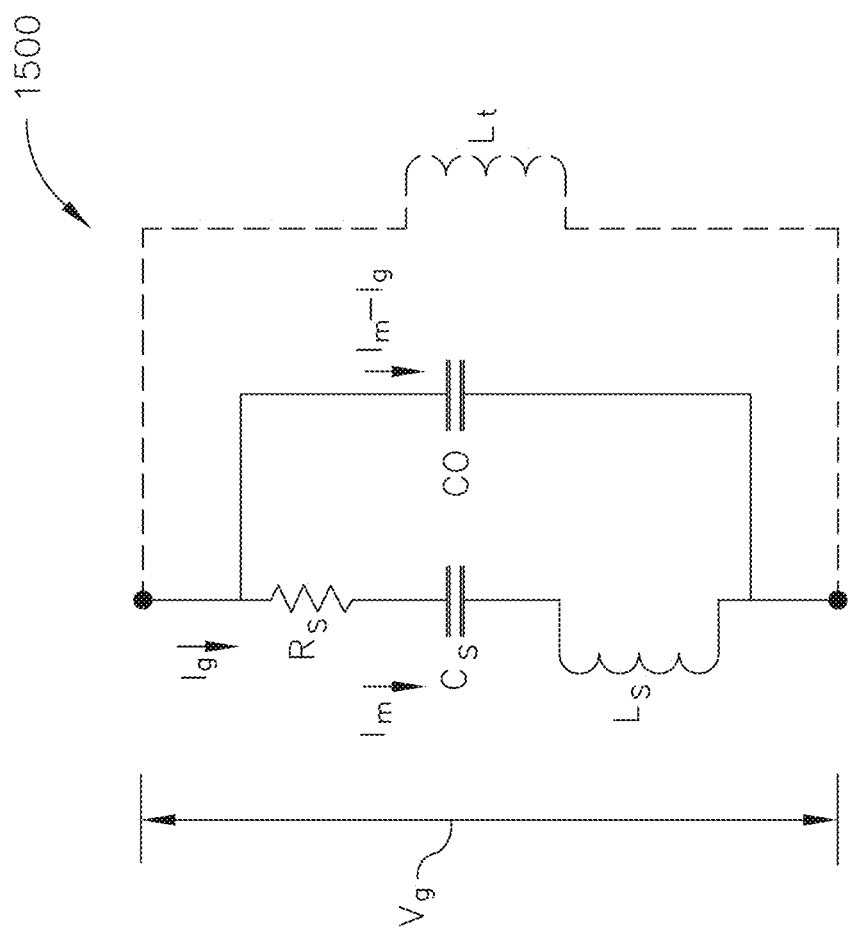
FIG. 25 is a model illustrating motional branch current, in accordance with at least one aspect of the present disclosure.

As shown in FIG. 25, the electromechanical properties of the ultrasonic transducer may be modeled as an equivalent circuit comprising a first branch having a static capacitance and a second "motional" branch having a serially connected inductance, resistance and capacitance that define the electromechanical properties of a resonator. Known ultrasonic generators may include a tuning inductor for tuning out the static capacitance at a resonant frequency so that substantially all of generator's drive signal current flows into the motional branch. Accordingly, by using a tuning inductor, the generator's drive signal current represents the motional branch current, and the generator is thus able to control its drive signal to maintain the ultrasonic transducer's resonant frequency. The tuning inductor may also transform the phase impedance plot of the ultrasonic transducer to improve the generator's frequency lock capabilities. However, the tuning inductor must be matched with the specific static capacitance of an ultrasonic transducer at the operational resonance frequency. In other words, a different ultrasonic transducer having a different static capacitance requires a different tuning inductor.

FIG. 25 illustrates an equivalent circuit 1500 of an ultrasonic transducer, such as the ultrasonic transducer 1120, according to one aspect. The circuit 1500 comprises a first "motional" branch having a serially connected inductance $L_s$, resistance $R_s$ and capacitance $C_s$ that define the electromechanical properties of the resonator, and a second capacitive branch having a static capacitance $C_0$. Drive current $I_g(t)$ may be received from a generator at a drive voltage $V_g(t)$, with motional current $I_m(t)$ flowing through the first branch and current $I_g(t)-I_m(t)$ flowing through the capacitive branch. Control of the electromechanical properties of the ultrasonic transducer may be achieved by suitably controlling $I_g(t)$ and $V_g(t)$. As explained above, known generator architectures may include a tuning inductor $L_t$ (shown in phantom in FIG. 25) in a parallel resonance circuit for tuning out the static capacitance $C_0$ at a resonant frequency so that substantially all of the generator's current output $I_g(t)$ flows through the motional branch. In this way, control of the motional branch current $I_m(t)$ is achieved by controlling the generator current output $I_g(t)$. The tuning inductor $L_t$ is specific to the static capacitance $C_0$ of an ultrasonic transducer, however, and a different ultrasonic transducer having a different static capacitance requires a different tuning inductor Lt. Moreover, because the tuning inductor $L_t$ is matched to the nominal value of the static capacitance $C_0$ at a single resonant frequency, accurate control of the motional branch current $I_m(t)$ is assured only at that frequency. As frequency shifts down with transducer temperature, accurate control of the motional branch current is compromised.

Various aspects of the generator 1100 may not rely on a tuning inductor $L_t$ to monitor the motional branch current $I_m(t)$. Instead, the generator 1100 may use the measured value of the static capacitance $C_0$ in between applications of power for a specific ultrasonic surgical device 1104 (along with drive signal voltage and current feedback data) to determine values of the motional branch current $I_m(t)$ on a dynamic and ongoing basis (e.g., in real-time). Such aspects of the generator 1100 are therefore able to provide virtual tuning to simulate a system that is tuned or resonant with any value of static capacitance $C_0$ at any frequency, and not just at a single resonant frequency dictated by a nominal value of the static capacitance $C_0$.

Figure 26:
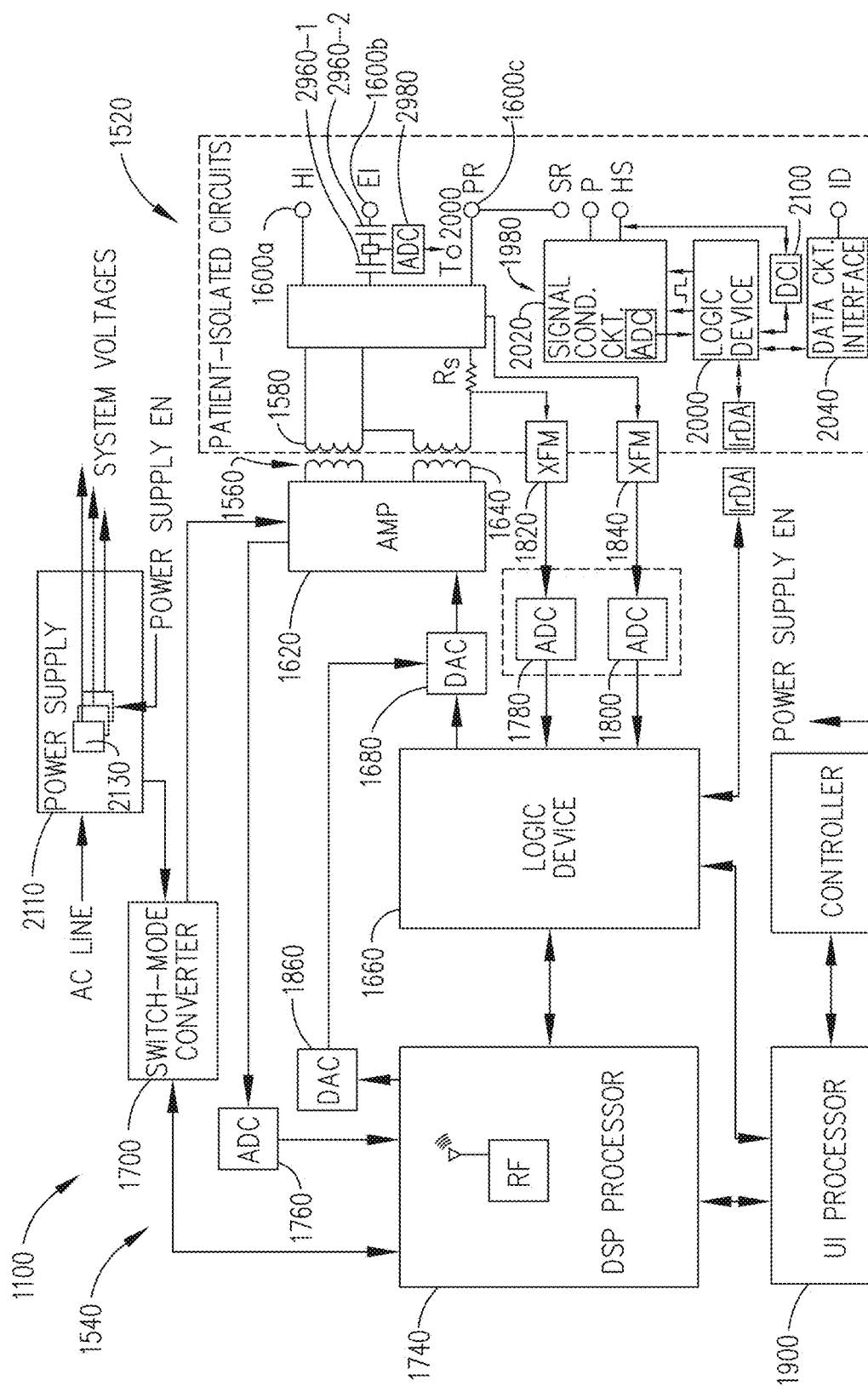
FIG. 26 is a structural view of a generator architecture, in accordance with at least one aspect of the present disclosure.
Figure 27A:
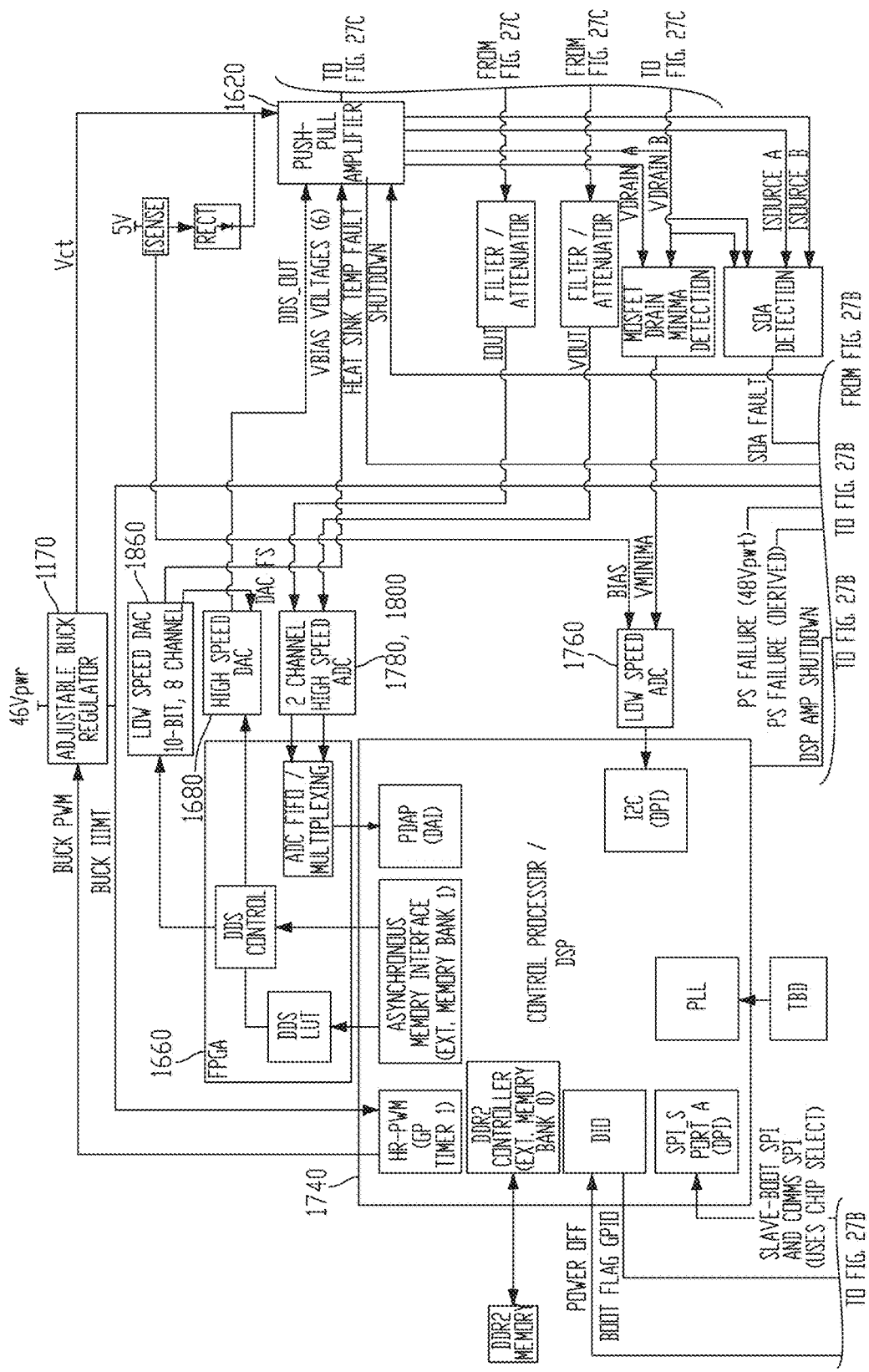
FIGS. 27A-27C are functional views of a generator architecture, in accordance with at least one aspect of the present disclosure.
Figure 27B:
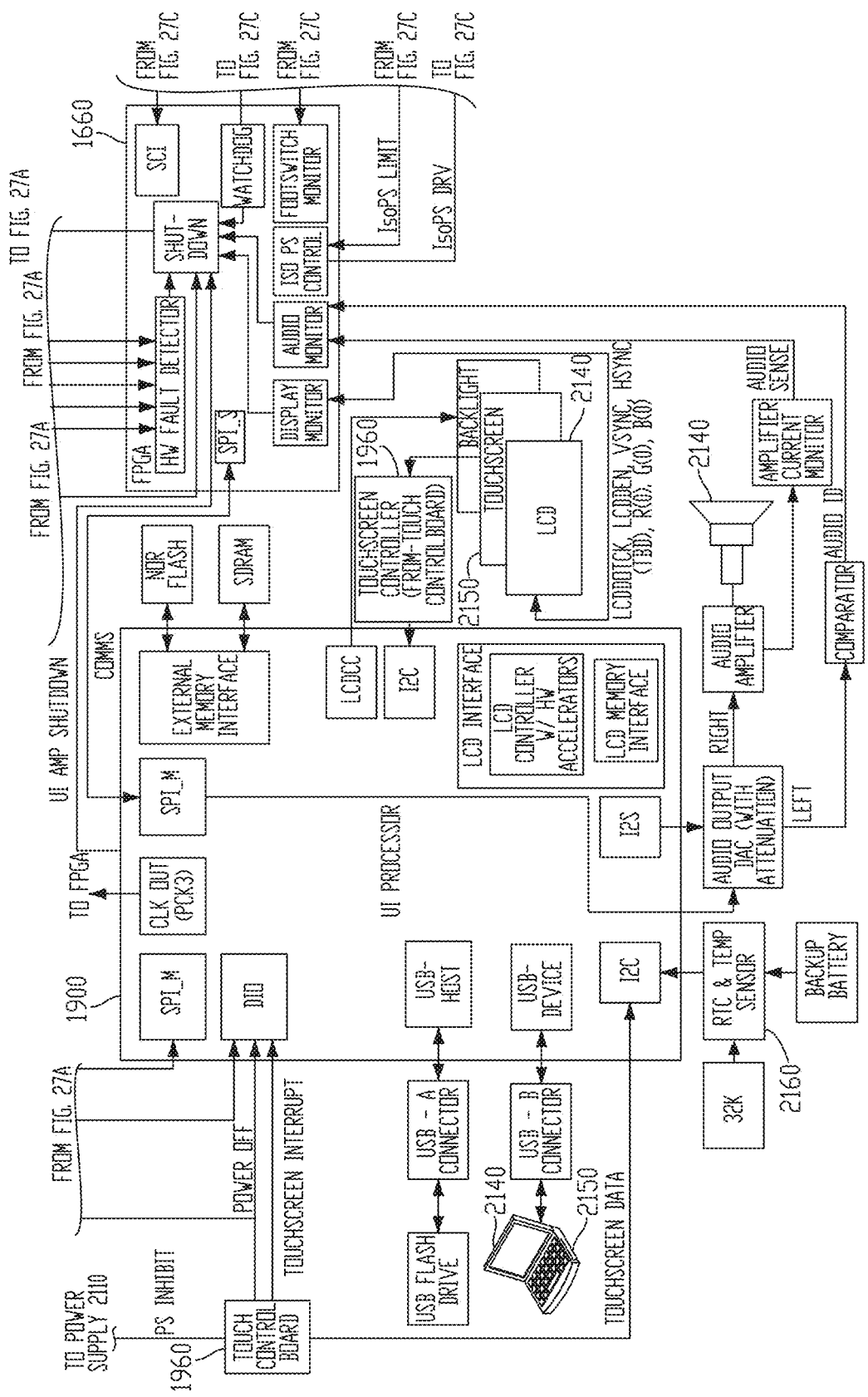
Figure 27C:
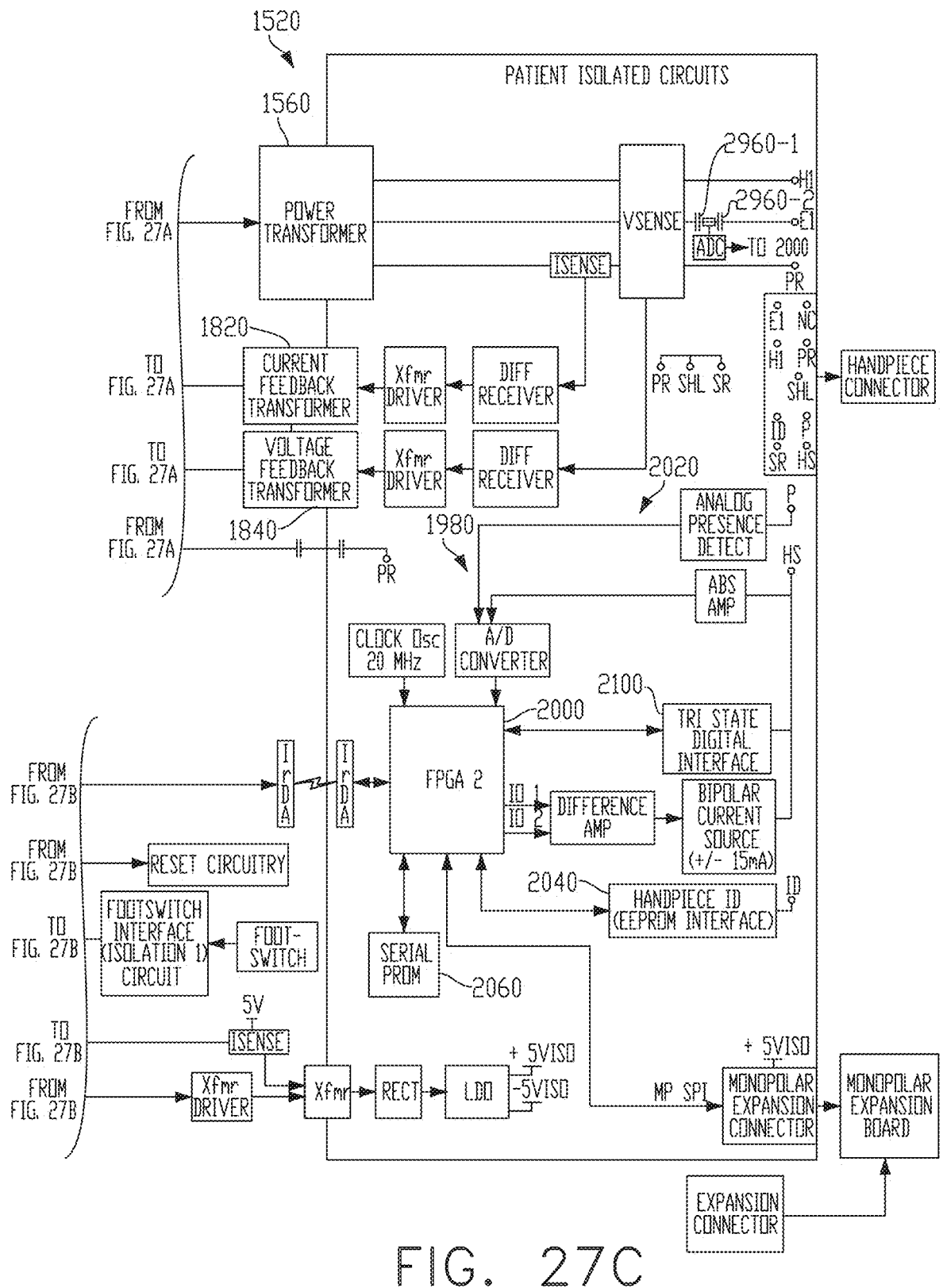

FIG. 26 is a simplified block diagram of one aspect of the generator 1100 for providing inductorless tuning as described above, among other benefits. FIGS. 27A-27C illustrate an architecture of the generator 1100 of FIG. 26 according to one aspect. With reference to FIG. 26, the generator 1100 may comprise a patient isolated stage 1520 in communication with a non-isolated stage 1540 via a power transformer 1560. A secondary winding 1580 of the power transformer 1560 is contained in the isolated stage 1520 and may comprise a tapped configuration (e.g., a center-tapped or non-center tapped configuration) to define drive signal outputs 1600*a*, 1600*b*, 1600*c* for outputting drive signals to different surgical devices, such as, for example, an ultrasonic surgical device 1104 and an electrosurgical device 1106. In particular, drive signal outputs 1600*a*, 1600*b*, 1600*c* may output a drive signal (e.g., a 420V RMS drive signal) to an ultrasonic surgical device 1104, and drive signal outputs 1600*a*, 1600*b*, 1600*c* may output a drive signal (e.g., a 100V RMS drive signal) to an electrosurgical device 1106, with output 1600*b* corresponding to the center tap of the power transformer 1560. The non-isolated stage 1540 may comprise a power amplifier 1620 having an output connected to a primary winding 1640 of the power transformer 1560. In certain aspects the power amplifier 1620 may comprise a push-pull amplifier, for example. The non-isolated stage 1540 may further comprise a programmable logic device 1660 for supplying a digital output to a digital-to-analog converter (DAC) 1680, which in turn supplies a corresponding analog signal to an input of the power amplifier 1620. In certain aspects the programmable logic device 1660 may comprise a field-programmable gate array (FPGA), for example. The programmable logic device 1660, by virtue of controlling the power amplifier's 1620 input via the DAC 1680, may therefore control any of a number of parameters (e.g., frequency, waveform shape, waveform amplitude) of drive signals appearing at the drive signal outputs 1600*a*, 1600*b*, 1600*c*. In certain aspects and as discussed below, the programmable logic device 1660, in conjunction with a processor (e.g., processor 1740 discussed below), may implement a number of digital signal processing (DSP)-based and/or other control algorithms to control parameters of the drive signals output by the generator 1100.

Power may be supplied to a power rail of the power amplifier 1620 by a switch-mode regulator 1700. In certain aspects the switch-mode regulator 1700 may comprise an adjustable buck regulator, for example. As discussed above, the non-isolated stage 1540 may further comprise a processor 1740, which in one aspect may comprise a DSP processor such as an ADSP-21469 SHARC DSP, available from Analog Devices, Norwood, Mass., for example. In certain aspects the processor 1740 may control operation of the switch-mode power converter 1700 responsive to voltage feedback data received from the power amplifier 1620 by the processor 1740 via an analog-to-digital converter (ADC) 1760. In one aspect, for example, the processor 1740 may receive as input, via the ADC 1760, the waveform envelope of a signal (e.g., an RF signal) being amplified by the power amplifier 1620. The processor 1740 may then control the switch-mode regulator 1700 (e.g., via a pulse-width modulated (PWM) output) such that the rail voltage supplied to the power amplifier 1620 tracks the waveform envelope of the amplified signal. By dynamically modulating the rail voltage of the power amplifier 1620 based on the waveform envelope, the efficiency of the power amplifier 1620 may be significantly improved relative to a fixed rail voltage amplifier scheme. The processor 1740 may be configured for wired or wireless communication.

In certain aspects and as discussed in further detail in connection with FIGS. 28A-28B, the programmable logic device 1660, in conjunction with the processor 1740, may implement a direct digital synthesizer (DDS) control scheme to control the waveform shape, frequency and/or amplitude of drive signals output by the generator 1100. In one aspect, for example, the programmable logic device 1660 may implement a DDS control algorithm 2680 (FIG. 28A) by recalling waveform samples stored in a dynamically-updated look-up table (LUT), such as a RAM LUT which may be embedded in an FPGA. This control algorithm is particularly useful for ultrasonic applications in which an ultrasonic transducer, such as the ultrasonic transducer 1120, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 1100 is impacted by various sources of distortion present in the output drive circuit (e.g., the power transformer 1560, the power amplifier 1620), voltage and current feedback data based on the drive signal may be input into an algorithm, such as an error control algorithm implemented by the processor 1740, which compensates for distortion by suitably pre-distorting or modifying the waveform samples stored in the LUT on a dynamic, ongoing basis (e.g., in real-time). In one aspect, the amount or degree of pre-distortion applied to the LUT samples may be based on the error between a computed motional branch current and a desired current waveform shape, with the error being determined on a sample-by sample basis. In this way, the pre-distorted LUT samples, when processed through the drive circuit, may result in a motional branch drive signal having the desired waveform shape (e.g., sinusoidal) for optimally driving the ultrasonic transducer. In such aspects, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 1540 may further comprise an ADC 1780 and an ADC 1800 coupled to the output of the power transformer 1560 via respective isolation transformers 1820, 1840 for respectively sampling the voltage and current of drive signals output by the generator 1100. In certain aspects, the ADCs 1780, 1800 may be configured to sample at high speeds (e.g., 80 Msps) to enable oversampling of the drive signals. In one aspect, for example, the sampling speed of the ADCs 1780, 1800 may enable approximately 200× (depending on drive frequency) oversampling of the drive signals. In certain aspects, the sampling operations of the ADCs 1780, 1800 may be performed by a single ADC receiving input voltage and current signals via a two-way multiplexer. The use of high-speed sampling in aspects of the generator 1100 may enable, among other things, calculation of the complex current flowing through the motional branch (which may be used in certain aspects to implement DDS-based waveform shape control described above), accurate digital filtering of the sampled signals, and calculation of real power consumption with a high degree of precision. Voltage and current feedback data output by the ADCs 1780, 1800 may be received and processed (e.g., FIFO buffering, multiplexing) by the programmable logic device 1660 and stored in data memory for subsequent retrieval by, for example, the processor 1740. As noted above, voltage and current feedback data may be used as input to an algorithm for pre-distorting or modifying LUT waveform samples on a dynamic and ongoing basis. In certain aspects, this may require each stored voltage and current feedback data pair to be indexed based on, or otherwise associated with, a corresponding LUT sample that was output by the programmable logic device 1660 when the voltage and current feedback data pair was acquired. Synchronization of the LUT samples and the voltage and current feedback data in this manner contributes to the correct timing and stability of the pre-distortion algorithm.

In certain aspects, the voltage and current feedback data may be used to control the frequency and/or amplitude (e.g., current amplitude) of the drive signals. In one aspect, for example, voltage and current feedback data may be used to determine impedance phase, e.g., the phase difference between the voltage and current drive signals. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy. The determination of phase impedance and a frequency control signal may be implemented in the processor 1740, for example, with the frequency control signal being supplied as input to a DDS control algorithm implemented by the programmable logic device 1660.

The impedance phase may be determined through Fourier analysis. In one aspect, the phase difference between the generator voltage $V_g(t)$ and generator current $I_g(t)$ driving signals may be determined using the Fast Fourier Transform (FFT) or the Discrete Fourier Transform (DFT) as follows:

$$V_g(t) = A_1 \cos(2\pi f_0 t + \varphi_1)$$

$$I_g(t) = A_2 \cos(2\pi f_0 t + \varphi_2)$$

$$V_g(f) = \frac{A_1}{2}(\delta(f - f_0) + \delta(f + f_0)) \exp\left(j2\pi f \frac{\varphi_1}{2\pi f_0}\right)$$

$$I_g(f) = \frac{A_2}{2}(\delta(f - f_0) + \delta(f + f_0)) \exp\left(j2\pi f \frac{\varphi_2}{2\pi f_0}\right)$$

Evaluating the Fourier Transform at the frequency of the sinusoid yields:

$$V_g(f_0) = \frac{A_1}{2}\delta(0)\exp(j\varphi_1) \quad \arg V(f_0) = \varphi_1$$

$$I_g(f_0) = \frac{A_2}{2}\delta(0)\exp(j\varphi_2) \quad \arg I(f_0) = \varphi_2$$

Other approaches include weighted least-squares estimation, Kalman filtering, and space-vector-based techniques. Virtually all of the processing in an FFT or DFT technique may be performed in the digital domain with the aid of the 2-channel high speed ADC 1780, 1800, for example. In one technique, the digital signal samples of the voltage and current signals are Fourier transformed with an FFT or a DFT. The phase angle φ at any point in time can be calculated by:

$$\varphi = 2\pi f t + \varphi_0$$

Where φ is the phase angle, f is the frequency, t is time, and $\varphi_0$ is the phase at t=0.

Another technique for determining the phase difference between the voltage $V_g(t)$ and current $I_g(t)$ signals is the zero-crossing method and produces highly accurate results. For voltage $V_g(t)$ and current $I_g(t)$ signals having the same frequency, each negative to positive zero-crossing of voltage signal $V_g(t)$ triggers the start of a pulse, while each negative to positive zero-crossing of current signal $I_g(t)$ triggers the end of the pulse. The result is a pulse train with a pulse width proportional to the phase angle between the voltage signal and the current signal. In one aspect, the pulse train may be passed through an averaging filter to yield a measure of the phase difference. Furthermore, if the positive to negative zero crossings also are used in a similar manner, and the results averaged, any effects of DC and harmonic components can be reduced. In one implementation, the analog voltage $V_g(t)$ and current $I_g(t)$ signals are converted to digital signals that are high if the analog signal is positive and low if the analog signal is negative. High accuracy phase estimates require sharp transitions between high and low. In one aspect, a Schmitt trigger along with an RC stabilization network may be employed to convert the analog signals into digital signals. In other aspects, an edge triggered RS flip-flop and ancillary circuitry may be employed. In yet another aspect, the zero-crossing technique may employ an eXclusive OR (XOR) gate.

Other techniques for determining the phase difference between the voltage and current signals include Lissajous figures and monitoring the image; methods such as the three-voltmeter method, the crossed-coil method, vector voltmeter and vector impedance methods; and using phase standard instruments, phase-locked loops, and other techniques as described in Phase Measurement, Peter O'Shea, 2000 CRC Press LLC, <http://www.engnetbase.com>, which is incorporated herein by reference.

In another aspect, for example, the current feedback data may be monitored in order to maintain the current amplitude of the drive signal at a current amplitude setpoint. The current amplitude setpoint may be specified directly or determined indirectly based on specified voltage amplitude and power setpoints. In certain aspects, control of the current amplitude may be implemented by control algorithm, such as, for example, a proportional-integral-derivative (PID) control algorithm, in the processor 1740. Variables controlled by the control algorithm to suitably control the current amplitude of the drive signal may include, for example, the scaling of the LUT waveform samples stored in the programmable logic device 1660 and/or the full-scale output voltage of the DAC 1680 (which supplies the input to the power amplifier 1620) via a DAC 1860.

The non-isolated stage 1540 may further comprise a processor 1900 for providing, among other things, user interface (UI) functionality. In one aspect, the processor 1900 may comprise an Atmel AT91 SAM9263 processor having an ARM 926EJ-S core, available from Atmel Corporation, San Jose, Calif., for example. Examples of UI functionality supported by the processor 1900 may include audible and visual user feedback, communication with peripheral devices (e.g., via a Universal Serial Bus (USB) interface), communication with a foot switch 1430, communication with an input device 2150 (e.g., a touch screen display) and communication with an output device 2140 (e.g., a speaker). The processor 1900 may communicate with the processor 1740 and the programmable logic device (e.g., via a serial peripheral interface (SPI) bus). Although the processor 1900 may primarily support UI functionality, it may also coordinate with the processor 1740 to implement hazard mitigation in certain aspects. For example, the processor 1900 may be programmed to monitor various aspects of user input and/or other inputs (e.g., touch screen inputs 2150, foot switch 1430 inputs, temperature sensor inputs 2160) and may disable the drive output of the generator 1100 when an erroneous condition is detected.

In certain aspects, both the processor 1740 (FIG. 26, 27A) and the processor 1900 (FIG. 26, 27B) may determine and monitor the operating state of the generator 1100. For processor 1740, the operating state of the generator 1100 may dictate, for example, which control and/or diagnostic processes are implemented by the processor 1740. For processor 1900, the operating state of the generator 1100 may dictate, for example, which elements of a user interface (e.g., display screens, sounds) are presented to a user. The processors 1740, 1900 may independently maintain the current operating state of the generator 1100 and recognize and evaluate possible transitions out of the current operating state. The processor 1740 may function as the master in this relationship and determine when transitions between operating states are to occur. The processor 1900 may be aware of valid transitions between operating states and may confirm if a particular transition is appropriate. For example, when the processor 1740 instructs the processor 1900 to transition to a specific state, the processor 1900 may verify that the requested transition is valid. In the event that a requested transition between states is determined to be invalid by the processor 1900, the processor 1900 may cause the generator 1100 to enter a failure mode.

The non-isolated stage 1540 may further comprise a controller 1960 (FIG. 26, 27B) for monitoring input devices 2150 (e.g., a capacitive touch sensor used for turning the generator 1100 on and off, a capacitive touch screen). In certain aspects, the controller 1960 may comprise at least one processor and/or other controller device in communication with the processor 1900. In one aspect, for example, the controller 1960 may comprise a processor (e.g., a Mega168 8-bit controller available from Atmel) configured to monitor user input provided via one or more capacitive touch sensors. In one aspect, the controller 1960 may comprise a touch screen controller (e.g., a QT5480 touch screen controller available from Atmel) to control and manage the acquisition of touch data from a capacitive touch screen.

In certain aspects, when the generator 1100 is in a "power off" state, the controller 1960 may continue to receive operating power (e.g., via a line from a power supply of the generator 1100, such as the power supply 2110 (FIG. 26) discussed below). In this way, the controller 1960 may continue to monitor an input device 2150 (e.g., a capacitive touch sensor located on a front panel of the generator 1100) for turning the generator 1100 on and off. When the generator 1100 is in the "power off" state, the controller 1960 may wake the power supply (e.g., enable operation of one or more DC/DC voltage converters 2130 (FIG. 26) of the power supply 2110) if activation of the "on/off" input device 2150 by a user is detected. The controller 1960 may therefore initiate a sequence for transitioning the generator 1100 to a "power on" state. Conversely, the controller 1960 may initiate a sequence for transitioning the generator 1100 to the "power off" state if activation of the "on/off" input device 2150 is detected when the generator 1100 is in the "power on" state. In certain aspects, for example, the controller 1960 may report activation of the "on/off" input device 2150 to the processor 1900, which in turn implements the necessary process sequence for transitioning the generator 1100 to the "power off" state. In such aspects, the controller 1960 may have no independent ability for causing the removal of power from the generator 1100 after its "power on" state has been established.

In certain aspects, the controller 1960 may cause the generator 1100 to provide audible or other sensory feedback for alerting the user that a "power on" or "power off" sequence has been initiated. Such an alert may be provided at the beginning of a "power on" or "power off" sequence and prior to the commencement of other processes associated with the sequence.

In certain aspects, the isolated stage 1520 may comprise an instrument interface circuit 1980 to, for example, provide a communication interface between a control circuit of a surgical device (e.g., a control circuit comprising handpiece switches) and components of the non-isolated stage 1540, such as, for example, the programmable logic device 1660, the processor 1740 and/or the processor 1900. The instrument interface circuit 1980 may exchange information with components of the non-isolated stage 1540 via a communication link that maintains a suitable degree of electrical isolation between the stages 1520, 1540, such as, for example, an infrared (IR)-based communication link. Power may be supplied to the instrument interface circuit 1980 using, for example, a low-dropout voltage regulator powered by an isolation transformer driven from the non-isolated stage 1540.

In one aspect, the instrument interface circuit 1980 may comprise a programmable logic device 2000 (e.g., an FPGA) in communication with a signal conditioning circuit 2020 (FIG. 26 and FIG. 27C). The signal conditioning circuit 2020 may be configured to receive a periodic signal from the programmable logic device 2000 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical device control circuit (e.g., by using a conductive pair in a cable that connects the generator 1100 to the surgical device) and monitored to determine a state or configuration of the control circuit. For example, the control circuit may comprise a number of switches, resistors and/or diodes to modify one or more characteristics (e.g., amplitude, rectification) of the interrogation signal such that a state or configuration of the control circuit is uniquely discernible based on the one or more characteristics. In one aspect, for example, the signal conditioning circuit 2020 may comprise an ADC for generating samples of a voltage signal appearing across inputs of the control circuit resulting from passage of interrogation signal therethrough. The programmable logic device 2000 (or a component of the non-isolated stage 1540) may then determine the state or configuration of the control circuit based on the ADC samples.

In one aspect, the instrument interface circuit 1980 may comprise a first data circuit interface 2040 to enable information exchange between the programmable logic device 2000 (or other element of the instrument interface circuit 1980) and a first data circuit disposed in or otherwise associated with a surgical device. In certain aspects, for example, a first data circuit 2060 may be disposed in a cable integrally attached to a surgical device handpiece, or in an adaptor for interfacing a specific surgical device type or model with the generator 1100. In certain aspects, the first data circuit may comprise a non-volatile storage device, such as an electrically erasable programmable read-only memory (EEPROM) device. In certain aspects and referring again to FIG. 26, the first data circuit interface 2040 may be implemented separately from the programmable logic device 2000 and comprise suitable circuitry (e.g., discrete logic devices, a processor) to enable communication between the programmable logic device 2000 and the first data circuit. In other aspects, the first data circuit interface 2040 may be integral with the programmable logic device 2000.

In certain aspects, the first data circuit 2060 may store information pertaining to the particular surgical device with which it is associated. Such information may include, for example, a model number, a serial number, a number of operations in which the surgical device has been used, and/or any other type of information. This information may be read by the instrument interface circuit 1980 (e.g., by the programmable logic device 2000), transferred to a component of the non-isolated stage 1540 (e.g., to programmable logic device 1660, processor 1740 and/or processor 1900) for presentation to a user via an output device 2140 and/or for controlling a function or operation of the generator 1100. Additionally, any type of information may be communicated to first data circuit 2060 for storage therein via the first data circuit interface 2040 (e.g., using the programmable logic device 2000). Such information may comprise, for example, an updated number of operations in which the surgical device has been used and/or dates and/or times of its usage.

As discussed previously, a surgical instrument may be detachable from a handpiece (e.g., instrument 1106 may be detachable from handpiece 1107) to promote instrument interchangeability and/or disposability. In such cases, known generators may be limited in their ability to recognize particular instrument configurations being used and to optimize control and diagnostic processes accordingly. The addition of readable data circuits to surgical device instruments to address this issue is problematic from a compatibility standpoint, however. For example, it may be impractical to design a surgical device to maintain backward compatibility with generators that lack the requisite data reading functionality due to, for example, differing signal schemes, design complexity and cost. Other aspects of instruments address these concerns by using data circuits that may be implemented in existing surgical instruments economically and with minimal design changes to preserve compatibility of the surgical devices with current generator platforms.

Additionally, aspects of the generator 1100 may enable communication with instrument-based data circuits. For example, the generator 1100 may be configured to communicate with a second data circuit (e.g., a data circuit) contained in an instrument (e.g., instrument 1104, 1106 or 1108) of a surgical device. The instrument interface circuit 1980 may comprise a second data circuit interface 2100 to enable this communication. In one aspect, the second data circuit interface 2100 may comprise a tri-state digital interface, although other interfaces may also be used. In certain aspects, the second data circuit may generally be any circuit for transmitting and/or receiving data. In one aspect, for example, the second data circuit may store information pertaining to the particular surgical instrument with which it is associated. Such information may include, for example, a model number, a serial number, a number of operations in which the surgical instrument has been used, and/or any other type of information. Additionally or alternatively, any type of information may be communicated to the second data circuit for storage therein via the second data circuit interface 2100 (e.g., using the programmable logic device 2000). Such information may comprise, for example, an updated number of operations in which the instrument has been used and/or dates and/or times of its usage. In certain aspects, the second data circuit may transmit data acquired by one or more sensors (e.g., an instrument-based temperature sensor). In certain aspects, the second data circuit may receive data from the generator 1100 and provide an indication to a user (e.g., an LED indication or other visible indication) based on the received data.

In certain aspects, the second data circuit and the second data circuit interface 2100 may be configured such that communication between the programmable logic device 2000 and the second data circuit can be effected without the need to provide additional conductors for this purpose (e.g., dedicated conductors of a cable connecting a handpiece to the generator 1100). In one aspect, for example, information may be communicated to and from the second data circuit using a one-wire bus communication scheme implemented on existing cabling, such as one of the conductors used transmit interrogation signals from the signal conditioning circuit 2020 to a control circuit in a handpiece. In this way, design changes or modifications to the surgical device that might otherwise be necessary are minimized or reduced. Moreover, because different types of communications can be implemented over a common physical channel (either with or without frequency-band separation), the presence of a second data circuit may be "invisible" to generators that do not have the requisite data reading functionality, thus enabling backward compatibility of the surgical device instrument.

In certain aspects, the isolated stage 1520 may comprise at least one blocking capacitor 2960-1 (FIG. 27C) connected to the drive signal output 1600b to prevent passage of DC current to a patient. A single blocking capacitor may be required to comply with medical regulations or standards, for example. While failure in single-capacitor designs is relatively uncommon, such failure may nonetheless have negative consequences. In one aspect, a second blocking capacitor 2960-2 may be provided in series with the blocking capacitor 2960-1, with current leakage from a point between the blocking capacitors 2960-1, 2960-2 being monitored by, for example, an ADC 2980 for sampling a voltage induced by leakage current. The samples may be received by the programmable logic device 2000, for example. Based on changes in the leakage current (as indicated by the voltage samples in the aspect of FIG. 26), the generator 1100 may determine when at least one of the blocking capacitors 2960-1, 2960-2 has failed. Accordingly, the aspect of FIG. 26 may provide a benefit over single-capacitor designs having a single point of failure.

In certain aspects, the non-isolated stage 1540 may comprise a power supply 2110 for outputting DC power at a suitable voltage and current. The power supply may comprise, for example, a 400 W power supply for outputting a 48 VDC system voltage. As discussed above, the power supply 2110 may further comprise one or more DC/DC voltage converters 2130 for receiving the output of the power supply to generate DC outputs at the voltages and currents required by the various components of the generator 1100. As discussed above in connection with the controller 1960, one or more of the DC/DC voltage converters 2130 may receive an input from the controller 1960 when activation of the "on/off" input device 2150 by a user is detected by the controller 1960 to enable operation of, or wake, the DC/DC voltage converters 2130.

Figure 28A:
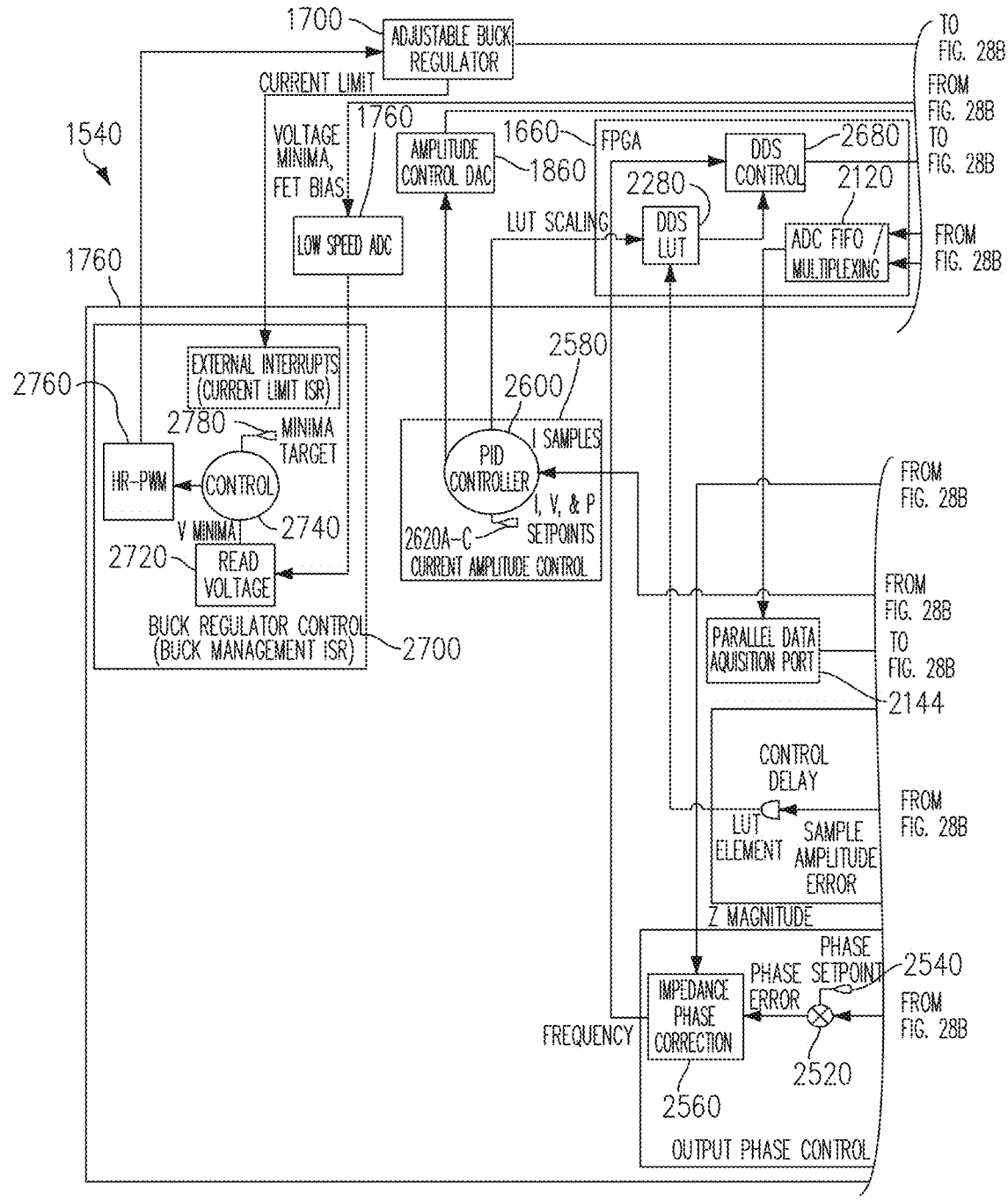
FIGS. 28A-28B are structural and functional aspects of a generator, in accordance with at least one aspect of the present disclosure.
Figure 28B:
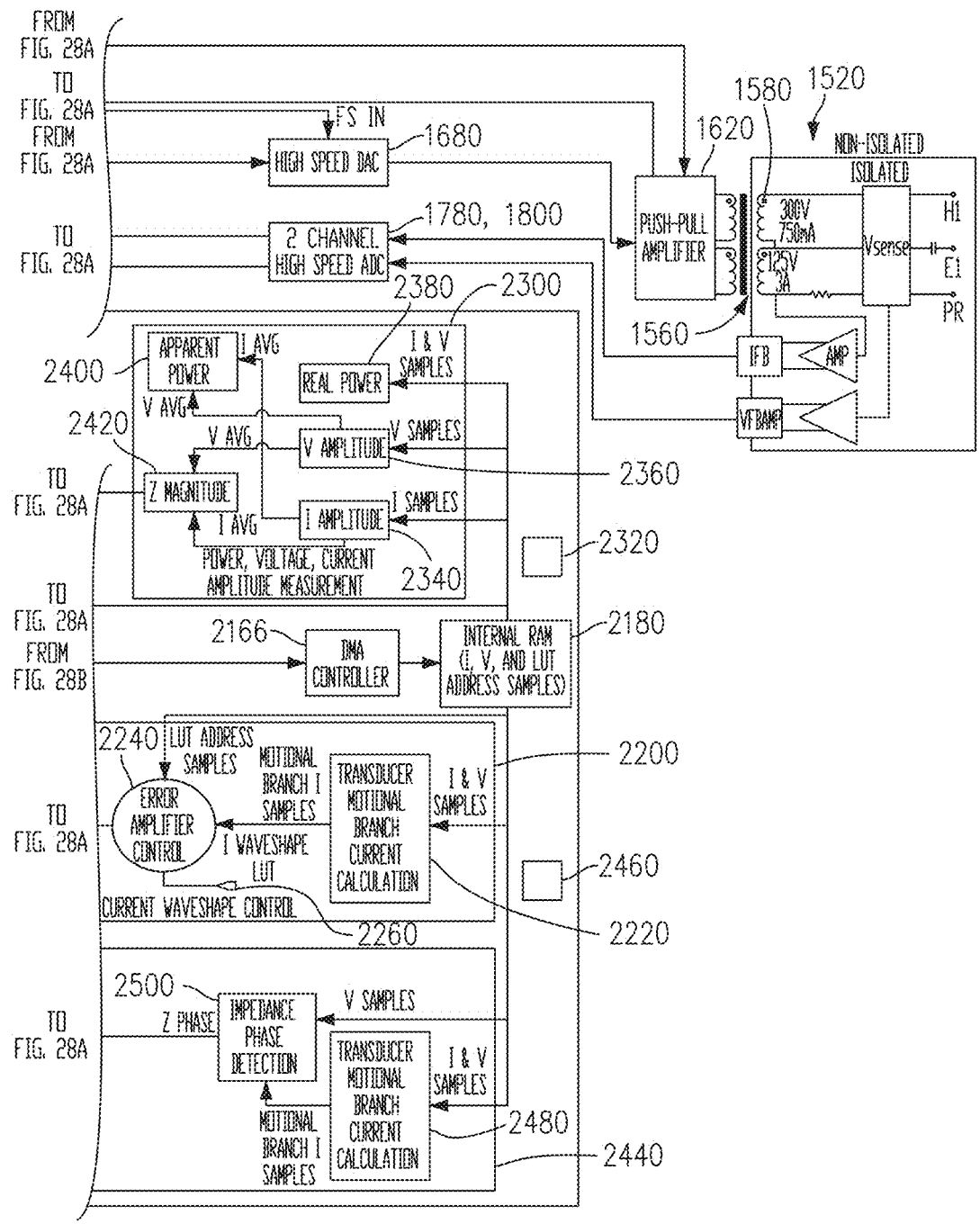

FIGS. 28A-28B illustrate certain functional and structural aspects of one aspect of the generator 1100. Feedback indicating current and voltage output from the secondary winding 1580 of the power transformer 1560 is received by the ADCs 1780, 1800, respectively. As shown, the ADCs 1780, 1800 may be implemented as a 2-channel ADC and may sample the feedback signals at a high speed (e.g., 80 Msps) to enable oversampling (e.g., approximately 200× oversampling) of the drive signals. The current and voltage feedback signals may be suitably conditioned in the analog domain (e.g., amplified, filtered) prior to processing by the ADCs 1780, 1800. Current and voltage feedback samples from the ADCs 1780, 1800 may be individually buffered and subsequently multiplexed or interleaved into a single data stream within block 2120 of the programmable logic device 1660. In the aspect of FIGS. 28A-28B, the programmable logic device 1660 comprises an FPGA.

The multiplexed current and voltage feedback samples may be received by a parallel data acquisition port (PDAP) implemented within block 2144 of the processor 1740. The PDAP may comprise a packing unit for implementing any of a number of methodologies for correlating the multiplexed feedback samples with a memory address. In one aspect, for example, feedback samples corresponding to a particular LUT sample output by the programmable logic device 1660 may be stored at one or more memory addresses that are correlated or indexed with the LUT address of the LUT sample. In another aspect, feedback samples corresponding to a particular LUT sample output by the programmable logic device 1660 may be stored, along with the LUT address of the LUT sample, at a common memory location. In any event, the feedback samples may be stored such that the address of the LUT sample from which a particular set of feedback samples originated may be subsequently ascertained. As discussed above, synchronization of the LUT sample addresses and the feedback samples in this way contributes to the correct timing and stability of the pre-distortion algorithm. A direct memory access (DMA) controller implemented at block 2166 of the processor 1740 may store the feedback samples (and any LUT sample address data, where applicable) at a designated memory location 2180 of the processor 1740 (e.g., internal RAM).

Block 2200 of the processor 1740 may implement a pre-distortion algorithm for pre-distorting or modifying the LUT samples stored in the programmable logic device 1660 on a dynamic, ongoing basis. As discussed above, pre-distortion of the LUT samples may compensate for various sources of distortion present in the output drive circuit of the generator 1100. The pre-distorted LUT samples, when processed through the drive circuit, will therefore result in a drive signal having the desired waveform shape (e.g., sinusoidal) for optimally driving the ultrasonic transducer.

At block 2220 of the pre-distortion algorithm, the current through the motional branch of the ultrasonic transducer is determined. The motional branch current may be determined using Kirchhoff's Current Law based on, for example, the current and voltage feedback samples stored at memory location 2180 (which, when suitably scaled, may be representative of $I_g$ and $V_g$ in the model of FIG. 25 discussed above), a value of the ultrasonic transducer static capacitance $C_0$ (measured or known a priori) and a known value of the drive frequency. A motional branch current sample for each set of stored current and voltage feedback samples associated with a LUT sample may be determined.

At block 2240 of the pre-distortion algorithm, each motional branch current sample determined at block 2220 is compared to a sample of a desired current waveform shape to determine a difference, or sample amplitude error, between the compared samples. For this determination, the sample of the desired current waveform shape may be supplied, for example, from a waveform shape LUT 2260 containing amplitude samples for one cycle of a desired current waveform shape. The particular sample of the desired current waveform shape from the LUT 2260 used for the comparison may be dictated by the LUT sample address associated with the motional branch current sample used in the comparison. Accordingly, the input of the motional branch current to block 2240 may be synchronized with the input of its associated LUT sample address to block 2240. The LUT samples stored in the programmable logic device 1660 and the LUT samples stored in the waveform shape LUT 2260 may therefore be equal in number. In certain aspects, the desired current waveform shape represented by the LUT samples stored in the waveform shape LUT 2260 may be a fundamental sine wave. Other waveform shapes may be desirable. For example, it is contemplated that a fundamental sine wave for driving main longitudinal motion of an ultrasonic transducer superimposed with one or more other drive signals at other frequencies, such as a third order harmonic for driving at least two mechanical resonances for beneficial vibrations of transverse or other modes, could be used.

Each value of the sample amplitude error determined at block 2240 may be transmitted to the LUT of the programmable logic device 1660 (shown at block 2280 in FIG. 28A) along with an indication of its associated LUT address. Based on the value of the sample amplitude error and its associated address (and, optionally, values of sample amplitude error for the same LUT address previously received), the LUT 2280 (or other control block of the programmable logic device 1660) may pre-distort or modify the value of the LUT sample stored at the LUT address such that the sample amplitude error is reduced or minimized. It will be appreciated that such pre-distortion or modification of each LUT sample in an iterative manner across the entire range of LUT addresses will cause the waveform shape of the generator's output current to match or conform to the desired current waveform shape represented by the samples of the waveform shape LUT 2260.

Current and voltage amplitude measurements, power measurements and impedance measurements may be determined at block 2300 of the processor 1740 based on the current and voltage feedback samples stored at memory location 2180. Prior to the determination of these quantities, the feedback samples may be suitably scaled and, in certain aspects, processed through a suitable filter 2320 to remove noise resulting from, for example, the data acquisition process and induced harmonic components. The filtered voltage and current samples may therefore substantially represent the fundamental frequency of the generator's drive output signal. In certain aspects, the filter 2320 may be a finite impulse response (FIR) filter applied in the frequency domain. Such aspects may use the Fast Fourier Transform (FFT) of the output drive signal current and voltage signals. In certain aspects, the resulting frequency spectrum may be used to provide additional generator functionality. In one aspect, for example, the ratio of the second and/or third order harmonic component relative to the fundamental frequency component may be used as a diagnostic indicator.

At block 2340 (FIG. 28B), a root mean square (RMS) calculation may be applied to a sample size of the current feedback samples representing an integral number of cycles of the drive signal to generate a measurement $I_{rms}$ representing the drive signal output current.

At block 2360, a root mean square (RMS) calculation may be applied to a sample size of the voltage feedback samples representing an integral number of cycles of the drive signal to determine a measurement $V_{rms}$ representing the drive signal output voltage.

At block 2380, the current and voltage feedback samples may be multiplied point by point, and a mean calculation is applied to samples representing an integral number of cycles of the drive signal to determine a measurement $P_r$ of the generator's real output power.

At block 2400, measurement $P_a$ of the generator's apparent output power may be determined as the product $V_{rms} \cdot I_{rms}$.

At block 2420, measurement $Z_m$ of the load impedance magnitude may be determined as the quotient $V_{rms}/I_{rms}$.

In certain aspects, the quantities $I_{rms}$, $V_{rms}$, $P_r$, $P_a$ and $Z_m$ determined at blocks 2340, 2360, 2380, 2400 and 2420 may be used by the generator 1100 to implement any of a number of control and/or diagnostic processes. In certain aspects, any of these quantities may be communicated to a user via, for example, an output device 2140 integral with the generator 1100 or an output device 2140 connected to the generator 1100 through a suitable communication interface (e.g., a USB interface). Various diagnostic processes may include, without limitation, handpiece integrity, instrument integrity, instrument attachment integrity, instrument overload, approaching instrument overload, frequency lock failure, over-voltage condition, over-current condition, over-power condition, voltage sense failure, current sense failure, audio indication failure, visual indication failure, short circuit condition, power delivery failure, or blocking capacitor failure, for example.

Block 2440 of the processor 1740 may implement a phase control algorithm for determining and controlling the impedance phase of an electrical load (e.g., the ultrasonic transducer) driven by the generator 1100. As discussed above, by controlling the frequency of the drive signal to minimize or reduce the difference between the determined impedance phase and an impedance phase setpoint (e.g., 0°), the effects of harmonic distortion may be minimized or reduced, and the accuracy of the phase measurement increased.

The phase control algorithm receives as input the current and voltage feedback samples stored in the memory location 2180. Prior to their use in the phase control algorithm, the feedback samples may be suitably scaled and, in certain aspects, processed through a suitable filter 2460 (which may be identical to filter 2320) to remove noise resulting from the data acquisition process and induced harmonic components, for example. The filtered voltage and current samples may therefore substantially represent the fundamental frequency of the generator's drive output signal.

At block 2480 of the phase control algorithm, the current through the motional branch of the ultrasonic transducer is determined. This determination may be identical to that described above in connection with block 2220 of the pre-distortion algorithm. The output of block 2480 may thus be, for each set of stored current and voltage feedback samples associated with a LUT sample, a motional branch current sample.

At block 2500 of the phase control algorithm, impedance phase is determined based on the synchronized input of motional branch current samples determined at block 2480 and corresponding voltage feedback samples. In certain aspects, the impedance phase is determined as the average of the impedance phase measured at the rising edge of the waveforms and the impedance phase measured at the falling edge of the waveforms.

At block 2520 of the of the phase control algorithm, the value of the impedance phase determined at block 2220 is compared to phase setpoint 2540 to determine a difference, or phase error, between the compared values.

At block 2560 (FIG. 28A) of the phase control algorithm, based on a value of phase error determined at block 2520 and the impedance magnitude determined at block 2420, a frequency output for controlling the frequency of the drive signal is determined. The value of the frequency output may be continuously adjusted by the block 2560 and transferred to a DDS control block 2680 (discussed below) in order to maintain the impedance phase determined at block 2500 at the phase setpoint (e.g., zero phase error). In certain aspects, the impedance phase may be regulated to a 0° phase setpoint. In this way, any harmonic distortion will be centered about the crest of the voltage waveform, enhancing the accuracy of phase impedance determination.

Block 2580 of the processor 1740 may implement an algorithm for modulating the current amplitude of the drive signal in order to control the drive signal current, voltage and power in accordance with user specified setpoints, or in accordance with requirements specified by other processes or algorithms implemented by the generator 1100. Control of these quantities may be realized, for example, by scaling the LUT samples in the LUT 2280 and/or by adjusting the full-scale output voltage of the DAC 1680 (which supplies the input to the power amplifier 1620) via a DAC 1860. Block 2600 (which may be implemented as a PID controller in certain aspects) may receive, as input, current feedback samples (which may be suitably scaled and filtered) from the memory location 2180. The current feedback samples may be compared to a "current demand" $I_d$ value dictated by the controlled variable (e.g., current, voltage or power) to determine if the drive signal is supplying the necessary current. In aspects in which drive signal current is the control variable, the current demand $I_d$ may be specified directly by a current setpoint 2620A ($I_{sp}$). For example, an RMS value of the current feedback data (determined as in block 2340) may be compared to user-specified RMS current setpoint $I_{sp}$ to determine the appropriate controller action. If, for example, the current feedback data indicates an RMS value less than the current setpoint $I_{sp}$, LUT scaling and/or the full-scale output voltage of the DAC 1680 may be adjusted by the block 2600 such that the drive signal current is increased. Conversely, block 2600 may adjust LUT scaling and/or the full-scale output voltage of the DAC 1680 to decrease the drive signal current when the current feedback data indicates an RMS value greater than the current setpoint $I_{sp}$.

In aspects in which the drive signal voltage is the control variable, the current demand $I_d$ may be specified indirectly, for example, based on the current required to maintain a desired voltage setpoint 2620B ($V_{sp}$) given the load impedance magnitude $Z_m$ measured at block 2420 (e.g. $I_d=V_{sp}/Z_m$). Similarly, in aspects in which drive signal power is the control variable, the current demand $I_d$ may be specified indirectly, for example, based on the current required to maintain a desired power setpoint 2620C ($P_{sp}$) given the voltage $V_{rms}$ measured at blocks 2360 (e.g. $d=P_{sp}/V_{rms}$).

Block 2680 (FIG. 28A) may implement a DDS control algorithm for controlling the drive signal by recalling LUT samples stored in the LUT 2280. In certain aspects, the DDS control algorithm may be a numerically-controlled oscillator (NCO) algorithm for generating samples of a waveform at a fixed clock rate using a point (memory location)-skipping technique. The NCO algorithm may implement a phase accumulator, or frequency-to-phase converter, that functions as an address pointer for recalling LUT samples from the LUT 2280. In one aspect, the phase accumulator may be a D step size, modulo N phase accumulator, where D is a positive integer representing a frequency control value, and N is the number of LUT samples in the LUT 2280. A frequency control value of D=1, for example, may cause the phase accumulator to sequentially point to every address of the LUT 2280, resulting in a waveform output replicating the waveform stored in the LUT 2280. When D>1, the phase accumulator may skip addresses in the LUT 2280, resulting in a waveform output having a higher frequency. Accordingly, the frequency of the waveform generated by the DDS control algorithm may therefore be controlled by suitably varying the frequency control value. In certain aspects, the frequency control value may be determined based on the output of the phase control algorithm implemented at block 2440. The output of block 2680 may supply the input of DAC 1680, which in turn supplies a corresponding analog signal to an input of the power amplifier 1620.

Block 2700 of the processor 1740 may implement a switch-mode converter control algorithm for dynamically modulating the rail voltage of the power amplifier 1620 based on the waveform envelope of the signal being amplified, thereby improving the efficiency of the power amplifier 1620. In certain aspects, characteristics of the waveform envelope may be determined by monitoring one or more signals contained in the power amplifier 1620. In one aspect, for example, characteristics of the waveform envelope may be determined by monitoring the minima of a drain voltage (e.g., a MOSFET drain voltage) that is modulated in accordance with the envelope of the amplified signal. A minima voltage signal may be generated, for example, by a voltage minima detector coupled to the drain voltage. The minima voltage signal may be sampled by ADC 1760, with the output minima voltage samples being received at block 2720 of the switch-mode converter control algorithm. Based on the values of the minima voltage samples, block 2740 may control a PWM signal output by a PWM generator 2760, which, in turn, controls the rail voltage supplied to the power amplifier 1620 by the switch-mode regulator 1700. In certain aspects, as long as the values of the minima voltage samples are less than a minima target 2780 input into block 2720, the rail voltage may be modulated in accordance with the waveform envelope as characterized by the minima voltage samples. When the minima voltage samples indicate low envelope power levels, for example, block 2740 may cause a low rail voltage to be supplied to the power amplifier 1620, with the full rail voltage being supplied only when the minima voltage samples indicate maximum envelope power levels. When the minima voltage samples fall below the minima target 2780, block 2740 may cause the rail voltage to be maintained at a minimum value suitable for ensuring proper operation of the power amplifier 1620.

Figure 29:
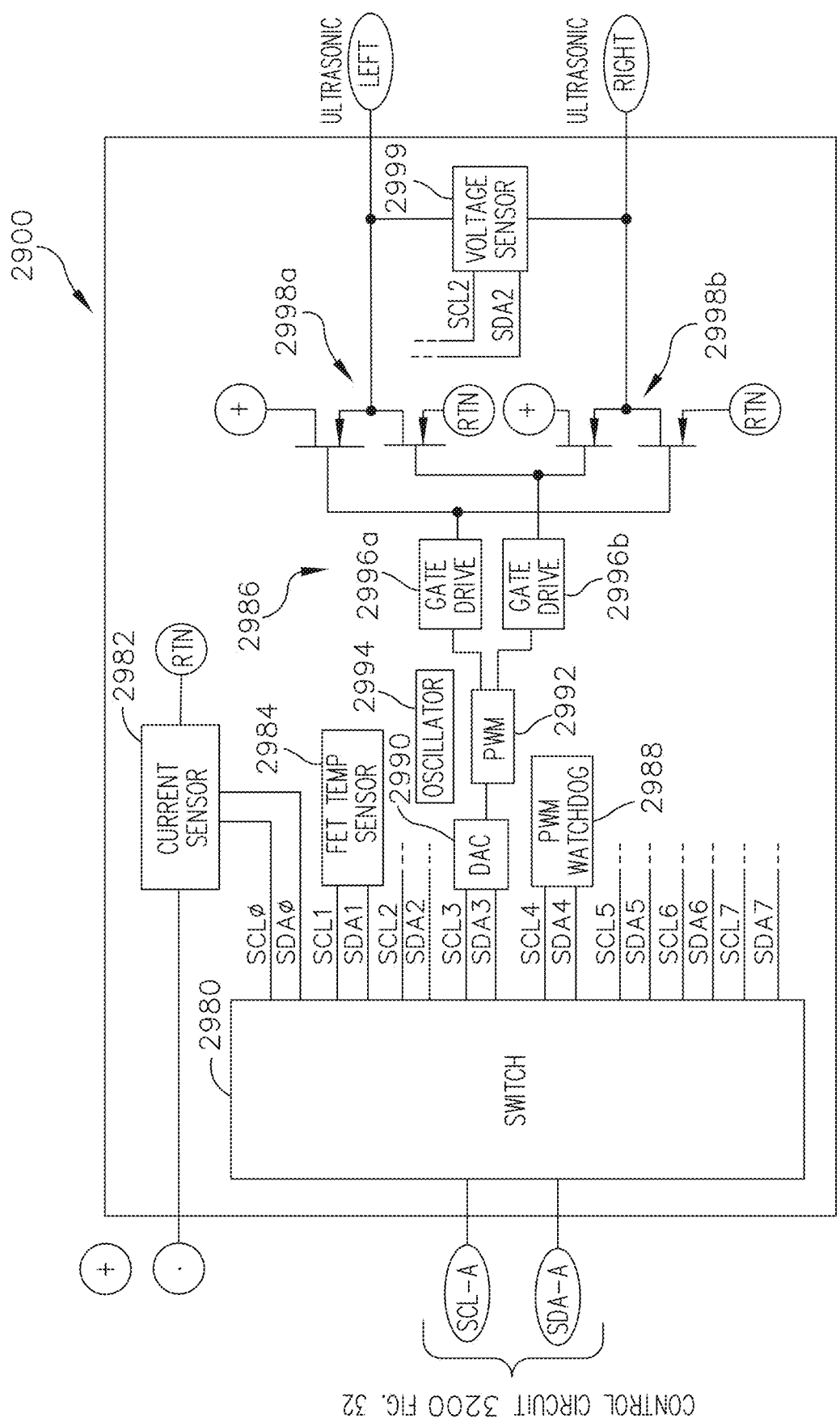
FIG. 29 is a schematic diagram of one aspect of an ultrasonic drive circuit

FIG. 29 is a schematic diagram of one aspect of an electrical circuit 2900, suitable for driving an ultrasonic transducer, such as ultrasonic transducer 1120, in accordance with at least one aspect of the present disclosure. The electrical circuit 2900 comprises an analog multiplexer 2980. The analog multiplexer 2980 multiplexes various signals from the upstream channels SCL-A, SDA-A such as ultrasonic, battery, and power control circuit. A current sensor 2982 is coupled in series with the return or ground leg of the power supply circuit to measure the current supplied by the power supply. A field effect transistor (FET) temperature sensor 2984 provides the ambient temperature. A pulse width modulation (PWM) watchdog timer 2988 automatically generates a system reset if the main program neglects to periodically service it. It is provided to automatically reset the electrical circuit 2900 when it hangs or freezes because of a software or hardware fault. It will be appreciated that the electrical circuit 2900 may be configured as an RF driver circuit for driving the ultrasonic transducer or for driving RF electrodes such as the electrical circuit 3600 shown in FIG. 36, for example. Accordingly, with reference now back to FIG. 29, the electrical circuit 2900 can be used to drive both ultrasonic transducers and RF electrodes interchangeably. If driven simultaneously, filter circuits may be provided in the corresponding first stage circuits 3404 (FIG. 34) to select either the ultrasonic waveform or the RF waveform. Such filtering techniques are described in commonly owned U.S. Pat. Pub. No. US-2017-0086910-A1, titled TECHNIQUES FOR CIRCUIT TOPOLOGIES FOR COMBINED GENERATOR, which is herein incorporated by reference in its entirety.

Figure 32:
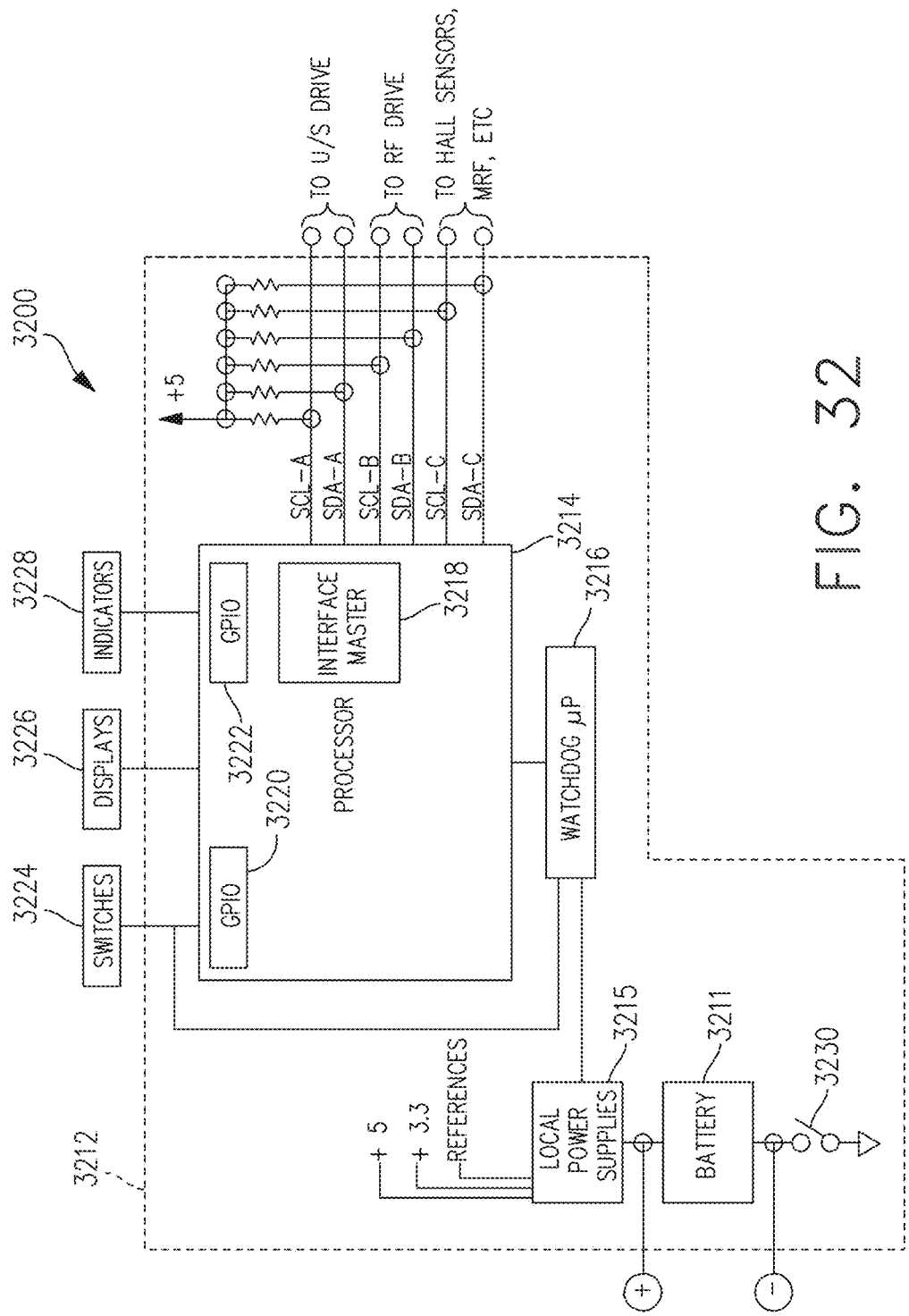
FIG. 32 is a schematic diagram of a control circuit, in accordance with at least one aspect of the present disclosure.
Figure 41:
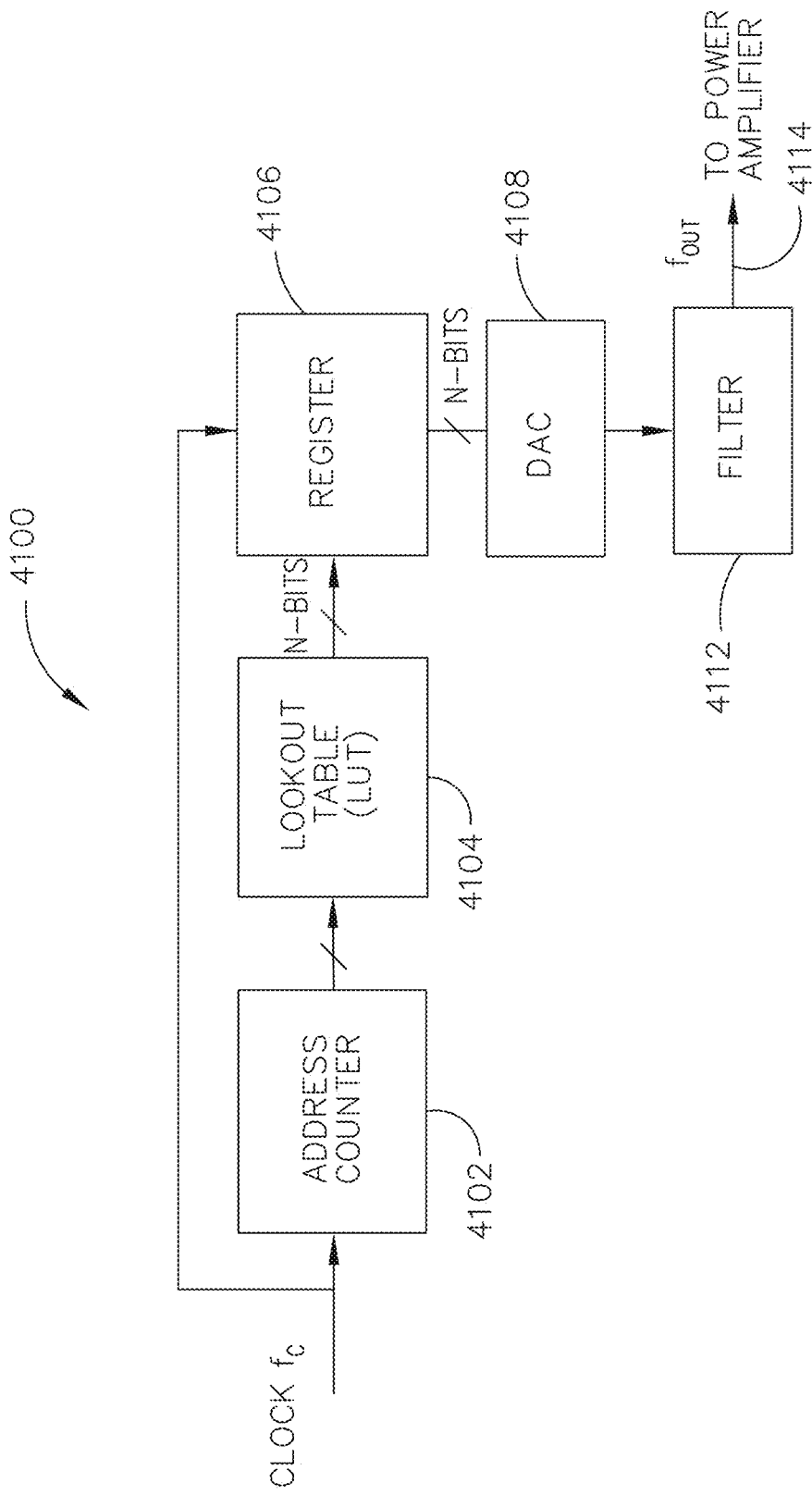
FIG. 41 illustrates one aspect of a fundamental architecture for a digital synthesis circuit such as a direct digital synthesis (DDS) circuit configured to generate a plurality of wave shapes for the electrical signal waveform for use in a surgical instrument, in accordance with at least one aspect of the present disclosure.
Figure 42:
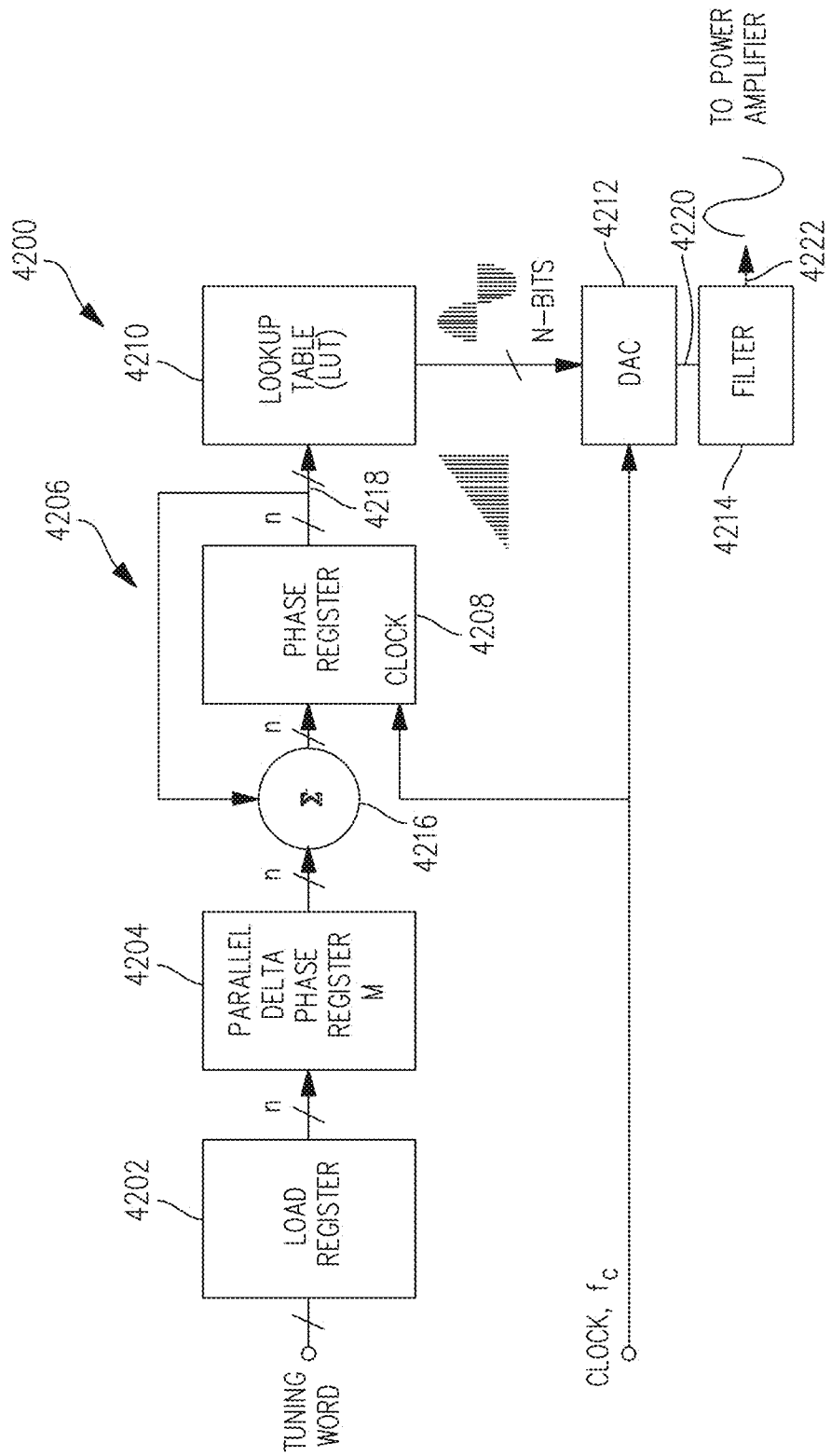
FIG. 42 illustrates one aspect of direct digital synthesis (DDS) circuit configured to generate a plurality of wave shapes for the electrical signal waveform for use in surgical instrument, in accordance with at least one aspect of the present disclosure.

A drive circuit 2986 provides left and right ultrasonic energy outputs. A digital signal that represents the signal waveform is provided to the SCL-A, SDA-A inputs of the analog multiplexer 2980 from a control circuit, such as the control circuit 3200 (FIG. 32). A digital-to-analog converter 2990 (DAC) converts the digital input to an analog output to drive a PWM circuit 2992 coupled to an oscillator 2994. The PWM circuit 2992 provides a first signal to a first gate drive circuit 2996*a* coupled to a first transistor output stage 2998*a* to drive a first Ultrasonic (LEFT) energy output. The PWM circuit 2992 also provides a second signal to a second gate drive circuit 2996*b* coupled to a second transistor output stage 2998*b* to drive a second Ultrasonic (RIGHT) energy output. A voltage sensor 2999 is coupled between the Ultrasonic LEFT/RIGHT output terminals to measure the output voltage. The drive circuit 2986, the first and second drive circuits 2996*a*, 2996*b*, and the first and second transistor output stages 2998*a*, 2998*b* define a first stage amplifier circuit. In operation, the control circuit 3200 (FIG. 32) generates a digital waveform 4300 (FIG. 43) employing circuits such as direct digital synthesis (DDS) circuits 4100, 4200 (FIGS. 41 and 42). The DAC 2990 receives the digital waveform 4300 and converts it into an analog waveform, which is received and amplified by the first stage amplifier circuit.

Figure 30:
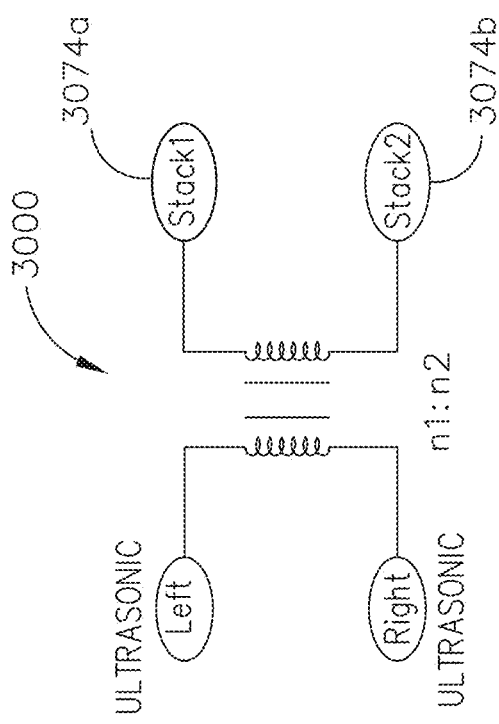
FIG. 30 is a schematic diagram of the transformer coupled to the ultrasonic drive circuit shown in FIG. 29, in accordance with at least one aspect of the present disclosure.

FIG. 30 is a schematic diagram of the transformer 3000 coupled to the electrical circuit 2900 shown in FIG. 29, in accordance with at least one aspect of the present disclosure.

The Ultrasonic LEFT/RIGHT input terminals (primary winding) of the transformer 3000 are electrically coupled to the Ultrasonic LEFT/RIGHT output terminals of the electrical circuit 2900. The secondary winding of the transformer 3000 are coupled to the positive and negative electrodes 3074a, 3074b. The positive and negative electrodes 3074a, 3074b of the transformer 3000 are coupled to the positive terminal (Stack 1) and the negative terminal (Stack 2) of an ultrasonic transducer. In one aspect, the transformer 3000 has a turns-ratio of $n_1:n_2$ of 1:50.

Figure 31:
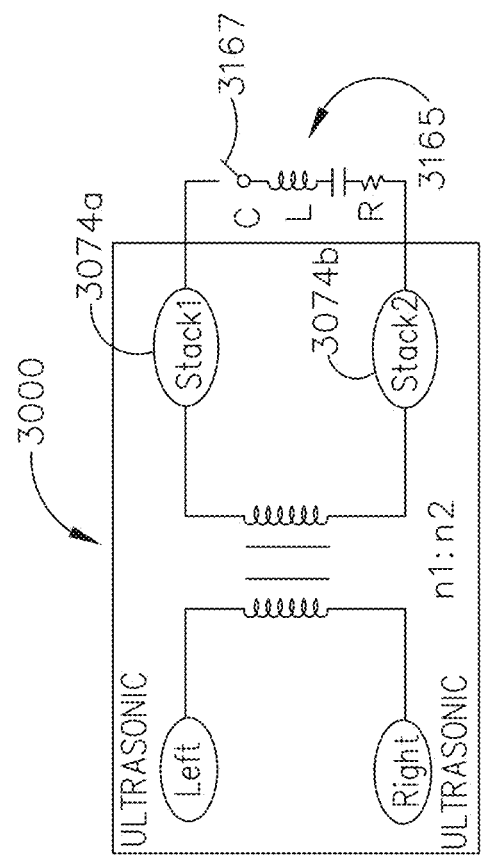
FIG. 31 is a schematic diagram of the transformer shown in FIG. 30 coupled to a test circuit, in accordance with at least one aspect of the present disclosure.

FIG. 31 is a schematic diagram of the transformer 3000 shown in FIG. 30 coupled to a test circuit 3165, in accordance with at least one aspect of the present disclosure. The test circuit 3165 is coupled to the positive and negative electrodes 3074a, 3074b. A switch 3167 is placed in series with an inductor/capacitor/resistor (LCR) load that simulates the load of an ultrasonic transducer.

FIG. 32 is a schematic diagram of a control circuit 3200, such as control circuit 3212, in accordance with at least one aspect of the present disclosure. The control circuit 3200 is located within a housing of the battery assembly. The battery assembly is the energy source for a variety of local power supplies 3215. The control circuit comprises a main processor 3214 coupled via an interface master 3218 to various downstream circuits by way of outputs SCL-A and SDA-A, SCL-B and SDA-B, SCL-C and SDA-C, for example. In one aspect, the interface master 3218 is a general purpose serial interface such as an I²C serial interface. The main processor 3214 also is configured to drive switches 3224 through general purposes input/output (GPIO) 3220, a display 3226 (e.g., and LCD display), and various indicators 3228 through GPIO 3222. A watchdog processor 3216 is provided to control the main processor 3214. A switch 3230 is provided in series with a battery 3211 to activate the control circuit 3212 upon insertion of the battery assembly into a handle assembly of a surgical instrument.

In one aspect, the main processor 3214 is coupled to the electrical circuit 2900 (FIG. 29) by way of output terminals SCL-A, SDA-A. The main processor 3214 comprises a memory for storing tables of digitized drive signals or waveforms that are transmitted to the electrical circuit 2900 for driving the ultrasonic transducer 1120, for example. In other aspects, the main processor 3214 may generate a digital waveform and transmit it to the electrical circuit 2900 or may store the digital waveform for later transmission to the electrical circuit 2900. The main processor 3214 also may provide RF drive by way of output terminals SCL-B, SDA-B and various sensors (e.g., Hall-effect sensors, magneto-rheological fluid (MRF) sensors, etc.) by way of output terminals SCL-C, SDA-C. In one aspect, the main processor 3214 is configured to sense the presence of ultrasonic drive circuitry and/or RF drive circuitry to enable appropriate software and user interface functionality.

In one aspect, the main processor 3214 may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QED analog, one or more 12-bit Analog-to-Digital Converters (ADC) with 12 analog input channels, among other features that are readily available from the product datasheet. Other processors may be readily substituted and, accordingly, the present disclosure should not be limited in this context.

Figure 33:
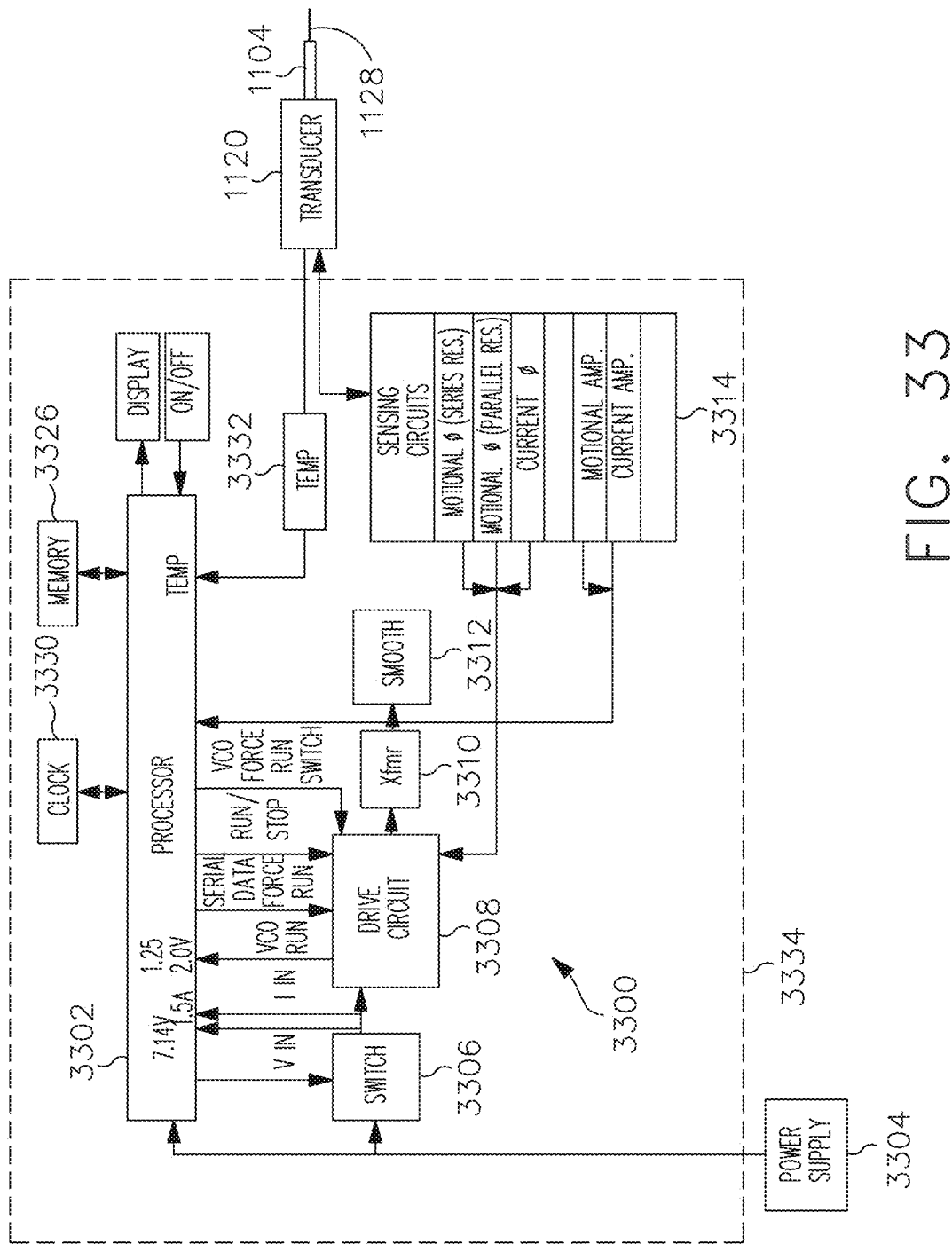
FIG. 33 shows a simplified block circuit diagram illustrating another electrical circuit contained within a modular ultrasonic surgical instrument, in accordance with at least one aspect of the present disclosure.

FIG. 33 shows a simplified block circuit diagram illustrating another electrical circuit 3300 contained within a modular ultrasonic surgical instrument 3334, in accordance with at least one aspect of the present disclosure. The electrical circuit 3300 includes a processor 3302, a clock 3330, a memory 3326, a power supply 3304 (e.g., a battery), a switch 3306, such as a metal-oxide semiconductor field effect transistor (MOSFET) power switch, a drive circuit 3308 (PLL), a transformer 3310, a signal smoothing circuit 3312 (also referred to as a matching circuit and can be, for example, a tank circuit), a sensing circuit 3314, a transducer 1120, and a shaft assembly (e.g. shaft assembly 1126, 1129) comprising an ultrasonic transmission waveguide that terminates at an ultrasonic blade (e.g. ultrasonic blade 1128, 1149) which may be referred to herein simply as the waveguide.

One feature of the present disclosure that severs dependency on high voltage (120 VAC) input power (a characteristic of general ultrasonic cutting devices) is the utilization of low-voltage switching throughout the wave-forming process and the amplification of the driving signal only directly before the transformer stage. For this reason, in one aspect of the present disclosure, power is derived from only a battery, or a group of batteries, small enough to fit either within a handle assembly. State-of-the-art battery technology provides powerful batteries of a few centimeters in height and width and a few millimeters in depth. By combining the features of the present disclosure to provide a self-contained and self-powered ultrasonic device, a reduction in manufacturing cost may be achieved.

The output of the power supply 3304 is fed to and powers the processor 3302. The processor 3302 receives and outputs signals and, as will be described below, functions according to custom logic or in accordance with computer programs that are executed by the processor 3302. As discussed above, the electrical circuit 3300 can also include a memory 3326, preferably, random access memory (RAM), that stores computer-readable instructions and data.

The output of the power supply 3304 also is directed to the switch 3306 having a duty cycle controlled by the processor 3302. By controlling the on-time for the switch 3306, the processor 3302 is able to dictate the total amount of power that is ultimately delivered to the transducer 1120. In one aspect, the switch 3306 is a MOSFET, although other switches and switching configurations are adaptable as well. The output of the switch 3306 is fed to a drive circuit 3308 that contains, for example, a phase detecting phase-locked loop (PLL) and/or a low-pass filter and/or a voltage-controlled oscillator. The output of the switch 3306 is sampled by the processor 3302 to determine the voltage and current of the output signal ($V_{IN}$ and $I_{IN}$, respectively). These values are used in a feedback architecture to adjust the pulse width modulation of the switch 3306. For instance, the duty cycle of the switch 3306 can vary from about 20% to about 80%, depending on the desired and actual output from the switch 3306.

The drive circuit 3308, which receives the signal from the switch 3306, includes an oscillatory circuit that turns the output of the switch 3306 into an electrical signal having an ultrasonic frequency, e.g., 55 kHz (VCO). As explained above, a smoothed-out version of this ultrasonic waveform is ultimately fed to the ultrasonic transducer 1120 to produce a resonant sine wave along an ultrasonic transmission waveguide.

At the output of the drive circuit 3308 is a transformer 3310 that is able to step up the low voltage signal(s) to a higher voltage. It is noted that upstream switching, prior to the transformer 3310, is performed at low (e.g., battery driven) voltages, something that, to date, has not been possible for ultrasonic cutting and cautery devices. This is at least partially due to the fact that the device advantageously uses low on-resistance MOSFET switching devices. Low on-resistance MOSFET switches are advantageous, as they produce lower switching losses and less heat than a traditional MOSFET device and allow higher current to pass through. Therefore, the switching stage (pre-transformer) can be characterized as low voltage/high current. To ensure the lower on-resistance of the amplifier MOSFET(s), the MOSFET(s) are run, for example, at 10 V. In such a case, a separate 10 VDC power supply can be used to feed the MOSFET gate, which ensures that the MOSFET is fully on and a reasonably low on resistance is achieved. In one aspect of the present disclosure, the transformer 3310 steps up the battery voltage to 120 V root-mean-square (RMS). Transformers are known in the art and are, therefore, not explained here in detail.

In the circuit configurations described, circuit component degradation can negatively impact the circuit performance of the circuit. One factor that directly affects component performance is heat. Known circuits generally monitor switching temperatures (e.g., MOSFET temperatures). However, because of the technological advancements in MOSFET designs, and the corresponding reduction in size, MOSFET temperatures are no longer a valid indicator of circuit loads and heat. For this reason, in accordance with at least one aspect of the present disclosure, the sensing circuit 3314 senses the temperature of the transformer 3310. This temperature sensing is advantageous as the transformer 3310 is run at or very close to its maximum temperature during use of the device. Additional temperature will cause the core material, e.g., the ferrite, to break down and permanent damage can occur. The present disclosure can respond to a maximum temperature of the transformer 3310 by, for example, reducing the driving power in the transformer 3310, signaling the user, turning the power off, pulsing the power, or other appropriate responses.

In one aspect of the present disclosure, the processor 3302 is communicatively coupled to the end effector (e.g. 1122, 1125), which is used to place material in physical contact with the ultrasonic blade (e.g. 1128, 1149). Sensors are provided that measure, at the end effector, a clamping force value (existing within a known range) and, based upon the received clamping force value, the processor 3302 varies the motional voltage $V_M$. Because high force values combined with a set motional rate can result in high blade temperatures, a temperature sensor 3332 can be communicatively coupled to the processor 3302, where the processor 3302 is operable to receive and interpret a signal indicating a current temperature of the blade from the temperature sensor 3336 and to determine a target frequency of blade movement based upon the received temperature. In another aspect, force sensors such as strain gages or pressure sensors may be coupled to the trigger (e.g. 1143, 1147) to measure the force applied to the trigger by the user. In another aspect, force sensors such as strain gages or pressure sensors may be coupled to a switch button such that displacement intensity corresponds to the force applied by the user to the switch button.

In accordance with at least one aspect of the present disclosure, the PLL portion of the drive circuit 3308, which is coupled to the processor 3302, is able to determine a frequency of waveguide movement and communicate that frequency to the processor 3302. The processor 3302 stores this frequency value in the memory 3326 when the device is turned off. By reading the clock 3330, the processor 3302 is able to determine an elapsed time after the device is shut off and retrieve the last frequency of waveguide movement if the elapsed time is less than a predetermined value. The device can then start up at the last frequency, which, presumably, is the optimum frequency for the current load.

Modular Battery Powered Handheld Surgical Instrument with Multistage Generator Circuits In another aspect, the present disclosure provides a modular battery powered handheld surgical instrument with multistage generator circuits. Disclosed is a surgical instrument that includes a battery assembly, a handle assembly, and a shaft assembly where the battery assembly and the shaft assembly are configured to mechanically and electrically connect to the handle assembly. The battery assembly includes a control circuit configured to generate a digital waveform. The handle assembly includes a first stage circuit configured to receive the digital waveform, convert the digital waveform into an analog waveform, and amplify the analog waveform. The shaft assembly includes a second stage circuit coupled to the first stage circuit to receive, amplify, and apply the analog waveform to a load.

In one aspect, the present disclosure provides a surgical instrument, comprising: a battery assembly, comprising a control circuit comprising a battery, a memory coupled to the battery, and a processor coupled to the memory and the battery, wherein the processor is configured to generate a digital waveform; a handle assembly comprising a first stage circuit coupled to the processor, the first stage circuit comprising a digital-to-analog (DAC) converter and a first stage amplifier circuit, wherein the DAC is configured to receive the digital waveform and convert the digital waveform into an analog waveform, wherein the first stage amplifier circuit is configured to receive and amplify the analog waveform; and a shaft assembly comprising a second stage circuit coupled to the first stage amplifier circuit to receive the analog waveform, amplify the analog waveform, and apply the analog waveform to a load; wherein the battery assembly and the shaft assembly are configured to mechanically and electrically connect to the handle assembly.

The load may comprise any one of an ultrasonic transducer, an electrode, or a sensor, or any combinations thereof. The first stage circuit may comprise a first stage ultrasonic drive circuit and a first stage high-frequency current drive circuit. The control circuit may be configured to drive the first stage ultrasonic drive circuit and the first stage high-frequency current drive circuit independently or simultaneously. The first stage ultrasonic drive circuit may be configured to couple to a second stage ultrasonic drive circuit. The second stage ultrasonic drive circuit may be configured to couple to an ultrasonic transducer. The first stage high-frequency current drive circuit may be configured to couple to a second stage high-frequency drive circuit. The second stage high-frequency drive circuit may be configured to couple to an electrode.

The first stage circuit may comprise a first stage sensor drive circuit. The first stage sensor drive circuit may be configured to a second stage sensor drive circuit. The second stage sensor drive circuit may be configured to couple to a sensor.

In another aspect, the present disclosure provides a surgical instrument, comprising: a battery assembly, comprising a control circuit comprising a battery, a memory coupled to the battery, and a processor coupled to the memory and the battery, wherein the processor is configured to generate a digital waveform; a handle assembly comprising a common first stage circuit coupled to the processor, the common first stage circuit comprising a digital-to-analog (DAC) converter and a common first stage amplifier circuit, wherein the DAC is configured to receive the digital waveform and convert the digital waveform into an analog waveform, wherein the common first stage amplifier circuit is configured to receive and amplify the analog waveform; and a shaft assembly comprising a second stage circuit coupled to the common first stage amplifier circuit to receive the analog waveform, amplify the analog waveform, and apply the analog waveform to a load; wherein the battery assembly and the shaft assembly are configured to mechanically and electrically connect to the handle assembly.

The load may comprise any one of an ultrasonic transducer, an electrode, or a sensor, or any combinations thereof. The common first stage circuit may be configured to drive ultrasonic, high-frequency current, or sensor circuits. The common first stage drive circuit may be configured to couple to a second stage ultrasonic drive circuit, a second stage high-frequency drive circuit, or a second stage sensor drive circuit. The second stage ultrasonic drive circuit may be configured to couple to an ultrasonic transducer, the second stage high-frequency drive circuit is configured to couple to an electrode, and the second stage sensor drive circuit is configured to couple to a sensor.

In another aspect, the present disclosure provides a surgical instrument, comprising a control circuit comprising a memory coupled to a processor, wherein the processor is configured to generate a digital waveform; a handle assembly comprising a common first stage circuit coupled to the processor, the common first stage circuit configured to receive the digital waveform, convert the digital waveform into an analog waveform, and amplify the analog waveform; and a shaft assembly comprising a second stage circuit coupled to the common first stage circuit to receive and amplify the analog waveform; wherein the shaft assembly is configured to mechanically and electrically connect to the handle assembly.

The common first stage circuit may be configured to drive ultrasonic, high-frequency current, or sensor circuits. The common first stage drive circuit may be configured to couple to a second stage ultrasonic drive circuit, a second stage high-frequency drive circuit, or a second stage sensor drive circuit. The second stage ultrasonic drive circuit may be configured to couple to an ultrasonic transducer, the second stage high-frequency drive circuit is configured to couple to an electrode, and the second stage sensor drive circuit is configured to couple to a sensor.

Figure 34:
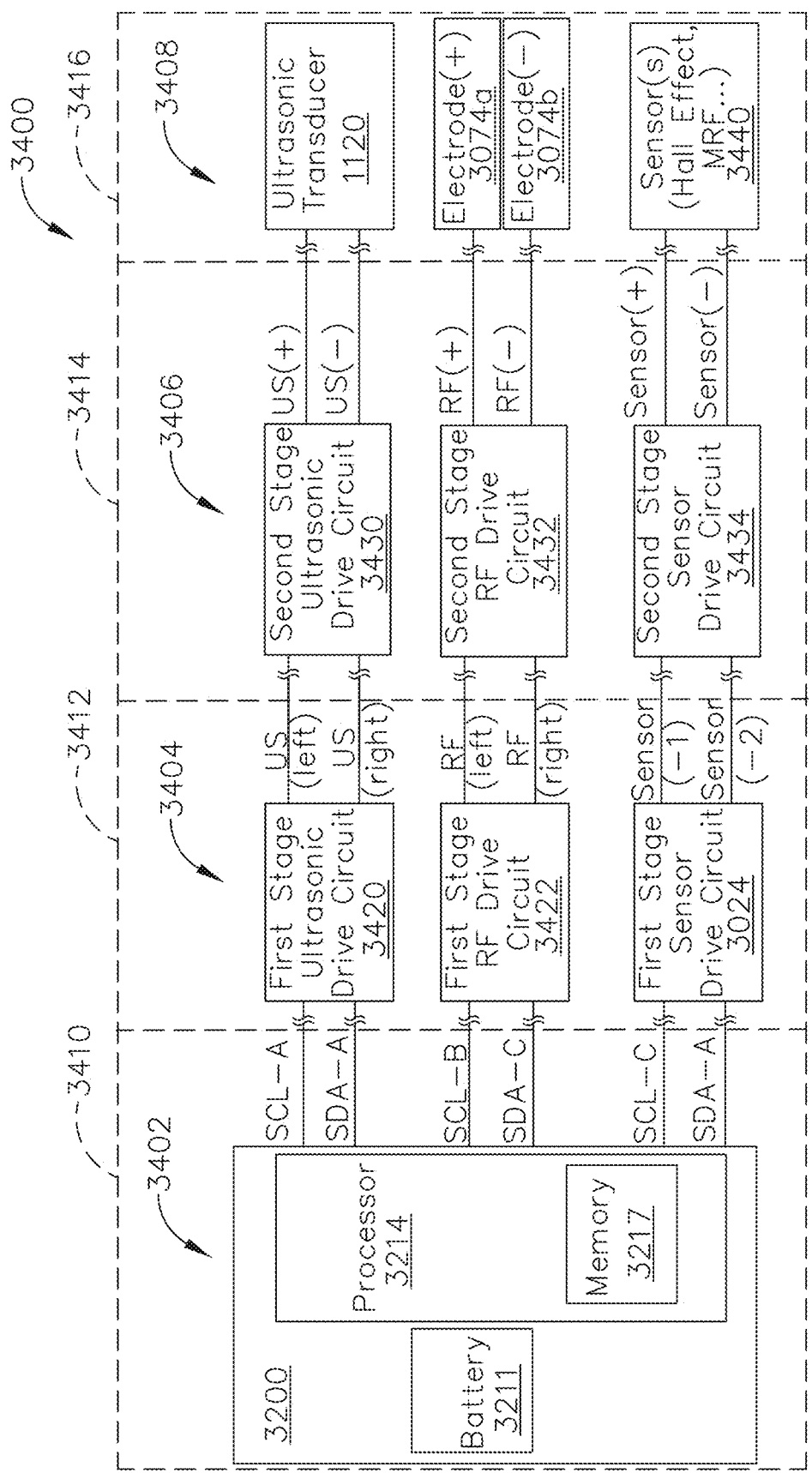
FIG. 34 illustrates a generator circuit partitioned into multiple stages, in accordance with at least one aspect of the present disclosure.

FIG. 34 illustrates a generator circuit 3400 partitioned into a first stage circuit 3404 and a second stage circuit 3406, in accordance with at least one aspect of the present disclosure. In one aspect, the surgical instruments of surgical system 1000 described herein may comprise a generator circuit 3400 partitioned into multiple stages. For example, surgical instruments of surgical system 1000 may comprise the generator circuit 3400 partitioned into at least two circuits: the first stage circuit 3404 and the second stage circuit 3406 of amplification enabling operation of RF energy only, ultrasonic energy only, and/or a combination of RF energy and ultrasonic energy. A combination modular shaft assembly 3414 may be powered by the common first stage circuit 3404 located within a handle assembly 3412 and the modular second stage circuit 3406 integral to the modular shaft assembly 3414. As previously discussed throughout this description in connection with the surgical instruments of surgical system 1000, a battery assembly 3410 and the shaft assembly 3414 are configured to mechanically and electrically connect to the handle assembly 3412. The end effector assembly is configured to mechanically and electrically connect the shaft assembly 3414.

Turning now to FIG. 34, the generator circuit 3400 is partitioned into multiple stages located in multiple modular assemblies of a surgical instrument, such as the surgical instruments of surgical system 1000 described herein. In one aspect, a control stage circuit 3402 may be located in the battery assembly 3410 of the surgical instrument. The control stage circuit 3402 is a control circuit 3200 as described in connection with FIG. 32. The control circuit 3200 comprises a processor 3214, which includes internal memory 3217 (FIG. 34) (e.g., volatile and non-volatile memory), and is electrically coupled to a battery 3211. The battery 3211 supplies power to the first stage circuit 3404, the second stage circuit 3406, and a third stage circuit 3408, respectively. As previously discussed, the control circuit 3200 generates a digital waveform 4300 (FIG. 43) using circuits and techniques described in connection with FIGS. 41 and 42. Returning to FIG. 34, the digital waveform 4300 may be configured to drive an ultrasonic transducer, high-frequency (e.g., RF) electrodes, or a combination thereof either independently or simultaneously. If driven simultaneously, filter circuits may be provided in the corresponding first stage circuits 3404 to select either the ultrasonic waveform or the RF waveform. Such filtering techniques are described in commonly owned U.S. Pat. Pub. No. US-2017-0086910-A1, titled TECHNIQUES FOR CIRCUIT TOPOLOGIES FOR COMBINED GENERATOR, which is herein incorporated by reference in its entirety.

The first stage circuits 3404 (e.g., the first stage ultrasonic drive circuit 3420, the first stage RF drive circuit 3422, and the first stage sensor drive circuit 3424) are located in a handle assembly 3412 of the surgical instrument. The control circuit 3200 provides the ultrasonic drive signal to the first stage ultrasonic drive circuit 3420 via outputs SCL-A, SDA-A of the control circuit 3200. The first stage ultrasonic drive circuit 3420 is described in detail in connection with FIG. 29. The control circuit 3200 provides the RF drive signal to the first stage RF drive circuit 3422 via outputs SCL-B, SDA-B of the control circuit 3200. The first stage RF drive circuit 3422 is described in detail in connection with FIG. 36. The control circuit 3200 provides the sensor drive signal to the first stage sensor drive circuit 3424 via outputs SCL-C, SDA-C of the control circuit 3200. Generally, each of the first stage circuits 3404 includes a digital-to-analog (DAC) converter and a first stage amplifier section to drive the second stage circuits 3406. The outputs of the first stage circuits 3404 are provided to the inputs of the second stage circuits 3406.

The control circuit 3200 is configured to detect which modules are plugged into the control circuit 3200. For example, the control circuit 3200 is configured to detect whether the first stage ultrasonic drive circuit 3420, the first stage RF drive circuit 3422, or the first stage sensor drive circuit 3424 located in the handle assembly 3412 is connected to the battery assembly 3410. Likewise, each of the first stage circuits 3404 can detect which second stage circuits 3406 are connected thereto and that information is provided back to the control circuit 3200 to determine the type of signal waveform to generate. Similarly, each of the second stage circuits 3406 can detect which third stage circuits 3408 or components are connected thereto and that information is provided back to the control circuit 3200 to determine the type of signal waveform to generate.

In one aspect, the second stage circuits 3406 (e.g., the ultrasonic drive second stage circuit 3430, the RF drive second stage circuit 3432, and the sensor drive second stage circuit 3434) are located in the shaft assembly 3414 of the surgical instrument. The first stage ultrasonic drive circuit 3420 provides a signal to the second stage ultrasonic drive circuit 3430 via outputs US-Left/US-Right. The second stage ultrasonic drive circuit 3430 is described in detail in connection with FIGS. 30 and 31. In addition to a transformer (FIGS. 30 and 31), the second stage ultrasonic drive circuit 3430 also may include filter, amplifier, and signal conditioning circuits. The first stage high-frequency (RF) current drive circuit 3422 provides a signal to the second stage RF drive circuit 3432 via outputs RF-Left/RF-Right. In addition to a transformer and blocking capacitors, the second stage RF drive circuit 3432 also may include filter, amplifier, and signal conditioning circuits. The first stage sensor drive circuit 3424 provides a signal to the second stage sensor drive circuit 3434 via outputs Sensor-1/Sensor-2. The second stage sensor drive circuit 3434 may include filter, amplifier, and signal conditioning circuits depending on the type of sensor. The outputs of the second stage circuits 3406 are provided to the inputs of the third stage circuits 3408.

In one aspect, the third stage circuits 3408 (e.g., the ultrasonic transducer 1120, the RF electrodes 3074*a*, 3074*b*, and the sensors 3440) may be located in various assemblies 3416 of the surgical instruments. In one aspect, the second stage ultrasonic drive circuit 3430 provides a drive signal to the ultrasonic transducer 1120 piezoelectric stack. In one aspect, the ultrasonic transducer 1120 is located in the ultrasonic transducer assembly of the surgical instrument. In other aspects, however, the ultrasonic transducer 1120 may be located in the handle assembly 3412, the shaft assembly 3414, or the end effector. In one aspect, the second stage RF drive circuit 3432 provides a drive signal to the RF electrodes 3074*a*, 3074*b*, which are generally located in the end effector portion of the surgical instrument. In one aspect, the second stage sensor drive circuit 3434 provides a drive signal to various sensors 3440 located throughout the surgical instrument.

Figure 35:
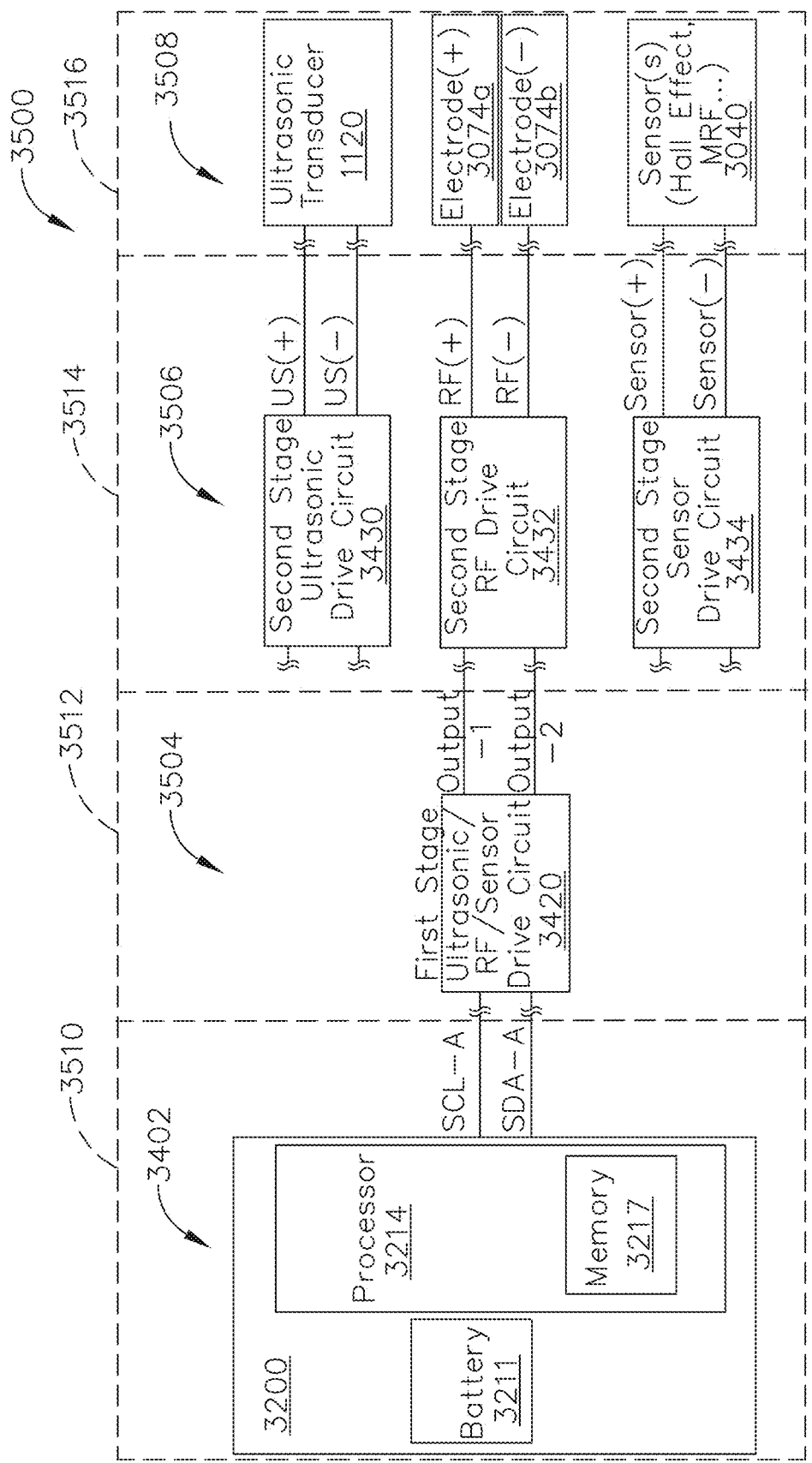
FIG. 35 illustrates a generator circuit partitioned into multiple stages where a first stage circuit is common to the second stage circuit, in accordance with at least one aspect of the present disclosure.

FIG. 35 illustrates a generator circuit 3500 partitioned into multiple stages where a first stage circuit 3504 is common to the second stage circuit 3506, in accordance with at least one aspect of the present disclosure. In one aspect, the surgical instruments of surgical system 1000 described herein may comprise generator circuit 3500 partitioned into multiple stages. For example, the surgical instruments of surgical system 1000 may comprise the generator circuit 3500 partitioned into at least two circuits: the first stage circuit 3504 and the second stage circuit 3506 of amplification enabling operation of high-frequency (RF) energy only, ultrasonic energy only, and/or a combination of RF energy and ultrasonic energy. A combination modular shaft assembly 3514 may be powered by a common first stage circuit 3504 located within the handle assembly 3512 and a modular second stage circuit 3506 integral to the modular shaft assembly 3514. As previously discussed throughout this description in connection with the surgical instruments of surgical system 1000, a battery assembly 3510 and the shaft assembly 3514 are configured to mechanically and electrically connect to the handle assembly 3512. The end effector assembly is configured to mechanically and electrically connect the shaft assembly 3514.

As shown in the example of FIG. 35, the battery assembly 3510 portion of the surgical instrument comprises a first control circuit 3502, which includes the control circuit 3200 previously described. The handle assembly 3512, which connects to the battery assembly 3510, comprises a common first stage drive circuit 3420. As previously discussed, the first stage drive circuit 3420 is configured to drive ultrasonic, high-frequency (RF) current, and sensor loads. The output of the common first stage drive circuit 3420 can drive any one of the second stage circuits 3506 such as the second stage ultrasonic drive circuit 3430, the second stage high-frequency (RF) current drive circuit 3432, and/or the second stage sensor drive circuit 3434. The common first stage drive circuit 3420 detects which second stage circuit 3506 is located in the shaft assembly 3514 when the shaft assembly 3514 is connected to the handle assembly 3512. Upon the shaft assembly 3514 being connected to the handle assembly 3512, the common first stage drive circuit 3420 determines which one of the second stage circuits 3506 (e.g., the second stage ultrasonic drive circuit 3430, the second stage RF drive circuit 3432, and/or the second stage sensor drive circuit 3434) is located in the shaft assembly 3514. The information is provided to the control circuit 3200 located in the handle assembly 3512 in order to supply a suitable digital waveform 4300 (FIG. 43) to the second stage circuit 3506 to drive the appropriate load, e.g., ultrasonic, RF, or sensor. It will be appreciated that identification circuits may be included in various assemblies 3516 in third stage circuit 3508 such as the ultrasonic transducer 1120, the electrodes 3074*a*, 3074*b*, or the sensors 3440. Thus, when a third stage circuit 3508 is connected to a second stage circuit 3506, the second stage circuit 3506 knows the type of load that is required based on the identification information.

Figure 36:
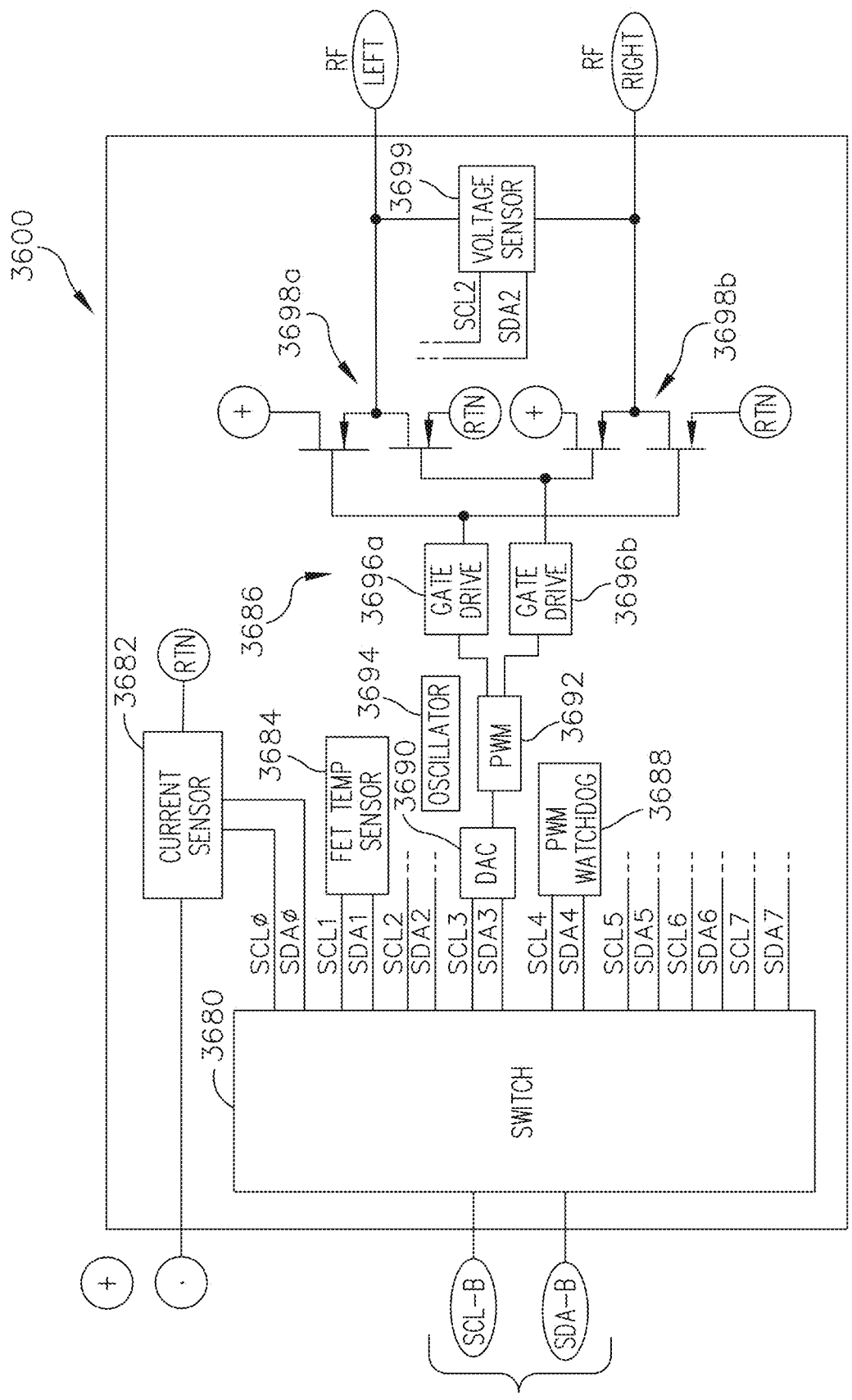
FIG. 36 is a schematic diagram of one aspect of a drive circuit configured for driving a high-frequency current (RF), in accordance with at least one aspect of the present disclosure.

FIG. 36 is a schematic diagram of one aspect of an electrical circuit 3600 configured to drive a high-frequency current (RF), in accordance with at least one aspect of the present disclosure. The electrical circuit 3600 comprises an analog multiplexer 3680. The analog multiplexer 3680 multiplexes various signals from the upstream channels SCL-A, SDA-A such as RF, battery, and power control circuit. A current sensor 3682 is coupled in series with the return or ground leg of the power supply circuit to measure the current supplied by the power supply. A field effect transistor (FET) temperature sensor 3684 provides the ambient temperature. A pulse width modulation (PWM) watchdog timer 3688 automatically generates a system reset if the main program neglects to periodically service it. It is provided to automatically reset the electrical circuit 3600 when it hangs or freezes because of a software or hardware fault. It will be appreciated that the electrical circuit 3600 may be configured for driving RF electrodes or for driving the ultrasonic transducer 1120 as described in connection with FIG. 29, for example. Accordingly, with reference now back to FIG. 36, the electrical circuit 3600 can be used to drive both ultrasonic and RF electrodes interchangeably.

A drive circuit 3686 provides Left and Right RF energy outputs. A digital signal that represents the signal waveform is provided to the SCL-A, SDA-A inputs of the analog multiplexer 3680 from a control circuit, such as the control circuit 3200 (FIG. 32). A digital-to-analog converter 3690 (DAC) converts the digital input to an analog output to drive a PWM circuit 3692 coupled to an oscillator 3694. The PWM circuit 3692 provides a first signal to a first gate drive circuit 3696a coupled to a first transistor output stage 3698a to drive a first RF+ (Left) energy output. The PWM circuit 3692 also provides a second signal to a second gate drive circuit 3696b coupled to a second transistor output stage 3698b to drive a second RF− (Right) energy output. A voltage sensor 3699 is coupled between the RF Left/RF output terminals to measure the output voltage. The drive circuit 3686, the first and second drive circuits 3696a, 3696b, and the first and second transistor output stages 3698a, 3698b define a first stage amplifier circuit. In operation, the control circuit 3200 (FIG. 32) generates a digital waveform 4300 (FIG. 43) employing circuits such as direct digital synthesis (DDS) circuits 4100, 4200 (FIGS. 41 and 42). The DAC 3690 receives the digital waveform 4300 and converts it into an analog waveform, which is received and amplified by the first stage amplifier circuit.

Figure 37:
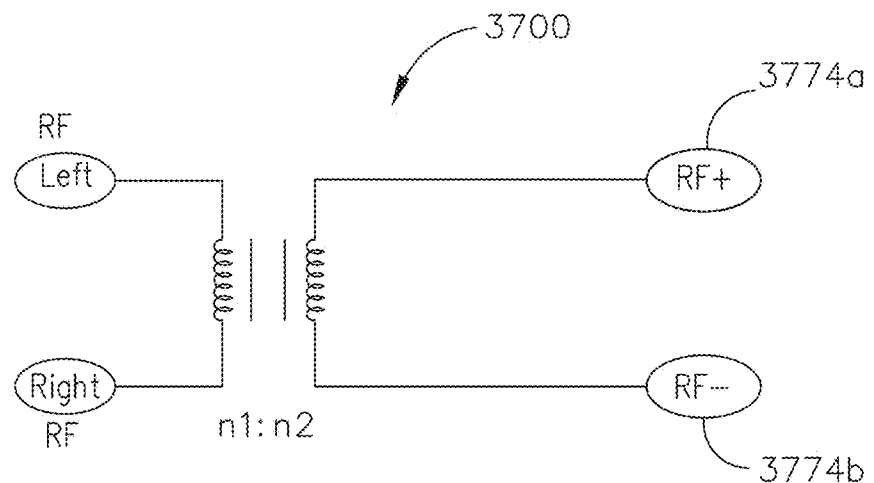
FIG. 37 is a schematic diagram of the transformer coupled to the RF drive circuit shown in FIG. 34, in accordance with at least one aspect of the present disclosure.

FIG. 37 is a schematic diagram of the transformer 3700 coupled to the electrical circuit 3600 shown in FIG. 36, in accordance with at least one aspect of the present disclosure. The RF+/RF input terminals (primary winding) of the transformer 3700 are electrically coupled to the RF Left/RF output terminals of the electrical circuit 3600. One side of the secondary winding is coupled in series with first and second blocking capacitors 3706, 3708. The second blocking capacitor is coupled to the second stage RF drive circuit 3774a positive terminal. The other side of the secondary winding is coupled to the second stage RF drive circuit 3774b negative terminal. The second stage RF drive circuit 3774a positive output is coupled to the ultrasonic blade and the second stage RF drive circuit 3774b negative ground terminal is coupled to an outer tube. In one aspect, a transformer has a turns-ratio of $n_1:n_2$ of 1:50.

Figure 38:
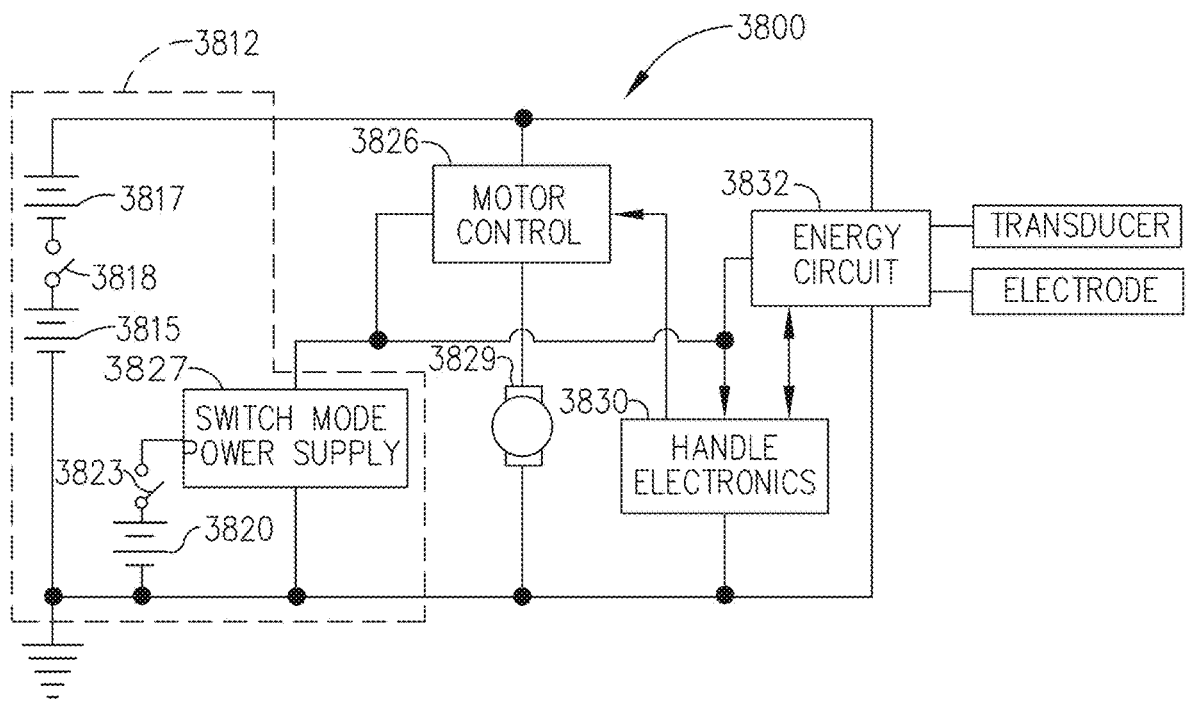
FIG. 38 is a schematic diagram of a circuit comprising separate power sources for high power energy/drive circuits and low power circuits, according to one aspect of the resent disclosure.

FIG. 38 is a schematic diagram of a circuit 3800 comprising separate power sources for high power energy/drive circuits and low power circuits, in accordance with at least one aspect of the present disclosure. A power supply 3812 includes a primary battery pack comprising first and second primary batteries 3815, 3817 (e.g., Li-ion batteries) that are connected into the circuit 3800 by a switch 3818 and a secondary battery pack comprising a secondary battery 3820 that is connected into the circuit by a switch 3823 when the power supply 3812 is inserted into the battery assembly. The secondary battery 3820 is a sag preventing battery that has componentry resistant to gamma or other radiation sterilization. For instance, a switch mode power supply 3827 and optional charge circuit within the battery assembly can be incorporated to allow the secondary battery 3820 to reduce the voltage sag of the primary batteries 3815, 3817. This guarantees full charged cells at the beginning of a surgery that are easy to introduce into the sterile field. The primary batteries 3815, 3817 can be used to power motor control circuits 3826 and energy circuits 3832 directly. The motor control circuits 3826 are configured to control a motor, such as motor 3829. The power supply/battery pack 3812 may comprise a dual type battery assembly including primary Li-ion batteries 3815, 3817 and secondary NiMH batteries 3820 with dedicated energy cells 3820 to control handle electronics circuits 3830 from dedicated energy cells 3815, 3817 to run the motor control circuits 3826 and the energy circuits 3832. In this case the circuit 3810 pulls from the secondary batteries 3820 involved in driving the handle electronics circuits 3830 when the primary batteries 3815, 3817 involved in driving the energy circuits 3832 and/or motor control circuits 3826 are dropping low. In one various aspect, the circuit 3810 may include a one way diode that would not allow for current to flow in the opposite direction (e.g., from the batteries involved in driving the energy and/or motor control circuits to the batteries involved in driving the electronics circuits).

Additionally, a gamma friendly charge circuit may be provided that includes a switch mode power supply 3827 using diodes and vacuum tube components to minimize voltage sag at a predetermined level. With the inclusion of a minimum sag voltage that is a division of the NiMH voltages (3 NiMH cells) the switch mode power supply 3827 could be eliminated. Additionally a modular system may be provided wherein the radiation hardened components are located in a module, making the module sterilizable by radiation sterilization. Other non-radiation hardened components may be included in other modular components and connections made between the modular components such that the componentry operates together as if the components were located together on the same circuit board. If only two NiMH cells are desired the switch mode power supply 3827 based on diodes and vacuum tubes allows for sterilizable electronics within the disposable primary battery pack.

Figure 39:
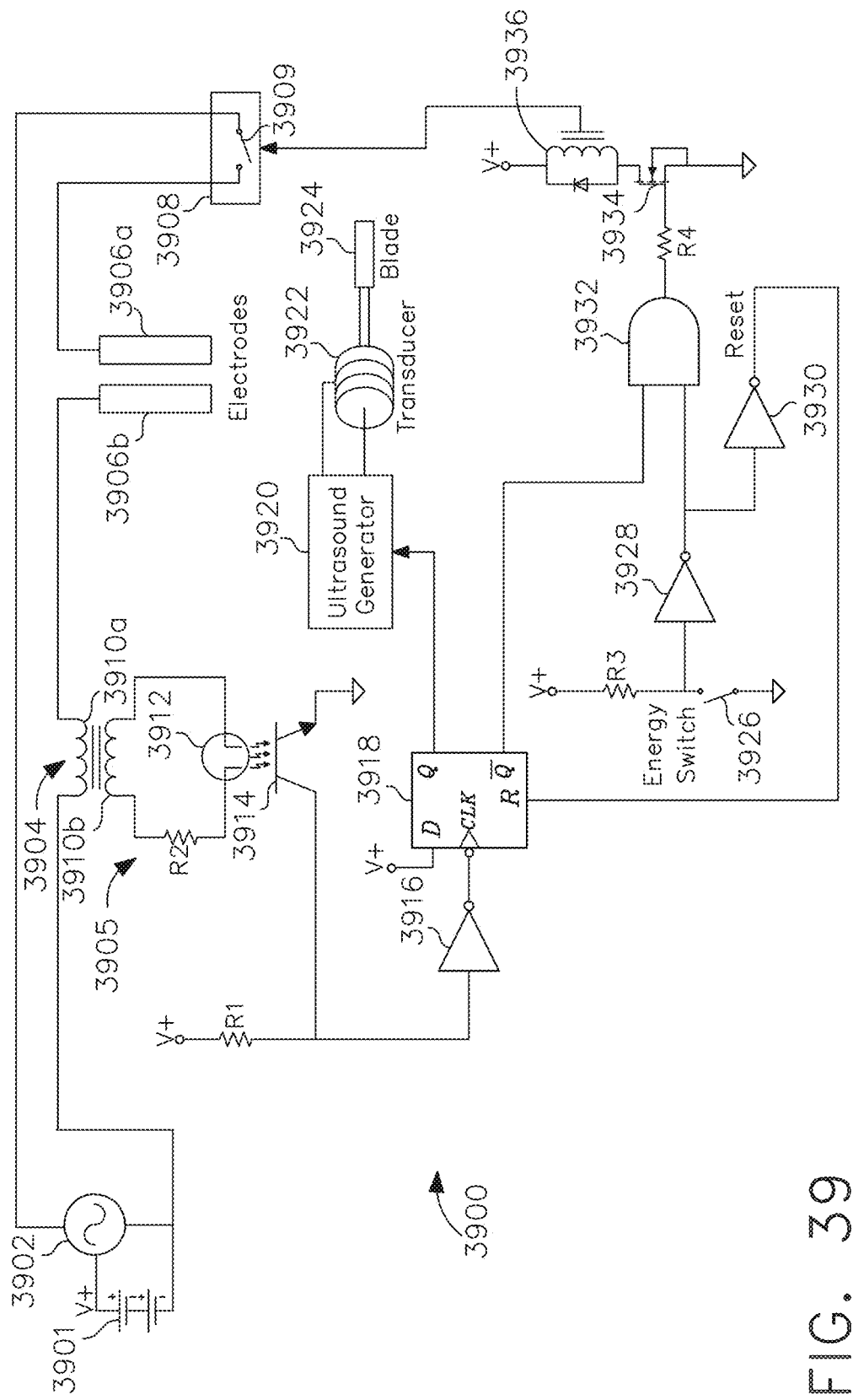
FIG. 39 illustrates a control circuit that allows a dual generator system to switch between the RF generator and the ultrasonic generator energy modalities for a surgical instrument.

Turning now to FIG. 39, there is shown a control circuit 3900 for operating a battery 3901 powered RF generator circuit 3902 for use with a surgical instrument, in accordance with at least one aspect of the present disclosure. The surgical instrument is configured to use both ultrasonic vibration and high-frequency current to carry out surgical coagulation/cutting treatments on living tissue, and uses high-frequency current to carry out a surgical coagulation treatment on living tissue.

FIG. 39 illustrates the control circuit 3900 that allows a dual generator system to switch between the RF generator circuit 3902 and the ultrasonic generator circuit 3920 energy modalities for a surgical instrument of the surgical system 1000. In one aspect, a current threshold in an RF signal is detected. When the impedance of the tissue is low the high-frequency current through tissue is high when RF energy is used as the treatment source for the tissue. According to one aspect, a visual indicator 3912 or light located on the surgical instrument of surgical system 1000 may be configured to be in an on-state during this high current period. When the current falls below a threshold, the visual indicator 3912 is in an off-state. Accordingly, a phototransistor 3914 may be configured to detect the transition from an on-state to an off-state and disengages the RF energy as shown in the control circuit 3900 shown in FIG. 39. Therefore, when the energy button is released and an energy switch 3926 is opened, the control circuit 3900 is reset and both the RF and ultrasonic generator circuits 3902, 3920 are held off.

With reference to FIG. 39, in one aspect, a method of managing an RF generator circuit 3902 and ultrasound generator circuit 3920 is provided. The RF generator circuit 3902 and/or the ultrasound generator circuit 3920 may be located in the handle assembly 1109, the ultrasonic transducer/RF generator assembly 1120, the battery assembly, the shaft assembly 1129, and/or the nozzle, of the multifunction electrosurgical instrument 1108, for example. The control circuit 3900 is held in a reset state if the energy switch 3926 is off (e.g., open). Thus, when the energy switch 3926 is opened, the control circuit 3900 is reset and both the RF and ultrasonic generator circuits 3902, 3920 are turned off. When the energy switch 3926 is squeezed and the energy switch 3926 is engaged (e.g., closed), RF energy is delivered to the tissue and the visual indicator 3912 operated by a current sensing step-up transformer 3904 will be lit while the tissue impedance is low. The light from the visual indicator 3912 provides a logic signal to keep the ultrasonic generator circuit 3920 in the off state. Once the tissue impedance increases above a threshold and the high-frequency current through the tissue decreases below a threshold, the visual indicator 3912 turns off and the light transitions to an off-state. A logic signal generated by this transition turns off a relay 3908, whereby the RF generator circuit 3902 is turned off and the ultrasonic generator circuit 3920 is turned on, to complete the coagulation and cut cycle.

Still with reference to FIG. 39, in one aspect, the dual generator circuit configuration employs the on-board RF generator circuit 3902, which is battery 3901 powered, for one modality and a second, on-board ultrasound generator circuit 3920, which may be on-board in the handle assembly 1109, battery assembly, shaft assembly 1129, nozzle, and/or the ultrasonic transducer/RF generator assembly 1120 of the multifunction electrosurgical instrument 1108, for example. The ultrasonic generator circuit 3920 also is battery 3901 operated. In various aspects, the RF generator circuit 3902 and the ultrasonic generator circuit 3920 may be an integrated or separable component of the handle assembly 1109. According to various aspects, having the dual RF/ultrasonic generator circuits 3902, 3920 as part of the handle assembly 1109 may eliminate the need for complicated wiring. The RF/ultrasonic generator circuits 3902, 3920 may be configured to provide the full capabilities of an existing generator while utilizing the capabilities of a cordless generator system simultaneously.

Either type of system can have separate controls for the modalities that are not communicating with each other. The surgeon activates the RF and Ultrasonic separately and at their discretion. Another approach would be to provide fully integrated communication schemes that share buttons, tissue status, instrument operating parameters (such as jaw closure, forces, etc.) and algorithms to manage tissue treatment. Various combinations of this integration can be implemented to provide the appropriate level of function and performance.

As discussed above, in one aspect, the control circuit 3900 includes the battery 3901 powered RF generator circuit 3902 comprising a battery as an energy source. As shown, RF generator circuit 3902 is coupled to two electrically conductive surfaces referred to herein as electrodes 3906a, 3906b (i.e., active electrode 3906a and return electrode 3906b) and is configured to drive the electrodes 3906a, 3906b with RF energy (e.g., high-frequency current). A first winding 3910a of the step-up transformer 3904 is connected in series with one pole of the bipolar RF generator circuit 3902 and the return electrode 3906b. In one aspect, the first winding 3910a and the return electrode 3906b are connected to the negative pole of the bipolar RF generator circuit 3902. The other pole of the bipolar RF generator circuit 3902 is connected to the active electrode 3906a through a switch contact 3909 of the relay 3908, or any suitable electromagnetic switching device comprising an armature which is moved by an electromagnet 3936 to operate the switch contact 3909. The switch contact 3909 is closed when the electromagnet 3936 is energized and the switch contact 3909 is open when the electromagnet 3936 is de-energized. When the switch contact is closed, RF current flows through conductive tissue (not shown) located between the electrodes 3906a, 3906b. It will be appreciated, that in one aspect, the active electrode 3906a is connected to the positive pole of the bipolar RF generator circuit 3902.

A visual indicator circuit 3905 comprises the step-up transformer 3904, a series resistor R2, and the visual indicator 3912. The visual indicator 3912 can be adapted for use with the surgical instrument 1108 and other electrosurgical systems and tools, such as those described herein. The first winding 3910a of the step-up transformer 3904 is connected in series with the return electrode 3906b and the second winding 3910b of the step-up transformer 3904 is connected in series with the resistor R2 and the visual indicator 3912 comprising a type NE-2 neon bulb, for example.

In operation, when the switch contact 3909 of the relay 3908 is open, the active electrode 3906a is disconnected from the positive pole of the bipolar RF generator circuit 3902 and no current flows through the tissue, the return electrode 3906b, and the first winding 3910a of the step-up transformer 3904. Accordingly, the visual indicator 3912 is not energized and does not emit light. When the switch contact 3909 of the relay 3908 is closed, the active electrode 3906a is connected to the positive pole of the bipolar RF generator circuit 3902 enabling current to flow through tissue, the return electrode 3906b, and the first winding 3910a of the step-up transformer 3904 to operate on tissue, for example cut and cauterize the tissue.

A first current flows through the first winding 3910a as a function of the impedance of the tissue located between the active and return electrodes 3906a, 3906b providing a first voltage across the first winding 3910a of the step-up transformer 3904. A stepped up second voltage is induced across the second winding 3910b of the step-up transformer 3904. The secondary voltage appears across the resistor R2 and energizes the visual indicator 3912 causing the neon bulb to light when the current through the tissue is greater than a predetermined threshold. It will be appreciated that the circuit and component values are illustrative and not limited thereto. When the switch contact 3909 of the relay 3908 is closed, current flows through the tissue and the visual indicator 3912 is turned on.

Turning now to the energy switch 3926 portion of the control circuit 3900, when the energy switch 3926 is open position, a logic high is applied to the input of a first inverter 3928 and a logic low is applied of one of the two inputs of the AND gate 3932. Thus, the output of the AND gate 3932 is low and a transistor 3934 is off to prevent current from flowing through the winding of the electromagnet 3936. With the electromagnet 3936 in the de-energized state, the switch contact 3909 of the relay 3908 remains open and prevents current from flowing through the electrodes 3906a, 3906b. The logic low output of the first inverter 3928 also is applied to a second inverter 3930 causing the output to go high and resetting a flip-flop 3918 (e.g., a D-Type flip-flop). At which time, the Q output goes low to turn off the ultrasound generator circuit 3920 circuit and the $\overline{Q}$ output goes high and is applied to the other input of the AND gate 3932.

When the user presses the energy switch 3926 on the instrument handle to apply energy to the tissue between the electrodes 3906a, 3906b, the energy switch 3926 closes and applies a logic low at the input of the first inverter 3928, which applies a logic high to other input of the AND gate 3932 causing the output of the AND gate 3932 to go high and turns on the transistor 3934. In the on state, the transistor 3934 conducts and sinks current through the winding of the electromagnet 3936 to energize the electromagnet 3936 and close the switch contact 3909 of the relay 3908. As discussed above, when the switch contact 3909 is closed, current can flow through the electrodes 3906a, 3906b and the first winding 3910a of the step-up transformer 3904 when tissue is located between the electrodes 3906a, 3906b.

As discussed above, the magnitude of the current flowing through the electrodes 3906a, 3906b depends on the impedance of the tissue located between the electrodes 3906a, 3906*b*. Initially, the tissue impedance is low and the magnitude of the current high through the tissue and the first winding 3910*a*. Consequently, the voltage impressed on the second winding 3910*b* is high enough to turn on the visual indicator 3912. The light emitted by the visual indicator 3912 turns on the phototransistor 3914, which pulls the input of an inverter 3916 low and causes the output of the inverter 3916 to go high. A high input applied to the CLK of the flip-flop 3918 has no effect on the Q or the $\overline{Q}$ outputs of the flip-flop 3918 and Q output remains low and the $\overline{Q}$ output remains high. Accordingly, while the visual indicator 3912 remains energized, the ultrasound generator circuit 3920 is turned OFF and an ultrasonic transducer 3922 and an ultrasonic blade 3924 of the multifunction electrosurgical instrument are not activated.

As the tissue between the electrodes 3906*a*, 3906*b* dries up, due to the heat generated by the current flowing through the tissue, the impedance of the tissue increases and the current therethrough decreases. When the current through the first winding 3910*a* decreases, the voltage across the second winding 3910*b* also decreases and when the voltage drops below a minimum threshold required to operate the visual indicator 3912, the visual indicator 3912 and the phototransistor 3914 turn off. When the phototransistor 3914 turns off, a logic high is applied to the input of the inverter 3916 and a logic low is applied to the CLK input of the flip-flop 3918 to clock a logic high to the Q output and a logic low to the $\overline{Q}$ output. The logic high at the Q output turns on the ultrasound generator circuit 3920 to activate the ultrasonic transducer 3922 and the ultrasonic blade 3924 to initiate cutting the tissue located between the electrodes 3906*a*, 3906*a*. Simultaneously or near simultaneously with the ultrasound generator circuit 3920 turning on, the $\overline{Q}$ output of the flip-flop 3918 goes low and causes the output of the AND gate 3932 to go low and turn off the transistor 3934, thereby deenergizing the electromagnet 3936 and opening the switch contact 3909 of the relay 3908 to cut off the flow of current through the electrodes 3906*a*, 3906*b*.

While the switch contact 3909 of the relay 3908 is open, no current flows through the electrodes 3906*a*, 3906*b*, tissue, and the first winding 3910*a* of the step-up transformer 3904. Therefore, no voltage is developed across the second winding 3910*b* and no current flows through the visual indicator 3912.

The state of the Q and the $\overline{Q}$ outputs of the flip-flop 3918 remain the same while the user squeezes the energy switch 3926 on the instrument handle to maintain the energy switch 3926 closed. Thus, the ultrasonic blade 3924 remains activated and continues cutting the tissue between the jaws of the end effector while no current flows through the electrodes 3906*a*, 3906*b* from the bipolar RF generator circuit 3902. When the user releases the energy switch 3926 on the instrument handle, the energy switch 3926 opens and the output of the first inverter 3928 goes low and the output of the second inverter 3930 goes high to reset the flip-flop 3918 causing the Q output to go low and turn off the ultrasound generator circuit 3920. At the same time, the $\overline{Q}$ output goes high and the circuit is now in an off state and ready for the user to actuate the energy switch 3926 on the instrument handle to close the energy switch 3926, apply current to the tissue located between the electrodes 3906*a*, 3906*b*, and repeat the cycle of applying RF energy to the tissue and ultrasonic energy to the tissue as described above.

Figure 40:
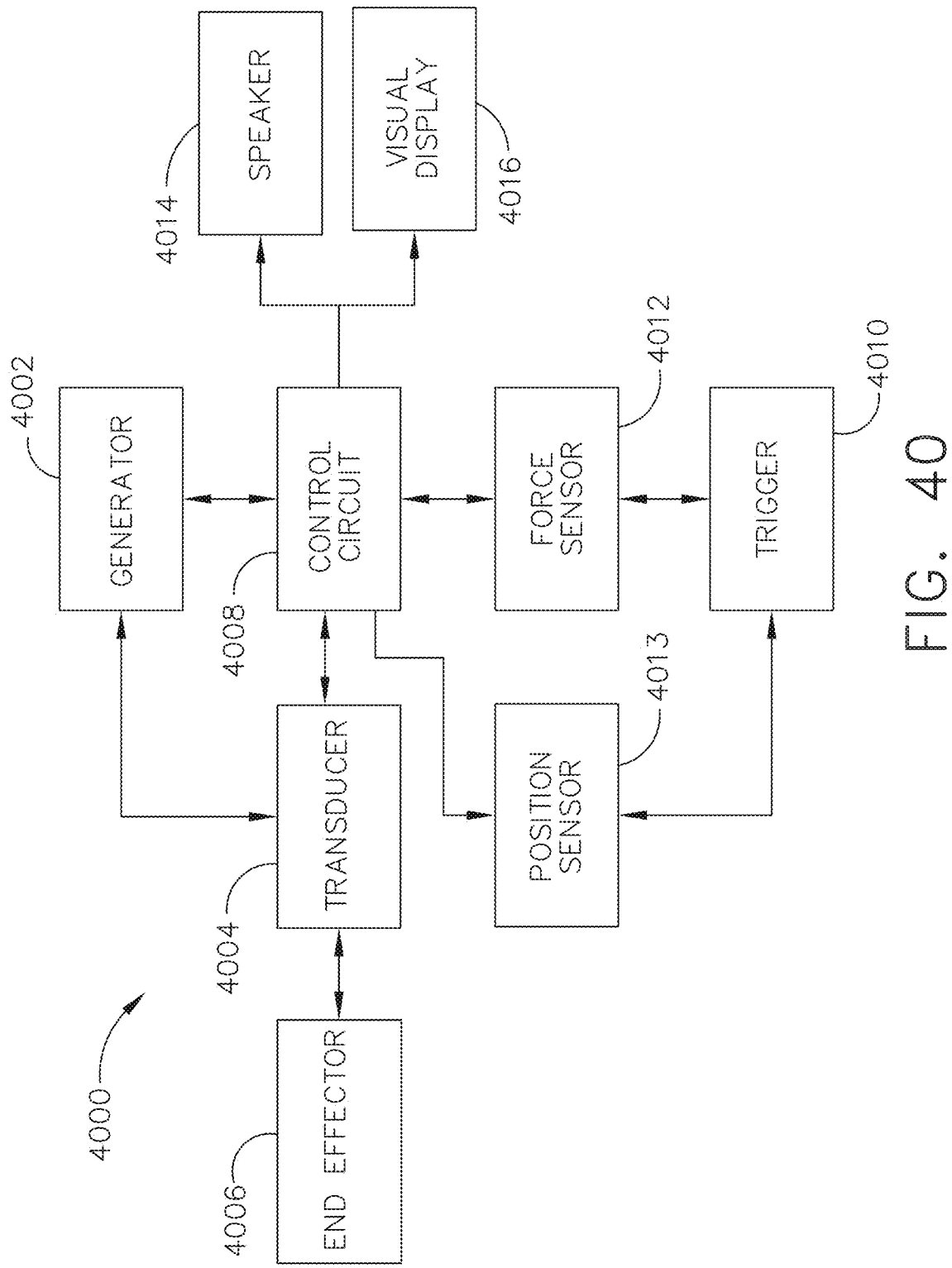
FIG. 40 illustrates a diagram of one aspect of a surgical instrument comprising a feedback system for use with a surgical instrument, according to one aspect of the resent disclosure.

FIG. 40 illustrates a diagram of a surgical system 4000, which represents one aspect of the surgical system 1000, comprising a feedback system for use with any one of the surgical instruments of surgical system 1000, which may include or implement many of the features described herein. The surgical system 4000 may include a generator 4002 coupled to a surgical instrument that includes an end effector 4006, which may be activated when a clinician operates a trigger 4010. In various aspects, the end effector 4006 may include an ultrasonic blade to deliver ultrasonic vibration to carry out surgical coagulation/cutting treatments on living tissue. In other aspects the end effector 4006 may include electrically conductive elements coupled to an electrosurgical high-frequency current energy source to carry out surgical coagulation or cauterization treatments on living tissue and either a mechanical knife with a sharp edge or an ultrasonic blade to carry out cutting treatments on living tissue. When the trigger 4010 is actuated, a force sensor 4012 may generate a signal indicating the amount of force being applied to the trigger 4010. In addition to, or instead of a force sensor 4012, the surgical instrument may include a position sensor 4013, which may generate a signal indicating the position of the trigger 4010 (e.g., how far the trigger has been depressed or otherwise actuated). In one aspect, the position sensor 4013 may be a sensor positioned with an outer tubular sheath or reciprocating tubular actuating member located within the outer tubular sheath of the surgical instrument. In one aspect, the sensor may be a Hall-effect sensor or any suitable transducer that varies its output voltage in response to a magnetic field. The Hall-effect sensor may be used for proximity switching, positioning, speed detection, and current sensing applications. In one aspect, the Hall-effect sensor operates as an analog transducer, directly returning a voltage. With a known magnetic field, its distance from the Hall plate can be determined.

A control circuit 4008 may receive the signals from the sensors 4012 and/or 4013. The control circuit 4008 may include any suitable analog or digital circuit components. The control circuit 4008 also may communicate with the generator 4002 and/or a transducer 4004 to modulate the power delivered to the end effector 4006 and/or the generator level or ultrasonic blade amplitude of the end effector 4006 based on the force applied to the trigger 4010 and/or the position of the trigger 4010 and/or the position of the outer tubular sheath described above relative to a reciprocating tubular actuating member located within an outer tubular sheath (e.g., as measured by a Hall-effect sensor and magnet combination). For example, as more force is applied to the trigger 4010, more power and/or higher ultrasonic blade amplitude may be delivered to the end effector 4006. According to various aspects, the force sensor 4012 may be replaced by a multi-position switch.

According to various aspects, the end effector 4006 may include a clamp or clamping mechanism. When the trigger 4010 is initially actuated, the clamping mechanism may close, clamping tissue between a clamp arm and the end effector 4006. As the force applied to the trigger increases (e.g., as sensed by force sensor 4012) the control circuit 4008 may increase the power delivered to the end effector 4006 by the transducer 4004 and/or the generator level or ultrasonic blade amplitude brought about in the end effector 4006. In one aspect, trigger position, as sensed by position sensor 4013 or clamp or clamp arm position, as sensed by position sensor 4013 (e.g., with a Hall-effect sensor), may be used by the control circuit 4008 to set the power and/or amplitude of the end effector 4006. For example, as the trigger is moved further towards a fully actuated position, or the clamp or clamp arm moves further towards the ultrasonic blade (or end effector 4006), the power and/or amplitude of the end effector 4006 may be increased.

According to various aspects, the surgical instrument of the surgical system 4000 also may include one or more feedback devices for indicating the amount of power delivered to the end effector 4006. For example, a speaker 4014 may emit a signal indicative of the end effector power. According to various aspects, the speaker 4014 may emit a series of pulse sounds, where the frequency of the sounds indicates power. In addition to, or instead of the speaker 4014, the surgical instrument may include a visual display 4016. The visual display 4016 may indicate end effector power according to any suitable method. For example, the visual display 4016 may include a series of LEDs, where end effector power is indicated by the number of illuminated LEDs. The speaker 4014 and/or visual display 4016 may be driven by the control circuit 4008. According to various aspects, the surgical instrument may include a ratcheting device connected to the trigger 4010. The ratcheting device may generate an audible sound as more force is applied to the trigger 4010, providing an indirect indication of end effector power. The surgical instrument may include other features that may enhance safety. For example, the control circuit 4008 may be configured to prevent power from being delivered to the end effector 4006 in excess of a predetermined threshold. Also, the control circuit 4008 may implement a delay between the time when a change in end effector power is indicated (e.g., by speaker 4014 or visual display 4016), and the time when the change in end effector power is delivered. In this way, a clinician may have ample warning that the level of ultrasonic power that is to be delivered to the end effector 4006 is about to change.

In one aspect, the ultrasonic or high-frequency current generators of the surgical system 1000 may be configured to generate the electrical signal waveform digitally such that the desired using a predetermined number of phase points stored in a lookup table to digitize the wave shape. The phase points may be stored in a table defined in a memory, a field programmable gate array (FPGA), or any suitable non-volatile memory. FIG. 41 illustrates one aspect of a fundamental architecture for a digital synthesis circuit such as a direct digital synthesis (DDS) circuit 4100 configured to generate a plurality of wave shapes for the electrical signal waveform. The generator software and digital controls may command the FPGA to scan the addresses in the lookup table 4104 which in turn provides varying digital input values to a DAC circuit 4108 that feeds a power amplifier. The addresses may be scanned according to a frequency of interest. Using such a lookup table 4104 enables generating various types of wave shapes that can be fed into tissue or into a transducer, an RF electrode, multiple transducers simultaneously, multiple RF electrodes simultaneously, or a combination of RF and ultrasonic instruments. Furthermore, multiple lookup tables 4104 that represent multiple wave shapes can be created, stored, and applied to tissue from a generator.

The waveform signal may be configured to control at least one of an output current, an output voltage, or an output power of an ultrasonic transducer and/or an RF electrode, or multiples thereof (e.g. two or more ultrasonic transducers and/or two or more RF electrodes). Further, where the surgical instrument comprises an ultrasonic components, the waveform signal may be configured to drive at least two vibration modes of an ultrasonic transducer of the at least one surgical instrument. Accordingly, a generator may be configured to provide a waveform signal to at least one surgical instrument wherein the waveform signal corresponds to at least one wave shape of a plurality of wave shapes in a table. Further, the waveform signal provided to the two surgical instruments may comprise two or more wave shapes. The table may comprise information associated with a plurality of wave shapes and the table may be stored within the generator. In one aspect or example, the table may be a direct digital synthesis table, which may be stored in an FPGA of the generator. The table may be addressed by anyway that is convenient for categorizing wave shapes. According to one aspect, the table, which may be a direct digital synthesis table, is addressed according to a frequency of the waveform signal. Additionally, the information associated with the plurality of wave shapes may be stored as digital information in the table.

The analog electrical signal waveform may be configured to control at least one of an output current, an output voltage, or an output power of an ultrasonic transducer and/or an RF electrode, or multiples thereof (e.g., two or more ultrasonic transducers and/or two or more RF electrodes). Further, where the surgical instrument comprises ultrasonic components, the analog electrical signal waveform may be configured to drive at least two vibration modes of an ultrasonic transducer of the at least one surgical instrument. Accordingly, the generator circuit may be configured to provide an analog electrical signal waveform to at least one surgical instrument wherein the analog electrical signal waveform corresponds to at least one wave shape of a plurality of wave shapes stored in a lookup table 4104. Further, the analog electrical signal waveform provided to the two surgical instruments may comprise two or more wave shapes. The lookup table 4104 may comprise information associated with a plurality of wave shapes and the lookup table 4104 may be stored either within the generator circuit or the surgical instrument. In one aspect or example, the lookup table 4104 may be a direct digital synthesis table, which may be stored in an FPGA of the generator circuit or the surgical instrument. The lookup table 4104 may be addressed by anyway that is convenient for categorizing wave shapes. According to one aspect, the lookup table 4104, which may be a direct digital synthesis table, is addressed according to a frequency of the desired analog electrical signal waveform. Additionally, the information associated with the plurality of wave shapes may be stored as digital information in the lookup table 4104.

With the widespread use of digital techniques in instrumentation and communications systems, a digitally-controlled method of generating multiple frequencies from a reference frequency source has evolved and is referred to as direct digital synthesis. The basic architecture is shown in FIG. 41. In this simplified block diagram, a DDS circuit is coupled to a processor, controller, or a logic device of the generator circuit and to a memory circuit located in the generator circuit of the surgical system 1000. The DDS circuit 4100 comprises an address counter 4102, lookup table 4104, a register 4106, a DAC circuit 4108, and a filter 4112. A stable clock $f_c$ is received by the address counter 4102 and the register 4106 drives a programmable-read-only-memory (PROM) which stores one or more integral number of cycles of a sinewave (or other arbitrary waveform) in a lookup table 4104. As the address counter 4102 steps through memory locations, values stored in the lookup table 4104 are written to the register 4106, which is coupled to the DAC circuit 4108. The corresponding digital amplitude of the signal at the memory location of the lookup table 4104 drives the DAC circuit 4108, which in turn generates an analog output signal 4110. The spectral purity of the analog output signal 4110 is determined primarily by the DAC circuit 4108. The phase noise is basically that of the reference clock fc. The first analog output signal 4110 output from the DAC circuit 4108 is filtered by the filter 4112 and a second analog output signal 4114 output by the filter 4112 is provided to an amplifier having an output coupled to the output of the generator circuit. The second analog output signal has a frequency foot.

Because the DDS circuit 4100 is a sampled data system, issues involved in sampling must be considered: quantization noise, aliasing, filtering, etc. For instance, the higher order harmonics of the DAC circuit 4108 output frequencies fold back into the Nyquist bandwidth, making them unfilterable, whereas, the higher order harmonics of the output of phase-locked-loop (PLL) based synthesizers can be filtered. The lookup table 4104 contains signal data for an integral number of cycles. The final output frequency $f_{out}$ can be changed changing the reference clock frequency $f_c$ or by reprogramming the PROM.

The DDS circuit 4100 may comprise multiple lookup tables 4104 where the lookup table 4104 stores a waveform represented by a predetermined number of samples, wherein the samples define a predetermined shape of the waveform. Thus multiple waveforms having a unique shape can be stored in multiple lookup tables 4104 to provide different tissue treatments based on instrument settings or tissue feedback. Examples of waveforms include high crest factor RF electrical signal waveforms for surface tissue coagulation, low crest factor RF electrical signal waveform for deeper tissue penetration, and electrical signal waveforms that promote efficient touch-up coagulation. In one aspect, the DDS circuit 4100 can create multiple wave shape lookup tables 4104 and during a tissue treatment procedure (e.g., "on-the-fly" or in virtual real time based on user or sensor inputs) switch between different wave shapes stored in separate lookup tables 4104 based on the tissue effect desired and/or tissue feedback.

Figure 43:
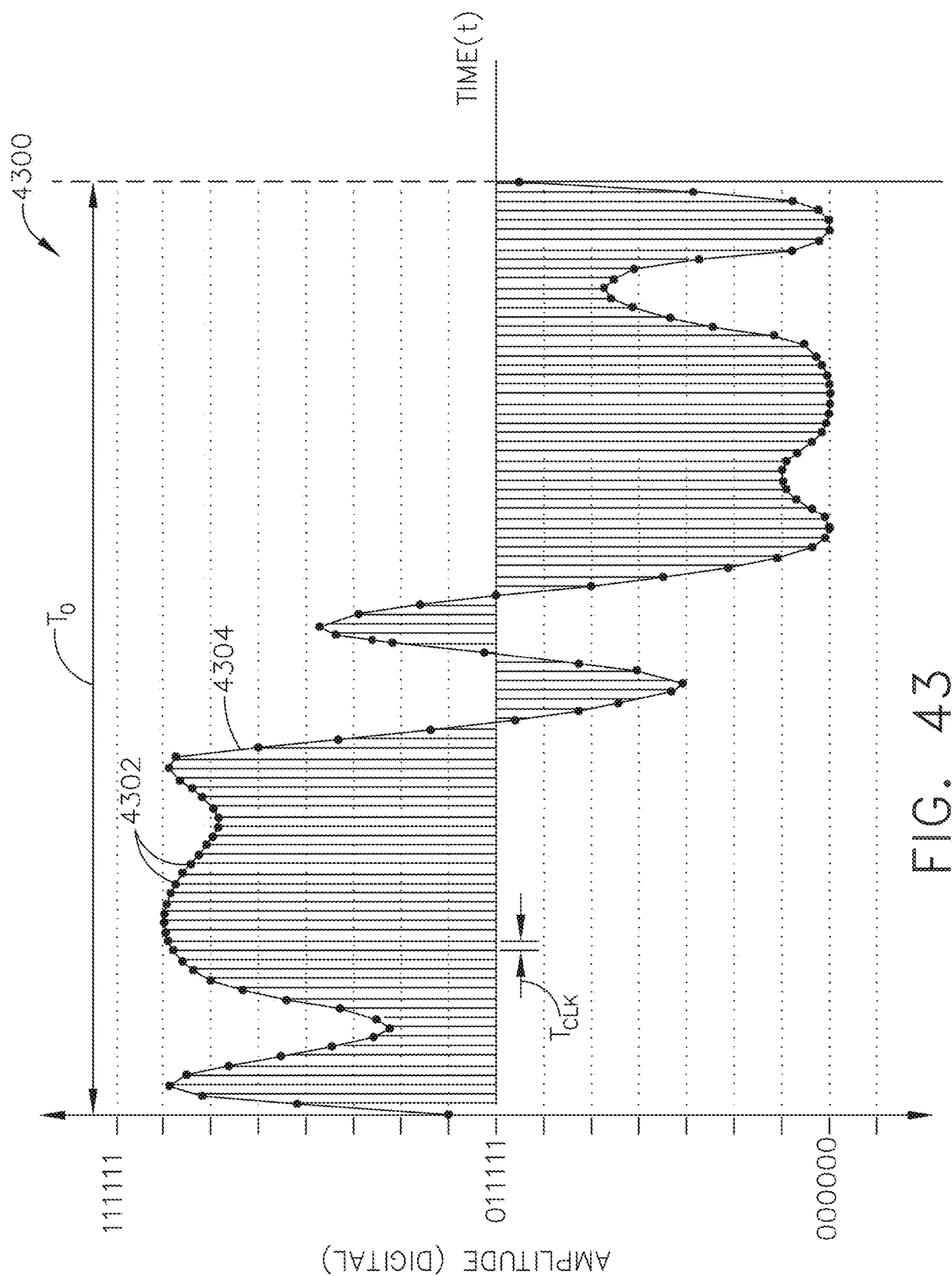
FIG. 43 illustrates one cycle of a discrete time digital electrical signal waveform, in accordance with at least one aspect of the present disclosure of an analog waveform (shown superimposed over a discrete time digital electrical signal waveform for comparison purposes), in accordance with at least one aspect of the present disclosure.

Accordingly, switching between wave shapes can be based on tissue impedance and other factors, for example. In other aspects, the lookup tables 4104 can store electrical signal waveforms shaped to maximize the power delivered into the tissue per cycle (i.e., trapezoidal or square wave). In other aspects, the lookup tables 4104 can store wave shapes synchronized in such way that they make maximizing power delivery by the multifunction surgical instrument of surgical system 1000 while delivering RF and ultrasonic drive signals. In yet other aspects, the lookup tables 4104 can store electrical signal waveforms to drive ultrasonic and RF therapeutic, and/or sub-therapeutic, energy simultaneously while maintaining ultrasonic frequency lock. Custom wave shapes specific to different instruments and their tissue effects can be stored in the non-volatile memory of the generator circuit or in the non-volatile memory (e.g., EEPROM) of the surgical system 1000 and be fetched upon connecting the multifunction surgical instrument to the generator circuit. An example of an exponentially damped sinusoid, as used in many high crest factor "coagulation" waveforms is shown in FIG. 43.

A more flexible and efficient implementation of the DDS circuit 4100 employs a digital circuit called a Numerically Controlled Oscillator (NCO). A block diagram of a more flexible and efficient digital synthesis circuit such as a DDS circuit 4200 is shown in FIG. 42. In this simplified block diagram, a DDS circuit 4200 is coupled to a processor, controller, or a logic device of the generator and to a memory circuit located either in the generator or in any of the surgical instruments of surgical system 1000. The DDS circuit 4200 comprises a load register 4202, a parallel delta phase register 4204, an adder circuit 4216, a phase register 4208, a lookup table 4210 (phase-to-amplitude converter), a DAC circuit 4212, and a filter 4214. The adder circuit 4216 and the phase register 4208 form part of a phase accumulator 4206. A clock frequency $f_c$ is applied to the phase register 4208 and a DAC circuit 4212. The load register 4202 receives a tuning word that specifies output frequency as a fraction of the reference clock frequency signal $f_c$. The output of the load register 4202 is provided to the parallel delta phase register 4204 with a tuning word M.

The DDS circuit 4200 includes a sample clock that generates the clock frequency $f_c$, the phase accumulator 4206, and the lookup table 4210 (e.g., phase to amplitude converter). The content of the phase accumulator 4206 is updated once per clock cycle fc. When time the phase accumulator 4206 is updated, the digital number, M, stored in the parallel delta phase register 4204 is added to the number in the phase register 4208 by the adder circuit 4216. Assuming that the number in the parallel delta phase register 4204 is 00 . . . 01 and that the initial contents of the phase accumulator 4206 is 00 . . . 00. The phase accumulator 4206 is updated by 00 . . . 01 per clock cycle. If the phase accumulator 4206 is 32-bits wide, 232 clock cycles (over 4 billion) are required before the phase accumulator 4206 returns to 00 . . . 00, and the cycle repeats.

A truncated output 4218 of the phase accumulator 4206 is provided to a phase-to amplitude converter lookup table 4210 and the output of the lookup table 4210 is coupled to a DAC circuit 4212. The truncated output 4218 of the phase accumulator 4206 serves as the address to a sine (or cosine) lookup table. An address in the lookup table corresponds to a phase point on the sinewave from 0° to 360°. The lookup table 4210 contains the corresponding digital amplitude information for one complete cycle of a sinewave. The lookup table 4210 therefore maps the phase information from the phase accumulator 4206 into a digital amplitude word, which in turn drives the DAC circuit 4212. The output of the DAC circuit is a first analog signal 4220 and is filtered by a filter 4214. The output of the filter 4214 is a second analog signal 4222, which is provided to a power amplifier coupled to the output of the generator circuit.

In one aspect, the electrical signal waveform may be digitized into 1024 (210) phase points, although the wave shape may be digitized is any suitable number of 2n phase points ranging from 256 (28) to 281,474,976,710,656 (248), where n is a positive integer, as shown in TABLE 1. The electrical signal waveform may be expressed as $\Delta_n(\theta_n)$, where a normalized amplitude $A_n$ at a point n is represented by a phase angle $\theta_n$ is referred to as a phase point at point n. The number of discrete phase points n determines the tuning resolution of the DDS circuit 4200 (as well as the DDS circuit 4100 shown in FIG. 41).

TABLE 1

| N | Number of Phase Points $2^n$ |
|---|---|
| 8 | 256 |
| 10 | 1,024 |
| 12 | 4,096 |
| 14 | 16,384 |
| 16 | 65,536 |
| 18 | 262,144 |
| 20 | 1,048,576 |
| 22 | 4,194,304 |
| 24 | 16,777,216 |
| 26 | 67,108,864 |
| 28 | 268,435,456 |
| . . . | . . . |
| 32 | 4,294,967,296 |
| . . . | . . . |
| 48 | 281,474,976,710,656 |
| . . . | . . . |

The generator circuit algorithms and digital control circuits scan the addresses in the lookup table 4210, which in turn provides varying digital input values to the DAC circuit

4212 that feeds the filter 4214 and the power amplifier. The addresses may be scanned according to a frequency of interest. Using the lookup table enables generating various types of shapes that can be converted into an analog output signal by the DAC circuit 4212, filtered by the filter 4214, amplified by the power amplifier coupled to the output of the generator circuit, and fed to the tissue in the form of RF energy or fed to an ultrasonic transducer and applied to the tissue in the form of ultrasonic vibrations which deliver energy to the tissue in the form of heat. The output of the amplifier can be applied to an RF electrode, multiple RF electrodes simultaneously, an ultrasonic transducer, multiple ultrasonic transducers simultaneously, or a combination of RF and ultrasonic transducers, for example. Furthermore, multiple wave shape tables can be created, stored, and applied to tissue from a generator circuit.

With reference back to FIG. 41, for n=32, and M=1, the phase accumulator 4206 steps through 2³² possible outputs before it overflows and restarts. The corresponding output wave frequency is equal to the input clock frequency divided by 2³². If M=2, then the phase register 1708 "rolls over" twice as fast, and the output frequency is doubled. This can be generalized as follows.

For a phase accumulator 4206 configured to accumulate n-bits (n generally ranges from 24 to 32 in most DDS systems, but as previously discussed n may be selected from a wide range of options), there are $2^n$ possible phase points. The digital word in the delta phase register, M, represents the amount the phase accumulator is incremented per clock cycle. If $f_c$ is the clock frequency, then the frequency of the output sinewave is equal to:

$$f_0 = \frac{M \cdot f_c}{2^n}$$

The above equation is known as the DDS "tuning equation." Note that the frequency resolution of the system is equal to $f_c/2^n$. For n=32, the resolution is greater than one part in four billion. In one aspect of the DDS circuit 4200, not all of the bits out of the phase accumulator 4206 are passed on to the lookup table 4210, but are truncated, leaving only the first 13 to 15 most significant bits (MSBs), for example. This reduces the size of the lookup table 4210 and does not affect the frequency resolution. The phase truncation only adds a small but acceptable amount of phase noise to the final output.

The electrical signal waveform may be characterized by a current, voltage, or power at a predetermined frequency. Further, where any one of the surgical instruments of surgical system 1000 comprises ultrasonic components, the electrical signal waveform may be configured to drive at least two vibration modes of an ultrasonic transducer of the at least one surgical instrument. Accordingly, the generator circuit may be configured to provide an electrical signal waveform to at least one surgical instrument wherein the electrical signal waveform is characterized by a predetermined wave shape stored in the lookup table 4210 (or lookup table 4104 FIG. 41). Further, the electrical signal waveform may be a combination of two or more wave shapes. The lookup table 4210 may comprise information associated with a plurality of wave shapes. In one aspect or example, the lookup table 4210 may be generated by the DDS circuit 4200 and may be referred to as a direct digital synthesis table. DDS works by first storing a large repetitive waveform in onboard memory. A cycle of a waveform (sine, triangle, square, arbitrary) can be represented by a predetermined number of phase points as shown in TABLE 1 and stored into memory. Once the waveform is stored into memory, it can be generated at very precise frequencies. The direct digital synthesis table may be stored in a non-volatile memory of the generator circuit and/or may be implemented with a FPGA circuit in the generator circuit. The lookup table 4210 may be addressed by any suitable technique that is convenient for categorizing wave shapes. According to one aspect, the lookup table 4210 is addressed according to a frequency of the electrical signal waveform. Additionally, the information associated with the plurality of wave shapes may be stored as digital information in a memory or as part of the lookup table 4210.

In one aspect, the generator circuit may be configured to provide electrical signal waveforms to at least two surgical instruments simultaneously. The generator circuit also may be configured to provide the electrical signal waveform, which may be characterized two or more wave shapes, via an output channel of the generator circuit to the two surgical instruments simultaneously. For example, in one aspect the electrical signal waveform comprises a first electrical signal to drive an ultrasonic transducer (e.g., ultrasonic drive signal), a second RF drive signal, and/or a combination thereof. In addition, an electrical signal waveform may comprise a plurality of ultrasonic drive signals, a plurality of RF drive signals, and/or a combination of a plurality of ultrasonic and RF drive signals.

In addition, a method of operating the generator circuit according to the present disclosure comprises generating an electrical signal waveform and providing the generated electrical signal waveform to any one of the surgical instruments of surgical system 1000, where generating the electrical signal waveform comprises receiving information associated with the electrical signal waveform from a memory. The generated electrical signal waveform comprises at least one wave shape. Furthermore, providing the generated electrical signal waveform to the at least one surgical instrument comprises providing the electrical signal waveform to at least two surgical instruments simultaneously.

The generator circuit as described herein may allow for the generation of various types of direct digital synthesis tables. Examples of wave shapes for RF/Electrosurgery signals suitable for treating a variety of tissue generated by the generator circuit include RF signals with a high crest factor (which may be used for surface coagulation in RF mode), a low crest factor RF signals (which may be used for deeper tissue penetration), and waveforms that promote efficient touch-up coagulation. The generator circuit also may generate multiple wave shapes employing a direct digital synthesis lookup table 4210 and, on the fly, can switch between particular wave shapes based on the desired tissue effect. Switching may be based on tissue impedance and/or other factors.

In addition to traditional sine/cosine wave shapes, the generator circuit may be configured to generate wave shape(s) that maximize the power into tissue per cycle (i.e., trapezoidal or square wave). The generator circuit may provide wave shape(s) that are synchronized to maximize the power delivered to the load when driving RF and ultrasonic signals simultaneously and to maintain ultrasonic frequency lock, provided that the generator circuit includes a circuit topology that enables simultaneously driving RF and ultrasonic signals. Further, custom wave shapes specific to instruments and their tissue effects can be stored in a non-volatile memory (NVM) or an instrument EEPROM and can be fetched upon connecting any one of the surgical instruments of surgical system 1000 to the generator circuit.

The DDS circuit 4200 may comprise multiple lookup tables 4104 where the lookup table 4210 stores a waveform represented by a predetermined number of phase points (also may be referred to as samples), wherein the phase points define a predetermined shape of the waveform. Thus multiple waveforms having a unique shape can be stored in multiple lookup tables 4210 to provide different tissue treatments based on instrument settings or tissue feedback. Examples of waveforms include high crest factor RF electrical signal waveforms for surface tissue coagulation, low crest factor RF electrical signal waveform for deeper tissue penetration, and electrical signal waveforms that promote efficient touch-up coagulation. In one aspect, the DDS circuit 4200 can create multiple wave shape lookup tables 4210 and during a tissue treatment procedure (e.g., "on-the-fly" or in virtual real time based on user or sensor inputs) switch between different wave shapes stored in different lookup tables 4210 based on the tissue effect desired and/or tissue feedback.

Accordingly, switching between wave shapes can be based on tissue impedance and other factors, for example. In other aspects, the lookup tables 4210 can store electrical signal waveforms shaped to maximize the power delivered into the tissue per cycle (i.e., trapezoidal or square wave). In other aspects, the lookup tables 4210 can store wave shapes synchronized in such way that they make maximizing power delivery by any one of the surgical instruments of surgical system 1000 when delivering RF and ultrasonic drive signals. In yet other aspects, the lookup tables 4210 can store electrical signal waveforms to drive ultrasonic and RF therapeutic, and/or sub-therapeutic, energy simultaneously while maintaining ultrasonic frequency lock. Generally, the output wave shape may be in the form of a sine wave, cosine wave, pulse wave, square wave, and the like. Nevertheless, the more complex and custom wave shapes specific to different instruments and their tissue effects can be stored in the non-volatile memory of the generator circuit or in the non-volatile memory (e.g., EEPROM) of the surgical instrument and be fetched upon connecting the surgical instrument to the generator circuit. One example of a custom wave shape is an exponentially damped sinusoid as used in many high crest factor "coagulation" waveforms, as shown in FIG. 43.

FIG. 43 illustrates one cycle of a discrete time digital electrical signal waveform 4300, in accordance with at least one aspect of the present disclosure of an analog waveform 4304 (shown superimposed over the discrete time digital electrical signal waveform 4300 for comparison purposes). The horizontal axis represents Time (t) and the vertical axis represents digital phase points. The digital electrical signal waveform 4300 is a digital discrete time version of the desired analog waveform 4304, for example. The digital electrical signal waveform 4300 is generated by storing an amplitude phase point 4302 that represents the amplitude per clock cycle $T_{clk}$ over one cycle or period $T_o$. The digital electrical signal waveform 4300 is generated over one period $T_o$ by any suitable digital processing circuit. The amplitude phase points are digital words stored in a memory circuit. In the example illustrated in FIGS. 41, 42, the digital word is a six-bit word that is capable of storing the amplitude phase points with a resolution of 26 or 64 bits. It will be appreciated that the examples shown in FIGS. 41, 42 is for illustrative purposes and in actual implementations the resolution can be much higher. The digital amplitude phase points 4302 over one cycle $T_o$ are stored in the memory as a string of string words in a lookup table 4104, 4210 as described in connection with FIGS. 41, 42, for example. To generate the analog version of the analog waveform 4304, the amplitude phase points 4302 are read sequentially from the memory from 0 to $T_o$ per clock cycle $T_{clk}$ and are converted by a DAC circuit 4108, 4212, also described in connection with FIGS. 41, 42. Additional cycles can be generated by repeatedly reading the amplitude phase points 4302 of the digital electrical signal waveform 4300 the from 0 to $T_o$ for as many cycles or periods as may be desired. The smooth analog version of the analog waveform 4304 is achieved by filtering the output of the DAC circuit 4108, 4212 by a filter 4112, 4214 (FIGS. 41 and 42). The filtered analog output signal 4114, 4222 (FIGS. 41 and 42) is applied to the input of a power amplifier.

Figure 44:
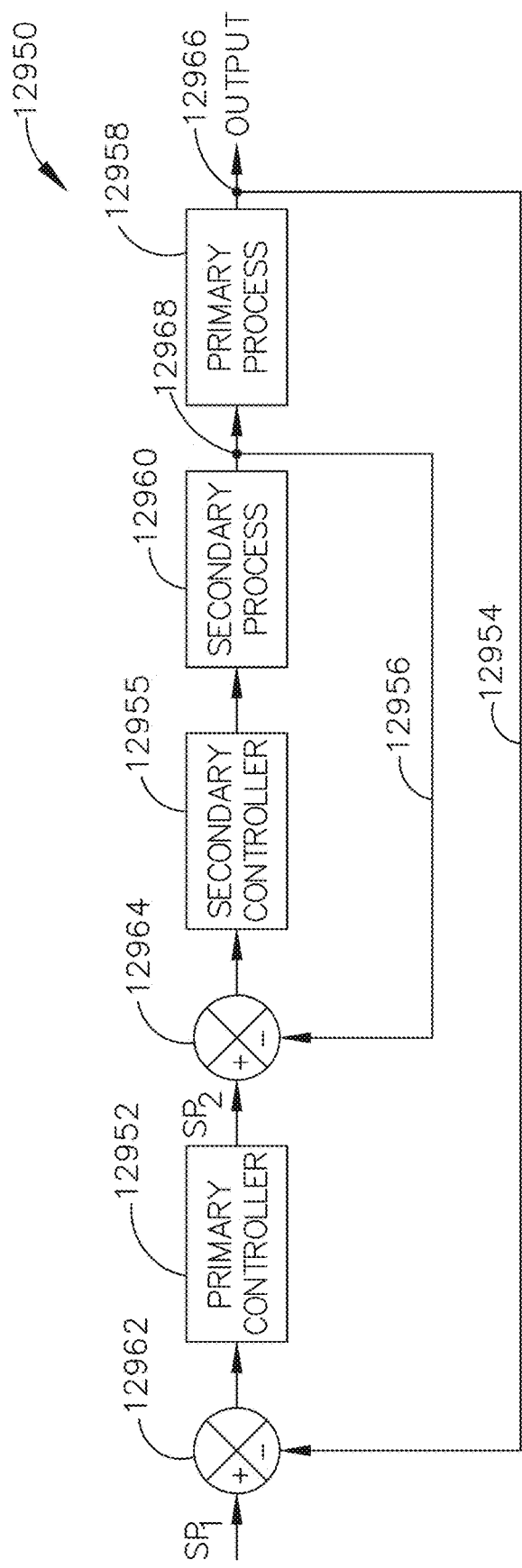
FIG. 44 is a diagram of a control system configured to provide progressive closure of a closure member as it advances distally to close the clamp arm to apply a closure force load at a desired rate according to one aspect of this disclosure.
Figure 45:
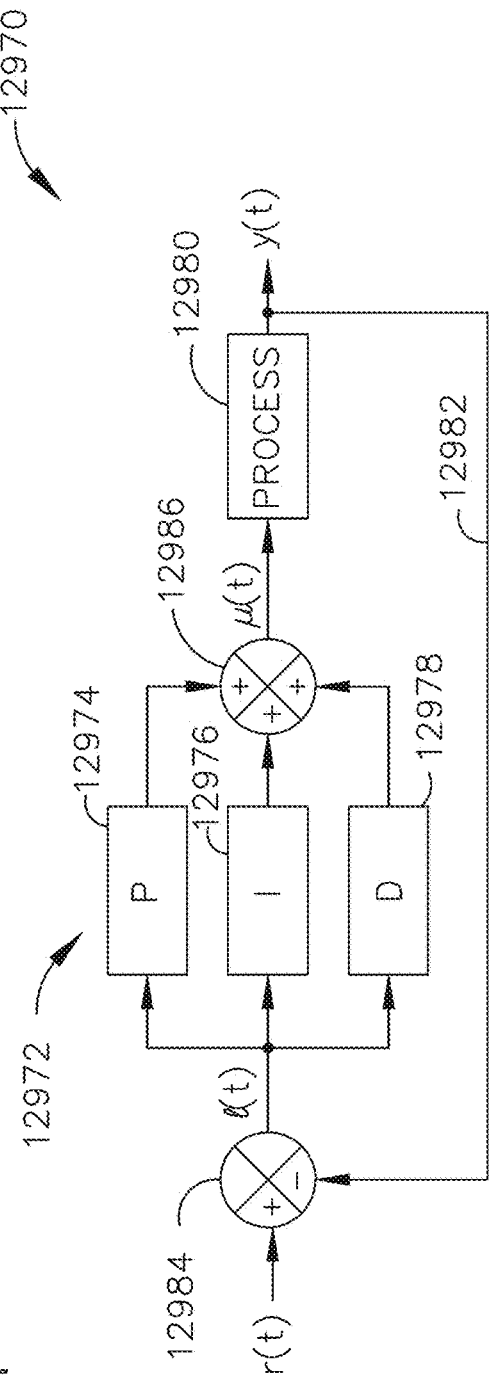
FIG. 45 illustrates a proportional-integral-derivative (PID) controller feedback control system according to one aspect of this disclosure.

FIG. 44 is a diagram of a control system 12950 configured to provide progressive closure of a closure member (e.g., closure tube) when the displacement member advances distally and couples into a clamp arm (e.g., anvil) to lower the closure force load on the closure member at a desired rate and decrease the firing force load on the firing member according to one aspect of this disclosure. In one aspect, the control system 12950 may be implemented as a nested PID feedback controller. A PID controller is a control loop feedback mechanism (controller) to continuously calculate an error value as the difference between a desired set point and a measured process variable and applies a correction based on proportional, integral, and derivative terms (sometimes denoted P, I, and D respectively). The nested PID controller feedback control system 12950 includes a primary controller 12952, in a primary (outer) feedback loop 12954 and a secondary controller 12955 in a secondary (inner) feedback loop 12956. The primary controller 12952 may be a PID controller 12972 as shown in FIG. 45, and the secondary controller 12955 also may be a PID controller 12972 as shown in FIG. 45. The primary controller 12952 controls a primary process 12958 and the secondary controller 12955 controls a secondary process 12960. The output 12966 of the primary process 12958 is subtracted from a primary set point $SP_1$ by a first summer 12962. The first summer 12962 produces a single sum output signal which is applied to the primary controller 12952. The output of the primary controller 12952 is the secondary set point $SP_2$. The output 12968 of the secondary process 12960 is subtracted from the secondary set point $SP_2$ by a second summer 12964.

In the context of controlling the displacement of a closure tube, the control system 12950 may be configured such that the primary set point $SP_1$ is a desired closure force value and the primary controller 12952 is configured to receive the closure force from a torque sensor coupled to the output of a closure motor and determine a set point $SP_2$ motor velocity for the closure motor. In other aspects, the closure force may be measured with strain gauges, load cells, or other suitable force sensors. The closure motor velocity set point $SP_2$ is compared to the actual velocity of the closure tube, which is determined by the secondary controller 12955. The actual velocity of the closure tube may be measured by comparing measuring the displacement of the closure tube with the position sensor and measuring elapsed time with a timer/counter. Other techniques, such as linear or rotary encoders may be employed to measure displacement of the closure tube. The output 12968 of the secondary process 12960 is the actual velocity of the closure tube. This closure tube velocity output 12968 is provided to the primary process 12958 which determines the force acting on the closure tube and is fed back to the adder 12962, which subtracts the measured closure force from the primary set point $SP_1$. The primary set point $SP_1$ may be an upper threshold or a lower threshold. Based on the output of the adder 12962, the primary controller 12952 controls the velocity and direction of the closure motor. The secondary controller 12955 controls the velocity of the closure motor based on the actual velocity of closure tube measured by the secondary process 12960 and the secondary set point $SP_2$, which is based on a comparison of the actual firing force and the firing force upper and lower thresholds.

FIG. 45 illustrates a PID feedback control system 12970 according to one aspect of this disclosure. The primary controller 12952 or the secondary controller 12955, or both, may be implemented as a PID controller 12972. In one aspect, the PID controller 12972 may comprise a proportional element 12974 (P), an integral element 12976 (I), and a derivative element 12978 (D). The outputs of the P, I, D elements 12974, 12976, 12978 are summed by a summer 12986, which provides the control variable $\mu(t)$ to the process 12980. The output of the process 12980 is the process variable $y(t)$. A summer 12984 calculates the difference between a desired set point $r(t)$ and a measured process variable $y(t)$, received by a feedback loop 12982. The PID controller 12972 continuously calculates an error value $e(t)$ (e.g., difference between closure force threshold and measured closure force) as the difference between a desired set point $r(t)$ (e.g., closure force threshold) and a measured process variable $y(t)$ (e.g., velocity and direction of closure tube) and applies a correction based on the proportional, integral, and derivative terms calculated by the proportional element 12974 (P), integral element 12976 (I), and derivative element 12978 (D), respectively. The PID controller 12972 attempts to minimize the error $e(t)$ over time by adjustment of the control variable $\mu(t)$ (e.g., velocity and direction of the closure tube).

In accordance with the PID algorithm, the "P" element 12974 accounts for present values of the error. For example, if the error is large and positive, the control output will also be large and positive. In accordance with the present disclosure, the error term $e(t)$ is the different between the desired closure force and the measured closure force of the closure tube. The "I" element 12976 accounts for past values of the error. For example, if the current output is not sufficiently strong, the integral of the error will accumulate over time, and the controller will respond by applying a stronger action. The "D" element 12978 accounts for possible future trends of the error, based on its current rate of change. For example, continuing the P example above, when the large positive control output succeeds in bringing the error closer to zero, it also puts the process on a path to large negative error in the near future. In this case, the derivative turns negative and the D module reduces the strength of the action to prevent this overshoot.

It will be appreciated that other variables and set points may be monitored and controlled in accordance with the feedback control systems 12950, 12970. For example, the adaptive closure member velocity control algorithm described herein may measure at least two of the following parameters: firing member stroke location, firing member load, displacement of cutting element, velocity of cutting element, closure tube stroke location, closure tube load, among others.

Various aspects are directed to improved ultrasonic surgical devices, electrosurgical devices and generators for use therewith. Aspects of the ultrasonic surgical devices can be configured for transecting and/or coagulating tissue during surgical procedures, for example. Aspects of the electrosurgical devices can be configured for transecting, coagulating, scaling, welding and/or desiccating tissue during surgical procedures, for example.

Aspects of the generator utilize high-speed analog-to-digital sampling (e.g., approximately 200× oversampling, depending on frequency) of the generator drive signal current and voltage, along with digital signal processing, to provide a number of advantages and benefits over known generator architectures. In one aspect, for example, based on current and voltage feedback data, a value of the ultrasonic transducer static capacitance, and a value of the drive signal frequency, the generator may determine the motional branch current of an ultrasonic transducer. This provides the benefit of a virtually tuned system, and simulates the presence of a system that is tuned or resonant with any value of the static capacitance (e.g., C0 in FIG. 4) at any frequency. Accordingly, control of the motional branch current may be realized by tuning out the effects of the static capacitance without the need for a tuning inductor. Additionally, the elimination of the tuning inductor may not degrade the generator's frequency lock capabilities, as frequency lock can be realized by suitably processing the current and voltage feedback data.

High-speed analog-to-digital sampling of the generator drive signal current and voltage, along with digital signal processing, may also enable precise digital filtering of the samples. For example, aspects of the generator may utilize a low-pass digital filter (e.g., a finite impulse response (FIR) filter) that rolls off between a fundamental drive signal frequency and a second-order harmonic to reduce the asymmetrical harmonic distortion and EMI-induced noise in current and voltage feedback samples. The filtered current and voltage feedback samples represent substantially the fundamental drive signal frequency, thus enabling a more accurate impedance phase measurement with respect to the fundamental drive signal frequency and an improvement in the generator's ability to maintain resonant frequency lock. The accuracy of the impedance phase measurement may be further enhanced by averaging falling edge and rising edge phase measurements, and by regulating the measured impedance phase to 0°.

Various aspects of the generator may also utilize the high-speed analog-to-digital sampling of the generator drive signal current and voltage, along with digital signal processing, to determine real power consumption and other quantities with a high degree of precision. This may allow the generator to implement a number of useful algorithms, such as, for example, controlling the amount of power delivered to tissue as the impedance of the tissue changes and controlling the power delivery to maintain a constant rate of tissue impedance increase. Some of these algorithms are used to determine the phase difference between the generator drive signal current and voltage signals. At resonance, the phase difference between the current and voltage signals is zero. The phase changes as the ultrasonic system goes off-resonance. Various algorithms may be employed to detect the phase difference and adjust the drive frequency until the ultrasonic system returns to resonance, i.e., the phase difference between the current and voltage signals goes to zero. The phase information also may be used to infer the conditions of the ultrasonic blade. As discussed with particularity below, the phase changes as a function of the temperature of the ultrasonic blade. Therefore, the phase information may be employed to control the temperature of the ultrasonic blade. This may be done, for example, by reducing the power delivered to the ultrasonic blade when the ultrasonic blade runs too hot and increasing the power delivered to the ultrasonic blade when the ultrasonic blade runs too cold.

Various aspects of the generator may have a wide frequency range and increased output power necessary to drive both ultrasonic surgical devices and electrosurgical devices. The lower voltage, higher current demand of electrosurgical devices may be met by a dedicated tap on a wideband power transformer, thereby eliminating the need for a separate power amplifier and output transformer. Moreover, sensing and feedback circuits of the generator may support a large dynamic range that addresses the needs of both ultrasonic and electrosurgical applications with minimal distortion.

Various aspects may provide a simple, economical means for the generator to read from, and optionally write to, a data circuit (e.g., a single-wire bus device, such as a one-wire protocol EEPROM known under the trade name "1-Wire") disposed in an instrument attached to the handpiece using existing multi-conductor generator/handpiece cables. In this way, the generator is able to retrieve and process instrument-specific data from an instrument attached to the handpiece. This may enable the generator to provide better control and improved diagnostics and error detection. Additionally, the ability of the generator to write data to the instrument makes possible new functionality in terms of, for example, tracking instrument usage and capturing operational data. Moreover, the use of frequency band permits the backward compatibility of instruments containing a bus device with existing generators.

Disclosed aspects of the generator provide active cancellation of leakage current caused by unintended capacitive coupling between non-isolated and patient-isolated circuits of the generator. In addition to reducing patient risk, the reduction of leakage current may also lessen electromagnetic emissions. These and other benefits of aspects of the present disclosure will be apparent from the description to follow.

It will be appreciated that the terms "proximal" and "distal" are used herein with reference to a clinician gripping a handpiece. Thus, an end effector is distal with respect to the more proximal handpiece. It will be further appreciated that, for convenience and clarity, spatial terms such as "top" and "bottom" may also be used herein with respect to the clinician gripping the handpiece. However, surgical devices are used in many orientations and positions, and these terms are not intended to be limiting and absolute.

Figure 46:
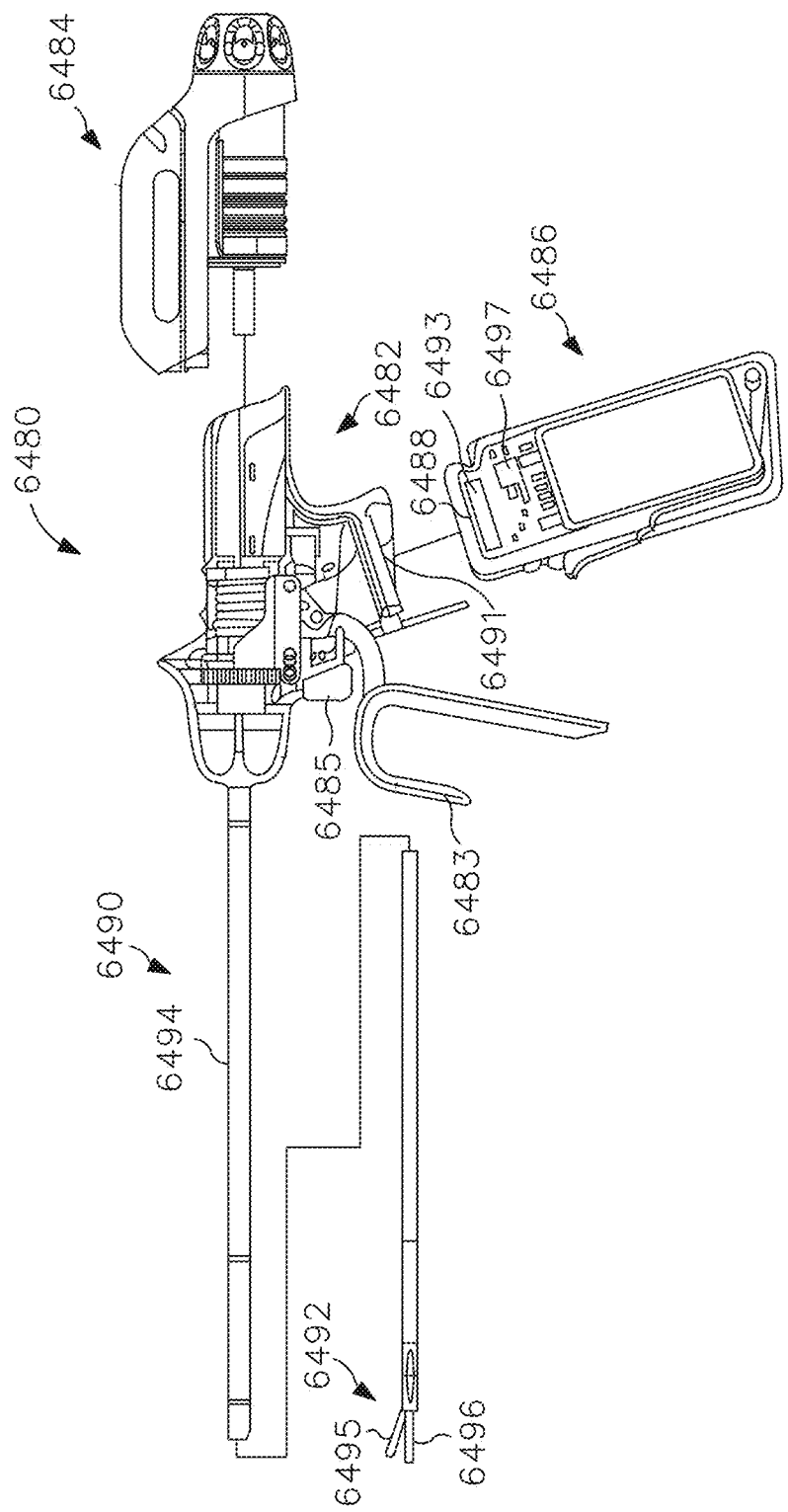
FIG. 46 is an elevational exploded view of modular handheld ultrasonic surgical instrument showing the left shell half removed from a handle assembly exposing a device identifier communicatively coupled to the multi-lead handle terminal assembly in accordance with one aspect of the present disclosure.

FIG. 46 is an elevational exploded view of modular handheld ultrasonic surgical instrument 6480 showing the left shell half removed from a handle assembly 6482 exposing a device identifier communicatively coupled to the multi-lead handle terminal assembly in accordance with one aspect of the present disclosure. In additional aspects of the present disclosure, an intelligent or smart battery is used to power the modular handheld ultrasonic surgical instrument 6480. However, the smart battery is not limited to the modular handheld ultrasonic surgical instrument 6480 and, as will be explained, can be used in a variety of devices, which may or may not have power requirements (e.g., current and voltage) that vary from one another. The smart battery assembly 6486, in accordance with one aspect of the present disclosure, is advantageously able to identify the particular device to which it is electrically coupled. It does this through encrypted or unencrypted identification methods. For instance, a smart battery assembly 6486 can have a connection portion, such as connection portion 6488. The handle assembly 6482 can also be provided with a device identifier communicatively coupled to the multi-lead handle terminal assembly 6491 and operable to communicate at least one piece of information about the handle assembly 6482. This information can pertain to the number of times the handle assembly 6482 has been used, the number of times an ultrasonic transducer/generator assembly 6484 (presently disconnected from the handle assembly 6482) has been used, the number of times a waveguide shaft assembly 6490 (presently connected to the handle assembly 6482) has been used, the type of the waveguide shaft assembly 6490 that is presently connected to the handle assembly 6482, the type or identity of the ultrasonic transducer/generator assembly 6484 that is presently connected to the handle assembly 6482, and/or many other characteristics. When the smart battery assembly 6486 is inserted in the handle assembly 6482, the connection portion 6488 within the smart battery assembly 6486 makes communicating contact with the device identifier of the handle assembly 6482. The handle assembly 6482, through hardware, software, or a combination thereof, is able to transmit information to the smart battery assembly 6486 (whether by self-initiation or in response to a request from the smart battery assembly 6486). This communicated identifier is received by the connection portion 6488 of the smart battery assembly 6486. In one aspect, once the smart battery assembly 6486 receives the information, the communication portion is operable to control the output of the smart battery assembly 6486 to comply with the device's specific power requirements.

In one aspect, the communication portion includes a processor 6493 and a memory 6497, which may be separate or a single component. The processor 6493, in combination with the memory, is able to provide intelligent power management for the modular handheld ultrasonic surgical instrument 6480. This aspect is particularly advantageous because an ultrasonic device, such as the modular handheld ultrasonic surgical instrument 6480, has a power requirement (frequency, current, and voltage) that may be unique to the modular handheld ultrasonic surgical instrument 6480. In fact, the modular handheld ultrasonic surgical instrument 6480 may have a particular power requirement or limitation for one dimension or type of outer tube 6494 and a second different power requirement for a second type of waveguide having a different dimension, shape, and/or configuration.

A smart battery assembly 6486, in accordance with at least one aspect of the present disclosure, therefore, allows a battery assembly to be used amongst several surgical instruments. Because the smart battery assembly 6486 is able to identify to which device it is attached and is able to alter its output accordingly, the operators of various different surgical instruments utilizing the smart battery assembly 6486 no longer need be concerned about which power source they are attempting to install within the electronic device being used. This is particularly advantageous in an operating environment where a battery assembly needs to be replaced or interchanged with another surgical instrument in the middle of a complex surgical procedure.

In a further aspect of the present disclosure, the smart battery assembly 6486 stores in a memory 6497 a record of each time a particular device is used. This record can be useful for assessing the end of a device's useful or permitted life. For instance, once a device is used 20 times, such batteries in the smart battery assembly 6486 connected to the device will refuse to supply power thereto-because the device is defined as a "no longer reliable" surgical instrument. Reliability is determined based on a number of factors. One factor can be wear, which can be estimated in a number of ways including the number of times the device has been used or activated. After a certain number of uses, the parts of the device can become worn and tolerances between parts exceeded. For instance, the smart battery assembly 6486 can sense the number of button pushes received by the handle assembly 6482 and can determine when a maximum number of button pushes has been met or exceeded. The smart battery assembly 6486 can also monitor an impedance of the button mechanism which can change, for instance, if the handle gets contaminated, for example, with saline.

This wear can lead to an unacceptable failure during a procedure. In some aspects, the smart battery assembly 6486 can recognize which parts are combined together in a device and even how many uses a part has experienced. For instance, if the smart battery assembly 6486 is a smart battery according to the present disclosure, it can identify the handle assembly 6482, the waveguide shaft assembly 6490, as well as the ultrasonic transducer/generator assembly 6484, well before the user attempts use of the composite device. The memory 6497 within the smart battery assembly 6486 can, for example, record a time when the ultrasonic transducer/generator assembly 6484 is operated, and how, when, and for how long it is operated. If the ultrasonic transducer/generator assembly 6484 has an individual identifier, the smart battery assembly 6486 can keep track of uses of the ultrasonic transducer/generator assembly 6484 and refuse to supply power to that the ultrasonic transducer/generator assembly 6484 once the handle assembly 6482 or the ultrasonic transducer/generator assembly 6484 exceeds its maximum number of uses. The ultrasonic transducer/generator assembly 6484, the handle assembly 6482, the waveguide shaft assembly 6490, or other components can include a memory chip that records this information as well. In this way, any number of smart batteries in the smart battery assembly 6486 can be used with any number of ultrasonic transducer/generator assemblies 6484, staplers, vessel sealers, etc. and still be able to determine the total number of uses, or the total time of use (through use of the clock), or the total number of actuations, etc. of the ultrasonic transducer/generator assembly 6484, the stapler, the vessel sealer, etc. or charge or discharge cycles. Smart functionality may reside outside the battery assembly 6486 and may reside in the handle assembly 6482, the ultrasonic transducer/generator assembly 6484, and/or the shaft assembly 6490, for example.

When counting uses of the ultrasonic transducer/generator assembly 6484, to intelligently terminate the life of the ultrasonic transducer/generator assembly 6484, the surgical instrument accurately distinguishes between completion of an actual use of the ultrasonic transducer/generator assembly 6484 in a surgical procedure and a momentary lapse in actuation of the ultrasonic transducer/generator assembly 6484 due to, for example, a battery change or a temporary delay in the surgical procedure. Therefore, as an alternative to simply counting the number of activations of the ultrasonic transducer/generator assembly 6484, a real-time clock (RTC) circuit can be implemented to keep track of the amount of time the ultrasonic transducer/generator assembly 6484 actually is shut down. From the length of time measured, it can be determined through appropriate logic if the shutdown was significant enough to be considered the end of one actual use or if the shutdown was too short in time to be considered the end of one use. Thus, in some applications, this method may be a more accurate determination of the useful life of the ultrasonic transducer/generator assembly 6484 than a simple "activations-based" algorithm, which for example, may provide that ten "activations" occur in a surgical procedure and, therefore, ten activations should indicate that the counter is incremented by one. Generally, this type and system of internal clocking will prevent misuse of the device that is designed to deceive a simple "activations-based" algorithm and will prevent incorrect logging of a complete use in instances when there was only a simple de-mating of the ultrasonic transducer/generator assembly 6484 or the smart battery assembly 6486 that was required for legitimate reasons.

Although the ultrasonic transducer/generator assemblies 6484 of the surgical instrument 6480 are reusable, in one aspect a finite number of uses may be set because the surgical instrument 6480 is subjected to harsh conditions during cleaning and sterilization. More specifically, the battery pack is configured to be sterilized. Regardless of the material employed for the outer surfaces, there is a limited expected life for the actual materials used. This life is determined by various characteristics which could include, for example, the amount of times the pack has actually been sterilized, the time from which the pack was manufactured, and the number of times the pack has been recharged, to name a few. Also, the life of the battery cells themselves is limited. Software of the present disclosure incorporates inventive algorithms that verify the number of uses of the ultrasonic transducer/generator assembly 6484 and smart battery assembly 6486 and disables the device when this number of uses has been reached or exceeded. Analysis of the battery pack exterior in each of the possible sterilizing methods can be performed. Based on the harshest sterilization procedure, a maximum number of permitted sterilizations can be defined and that number can be stored in a memory of the smart battery assembly 6486. If it is assumed that a charger is non-sterile and that the smart battery assembly 6486 is to be used after it is charged, then the charge count can be defined as being equal to the number of sterilizations encountered by that particular pack.

In one aspect, the hardware in the battery pack may be to disabled to minimize or eliminate safety concerns due to continuous drain in from the battery cells after the pack has been disabled by software. A situation can exist where the battery's internal hardware is incapable of disabling the battery under certain low voltage conditions. In such a situation, in an aspect, the charger can be used to "kill" the battery. Due to the fact that the battery microcontroller is OFF while the battery is in its charger, a non-volatile, System Management Bus (SMB) based electrically erasable programmable read only memory (EEPROM) can be used to exchange information between the battery microcontroller and the charger. Thus, a serial EEPROM can be used to store information that can be written and read even when the battery microcontroller is OFF, which is very beneficial when trying to exchange information with the charger or other peripheral devices. This example EEPROM can be configured to contain enough memory registers to store at least (a) a use-count limit at which point the battery should be disabled (Battery Use Count), (b) the number of procedures the battery has undergone (Battery Procedure Count), and/or (c) a number of charges the battery has undergone (Charge Count), to name a few. Some of the information stored in the EEPROM, such as the Use Count Register and Charge Count Register are stored in write-protected sections of the EEPROM to prevent users from altering the information. In an aspect, the use and counters are stored with corresponding bit-inverted minor registers to detect data corruption.

Any residual voltage in the SMBus lines could damage the microcontroller and corrupt the SMBus signal. Therefore, to ensure that the SMBus lines of a battery controller do not carry a voltage while the microcontroller is OFF, relays are provided between the external SMBus lines and the battery microcontroller board.

During charging of the smart battery assembly 6486, an "end-of-charge" condition of the batteries within the smart battery assembly 6486 is determined when, for example, the current flowing into the battery falls below a given threshold in a tapering manner when employing a constant-current/constant-voltage charging scheme. To accurately detect this "end-of-charge" condition, the battery microcontroller and buck boards are powered down and turned OFF during charging of the battery to reduce any current drain that may be caused by the boards and that may interfere with the tapering current detection. Additionally, the microcontroller and buck boards are powered down during charging to prevent any resulting corruption of the SMBus signal.

With regard to the charger, in one aspect the smart battery assembly 6486 is prevented from being inserted into the charger in any way other than the correct insertion position. Accordingly, the exterior of the smart battery assembly 6486 is provided with charger-holding features. A cup for holding the smart battery assembly 6486 securely in the charger is configured with a contour-matching taper geometry to prevent the accidental insertion of the smart battery assembly 6486 in any way other than the correct (intended) way. It is further contemplated that the presence of the smart battery assembly 6486 may be detectable by the charger itself. For example, the charger may be configured to detect the presence of the SMBus transmission from the battery protection circuit, as well as resistors that are located in the protection board. In such case, the charger would be enabled to control the voltage that is exposed at the charger's pins until the smart battery assembly 6486 is correctly seated or in place at the charger. This is because an exposed voltage at the charger's pins would present a hazard and a risk that an electrical short could occur across the pins and cause the charger to inadvertently begin charging.

In some aspects, the smart battery assembly 6486 can communicate to the user through audio and/or visual feedback. For example, the smart battery assembly 6486 can cause the LEDs to light in a pre-set way. In such a case, even though the microcontroller in the ultrasonic transducer/generator assembly 6484 controls the LEDs, the microcontroller receives instructions to be carried out directly from the smart battery assembly 6486.

In yet a further aspect of the present disclosure, the microcontroller in the ultrasonic transducer/generator assembly 6484, when not in use for a predetermined period of time, goes into a sleep mode. Advantageously, when in the sleep mode, the clock speed of the microcontroller is reduced, cutting the current drain significantly. Some current continues to be consumed because the processor continues pinging waiting to sense an input. Advantageously, when the microcontroller is in this power-saving sleep mode, the microcontroller and the battery controller can directly control the LEDs. For example, a decoder circuit could be built into the ultrasonic transducer/generator assembly 6484 and connected to the communication lines such that the LEDs can be controlled independently by the processor 6493 while the ultrasonic transducer/generator assembly 6484 microcontroller is "OFF" or in a "sleep mode." This is a power-saving feature that eliminates the need for waking up the microcontroller in the ultrasonic transducer/generator assembly 6484. Power is conserved by allowing the generator to be turned off while still being able to actively control the user-interface indicators.

Another aspect slows down one or more of the microcontrollers to conserve power when not in use. For example, the clock frequencies of both microcontrollers can be reduced to save power. To maintain synchronized operation, the microcontrollers coordinate the changing of their respective clock frequencies to occur at about the same time, both the reduction and, then, the subsequent increase in frequency when full speed operation is required. For example, when entering the idle mode, the clock frequencies are decreased and, when exiting the idle mode, the frequencies are increased.

In an additional aspect, the smart battery assembly 6486 is able to determine the amount of usable power left within its cells and is programmed to only operate the surgical instrument to which it is attached if it determines there is enough battery power remaining to predictably operate the device throughout the anticipated procedure. For example, the smart battery assembly 6486 is able to remain in a non-operational state if there is not enough power within the cells to operate the surgical instrument for 20 seconds. According to one aspect, the smart battery assembly 6486 determines the amount of power remaining within the cells at the end of its most recent preceding function, e.g., a surgical cutting. In this aspect, therefore, the smart battery assembly 6486 would not allow a subsequent function to be carried out if, for example, during that procedure, it determines that the cells have insufficient power. Alternatively, if the smart battery assembly 6486 determines that there is sufficient power for a subsequent procedure and goes below that threshold during the procedure, it would not interrupt the ongoing procedure and, instead, will allow it to finish and thereafter prevent additional procedures from occurring.

The following explains an advantage to maximizing use of the device with the smart battery assembly 6486 of the present disclosure. In this example, a set of different devices have different ultrasonic transmission waveguides. By definition, the waveguides could have a respective maximum allowable power limit where exceeding that power limit overstresses the waveguide and eventually causes it to fracture. One waveguide from the set of waveguides will naturally have the smallest maximum power tolerance. Because prior-art batteries lack intelligent battery power management, the output of prior-art batteries must be limited by a value of the smallest maximum allowable power input for the smallest/thinnest/most-frail waveguide in the set that is envisioned to be used with the device/battery. This would be true even though larger, thicker waveguides could later be attached to that handle and, by definition, allow a greater force to be applied. This limitation is also true for maximum battery power. For example, if one battery is designed to be used in multiple devices, its maximum output power will be limited to the lowest maximum power rating of any of the devices in which it is to be used. With such a configuration, one or more devices or device configurations would not be able to maximize use of the battery because the battery does not know the particular device's specific limits.

In one aspect, the smart battery assembly 6486 may be employed to intelligently circumvent the above-mentioned ultrasonic device limitations. The smart battery assembly 6486 can produce one output for one device or a particular device configuration and the same smart battery assembly 6486 can later produce a different output for a second device or device configuration. This universal smart battery surgical system lends itself well to the modern operating room where space and time are at a premium. By having a smart battery pack operate many different devices, the nurses can easily manage the storage, retrieval, and inventory of these packs.

Advantageously, in one aspect the smart battery system according to the present disclosure may employ one type of charging station, thus increasing ease and efficiency of use and decreasing cost of surgical room charging equipment.

In addition, other surgical instruments, such as an electric stapler, may have a different power requirement than that of the modular handheld ultrasonic surgical instrument 6480. In accordance with various aspects of the present disclosure, a smart battery assembly 6486 can be used with any one of a series of surgical instruments and can be made to tailor its own power output to the particular device in which it is installed. In one aspect, this power tailoring is performed by controlling the duty cycle of a switched mode power supply, such as buck, buck-boost, boost, or other configuration, integral with or otherwise coupled to and controlled by the smart battery assembly 6486. In other aspects, the smart battery assembly 6486 can dynamically change its power output during device operation. For instance, in vessel sealing devices, power management provides improved tissue sealing. In these devices, large constant current values are needed. The total power output needs to be adjusted dynamically because, as the tissue is sealed, its impedance changes. Aspects of the present disclosure provide the smart battery assembly 6486 with a variable maximum current limit. The current limit can vary from one application (or device) to another, based on the requirements of the application or device.

Figures 47, 48:
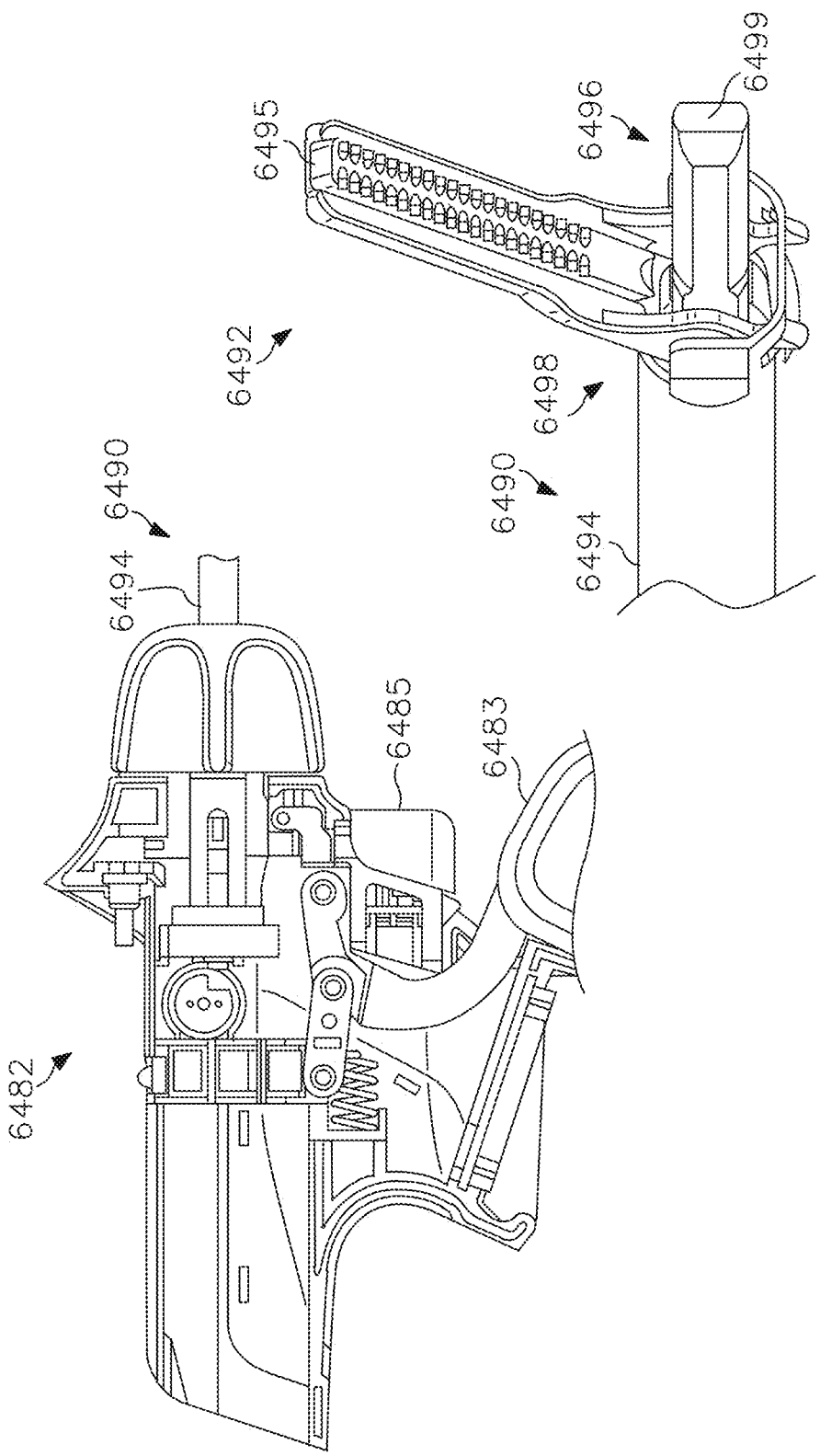
FIG. 47 is a detail view of a trigger portion and switch of the ultrasonic surgical instrument shown in FIG. 46, in accordance with at least one aspect of the present disclosure.
FIG. 48 is a fragmentary, enlarged perspective view of an end effector from a distal end with a jaw member in an open position, in accordance with at least one aspect of the present disclosure.

FIG. 47 is a detail view of a trigger 6483 portion and switch of the ultrasonic surgical instrument 6480 shown in FIG. 46, in accordance with at least one aspect of the present disclosure. The trigger 6483 is operably coupled to the jaw member 6495 of the end effector 6492. The ultrasonic blade 6496 is energized by the ultrasonic transducer/generator assembly 6484 upon activating the activation switch 6485. Continuing now with FIG. 46 and also looking to FIG. 47, the trigger 6483 and the activation switch 6485 are shown as components of the handle assembly 6482. The trigger 6483 activates the end effector 6492, which has a cooperative association with the ultrasonic blade 6496 of the waveguide shaft assembly 6490 to enable various kinds of contact between the end effector jaw member 6495 and the ultrasonic blade 6496 with tissue and/or other substances. The jaw member 6495 of the end effector 6492 is usually a pivoting jaw that acts to grasp or clamp onto tissue disposed between the jaw and the ultrasonic blade 6496. In one aspect, an audible feedback is provided in the trigger that clicks when the trigger is fully depressed. The noise can be generated by a thin metal part that the trigger snaps over while closing. This feature adds an audible component to user feedback that informs the user that the jaw is fully compressed against the waveguide and that sufficient clamping pressure is being applied to accomplish vessel sealing. In another aspect, force sensors such as strain gages or pressure sensors may be coupled to the trigger 6483 to measure the force applied to the trigger 6483 by the user. In another aspect, force sensors such as strain gages or pressure sensors may be coupled to the switch 6485 button such that displacement intensity corresponds to the force applied by the user to the switch 6485 button.

The activation switch 6485, when depressed, places the modular handheld ultrasonic surgical instrument 6480 into an ultrasonic operating mode, which causes ultrasonic motion at the waveguide shaft assembly 6490. In one aspect, depression of the activation switch 6485 causes electrical contacts within a switch to close, thereby completing a circuit between the smart battery assembly 6486 and the ultrasonic transducer/generator assembly 6484 so that electrical power is applied to the ultrasonic transducer, as previously described. In another aspect, depression of the activation switch 6485 closes electrical contacts to the smart battery assembly 6486. Of course, the description of closing electrical contacts in a circuit is, here, merely an example general description of switch operation. There are many alternative aspects that can include opening contacts or processor-controlled power delivery that receives information from the switch and directs a corresponding circuit reaction based on the information.

FIG. 48 is a fragmentary, enlarged perspective view of an end effector 6492, in accordance with at least one aspect of the present disclosure, from a distal end with a jaw member 6495 in an open position. Referring to FIG. 48, a perspective partial view of the distal end 6498 of the waveguide shaft assembly 6490 is shown. The waveguide shaft assembly 6490 includes an outer tube 6494 surrounding a portion of the waveguide. The ultrasonic blade 6496 portion of the waveguide 6499 protrudes from the distal end 6498 of the outer tube 6494. It is the ultrasonic blade 6496 portion that contacts the tissue during a medical procedure and transfers its ultrasonic energy to the tissue. The waveguide shaft assembly 6490 also includes a jaw member 6495 that is coupled to the outer tube 6494 and an inner tube (not visible in this view). The jaw member 6495, together with the inner and outer tubes and the ultrasonic blade 6496 portion of the waveguide 6499, can be referred to as an end effector 6492. As will be explained below, the outer tube 6494 and the non-illustrated inner tube slide longitudinally with respect to each other. As the relative movement between the outer tube 6494 and the non-illustrated inner tube occurs, the jaw member 6495 pivots upon a pivot point, thereby causing the jaw member 6495 to open and close. When closed, the jaw member 6495 imparts a pinching force on tissue located between the jaw member 6495 and the ultrasonic blade 6496, insuring positive and efficient blade-to-tissue contact.

Figure 49:
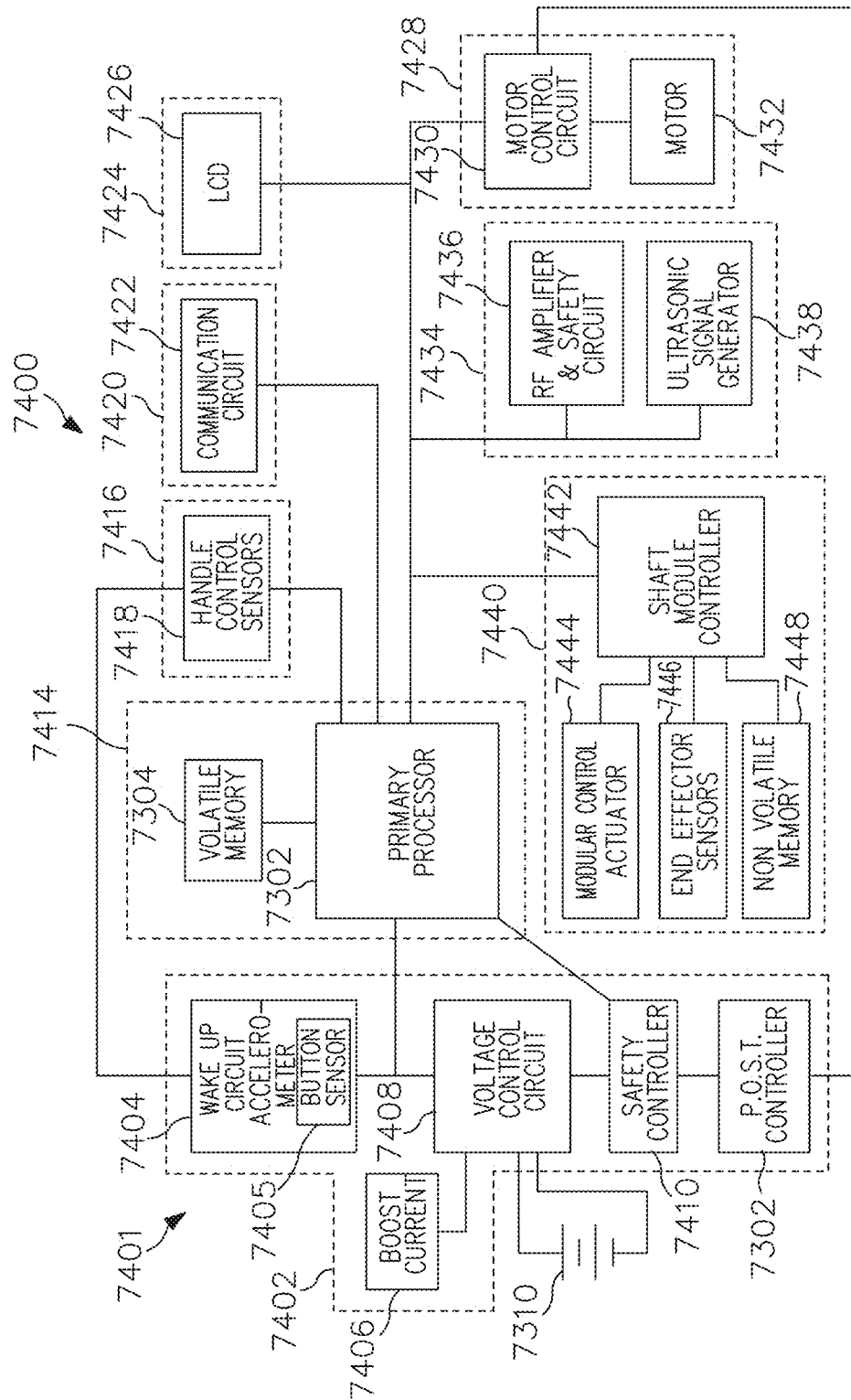
FIG. 49 is a system diagram of a segmented circuit comprising a plurality of independently operated circuit segments, in accordance with at least one aspect of the present disclosure.

FIG. 49 is a system diagram 7400 of a segmented circuit 7401 comprising a plurality of independently operated circuit segments 7402, 7414, 7416, 7420, 7424, 7428, 7434, 7440, in accordance with at least one aspect of the present disclosure. A circuit segment of the plurality of circuit segments of the segmented circuit 7401 comprises one or more circuits and one or more sets of machine executable instructions stored in one or more memory devices. The one or more circuits of a circuit segment are coupled to for electrical communication through one or more wired or wireless connection media. The plurality of circuit segments are configured to transition between three modes comprising a sleep mode, a standby mode and an operational mode.

In one aspect shown, the plurality of circuit segments 7402, 7414, 7416, 7420, 7424, 7428, 7434, 7440 start first in the standby mode, transition second to the sleep mode, and transition third to the operational mode. However, in other aspects, the plurality of circuit segments may transition from any one of the three modes to any other one of the three modes. For example, the plurality of circuit segments may transition directly from the standby mode to the operational mode. Individual circuit segments may be placed in a particular state by the voltage control circuit 7408 based on the execution by a processor of machine executable instructions. The states comprise a deenergized state, a low energy state, and an energized state. The deenergized state corresponds to the sleep mode, the low energy state corresponds to the standby mode, and the energized state corresponds to the operational mode. Transition to the low energy state may be achieved by, for example, the use of a potentiometer.

In one aspect, the plurality of circuit segments 7402, 7414, 7416, 7420, 7424, 7428, 7434, 7440 may transition from the sleep mode or the standby mode to the operational mode in accordance with an energization sequence. The plurality of circuit segments also may transition from the operational mode to the standby mode or the sleep mode in accordance with a deenergization sequence. The energization sequence and the deenergization sequence may be different. In some aspects, the energization sequence comprises energizing only a subset of circuit segments of the plurality of circuit segments. In some aspects, the deenergization sequence comprises deenergizing only a subset of circuit segments of the plurality of circuit segments.

Referring back to the system diagram 7400 in FIG. 49, the segmented circuit 7401 comprise a plurality of circuit segments comprising a transition circuit segment 7402, a processor circuit segment 7414 comprising a primary processor 7302 and a volatile memory unit 7304, a handle circuit segment 7416, a communication circuit segment 7420, a display circuit segment 7424, a motor control circuit segment 7428, an energy treatment circuit segment 7434, and a shaft circuit segment 7440. The transition circuit segment comprises a wake up circuit 7404, a boost current circuit 7406, a voltage control circuit 7408, a safety controller 7410 and a POST controller 7412. The transition circuit segment 7402 is configured to implement a deenergization and an energization sequence, a safety detection protocol, and a POST.

In some aspects, the wake up circuit 7404 comprises an accelerometer button sensor 7405. In aspects, the transition circuit segment 7402 is configured to be in an energized state while other circuit segments of the plurality of circuit segments of the segmented circuit 7401 are configured to be in a low energy state, a deenergized state or an energized state. The accelerometer button sensor 7405 may monitor movement or acceleration of the surgical instrument 6480 described herein. For example, the movement may be a change in orientation or rotation of the surgical instrument. The surgical instrument may be moved in any direction relative to a three dimensional Euclidean space by for example, a user of the surgical instrument. When the accelerometer button sensor 7405 senses movement or acceleration, the accelerometer button sensor 7405 sends a signal to the voltage control circuit 7408 to cause the voltage control circuit 7408 to apply voltage to the processor circuit segment 7414 to transition the processor and a volatile memory to an energized state. In aspects, the processor and the volatile memory are in an energized state before the voltage control circuit 7409 applies voltage to the processor and the volatile memory. In the operational mode, the processor may initiate an energization sequence or a deenergization sequence. In various aspects, the accelerometer button sensor 7405 may also send a signal to the processor to cause the processor to initiate an energization sequence or a deenergization sequence. In some aspects, the processor initiates an energization sequence when the majority of individual circuit segments are in a low energy state or a deenergized state. In other aspects, the processor initiates a deenergization sequence when the majority of individual circuit segments are in an energized state.

Additionally or alternatively, the accelerometer button sensor 7405 may sense external movement within a predetermined vicinity of the surgical instrument. For example, the accelerometer button sensor 7405 may sense a user of the surgical instrument 6480 described herein moving a hand of the user within the predetermined vicinity. When the accelerometer button sensor 7405 senses this external movement, the accelerometer button sensor 7405 may send a signal to the voltage control circuit 7408 and a signal to the processor, as previously described. After receiving the sent signal, the processor may initiate an energization sequence or a deenergization sequence to transition one or more circuit segments between the three modes. In aspects, the signal sent to the voltage control circuit 7408 is sent to verify that the processor is in operational mode. In some aspects, the accelerometer button sensor 7405 may sense when the surgical instrument has been dropped and send a signal to the processor based on the sensed drop. For example, the signal can indicate an error in the operation of an individual circuit segment. One or more sensors may sense damage or malfunctioning of the affected individual circuit segments. Based on the sensed damage or malfunctioning, the POST controller 7412 may perform a POST of the corresponding individual circuit segments.

An energization sequence or a deenergization sequence may be defined based on the accelerometer button sensor 7405. For example, the accelerometer button sensor 7405 may sense a particular motion or a sequence of motions that indicates the selection of a particular circuit segment of the plurality of circuit segments. Based on the sensed motion or series of sensed motions, the accelerometer button sensor 7405 may transmit a signal comprising an indication of one or more circuit segments of the plurality of circuit segments to the processor when the processor is in an energized state. Based on the signal, the processor determines an energization sequence comprising the selected one or more circuit segments. Additionally or alternatively, a user of the surgical instruments 6480 described herein may select a number and order of circuit segments to define an energization sequence or a deenergization sequence based on interaction with a graphical user interface (GUI) of the surgical instrument.

In various aspects, the accelerometer button sensor 7405 may send a signal to the voltage control circuit 7408 and a signal to the processor only when the accelerometer button sensor 7405 detects movement of the surgical instrument 6480 described herein or external movement within a predetermined vicinity above a predetermined threshold. For example, a signal may only be sent if movement is sensed for 5 or more seconds or if the surgical instrument is moved 5 or more inches. In other aspects, the accelerometer button sensor 7405 may send a signal to the voltage control circuit 7408 and a signal to the processor only when the accelerometer button sensor 7405 detects oscillating movement of the surgical instrument. A predetermined threshold reduces inadvertent transition of circuit segments of the surgical instrument. As previously described, the transition may comprise a transition to operational mode according to an energization sequence, a transition to low energy mode according to a deenergization sequence, or a transition to sleep mode according to a deenergization sequence. In some aspects, the surgical instrument comprises an actuator that may be actuated by a user of the surgical instrument. The actuation is sensed by the accelerometer button sensor 7405. The actuator may be a slider, a toggle switch, or a momentary contact switch. Based on the sensed actuation, the accelerometer button sensor 7405 may send a signal to the voltage control circuit 7408 and a signal to the processor.

The boost current circuit 7406 is coupled to a battery. The boost current circuit 7406 is a current amplifier, such as a relay or transistor, and is configured to amplify the magnitude of a current of an individual circuit segment. The initial magnitude of the current corresponds to the source voltage provided by the battery to the segmented circuit 7401. Suitable relays include solenoids. Suitable transistors include field-effect transistors (FET), MOSFET, and bipolar junction transistors (BJT). The boost current circuit 7406 may amplify the magnitude of the current corresponding to an individual circuit segment or circuit which requires more current draw during operation of the surgical instruments 6480 described herein. For example, an increase in current to the motor control circuit segment 7428 may be provided when a motor of the surgical instrument requires more input power. The increase in current provided to an individual circuit segment may cause a corresponding decrease in current of another circuit segment or circuit segments. Additionally or alternatively, the increase in current may correspond to voltage provided by an additional voltage source operating in conjunction with the battery.

The voltage control circuit 7408 is coupled to the battery 7310. The voltage control circuit 7408 is configured to provide voltage to or remove voltage from the plurality of circuit segments. The voltage control circuit 7408 is also configured to increase or reduce voltage provided to the plurality of circuit segments of the segmented circuit 7401. In various aspects, the voltage control circuit 7408 comprises a combinational logic circuit such as a multiplexer (MUX) to select inputs, a plurality of electronic switches, and a plurality of voltage converters. An electronic switch of the plurality of electronic switches may be configured to switch between an open and closed configuration to disconnect or connect an individual circuit segment to or from the battery. The plurality of electronic switches may be solid state devices such as transistors or other types of switches such as wireless switches, ultrasonic switches, accelerometers, inertial sensors, among others. The combinational logic circuit is configured to select an individual electronic switch for switching to an open configuration to enable application of voltage to the corresponding circuit segment. The combination logic circuit also is configured to select an individual electronic switch for switching to a closed configuration to enable removal of voltage from the corresponding circuit segment. By selecting a plurality of individual electronic switches, the combination logic circuit may implement a deenergization sequence or an energization sequence. The plurality of voltage converters may provide a stepped-up voltage or a stepped-down voltage to the plurality of circuit segments. The voltage control circuit 7408 may also comprise a microprocessor and memory device.

The safety controller 7410 is configured to perform safety checks for the circuit segments. In some aspects, the safety controller 7410 performs the safety checks when one or more individual circuit segments are in the operational mode. The safety checks may be performed to determine whether there are any errors or defects in the functioning or operation of the circuit segments. The safety controller 7410 may monitor one or more parameters of the plurality of circuit segments. The safety controller 7410 may verify the identity and operation of the plurality of circuit segments by comparing the one or more parameters with predefined parameters. For example, if an RF energy modality is selected, the safety controller 7410 may verify that an articulation parameter of the shaft matches a predefined articulation parameter to verify the operation of the RF energy modality of the surgical instrument 6480 described herein. In some aspects, the safety controller 7410 may monitor, by the sensors, a predetermined relationship between one or more properties of the surgical instrument to detect a fault. A fault may arise when the one or more properties are inconsistent with the predetermined relationship. When the safety controller 7410 determines that a fault exists, an error exists, or that some operation of the plurality of circuit segments was not verified, the safety controller 7410 prevents or disables operation of the particular circuit segment where the fault, error or verification failure originated.

The POST controller 7412 performs a POST to verify proper operation of the plurality of circuit segments. In some aspects, the POST is performed for an individual circuit segment of the plurality of circuit segments prior to the voltage control circuit 7408 applying a voltage to the individual circuit segment to transition the individual circuit segment from standby mode or sleep mode to operational mode. If the individual circuit segment does not pass the POST, the particular circuit segment does not transition from standby mode or sleep mode to operational mode. POST of the handle circuit segment 7416 may comprise, for example, testing whether the handle control sensors 7418 sense an actuation of a handle control of the surgical instrument 6480 described herein. In some aspects, the POST controller 7412 may transmit a signal to the accelerometer button sensor 7405 to verify the operation of the individual circuit segment as part of the POST. For example, after receiving the signal, the accelerometer button sensor 7405 may prompt a user of the surgical instrument to move the surgical instrument to a plurality of varying locations to confirm operation of the surgical instrument. The accelerometer button sensor 7405 may also monitor an output of a circuit segment or a circuit of a circuit segment as part of the POST. For example, the accelerometer button sensor 7405 can sense an incremental motor pulse generated by the motor 7432 to verify operation. A motor controller of the motor control circuit 7430 may be used to control the motor 7432 to generate the incremental motor pulse.

In various aspects, the surgical instrument 6480 described herein may comprise additional accelerometer button sensors. The POST controller 7412 may also execute a control program stored in the memory device of the voltage control circuit 7408. The control program may cause the POST controller 7412 to transmit a signal requesting a matching encrypted parameter from a plurality of circuit segments. Failure to receive a matching encrypted parameter from an individual circuit segment indicates to the POST controller 7412 that the corresponding circuit segment is damaged or malfunctioning. In some aspects, if the POST controller 7412 determines based on the POST that the processor is damaged or malfunctioning, the POST controller 7412 may send a signal to one or more secondary processors to cause one or more secondary processors to perform critical functions that the processor is unable to perform. In some aspects, if the POST controller 7412 determines based on the POST that one or more circuit segments do not operate properly, the POST controller 7412 may initiate a reduced performance mode of those circuit segments operating properly while locking out those circuit segments that fail POST or do not operate properly. A locked out circuit segment may function similarly to a circuit segment in standby mode or sleep mode.

The processor circuit segment 7414 comprises the processor and the volatile memory. The processor is configured to initiate an energization or a deenergization sequence. To initiate the energization sequence, the processor transmits an energizing signal to the voltage control circuit 7408 to cause the voltage control circuit 7408 to apply voltage to the plurality or a subset of the plurality of circuit segments in accordance with the energization sequence. To initiate the deenergization sequence, the processor transmits a deenergizing signal to the voltage control circuit 7408 to cause the voltage control circuit 7408 to remove voltage from the plurality or a subset of the plurality of circuit segments in accordance with the deenergization sequence.

The handle circuit segment 7416 comprises handle control sensors 7418. The handle control sensors 7418 may sense an actuation of one or more handle controls of the surgical instrument 6480 described herein. In various aspects, the one or more handle controls comprise a clamp control, a release button, an articulation switch, an energy activation button, and/or any other suitable handle control. The user may activate the energy activation button to select between an RF energy mode, an ultrasonic energy mode or a combination RF and ultrasonic energy mode. The handle control sensors 7418 may also facilitate attaching a modular handle to the surgical instrument. For example, the handle control sensors 7418 may sense proper attachment of the modular handle to the surgical instrument and indicate the sensed attachment to a user of the surgical instrument. The LCD display 7426 may provide a graphical indication of the sensed attachment. In some aspects, the handle control sensors 7418 senses actuation of the one or more handle controls. Based on the sensed actuation, the processor may initiate either an energization sequence or a deenergization sequence.

The communication circuit segment 7420 comprises a communication circuit 7422. The communication circuit 7422 comprises a communication interface to facilitate signal communication between the individual circuit segments of the plurality of circuit segments. In some aspects, the communication circuit 7422 provides a path for the modular components of the surgical instrument 6480 described herein to communicate electrically. For example, a modular shaft and a modular transducer, when attached together to the handle of the surgical instrument, can upload control programs to the handle through the communication circuit 7422.

The display circuit segment 7424 comprises a LCD display 7426. The LCD display 7426 may comprise a liquid crystal display screen, LED indicators, etc. In some aspects, the LCD display 7426 is an organic light-emitting diode (OLED) screen. A display may be placed on, embedded in, or located remotely from the surgical instrument 6480 described herein. For example, the display can be placed on the handle of the surgical instrument. The display is configured to provide sensory feedback to a user. In various aspects, the LCD display 7426 further comprises a backlight. In some aspects, the surgical instrument may also comprise audio feedback devices such as a speaker or a buzzer and tactile feedback devices such as a haptic actuator.

The motor control circuit segment 7428 comprises a motor control circuit 7430 coupled to a motor 7432. The motor 7432 is coupled to the processor by a driver and a transistor, such as a FET. In various aspects, the motor control circuit 7430 comprises a motor current sensor in signal communication with the processor to provide a signal indicative of a measurement of the current draw of the motor to the processor. The processor transmits the signal to the display. The display receives the signal and displays the measurement of the current draw of the motor 7432. The processor may use the signal, for example, to monitor that the current draw of the motor 7432 exists within an acceptable range, to compare the current draw to one or more parameters of the plurality of circuit segments, and to determine one or more parameters of a patient treatment site. In various aspects, the motor control circuit 7430 comprises a motor controller to control the operation of the motor. For example, the motor control circuit 7430 controls various motor parameters, such as by adjusting the velocity, torque and acceleration of the motor 7432. The adjusting is done based on the current through the motor 7432 measured by the motor current sensor.

In various aspects, the motor control circuit 7430 comprises a force sensor to measure the force and torque generated by the motor 7432. The motor 7432 is configured to actuate a mechanism of the surgical instruments 6480 described herein. For example, the motor 7432 is configured to control actuation of the shaft of the surgical instrument to realize clamping, rotation and articulation functionality. For example, the motor 7432 may actuate the shaft to realize a clamping motion with jaws of the surgical instrument. The motor controller may determine whether the material clamped by the jaws is tissue or metal. The motor controller may also determine the extent to which the jaws clamp the material. For example, the motor controller may determine how open or closed the jaws are based on the derivative of sensed motor current or motor voltage. In some aspects, the motor 7432 is configured to actuate the transducer to cause the transducer to apply torque to the handle or to control articulation of the surgical instrument. The motor current sensor may interact with the motor controller to set a motor current limit. When the current meets the predefined threshold limit, the motor controller initiates a corresponding change in a motor control operation. For example, exceeding the motor current limit causes the motor controller to reduce the current draw of the motor.

The energy treatment circuit segment 7434 comprises a RF amplifier and safety circuit 7436 and an ultrasonic signal generator circuit 7438 to implement the energy modular functionality of the surgical instrument 6480 described herein. In various aspects, the RF amplifier and safety circuit 7436 is configured to control the RF modality of the surgical instrument by generating an RF signal. The ultrasonic signal generator circuit 7438 is configured to control the ultrasonic energy modality by generating an ultrasonic signal. The RF amplifier and safety circuit 7436 and an ultrasonic signal generator circuit 7438 may operate in conjunction to control the combination RF and ultrasonic energy modality.

The shaft circuit segment 7440 comprises a shaft module controller 7442, a modular control actuator 7444, one or more end effector sensors 7446, and a non volatile memory 7448. The shaft module controller 7442 is configured to control a plurality of shaft modules comprising the control programs to be executed by the processor. The plurality of shaft modules implements a shaft modality, such as ultrasonic, combination ultrasonic and RF, RF I-blade, and RF-opposable jaw. The shaft module controller 7442 can select shaft modality by selecting the corresponding shaft module for the processor to execute. The modular control actuator 7444 is configured to actuate the shaft according to the selected shaft modality. After actuation is initiated, the shaft articulates the end effector according to the one or more parameters, routines or programs specific to the selected shaft modality and the selected end effector modality. The one or more end effector sensors 7446 located at the end effector may include force sensors, temperature sensors, current sensors or motion sensors. The one or more end effector sensors 7446 transmit data about one or more operations of the end effector, based on the energy modality implemented by the end effector. In various aspects, the energy modalities include an ultrasonic energy modality, a RF energy modality, or a combination of the ultrasonic energy modality and the RF energy modality. The non volatile memory 7448 stores the shaft control programs. A control program comprises one or more parameters, routines or programs specific to the shaft. In various aspects, the non volatile memory 7448 may be an ROM, EPROM, EEPROM or flash memory. The non volatile memory 7448 stores the shaft modules corresponding to the selected shaft of the surgical instrument 6480 described herein in. The shaft modules may be changed or upgraded in the non volatile memory 7448 by the shaft module controller 7442, depending on the surgical instrument shaft to be used in operation.

Figure 50:
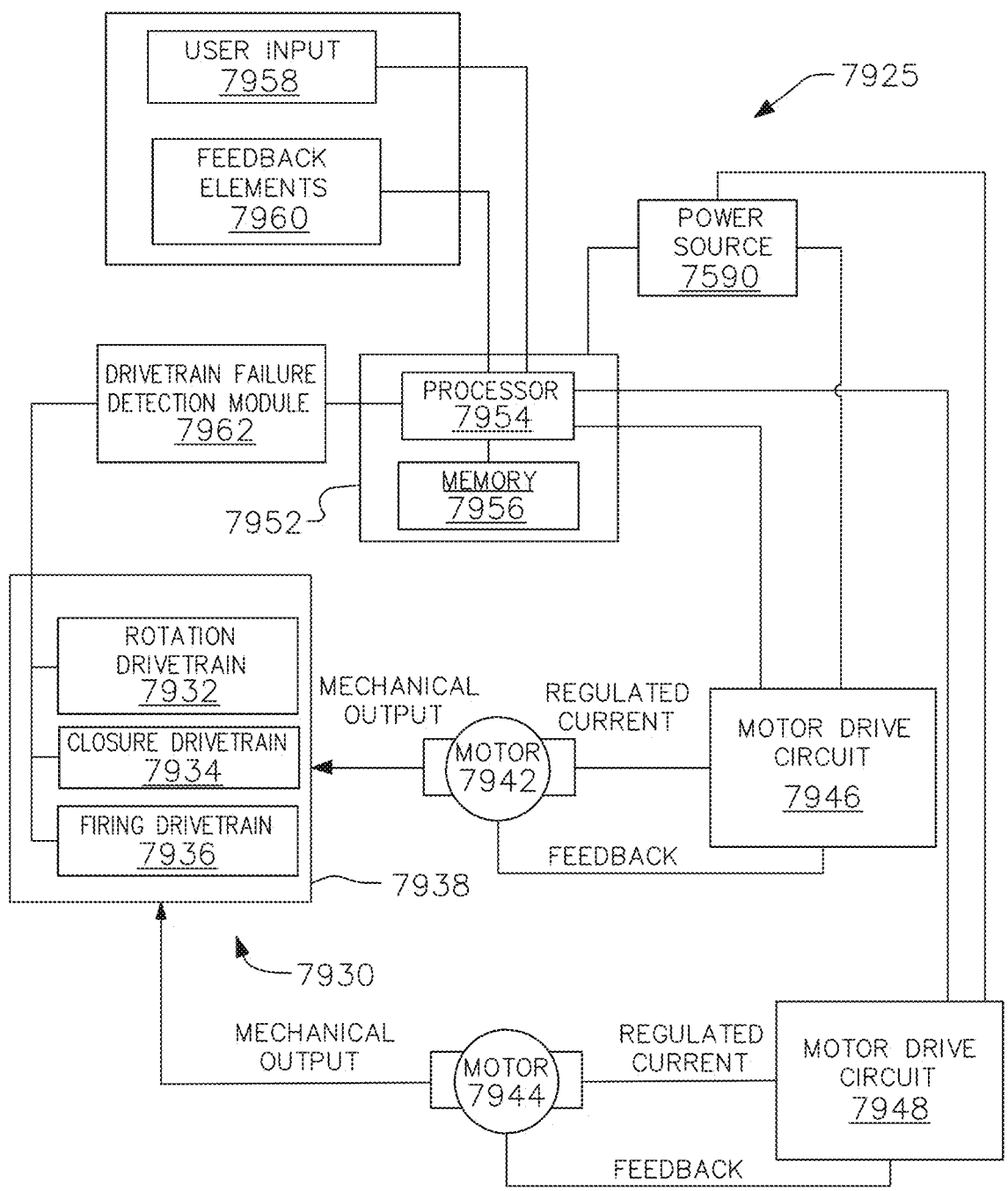
FIG. 50 is a circuit diagram of various components of a surgical instrument with motor control functions, in accordance with at least one aspect of the present disclosure.

FIG. 50 is a schematic diagram of a circuit 7925 of various components of a surgical instrument with motor control functions, in accordance with at least one aspect of the present disclosure. In various aspects, the surgical instrument 6480 described herein may include a drive mechanism 7930 which is configured to drive shafts and/or gear components in order to perform the various operations associated with the surgical instrument 6480. In one aspect, the drive mechanism 7930 includes a rotation drivetrain 7932 configured to rotate an end effector, for example, about a longitudinal axis relative to handle housing. The drive mechanism 7930 further includes a closure drivetrain 7934 configured to close a jaw member to grasp tissue with the end effector. In addition, the drive mechanism 7930 includes a firing drive train 7936 configured to open and close a clamp arm portion of the end effector to grasp tissue with the end effector.

The drive mechanism 7930 includes a selector gearbox assembly 7938 that can be located in the handle assembly of the surgical instrument. Proximal to the selector gearbox assembly 7938 is a function selection module which includes a first motor 7942 that functions to selectively move gear elements within the selector gearbox assembly 7938 to selectively position one of the drivetrains 7932, 7934, 7936 into engagement with an input drive component of an optional second motor 7944 and motor drive circuit 7946 (shown in dashed line to indicate that the second motor 7944 and motor drive circuit 7946 are optional components).

Still referring to FIG. 50, the motors 7942, 7944 are coupled to motor control circuits 7946, 7948, respectively, which are configured to control the operation of the motors 7942, 7944 including the flow of electrical energy from a power source 7950 to the motors 7942, 7944. The power source 7950 may be a DC battery (e.g., rechargeable lead-based, nickel-based, lithium-ion based, battery etc.) or any other power source suitable for providing electrical energy to the surgical instrument.

The surgical instrument further includes a microcontroller 7952 ("controller"). In certain instances, the controller 7952 may include a microprocessor 7954 ("processor") and one or more computer readable mediums or memory units 7956 ("memory"). In certain instances, the memory 7956 may store various program instructions, which when executed may cause the processor 7954 to perform a plurality of functions and/or calculations described herein. The power source 7950 can be configured to supply power to the controller 7952, for example.

The processor 7954 may be in communication with the motor control circuit 7946. In addition, the memory 7956 may store program instructions, which when executed by the processor 7954 in response to a user input 7958 or feedback elements 7960, may cause the motor control circuit 7946 to motivate the motor 7942 to generate at least one rotational motion to selectively move gear elements within the selector gearbox assembly 7938 to selectively position one of the drivetrains 7932, 7934, 7936 into engagement with the input drive component of the second motor 7944. Furthermore, the processor 7954 can be in communication with the motor control circuit 7948. The memory 7956 also may store program instructions, which when executed by the processor 7954 in response to a user input 7958, may cause the motor control circuit 7948 to motivate the motor 7944 to generate at least one rotational motion to drive the drivetrain engaged with the input drive component of the second motor 7948, for example.

The controller 7952 and/or other controllers of the present disclosure may be implemented using integrated and/or discrete hardware elements, software elements, and/or a combination of both. Examples of integrated hardware elements may include processors, microprocessors, microcontrollers, integrated circuits, ASICs, PLDs, DSPs, FPGAs, logic gates, registers, semiconductor devices, chips, microchips, chip sets, microcontrollers, system on a chip (SoC), and/or single in-line package (SIP). Examples of discrete hardware elements may include circuits and/or circuit elements such as logic gates, field effect transistors, bipolar transistors, resistors, capacitors, inductors, and/or relays. In certain instances, the controller 7952 may include a hybrid circuit comprising discrete and integrated circuit elements or components on one or more substrates, for example.

In certain instances, the controller 7952 and/or other controllers of the present disclosure may be an LM 4F230H5QR, available from Texas Instruments, for example. In certain instances, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle SRAM, internal ROM loaded with StellarisWare® software, 2 KB EEPROM, one or more PWM modules, one or more QEI analog, one or more 12-bit ADC with 12 analog input channels, among other features that are readily available. Other microcontrollers may be readily substituted for use with the present disclosure. Accordingly, the present disclosure should not be limited in this context.

In various instances, one or more of the various steps described herein can be performed by a finite state machine comprising either a combinational logic circuit or a sequential logic circuit, where either the combinational logic circuit or the sequential logic circuit is coupled to at least one memory circuit. The at least one memory circuit stores a current state of the finite state machine. The combinational or sequential logic circuit is configured to cause the finite state machine to the steps. The sequential logic circuit may be synchronous or asynchronous. In other instances, one or more of the various steps described herein can be performed by a circuit that includes a combination of the processor 7958 and the finite state machine, for example.

In various instances, it can be advantageous to be able to assess the state of the functionality of a surgical instrument to ensure its proper function. It is possible, for example, for the drive mechanism, as explained above, which is configured to include various motors, drivetrains, and/or gear components in order to perform the various operations of the surgical instrument, to wear out over time. This can occur through normal use, and in some instances the drive mechanism can wear out faster due to abuse conditions. In certain instances, a surgical instrument can be configured to perform self-assessments to determine the state, e.g. health, of the drive mechanism and it various components.

For example, the self-assessment can be used to determine when the surgical instrument is capable of performing its function before a re-sterilization or when some of the components should be replaced and/or repaired. Assessment of the drive mechanism and its components, including but not limited to the rotation drivetrain 7932, the closure drivetrain 7934, and/or the firing drivetrain 7936, can be accomplished in a variety of ways. The magnitude of deviation from a predicted performance can be used to determine the likelihood of a sensed failure and the severity of such failure. Several metrics can be used including: Periodic analysis of repeatably predictable events, Peaks or drops that exceed an expected threshold, and width of the failure.

In various instances, a signature waveform of a properly functioning drive mechanism or one or more of its components can be employed to assess the state of the drive mechanism or the one or more of its components. One or more vibration sensors can be arranged with respect to a properly functioning drive mechanism or one or more of its components to record various vibrations that occur during operation of the properly functioning drive mechanism or the one or more of its components. The recorded vibrations can be employed to create the signature waveform. Future waveforms can be compared against the signature waveform to assess the state of the drive mechanism and its components.

Still referring to FIG. 50, the surgical instrument 7930 includes a drivetrain failure detection module 7962 configured to record and analyze one or more acoustic outputs of one or more of the drivetrains 7932, 7934, 7936. The processor 7954 can be in communication with or otherwise control the module 7962. As described below in greater detail, the module 7962 can be embodied as various means, such as circuitry, hardware, a computer program product comprising a computer readable medium (for example, the memory 7956) storing computer readable program instructions that are executable by a processing device (for example, the processor 7954), or some combination thereof. In some aspects, the processor 36 can include, or otherwise control the module 7962.

Figure 51:
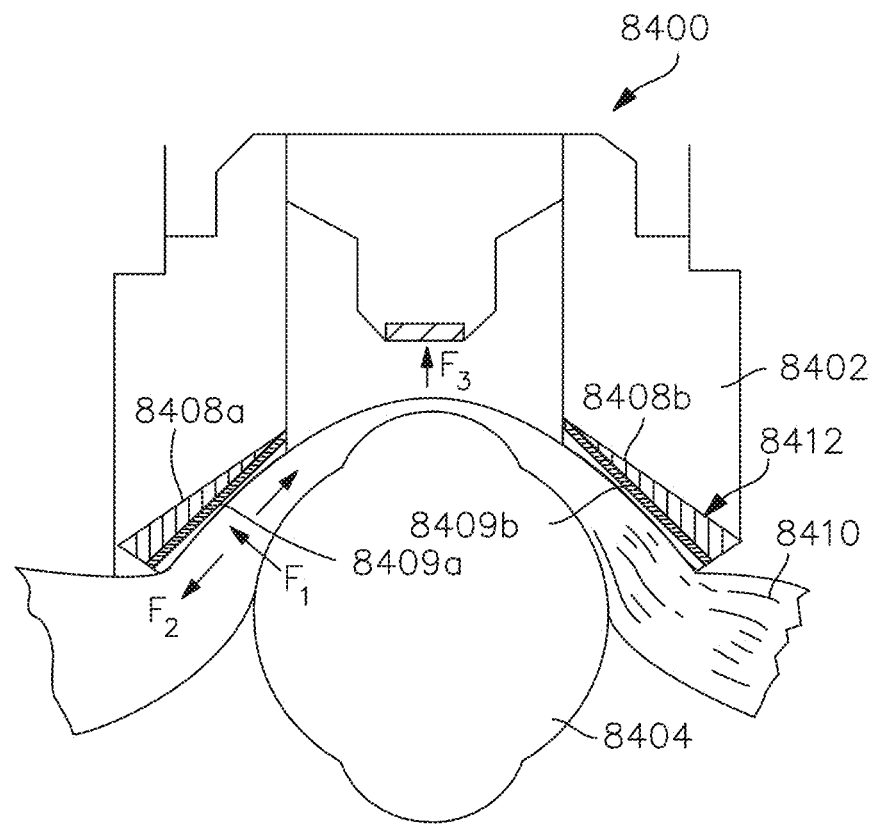
FIG. 51 illustrates one aspect of an end effector comprising RF data sensors located on the jaw member, in accordance with at least one aspect of the present disclosure.

Turning now to FIG. 51, the end effector 8400 comprises RF data sensors 8406, 8408*a*, 8408*b* located on the jaw member 8402. The end effector 8400 comprises a jaw member 8402 and an ultrasonic blade 8404. The jaw member 8402 is shown clamping tissue 8410 located between the jaw member 8402 and the ultrasonic blade 8404. A first sensor 8406 is located in a center portion of the jaw member 8402. Second and third sensors 8408*a*, 8408*b* are located on lateral portions of the jaw member 8402. The sensors 8406, 8408*a*, 8408*b* are mounted or formed integrally with a flexible circuit 8412 (shown more particularly in FIG. 52) configured to be fixedly mounted to the jaw member 8402.

The end effector 8400 is an example end effector for a surgical instrument. The sensors 8406, 8408*a*, 8408*b* are electrically connected to a control circuit such as the control circuit 7400 (FIG. 63) via interface circuits. The sensors 8406, 8408*a*, 8408*b* are battery powered and the signals generated by the sensors 8406, 8408*a*, 8408*b* are provided to analog and/or digital processing circuits of the control circuit.

In one aspect, the first sensor 8406 is a force sensor to measure a normal force F3 applied to the tissue 8410 by the jaw member 8402. The second and third sensors 8408*a*, 8408*b* include one or more elements to apply RF energy to the tissue 8410, measure tissue impedance, down force F1, transverse forces F2, and temperature, among other parameters. Electrodes 8409*a*, 8409*b* are electrically coupled to an energy source and apply RF energy to the tissue 8410. In one aspect, the first sensor 8406 and the second and third sensors 8408*a*, 8408*b* are strain gauges to measure force or force per unit area. It will be appreciated that the measurements of the down force F1, the lateral forces F2, and the normal force F3 may be readily converted to pressure by determining the surface area upon which the force sensors 8406, 8408*a*, 8408*b* are acting upon. Additionally, as described with particularity herein, the flexible circuit 8412 may comprise temperature sensors embedded in one or more layers of the flexible circuit 8412. The one or more temperature sensors may be arranged symmetrically or asymmetrically and provide tissue 8410 temperature feedback to control circuits of an ultrasonic drive circuit and an RF drive circuit.

Figure 52:
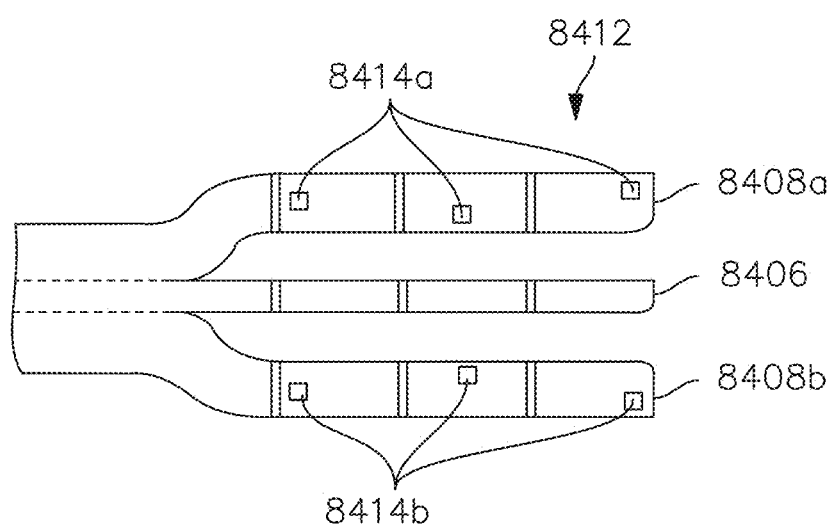
FIG. 52 illustrates one aspect of the flexible circuit shown in FIG. 51 in which the sensors may be mounted to or formed integrally therewith, in accordance with at least one aspect of the present disclosure.

FIG. 52 illustrates one aspect of the flexible circuit 8412 shown in FIG. 51 in which the sensors 8406, 8408*a*, 8408*b* may be mounted to or formed integrally therewith. The flexible circuit 8412 is configured to fixedly attach to the jaw member 8402. As shown particularly in FIG. 52, asymmetric temperature sensors 8414*a*, 8414*b* are mounted to the flexible circuit 8412 to enable measuring the temperature of the tissue 8410 (FIG. 51).

Figure 53:
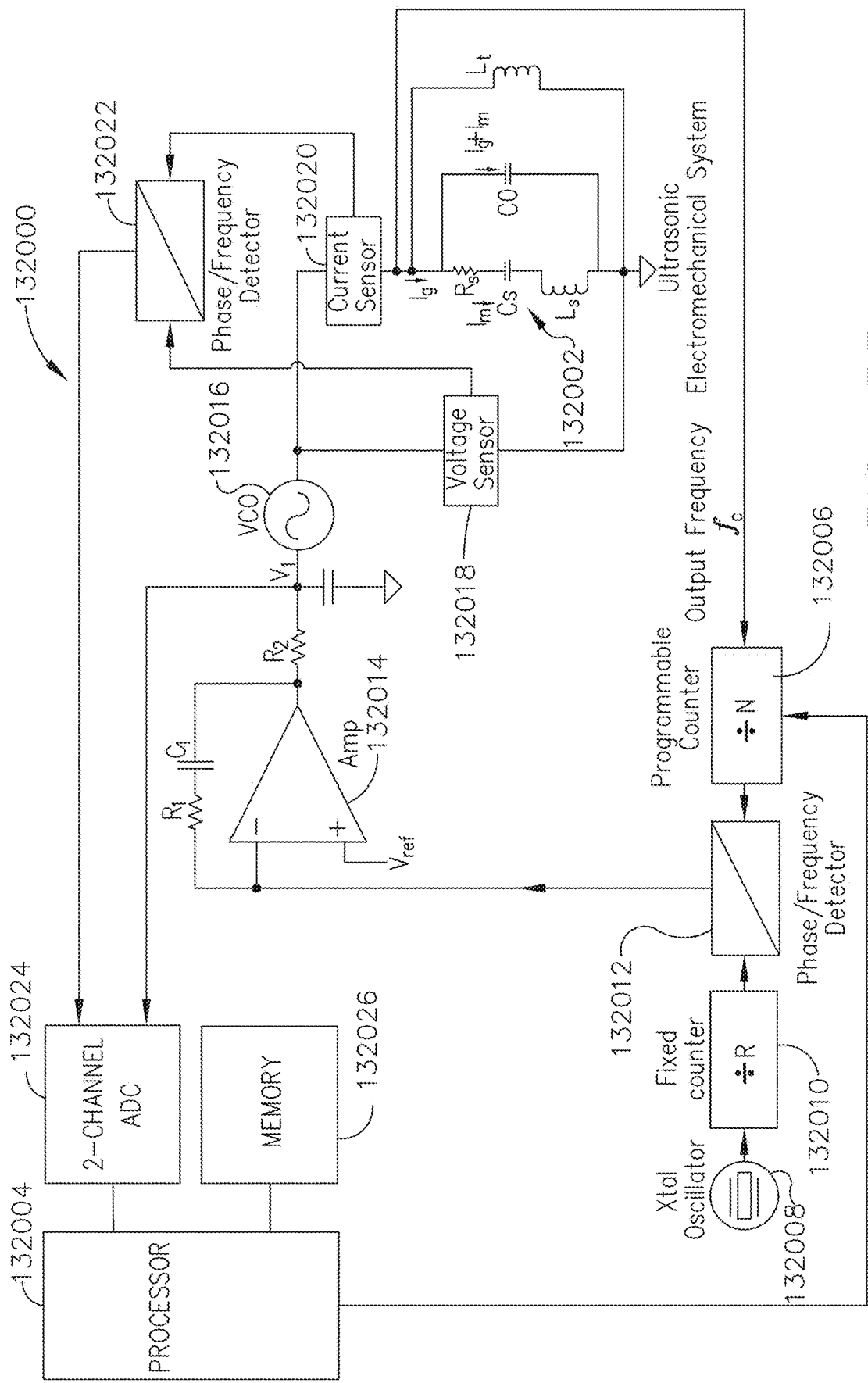
FIG. 53 is an alternative system for controlling the frequency of an ultrasonic electromechanical system and detecting the impedance thereof, in accordance with at least one aspect of the present disclosure.

FIG. 53 is an alternative system 132000 for controlling the frequency of an ultrasonic electromechanical system 132002 and detecting the impedance thereof, in accordance with at least one aspect of the present disclosure. The system 132000 may be incorporated into a generator. A processor 132004 coupled to a memory 132026 programs a programmable counter 132006 to tune to the output frequency $f_o$ of the ultrasonic electromechanical system 132002. The input frequency is generated by a crystal oscillator 132008 and is input into a fixed counter 132010 to scale the frequency to a suitable value. The outputs of the fixed counter 132010 and the programmable counter 132006 are applied to a phase/frequency detector 132012. The output of the phase/frequency detector 132012 is applied to an amplifier/active filter circuit 132014 to generate a tuning voltage $V_t$ that is applied to a voltage controlled oscillator 132016 (VCO). The VCO 132016 applies the output frequency $f_o$ to an ultrasonic transducer portion of the ultrasonic electromechanical system 132002, shown here modeled as an equivalent electrical circuit. The voltage and current signals applied to the ultrasonic transducer are monitored by a voltage sensor 132018 and a current sensor 132020.

The outputs of the voltage and current sensors 132018, 132020 are applied to another phase/frequency detector 132022 to determine the phase angle between the voltage and current as measured by the voltage and current sensors 132018, 132020. The output of the phase/frequency detector 132022 is applied to one channel of a high speed analog to digital converter 132024 (ADC) and is provided to the processor 132004 therethrough. Optionally, the outputs of the voltage and current sensors 132018, 132020 may be applied to respective channels of the two-channel ADC 132024 and provided to the processor 132004 for zero crossing, FFT, or other algorithm described herein for determining the phase angle between the voltage and current signals applied to the ultrasonic electromechanical system 132002.

Optionally the tuning voltage $V_t$, which is proportional to the output frequency $f_o$, may be fed back to the processor 132004 via the ADC 132024. This provides the processor 132004 with a feedback signal proportional to the output frequency $f_o$ and can use this feedback to adjust and control the output frequency $f_o$.

Estimating the State of the Jaw (Pad Burn Through, Staples, Broken Blade, Bone in Jaw, Tissue in Jaw)

A challenge with ultrasonic energy delivery is that ultrasonic acoustics applied on the wrong materials or the wrong tissue can result in device failure, for example, clamp arm pad burn through or ultrasonic blade breakage. It is also desirable to detect what is located in the jaws of an end effector of an ultrasonic device and the state of the jaws without adding additional sensors in the jaws. Locating sensors in the jaws of an ultrasonic end effector poses reliability, cost, and complexity challenges.

Ultrasonic spectroscopy smart blade algorithm techniques may be employed for estimating the state of the jaw (clamp arm pad burn through, staples, broken blade, bone in jaw, tissue in jaw, back-cutting with jaw closed, etc.) based on the impedance $$Z_g(t) = \frac{V_g(t)}{I_g(t)}$$

of an ultrasonic transducer configured to drive an ultrasonic transducer blade, in accordance with at least one aspect of the present disclosure. The impedance $Z_g(t)$, magnitude |Z|, and phase φ are plotted as a function of frequency f.

Dynamic mechanical analysis (DMA), also known as dynamic mechanical spectroscopy or simply mechanical spectroscopy, is a technique used to study and characterize materials. A sinusoidal stress is applied to a material, and the strain in the material is measured, allowing the determination of the complex modulus of the material. The spectroscopy as applied to ultrasonic devices includes exciting the tip of the ultrasonic blade with a sweep of frequencies (compound signals or traditional frequency sweeps) and measuring the resulting complex impedance at each frequency. The complex impedance measurements of the ultrasonic transducer across a range of frequencies are used in a classifier or model to infer the characteristics of the ultrasonic end effector. In one aspect, the present disclosure provides a technique for determining the state of an ultrasonic end effector (clamp arm, jaw) to drive automation in the ultrasonic device (such as disabling power to protect the device, executing adaptive algorithms, retrieving information, identifying tissue, etc.).

Figure 54:
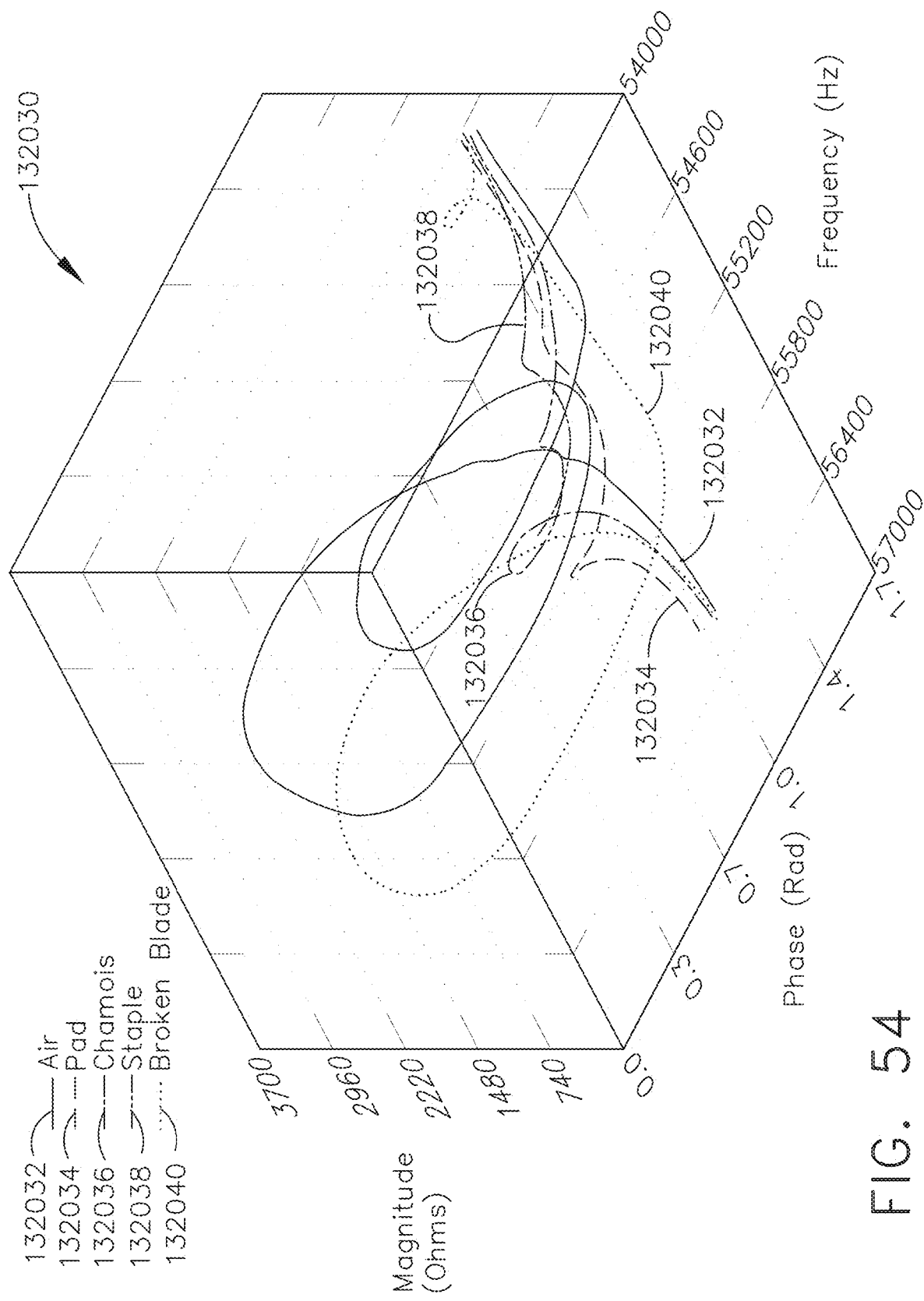
FIG. 54 is a spectra of the same ultrasonic device with a variety of different states and conditions of the end effector where phase and magnitude of the impedance of an ultrasonic transducer are plotted as a function of frequency, in accordance with at least one aspect of the present disclosure.

FIG. 54 is a spectra 132030 of an ultrasonic device with a variety of different states and conditions of the end effector where the impedance $Z_g(t)$, magnitude |Z|, and phase φ are plotted as a function of frequency f, in accordance with at least one aspect of the present disclosure. The spectra 132030 is plotted in three-dimensional space where frequency (Hz) is plotted along the x-axis, phase (Rad) is plotted along the y-axis, and magnitude (Ohms) is plotted along the z-axis.

Spectral analysis of different jaw bites and device states produces different complex impedance characteristic patterns (fingerprints) across a range of frequencies for different conditions and states. Each state or condition has a different characteristic pattern in 3D space when plotted. These characteristic patterns can be used to estimate the condition and state of the end effector. FIG. 54 shows the spectra for air 132032, clamp arm pad 132034, chamois 132036, staple 132038, and broken blade 132040. The chamois 132036 may be used to characterize different types of tissue.

The spectra 132030 can be evaluated by applying a low-power electrical signal across the ultrasonic transducer to produce a non-therapeutic excitation of the ultrasonic blade. The low-power electrical signal can be applied in the form of a sweep or a compound Fourier series to measure the impedance $$Z_g(t) = \frac{V_g(t)}{I_g(t)}$$

across the ultrasonic transducer at a range of frequencies in series (sweep) or in parallel (compound signal) using an FFT.

Methods of Classification of New Data

For each characteristic pattern, a parametric line can be fit to the data used for training using a polynomial, a Fourier series, or any other form of parametric equation as may be dictated by convenience. A new data point is then received and is classified by using the Euclidean perpendicular distance from the new data point to the trajectory that has been fitted to the characteristic pattern training data. The perpendicular distance of the new data point to each of the trajectories (each trajectory representing a different state or condition) is used to assign the point to a state or condition.

The probability distribution of distance of each point in the training data to the fitted curve can be used to estimate the probability of a correctly classified new data point. This essentially constructs a two-dimensional probability distribution in a plane perpendicular to the fitted trajectory at each new data point of the fitted trajectory. The new data point can then be included in the training set based on its probability of correct classification to make an adaptive, learning classifier that readily detects high-frequency changes in states but adapts to slow occurring deviations in system performance, such as a device getting dirty or the pad wearing out.

Figure 55:
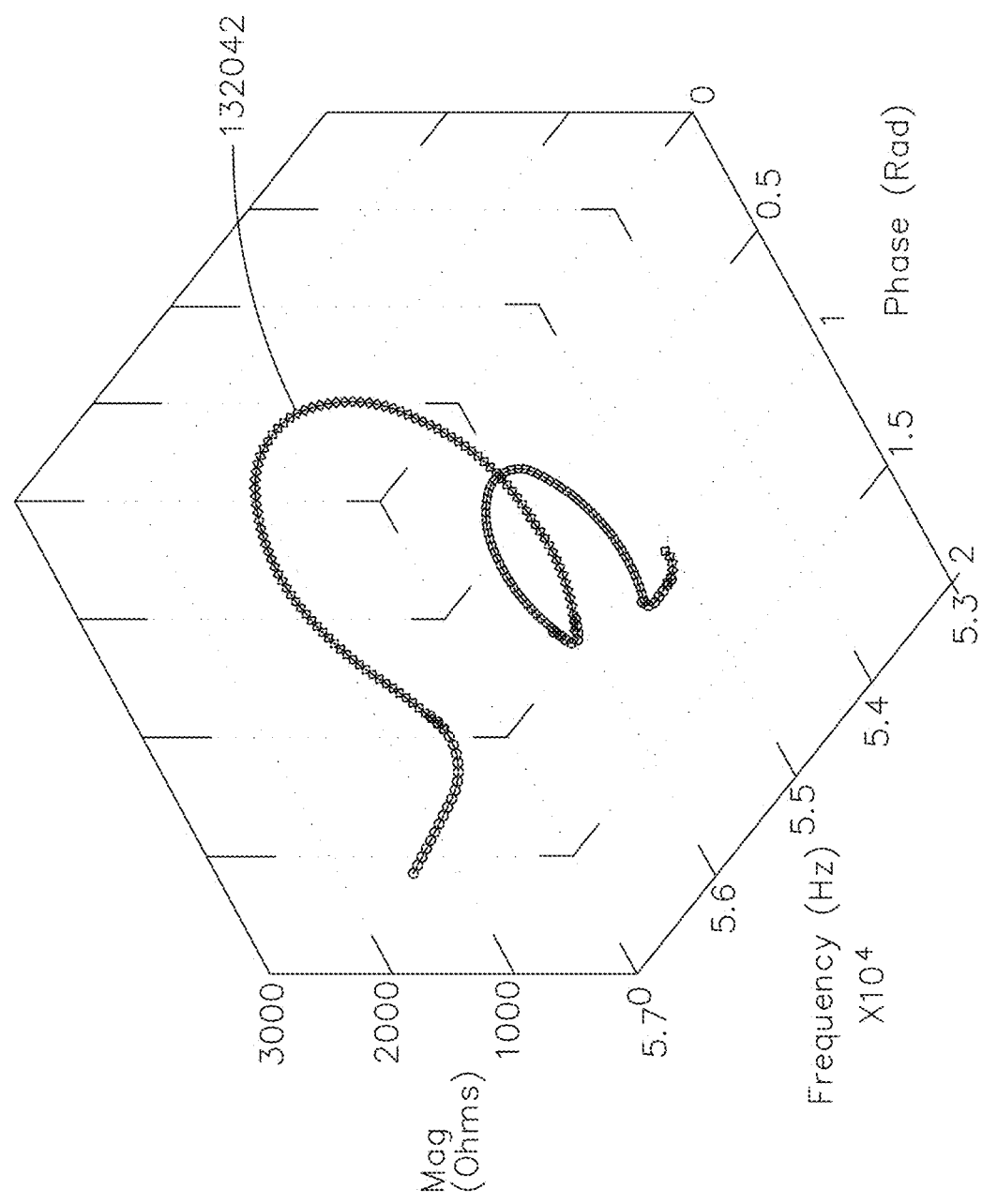
FIG. 55 is a graphical representation of a plot of a set of 3D training data S, where ultrasonic transducer impedance magnitude and phase are plotted as a function of frequency, in accordance with at least one aspect of the present disclosure.

FIG. 55 is a graphical representation of a plot 132042 of a set of 3D training data set (S), where ultrasonic transducer impedance $Z_g(t)$, magnitude |Z|, and phase φ are plotted as a function of frequency f, in accordance with at least one aspect of the present disclosure. The 3D training data set (S) plot 132042 is graphically depicted in three-dimensional space where phase (Rad) is plotted along the x-axis, frequency (Hz) is plotted along the y-axis, magnitude (Ohms) is plotted along the z-axis, and a parametric Fourier series is fit to the 3D training data set (S). A methodology for classifying data is based on the 3D training data set (S0 is used to generate the plot 132042).

The parametric Fourier series fit to the 3D training data set (S) is defined by:

$$\vec{p} = \vec{a}_0 + \sum_{n=1}^{\infty}\left(\vec{a}_n \cos\frac{n\pi t}{L} + \vec{b}_n \sin\frac{n\pi t}{L}\right)$$

For a new point $\vec{z}$, the perpendicular distance from $\vec{p}$ to $\vec{z}$ is found by:

$$D = \|\vec{p} - \vec{z}\|$$

When:

$$\frac{\partial D}{\partial T} = 0$$

Then:

$$D = D_\perp$$

A probability distribution of D can be used to estimate the probability of a data point z belonging to the group S.

Control

Based on the classification of data measured before, during, or after activation of the ultrasonic transducer/ultrasonic blade, a variety of automated tasks and safety measures can be implemented. Similarly, the state of the tissue located in the end effector and temperature of the ultrasonic blade also can be inferred to some degree, and used to better inform the user of the state of the ultrasonic device or protect critical structures, etc. Temperature control of an ultrasonic blade is described in commonly owned U.S. Provisional Patent Application Ser. No. 62/640,417, filed Mar. 8, 2018, titled TEMPERATURE CONTROL IN ULTRASONIC DEVICE AND CONTROL SYSTEM THEREFOR, which is incorporated herein by reference in its entirety.

Similarly, power delivery can be reduced when there is a high probability that the ultrasonic blade is contacting the clamp arm pad (e.g., without tissue in between) or if there is a probability that the ultrasonic blade has broken or that the ultrasonic blade is touching metal (e.g., a staple). Furthermore, back-cutting can be disallowed if the jaw is closed and no tissue is detected between the ultrasonic blade and the clamp arm pad.

Integration of Other Data to Improve Classification

This system can be used in conjunction with other information provided by sensors, the user, metrics on the patient, environmental factors, etc., by combing the data from this process with the aforementioned data using probability functions and a Kalman filter. The Kalman filter determines the maximum likelihood of a state or condition occurring given a plethora of uncertain measurements of varying confidence. Since this method allows for an assignment of probability to a newly classified data point, this algorithm's information can be implemented with other measures or estimates in a Kalman filter.

Figure 56:
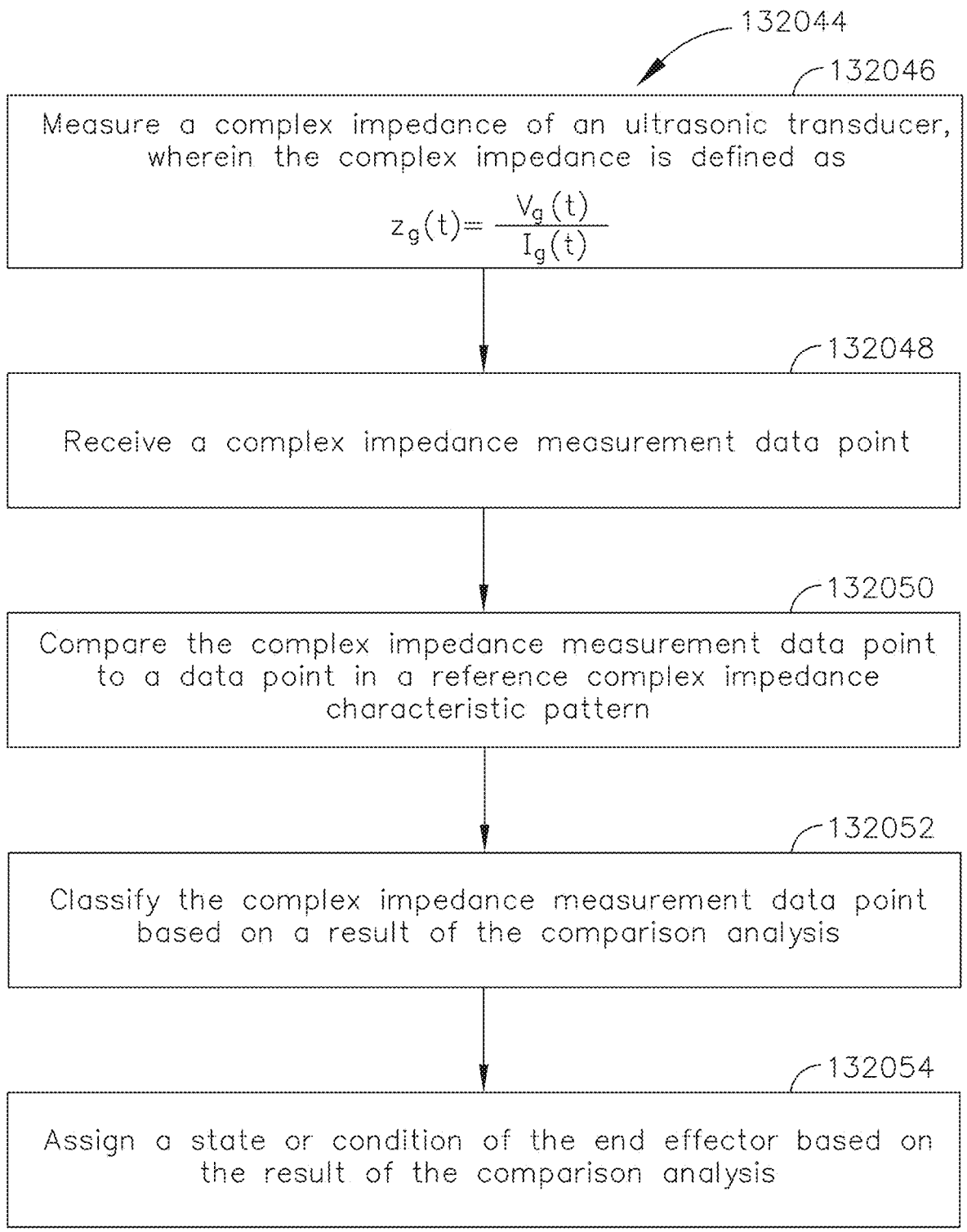
FIG. 56 is a logic flow diagram depicting a control program or a logic configuration to determine jaw conditions based on the complex impedance characteristic pattern (fingerprint), in accordance with at least one aspect of the present disclosure.

FIG. 56 is a logic flow diagram 132044 depicting a control program or a logic configuration to determine jaw conditions based on the complex impedance characteristic pattern (fingerprint), in accordance with at least one aspect of the present disclosure. Prior to determining jaw conditions based on the complex impedance characteristic pattern (fingerprint), a database is populated with reference complex impedance characteristic patterns or a training data sets (S) that characterize various jaw conditions, including, without limitation, air 132032, clamp arm pad 132034, chamois 132036, staple 132038, broken blade 132040, as shown in FIG. 82, and a variety of tissue types and conditions. The chamois dry or wet, full byte or tip, may be used to characterize different types of tissue. The data points used to generate reference complex impedance characteristic patterns or a training data set (S) are obtained by applying a sub-therapeutic drive signal to the ultrasonic transducer, sweeping the driving frequency over a predetermined range of frequencies from below resonance to above resonance, measuring the complex impedance at each of the frequencies, and recording the data points. The data points are then fit to a curve using a variety of numerical methods including polynomial curve fit, Fourier series, and/or parametric equation. A parametric Fourier series fit to the reference complex impedance characteristic patterns or a training data set (S) is described herein.

Once the reference complex impedance characteristic patterns or a training data sets (S) are generated, the ultrasonic instrument measures new data points, classifies the new points, and determines whether the new data points should be added to the reference complex impedance characteristic patterns or a training data sets (S).

Turning now to the logic flow diagram of FIG. 56, in one aspect, the control circuit measures 132046 a complex impedance of an ultrasonic transducer, wherein the complex impedance is defined as $$Z_g(t) = \frac{V_g(t)}{I_g(t)}.$$

The control circuit receives 132048 a complex impedance measurement data point and compares 132050 the complex impedance measurement data point to a data point in a reference complex impedance characteristic pattern. The control circuit classifies 132052 the complex impedance measurement data point based on a result of the comparison analysis and assigns 132054 a state or condition of the end effector based on the result of the comparison analysis.

In one aspect, the control circuit receives the reference complex impedance characteristic pattern from a database or memory coupled to the processor. In one aspect, the control circuit generates the reference complex impedance characteristic pattern as follows. A drive circuit coupled to the control circuit applies a nontherapeutic drive signal to the ultrasonic transducer starting at an initial frequency, ending at a final frequency, and at a plurality of frequencies therebetween. The control circuit measures the impedance of the ultrasonic transducer at each frequency and stores a data point corresponding to each impedance measurement. The control circuit curve fits a plurality of data points to generate a three-dimensional curve of representative of the reference complex impedance characteristic pattern, wherein the magnitude $|Z|$ and phase $\varphi$ are plotted as a function of frequency f. The curve fitting includes a polynomial curve fit, a Fourier series, and/or a parametric equation.

In one aspect, the control circuit receives a new impedance measurement data point and classifies the new impedance measurement data point using a Euclidean perpendicular distance from the new impedance measurement data point to a trajectory that has been fitted to the reference complex impedance characteristic pattern. The control circuit estimates a probability that the new impedance measurement data point is correctly classified. The control circuit adds the new impedance measurement data point to the reference complex impedance characteristic pattern based on the probability of the estimated correct classification of the new impedance measurement data point. In one aspect, the control circuit classifies data based on a training data set (S), where the training data set (S) comprises a plurality of complex impedance measurement data, and curve fits the training data set (S) using a parametric Fourier series, wherein S is defined herein and wherein the probability distribution is used to estimate the probability of the new impedance measurement data point belonging to the group S.

State of Jaw Classifier Based on Model

There has been an existing interest in classifying matter located within the jaws of an ultrasonic device including tissue types and condition. In various aspects, it can be shown that with high data sampling and sophisticated pattern recognition this classification is possible. The approach is based on impedance as a function of frequency, where magnitude, phase, and frequency are plotted in 3D the patterns look like ribbons as shown in FIGS. 54 and 55 and the logic flow diagram of FIG. 56. This disclosure provides an alternative smart blade algorithm approach that is based on a well-established model for piezoelectric transducers.

Figure 57:
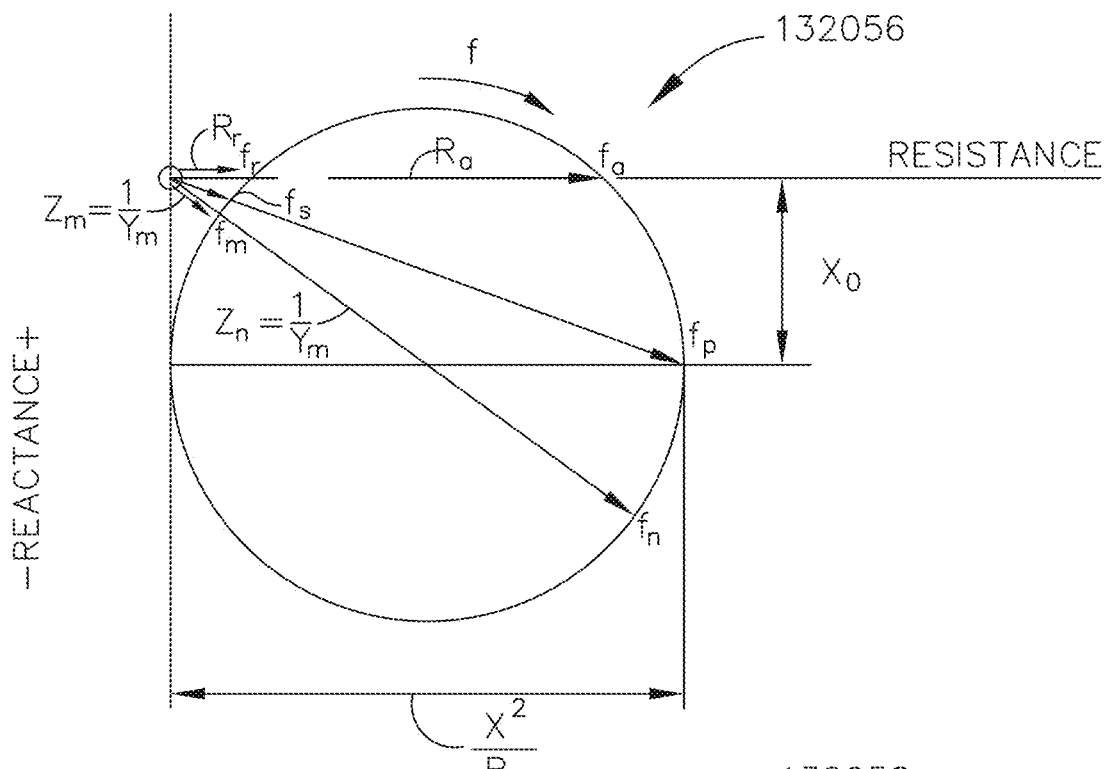
FIG. 57 is a circle plot of complex impedance plotted as an imaginary component versus real components of a piezoelectric vibrator, in accordance with at least one aspect of the present disclosure.
Figure 58:
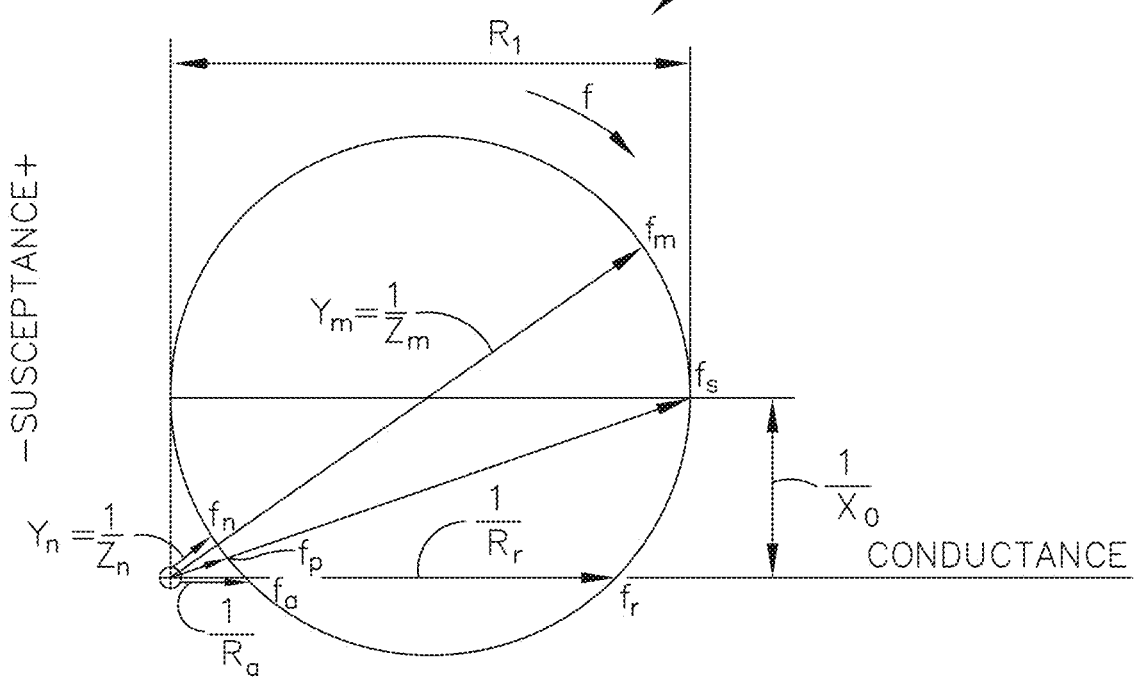
FIG. 58 is a circle plot of complex admittance plotted as an imaginary component versus real components of a piezoelectric vibrator, in accordance with at least one aspect of the present disclosure.

By way of example, the equivalent electrical lumped parameter model is known to be an accurate model of the physical piezoelectric transducer. It is based on the Mittag-Leffler expansion of a tangent near a mechanical resonance. When the complex impedance or the complex admittance is plotted as an imaginary component versus a real component, circles are formed. FIG. 57 is a circle plot 132056 of complex impedance plotted as an imaginary component versus real components of a piezoelectric vibrator, in accordance with at least one aspect of the present disclosure. FIG. 58 is a circle plot 132058 of complex admittance plotted as an imaginary component versus real components of a piezoelectric vibrator, in accordance with at least one aspect of the present disclosure. The circles depicted in FIGS. 57 and 58 are taken from the IEEE 177 Standard, which is incorporated herein by reference in its entirety. Tables 1-4 are taken from the IEEE 177 Standard and disclosed herein for completeness.

The circle is created as the frequency is swept from below resonance to above resonance. Rather than stretching the circle out in 3D, a circle is identified and the radius (r) and offsets (a, b) of the circle are estimated. These values are then compared with established values for given conditions. These conditions may be: 1) open nothing in jaws, 2) tip bite 3) full bite and staple in jaws. If the sweep generates multiple resonances, circles of different characteristics will be present for each resonance. Each circle will be drawn out before the next if the resonances are separated. Rather than fitting a 3D curve with a series approximation, the data is fitted with a circle. The radius (r) and offsets (a, b) can be calculated using a processor programmed to execute a variety of mathematical or numerical techniques described below. These values may be estimated by capturing an image of a circle and, using image processing techniques, the radius (r) and offsets (a, b) that define the circle are estimated.

Figure 59:
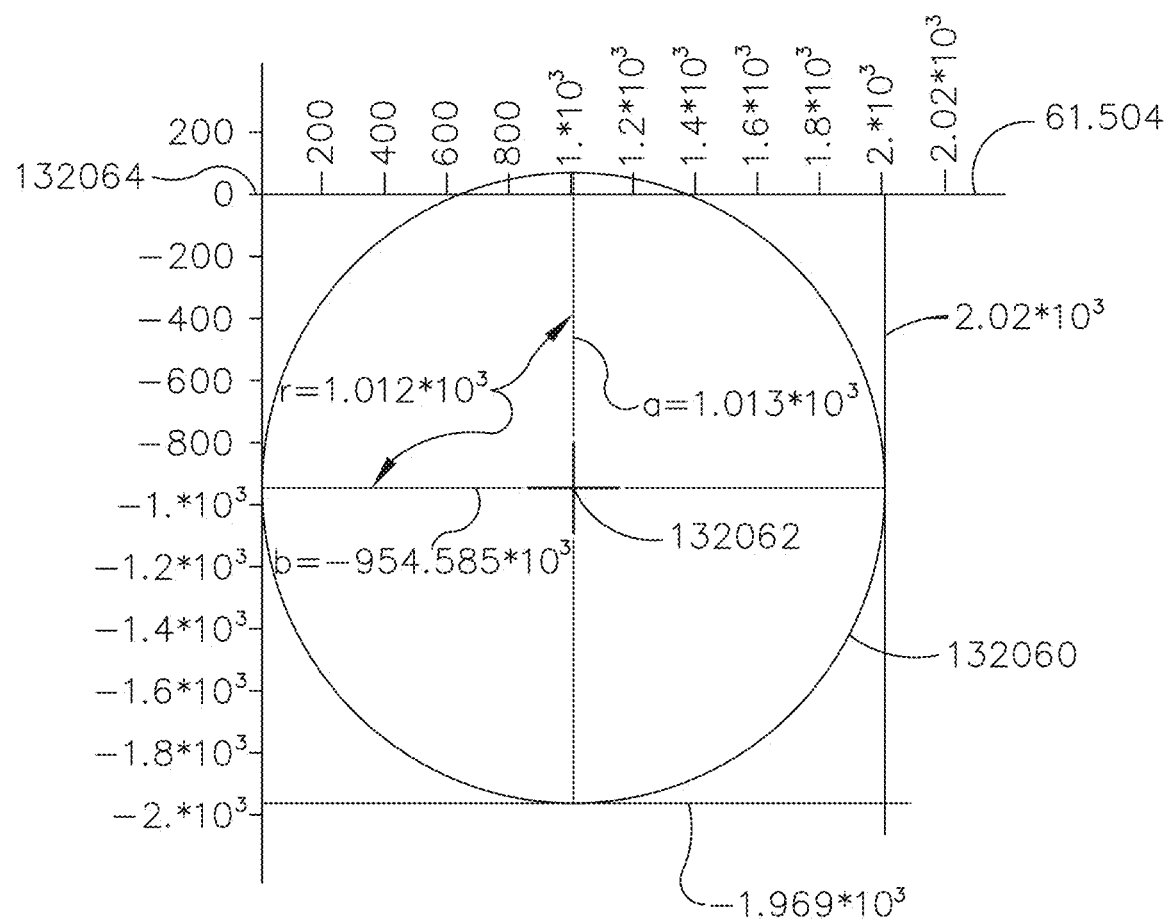
FIG. 59 is a circle plot of complex admittance for a 55.5 kHz ultrasonic piezoelectric transducer.

FIG. 59 is a circle plot 132060 of complex admittance for a 55.5 kHz ultrasonic piezoelectric transducer for lumped parameters inputs and outputs specified hereinbelow. Values for a lumped parameter model were used to generate the complex admittance. A moderate load was applied in the model. The obtained admittance circle generated in MathCad is shown in FIG. 59. The circle plot 132060 is formed when the frequency is swept from 54 to 58 kHz.

The lumped parameter input values are:
Co=3.0 nF
Cs=8.22 pF
Ls=1.0 H
Rs=450Ω

The outputs of the model based on the inputs are:

$$am = \frac{D \cdot C - B \cdot C}{A \cdot C - B^2} = 1.013 \cdot 10^3$$

$$bm = \frac{A \cdot E - B \cdot D}{A \cdot C - B^2} = -954.585$$

$$rm = \frac{1}{fpts}\left(\sum_i^{fpts} \sqrt[2]{((Zout_{1,i} = am)^2 + (Zout_{2,i} - bm)^2)}\right) = 1.012 \cdot 10^3$$

The output values are used to plot the circle plot 132060 shown in FIG. 59. The circle plot 132060 has a radius (r) and the center 132062 is offset (a, b) from the origin 132064 as follows:

$$r = 1.012 * 10^3$$
$$a = 1.013 * 10^3$$
$$b = -954.585$$

The summations A-E specified below are needed to estimate the circle plot 132060 plot for the example given in FIG. 59, in accordance with at least one aspect of the present disclosure. Several algorithms exist to calculate a fit to a circle. A circle is defined by its radius (r) and offsets (a, b) of the center from the origin:

$$r^2 = (x - a)^2 + (y - b)^2$$

The modified least squares method (Umbach and Jones) is convenient in that there a simple close formed solution for a, b, and r.

$$\hat{a} = \frac{DC - BE}{AC - B^2}$$

$$\hat{b} = \frac{AE - BD}{AC - B^2}$$

$$\hat{r} = \frac{1}{n}\sum_{i=1}^{n}\sqrt{(x_i - \hat{a})^2 + (y_i - \hat{b})^2}$$

The caret symbol over the variable "a" indicates an estimate of the true value. A, B, C, D, and E are summations of various products which are calculated from the data. They are included herein for completeness as follows:

$$A := fpts \cdot \sum_i^{fpts}(Zout_{1,i})^2 - \left(\sum_i^{fpts}(Zout_{1,i})\right)^2 = 5.463 \cdot 10^{10}$$

$$B := fpts\sum_i^{fpts}(Zout_{1,i} \cdot Zout_{2,i}) - \left(\left(\sum_i^{fpts}(Zout_{1,i})\right) \cdot \left(\sum_i^{fpts}(Zout_{2,i})\right)\right) = 5.461 \cdot 10^7$$

$$C := fpts\sum_i^{fpts}(Zout_{2,i})^2 - \left(\sum_i^{fpts}(Zout_{2,i})\right)^2 = 5.445 \cdot 10^{10}$$

$$D := 0.5 \cdot \left(fpts\sum_i^{fpts}(Zout_{1,i} \cdot (Zout_{2,i})^2) - \left(\sum_i^{fpts}(Zout_{1,i})\right) \cdot \left(\sum_i^{fpts}(Zout_{2,i})^2\right) + fpts\sum_i^{fpts}(Zout_{1,i}^3) - \left(\sum_i^{fpts}(Zout_{1,i})\right) \cdot \left(\sum_i^{fpts}(Zout_{1,i})^2\right)\right) = 5.529 \cdot 10^3$$

$$E := 0.5 \cdot \left(fpts\sum_i^{fpts}(Zout_{2,i} \cdot (Zout_{1,i})^2) - \left(\sum_i^{fpts}(Zout_{2,i})\right) \cdot \left(\sum_i^{fpts}(Zout_{1,i})^2\right) + fpts\sum_i^{fpts}(Zout_{2,i}^3) - \left(\sum_i^{fpts}(Zout_{2,i})\right) \cdot \left(\sum_i^{fpts}(Zout_{2,i})^2\right)\right) = -5.192 \cdot 10^{13}$$

Z1,i is a first vector of the real components referred to as conductance;

Z2,i is a second of the imaginary components referred to as susceptance; and

Z3,i is a third vector that represents the frequencies at which admittances are calculated.

This disclosure will work for ultrasonic systems and may possibly be applied to electrosurgical systems, even though electrosurgical systems do not rely on a resonance.

FIGS. 60-64 illustrate images taken from an impedance analyzer showing impedance/admittance circle plots for an ultrasonic device with the end effector jaw in various open or closed configurations and loading. The circle plots in solid line depict impedance and the circle plots in broken lines depict admittance, in accordance with at least one aspect of the present disclosure. By way of example, the impedance/admittance circle plots are generated by connecting an ultrasonic device to an impedance analyzer. The display of the impedance analyzer is set to complex impedance and complex admittance, which can be selectable from the front panel of the impedance analyzer. An initial display may be obtained with the jaw of the ultrasonic end effector in an open position and the ultrasonic device in an unloaded state, as described below in connection with FIG. 60, for example. The autoscale display function of the impedance analyzer may be used to generate both the complex impedance and admittance circle plots. The same display is used for subsequent runs of the ultrasonic device with different loading conditions as shown in the subsequent FIGS. 60-64. A LabVIEW application may be employed to upload the data files. In another technique, the display images may be captured with a camera, such as a smartphone camera, like an Phone or Android. As such, the image of the display may include some "keystone-ing" and in general may not appear to be parallel to the screen. Using this technique, the circle plot traces on the display will appear distorted in the captured image. With this approach, the material located in the jaws of the ultrasonic end effector can be classified.

The complex impedance and complex admittance are just the reciprocal of one another. No new information should be added by looking at both. Another consideration includes determining how sensitive the estimates are to noise when using complex impedance or complex admittance.

In the examples illustrated in FIGS. 60-64, the impedance analyzer is set up with a range to just capture the main resonance. By scanning over a wider range of frequencies more resonances may be encountered and multiple circle plots may be formed. An equivalent circuit of an ultrasonic transducer may be modeled by a first "motional" branch having a serially connected inductance Ls, resistance Rs and capacitance Cs that define the electromechanical properties of the resonator, and a second capacitive branch having a static capacitance C0. In the impedance/admittance plots shown in FIGS. 60-64 that follow, the values of the components of the equivalent circuit are:

$$Ls = L1 = 1.1068H$$
$$Rs = R1 = 311.352\Omega$$
$$Cs = C1 = 7.43265 \text{ pF}$$
$$C0 = C0 = 3.64026 \text{ nF}$$

The oscillator voltage applied to the ultrasonic transducer is 500 mV and the frequency is swept from 55 kHz to 56 kHz. The impedance (Z) scale is 200 Ω/div and the admittance (Y) scale is 500 µS/div. Measurements of values that may characterize the impedance (Z) and admittance (Y) circle plots may be obtained at the locations on the circle plots as indicated by an impedance cursor and an admittance cursor.

State of Jaw: Open with No Loading

Figure 60:
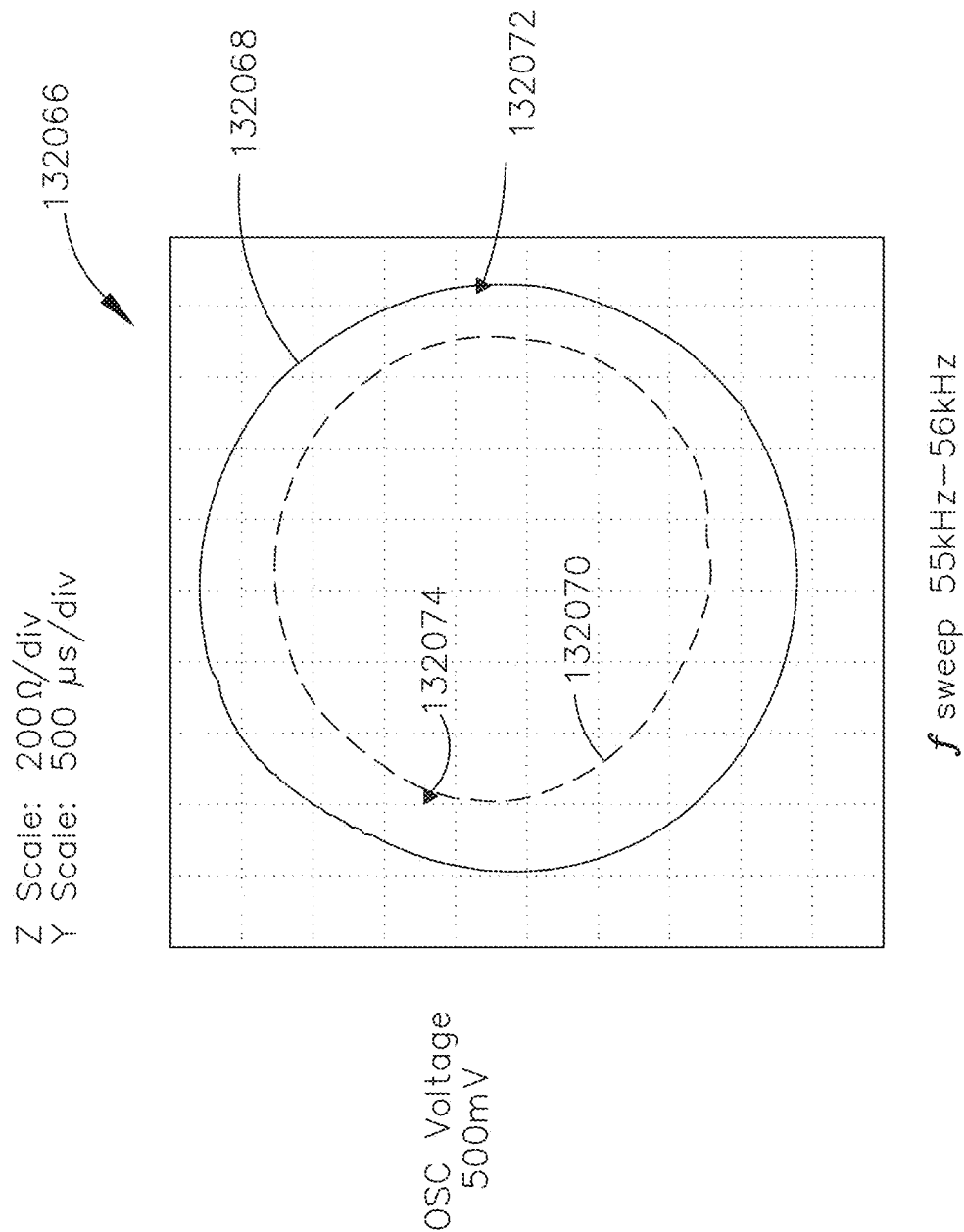
FIG. 60 is a graphical display of an impedance analyzer showing impedance/admittance circle plots for an ultrasonic device with the jaw open and no loading where red depicts admittance and blue depicts impedance, in accordance with at least one aspect of the present disclosure.

FIG. 60 is a graphical display 132066 of an impedance analyzer showing complex impedance (Z)/admittance (Y) circle plots 132068, 132070 for an ultrasonic device with the jaw open and no loading where a circle plot 132068 in solid line depicts complex impedance and a circle plot 132070 in broken line depicts complex admittance, in accordance with at least one aspect of the present disclosure. The oscillator voltage applied to the ultrasonic transducer is 500 mV and the frequency is swept from 55 kHz to 56 kHz. The impedance (Z) scale is 200 Ω/div and the admittance (Y) scale is 500 µS/div. Measurements of values that may characterize the complex impedance (Z) and admittance (Y) circle plots 132068, 132070 may be obtained at locations on the circle plots 132068, 132070 as indicated by the impedance cursor 132072 and the admittance cursor 132074. Thus, the impedance cursor 132072 is located at a portion of the impedance circle plot 132068 that is equivalent to about 55.55 kHz, and the admittance cursor 132074 is located at a portion of the admittance circle plot 132070 that is equivalent to about 55.29 kHz. As depicted in FIG. 60, the position of the impedance cursor 132072 corresponds to values of:

$$R = 1.66026\Omega$$
$$X = -697.309\Omega$$

Where R is the resistance (real value) and X is the reactance (imaginary value). Similarly, the position of the admittance cursor 132074 corresponds to values of:

G=64.0322 µS

B=1.63007 mS

Where G is the conductance (real value) and B is susceptance (imaginary value).

State of Jaw: Clamped on Dry Chamois

Figure 61:
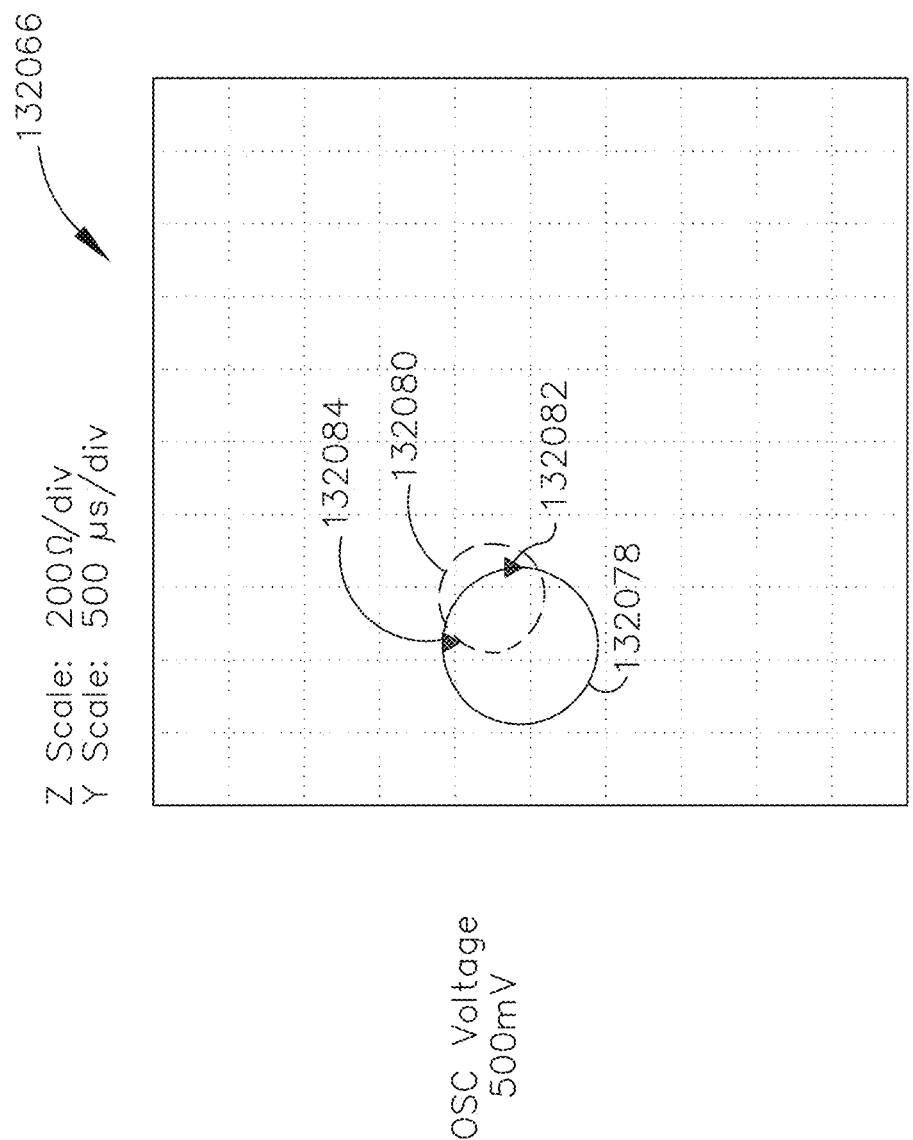
FIG. 61 is a graphical display of an impedance analyzer showing impedance/admittance circle plots for an ultrasonic device with the jaw clamped on dry chamois where red depicts admittance and blue depicts impedance, in accordance with at least one aspect of the present disclosure.

FIG. 61 is a graphical display 132076 of an impedance analyzer showing complex impedance (Z)/admittance (Y) circle plots 132078, 132080 for an ultrasonic device with the jaw of the end effector clamped on dry chamois where the impedance circle plot 132078 is shown in solid line and the admittance circle plot 132080 is shown in broken line, in accordance with at least one aspect of the present disclosure. The voltage applied to the ultrasonic transducer is 500 mV and the frequency is swept from 55 kHz to 56 kHz. The impedance (Z) scale is 200 Ω/div and the admittance (Y) scale is 500 µS/div.

Measurements of values that may characterize the complex impedance (Z) and admittance (Y) circle pots 132078, 132080 may be obtained at locations on the circle plots 132078, 132080 as indicated by the impedance cursor 132082 and the admittance cursor 132084. Thus, the impedance cursor 132082 is located at a portion of the impedance circle plot 132078 that is equivalent to about 55.68 kHz, and the admittance cursor 132084 is located at a portion of the admittance circle plot 132080 that is equivalent to about 55.29 kHz. As depicted in FIG. 61, the position of the impedance cursor 132082 corresponds to values of:

$$R = 434.577\,\Omega$$

$$X = -758.772\,\Omega$$

Where R is the resistance (real value) and X is the reactance (imaginary value).

Similarly, the position of the admittance cursor 132084 corresponds to values of:

G=85.1712 µS
B=1.49569 mS

Where G is the conductance (real value) and B is susceptance (imaginary value).

State of Jaw: Tip Clamped on Moist Chamois

Figure 62:
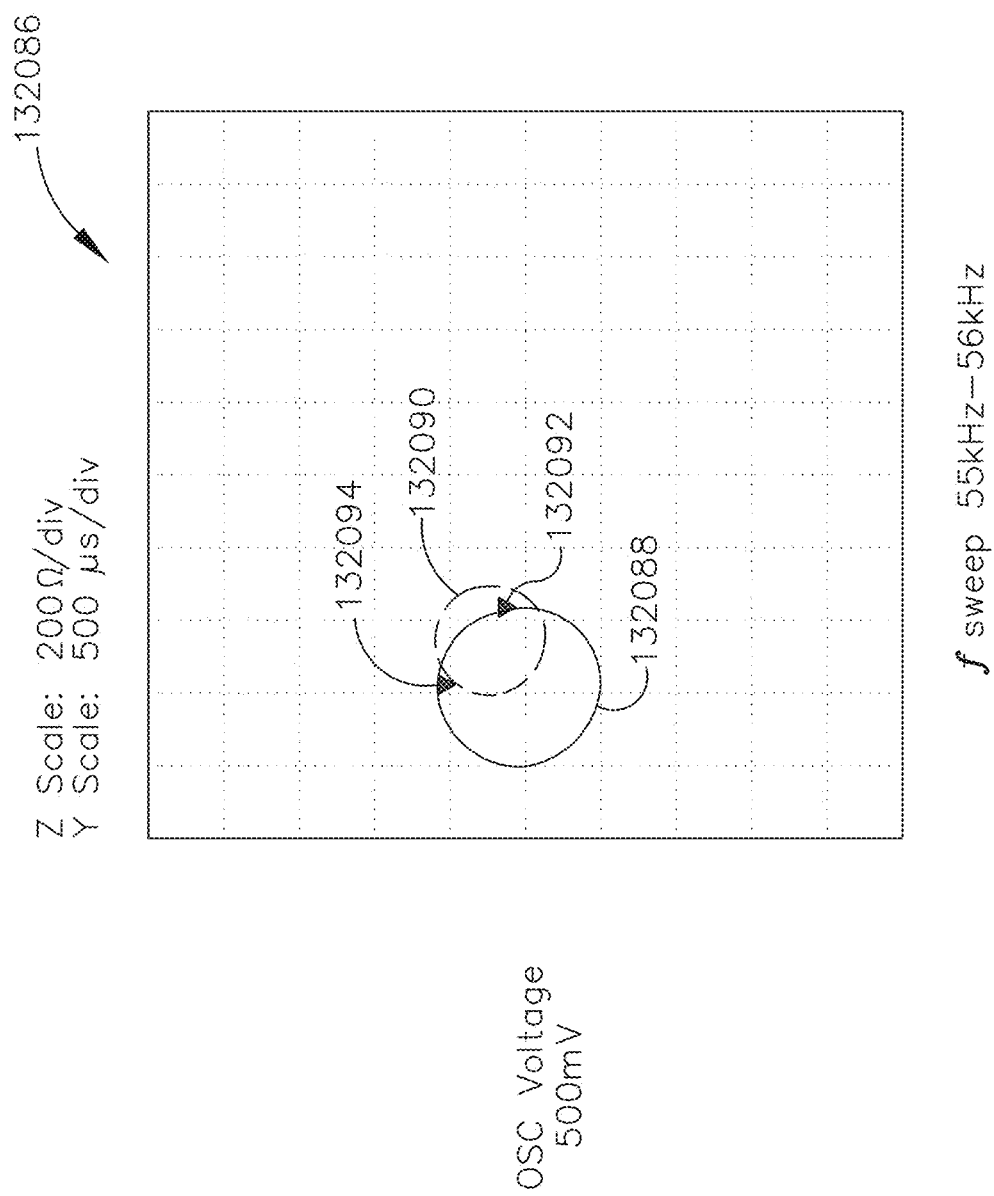
FIG. 62 is a graphical display of an impedance analyzer showing impedance/admittance circle plots for an ultrasonic device with the jaw tip clamped on moist chamois where red depicts admittance and blue depicts impedance, in accordance with at least one aspect of the present disclosure.

FIG. 62 is a graphical display 132086 of an impedance analyzer showing complex impedance (Z)/admittance (Y) circle plots 132098, 132090 for an ultrasonic device with the jaw tip clamped on moist chamois where the impedance circle plot 132088 is shown in solid line and the admittance circle plot 132090 is shown in broken line, in accordance with at least one aspect of the present disclosure. The voltage applied to the ultrasonic transducer is 500 mV and the frequency is swept from 55 kHz to 56 kHz. The impedance (Z) scale is 200 Ω/div and the admittance (Y) scale is 500 µS/div.

Figure 63:
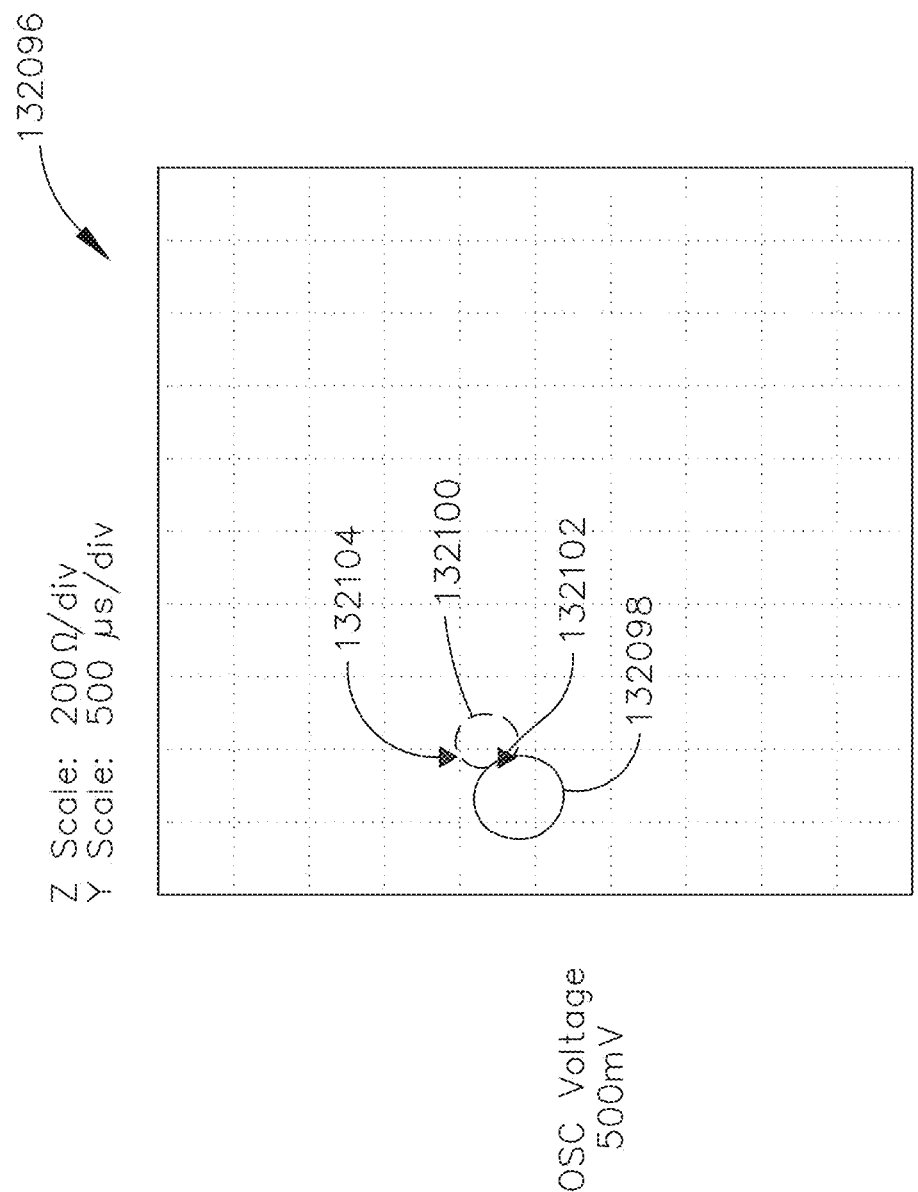
FIG. 63 is a graphical display of an impedance analyzer showing impedance/admittance circle plots for an ultrasonic device with the jaw fully clamped on moist chamois where red depicts admittance and blue depicts impedance, in accordance with at least one aspect of the present disclosure.

Measurements of values that may characterize the complex impedance (Z) and complex admittance (Y) circle plots 132088, 132090 may be obtained at locations on the circle plots 132088, 132090 as indicated by the impedance cursor 132092 and the admittance cursor 132094. Thus, the impedance cursor 132092 is located at a portion of the impedance circle plot 132088 that is equivalent to about 55.68 kHz, and the admittance cursor 132094 is located at a portion of the admittance circle plot 132090 that is equivalent to about 55.29 kHz. As depicted in FIG. 63, the impedance cursor 132092 corresponds to values of:

$$R = 445.259\,\Omega$$

$$X = -750.082\,\Omega$$

Where R is the resistance (real value) and X is the reactance (imaginary value). Similarly, the admittance cursor 132094 corresponds to values of:

G=96.2179 µS
B=1.50236 mS

Where G is the conductance (real value) and B is susceptance (imaginary value).

State of Jaw: Fully Clamped on Moist Chamois

FIG. 63 is a graphical display 132096 of an impedance analyzer showing complex impedance (Z)/admittance (Y) circle plots 132098, 132100 for an ultrasonic device with the jaw fully clamped on moist chamois where the impedance circle plot 132098 is shown in solid line and the admittance circle plot 132100 is shown in broken line, in accordance with at least one aspect of the present disclosure. The voltage applied to the ultrasonic transducer is 500 mV and the frequency is swept from 55 kHz to 56 kHz. The impedance (Z) scale is 200 Ω/div and the admittance (Y) scale is 500 µS/div.

Measurements of values that may characterize the impedance and admittance circle plots 132098, 132100 may be obtained at locations on the circle plots 132098, 1332100 as indicated by the impedance cursor 13212 and admittance cursor 132104. Thus, the impedance cursor 132102 is located at a portion of the impedance circle plot 132098 equivalent to about 55.63 kHz, and the admittance cursor 132104 is located at a portion of the admittance circle plot 132100 equivalent to about 55.29 kHz. As depicted in FIG. 63, the impedance cursor 132102 corresponds to values of R, the resistance (real value, not shown), and X, the reactance (imaginary value, also not shown).

Similarly, the admittance cursor 132104 corresponds to values of:

G=137.272 µS
B=1.48481 mS

Where G is the conductance (real value) and B is susceptance (imaginary value).

State of Jaw: Open with No Loading

Figure 64:
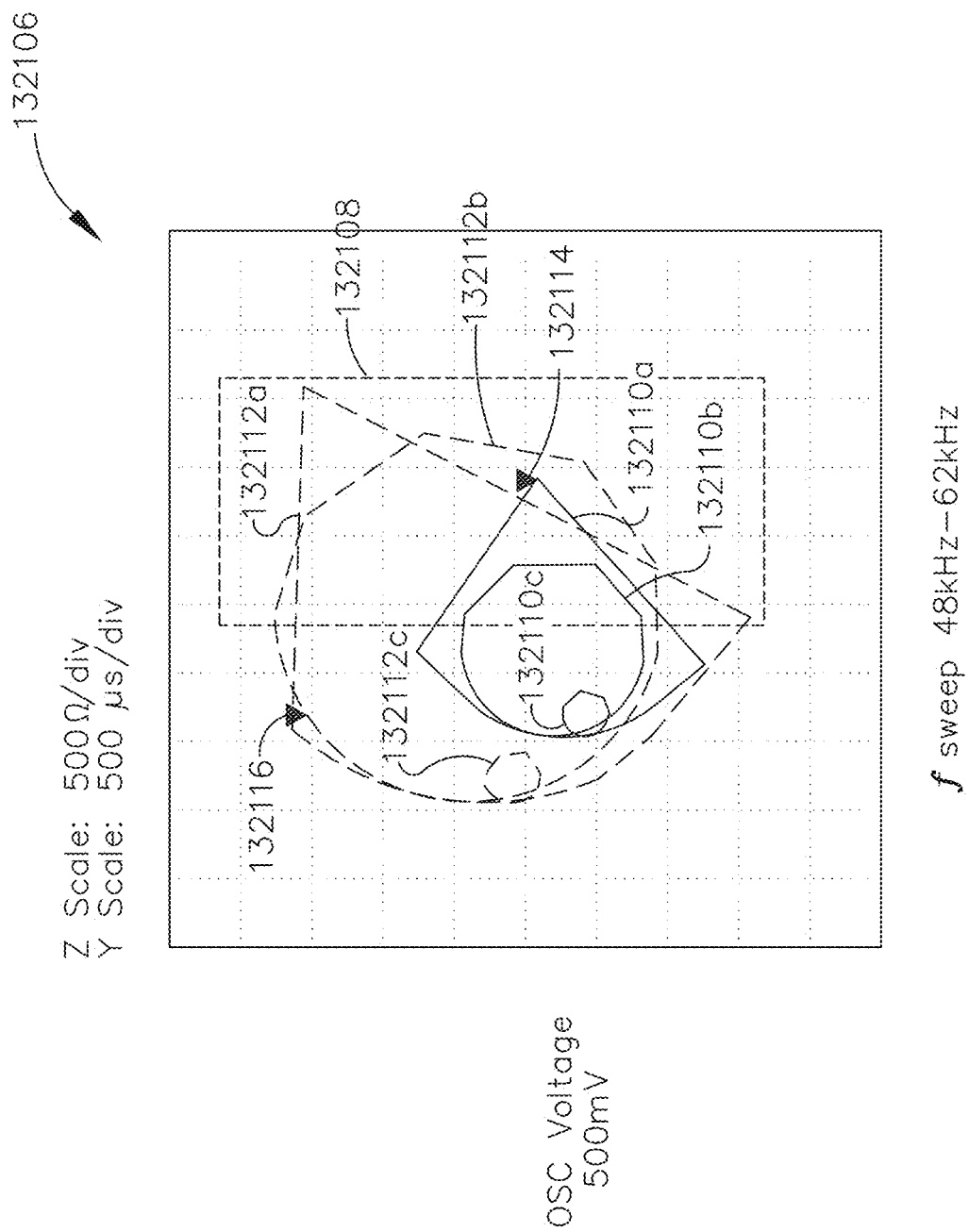
FIG. 64 is a graphical display of an impedance analyzer showing impedance/admittance plots where frequency is swept from 48 kHz to 62 kHz to capture multiple resonances of an ultrasonic device with the jaw open where the gray overlay is to help see the circles, in accordance with at least one aspect of the present disclosure.

FIG. 64 is a graphical display 132106 of an impedance analyzer showing impedance (Z)/admittance (Y) circle plots where frequency is swept from 48 kHz to 62 kHz to capture multiple resonances of an ultrasonic device with the jaw open and no loading where the area designated by the rectangle 132108 shown in broken line is to help see the impedance circle plots 132110*a*, 132110*b*, 132110*c* shown in solid line and the admittance circle plots 132112*a*, 132112*b*, 132112*c*, in accordance with at least one aspect of the present disclosure. The voltage applied to the ultrasonic transducer is 500 mV and the frequency is swept from 48 kHz to 62 kHz. The impedance (Z) scale is 500 Ω/div and the admittance (Y) scale is 500 µS/div.

Measurements of values that may characterize the impedance and admittance circle plots 132110*a-c*, 132112*a-c* may be obtained at locations on the impedance and admittance circle plots 132110*a-c*, 132112*a-c* as indicated by the impedance cursor 132114 and the admittance cursor 132116. Thus, the impedance cursor 132114 is located at a portion of the impedance circle plots 132110*a-c* equivalent to about 55.52 kHz, and the admittance cursor 132116 is located at a portion of the admittance circle plot 132112*a-c* equivalent to about 59.55 kHz. As depicted in FIG. 64, the impedance cursor 132114 corresponds to values of:

$$R = 1.86163\,k\Omega$$

$$X = -536.229\,\Omega$$

Where R is the resistance (real value) and X is the reactance (imaginary value). Similarly, the admittance cursor 132116 corresponds to values of:

G=649.956 µS
B=2.51975 mS

Where G is the conductance (real value) and B is susceptance (imaginary value).

Because there are only 400 samples across the sweep range of the impedance analyzer, there are only a few points about a resonance. So, the circle on the right side becomes choppy. But this is only due to the impedance analyzer and the settings used to cover multiple resonances.

When multiple resonances are present, there is more information to improve the classifier. The circle plots 132110*a-c*, 132112*a-c* fit can be calculated for each as encountered to keep the algorithm running fast. So once there is a cross of the complex admittance, which implies a circle, during the sweep, a fit can be calculated.

Benefits include in-the-jaw classifier based on data and a well-known model for ultrasonic systems. Count and characterizations of circles are well known in vision systems. So data processing is readily available. For example, a closed form solution exists to calculate the radius and axes' offsets for a circle. This technique can be relatively fast.

TABLE 2 is a list of symbols used for lumped parameter model of a piezoelectric transducer (from IEEE 177 Standard).

TABLE 2

| Symbols | Meaning | SI Units | References Equations | Tables | FIGS. |
|---|---|---|---|---|---|
| $B_p$ | Equivalent parallel susceptance of vibrator | mho | | 2 | |
| $C_o$ | Shunt (parallel) capacitance in the equivalent electric circuit | farad | 2, 3, 4, 8 | 5 | 1, 4 |
| $C_1$ | Motional capacitance in the equivalent electric circuit | farad | 2, 3, 4, 6, 8, 9 | 5 | 1, 4 |
| f | Frequency | hertz | | | 3 |
| $f_a$ | Antiresonance frequency, zero susceptance | hertz | | 2, 4 | 2, 3 |
| $f_m$ | Frequency of maximum admittance (minimum impedance) | hertz | | 2, 4 | 2, 3 |
| $f_n$ | Frequency of minimum admittance (maximum impedance) | hertz | | 2, 4 | 2, 3 |
| $f_p$ | Parallel resonance frequency (lossless) = $\dfrac{1}{2\pi\sqrt{L_1 \dfrac{C_1 C_O}{C_1 + C_O}}}$ | hertz | 2, 3 | 2, 4 | 2 |
| $f_r$ | Resonance frequency, zero substance | hertz | | 2, 4 | 2, 3 |
| $f_s$ | Motional (series) resonance frequency $\dfrac{1}{2}$ | hertz | 2, 3, 6, 7, 9, 11a, 11b, 11c, 12, | 2, 4 | 2, 3, 6, 8 |
| $G_p$ | Equivalent parallel conductance of vibrator | | 1 | | |
| $L_1$ | Motional inductance in the equivalent electric circuit | henry | 8, 9 | | 1, 4, 5 |
| M | Figure of merit of a vibrator = $\dfrac{Q}{r}$ $M = \dfrac{1}{\omega_s C_O R_1}$ | dimensionless | 10, 11a, 11b | 3, 4, 5 | |
| Q | Quality factor $Q = \dfrac{\omega_s L_1}{R_1} = \dfrac{1}{\omega_s C_1 R_1} = rM$ | dimensionless | 12 | 3 | 6, 8 |
| r | Capacitance ratio $r = \dfrac{C_o}{C_1}$ | dimensionless | 2, 3, 10, 11 | 2, 3, 4, 5 | 8 |
| $R_a$ | Impedance at zero phase angle near antiresonance | ohm | | | 2, 3 |
| $R_e$ | Equivalent series resistance of vibrator | ohm | | | 1, 2 |
| $R_r$ | Impedance at $f_r$ zero phase angle | ohm | | | 2, 3 |
| $R_1$ | Motional resistance in the equivalent electric circuit | ohm | 4, 8, 10, 11a, 11b, 11c, 12 | 2, 5 | 1, 3, 4, 6, 7, 8 |
| $X_e$ | Equivalent series reactance of vibrator | ohm | | | 1, 2 |
| $X_o$ | Reactance of shunt (parallel) capacitance at series resonance = $\dfrac{1}{\omega_s C_o}$ | ohm | 1, 4, 5 | 5 | 3, 7 |
| $X_1$ | Reactance of motional (series) arm of vibrator $X_1 = \omega L_1 - \dfrac{1}{\omega C_1}$ | ohm | | 2 | 2 |

TABLE 2-continued

| Symbols | Meaning | SI Units | References Equations | Tables | FIGS. |
|---|---|---|---|---|---|
| Y | Admittance of vibrator $Y = G_p + jB_p = \dfrac{1}{Z}$ | mho | 1 | | |
| $Y_m$ | Maximum admittance of vibrator | mho | | | 3 |
| $Y_n$ | Minimum admittance of vibrator | mho | | | 3 |
| Z | Impedance of vibrator $Z = R_e + jX_e$ | ohm | 1 | | |
| $Z_m$ | Minimum impedance of vibrator | ohm | | | 3 |
| $Z_n$ | Maximum impedance of vibrator | ohm | | | 3 |
| | Absolute value of impedance of vibrator $Z = \sqrt{R_e^2 + X_e^2}$ | ohm | | 2 | 2 |
| | Absolute value of impedance at $f_m$ (minimum impedance) | ohm | | | 2 |
| | Absolute value of impedance at $f_n$ (maximum impedance) | ohm | | | 2 |
| δ | Normalized damping factor $\delta = {}_wC_oR_1$ | dimensionless | 1 | 2 | |
| Ω | Normalized frequency factor $\Omega = \dfrac{f^2 - f_s^2}{f_p^2 - f_s^2}$ | dimensionless | 1 | 2 | |
| ω | Circular (angular) frequency $\omega = 2\pi f$ | hertz | | 2 | |
| $\omega_s$ | Circular frequency at motional resonance $\omega_s = 2\pi f_s$ | hertz | | | |

TABLE 3 is a list of symbols for the transmission network (from IEEE 177 Standard).

TABLE 3

| Symbols | Meaning | SI Units | References Equations | Tables | FIGS. |
|---|---|---|---|---|---|
| b | Normalized compensation factor $1 - \dfrac{1}{4\pi^2 f_s^2 C_0 L_0}$ | dimensionless | 4, 10 | 5 | |
| B | Normalized admittance factor | dimensionless | 10 | 5 | |
| C | Normalized admittance factor | dimensionless | 10 | 5 | |
| $C_{A-B}$ | Stray capacitance between the terminals A-B (Figure 4) | farad | | | |
| $C_L$ | Load capacitance | farad | 6 | | 4 |
| $C_T$ | Shunt capacitance terminating transmission circuit | farad | 4, 10 | 5 | 4 |
| $C_{L1}$ | Load capacitance | farad | 7 | | |
| $C_{L2}$ | Load capacitance | farad | 7 | | |
| $e_2$ | Output voltage of transmission network | volt | | | 4 |
| $f_{mT}$ | Frequency of maximum transmission | hertz | 10 | | |
| $F_{sL1}$ | Motional resonance frequency of combination of vibrator and $C_{L1}$ | hertz | 7 | | |
| $F_{sL2}$ | Motional resonance frequency of combination of vibrator and $C_{L2}$ | hertz | 7 | | |
| $i_1$ | Input current to transmission network | ampere | | | 4 |
| $L_0$ | Compensation inductance shunting vibrator | henry | | | 4 |

TABLE 3-continued

| Symbols | Meaning | SI Units | References Equations | Tables | FIGS. |
|---|---|---|---|---|---|
| $M_T$ | Figure of merit of transmission network termination = $\dfrac{1}{2\pi f_s C_T R_T} = \dfrac{X_T}{R_T}$ | dimensionless | 4, 10 | 5 | |
| $R_T$ | Shunt resistance termination of transmission network | ohm | 4, 11a, 11b, 11c, 12 | 5 | 4, 6, 7, 8 |
| $R_{sL2}$ | Standard resistor | ohm | 4, 5 | 5 | 7 |
| S | Detector sensitivity smallest detectable current change/current | dimensionless | 12 | | 6 |
| x | Normalized frequency factor $x = \dfrac{f^2}{f_s^2} - 1 = \dfrac{\Omega}{r}$ | dimensionless | 12 | | |
| $X_{A-B}$ | Reactance of stray capacitance $C_{A-B}$ | ohm | | | |
| $X_T$ | Reactance of $C_T$ at the motional resonance frequency $X_T = \dfrac{1}{2\pi f_s C_T}$ | ohm | 4 | 5 | |
| $x_{mT}$ | Normalized frequency factor at the frequency of maximum transmission | dimensionless | | 5 | |
| $\Delta C_L$ | $\Delta C_L = C_{L2} - C_{L1}$ | farad | 6, 7 | | |
| $\Delta f$ | $\Delta f_1 = f_{sL1} - f_{sL2}$ | hertz | 6, 7 | | 6, 8 |
| $\Delta f_1$ | $\Delta f_1 = f_{sL1} - f_s$ | hertz | 6, 7 | | |
| $\Delta f_2$ | $\Delta f_1 = f_{sL2} - f_s$ | hertz | 6, 7 | | |

*Refers to real roots; complex roots to be disregarded.

TABLE 4 is a list of solutions for various characteristic frequencies (from IEEE 177 Standard).

TABLE 4

SOLUTIONS FOR THE VARIOUS CHARACTERISTIC FREQUENCIES

| Characteristic Frequencies | Meaning | Condition | Constituent Equasion for Frequency | Root | 57 IEEE 14.S1[1] |
|---|---|---|---|---|---|
| $f_m$ | Frequency of maximum admittance (minimum impedance) | = 0 | $-2\delta^2(\Omega + r) - 2\Omega r(1 - \Omega) - \Omega^2 = 0$ | lower* | $f_m$ |
| $f_a$ | Motional (series) resonance frequency | $X_1 = 0$ | $\Omega = 0$ | | $f_a$ |
| $f_r$ | Resonance frequency | $X_e = B_p = 0$ | $\Omega(1 - \Omega) - \delta^2 = 0$ | lower | $f_r$ |
| $f_a$ | Antiresonance frequency | $X_e = B_p = 0$ | $\Omega(1 - \Omega) - \delta^2 = 0$ | upper | $f_a$ |
| $f_p$ | Parallel resonance frequency (lossless) | $I = \infty \mid R1 = 0$ | $\Omega = 1$ | | $f_p$ |
| $f_n$ | Frequency of minimum admittance (maximum impedance) | = 0 | $-2\delta^2(\Omega + r) - 2\Omega r(1 - \Omega) - \Omega^2 = 0$ | upper* | $f_n$ |

*Refers to real roots; complex roots to be disregarded

TABLE 5 is a list of losses of three classes of piezoelectric materials.

TABLE 5

Minimum Values for the Ratio Q'/r to be Expected for Various Types of Piezoelectric Vibrators

| Type of Piezoelectric Vibrator | Q = Mr | r | Q'/r min |
|---|---|---|---|
| Piezoelectric Ceramics | 90-500 | 2-40 | 200 |
| Water-Soluble Piezoelectric Crystals | 200-50,000 | 3-500 | 80 |
| Quartz | $10^4$-$10^7$ | 100-50,000 | 2000 |

TABLE 6 illustrates jaw conditions, estimated parameters of a circle based on real time measurements of complex impedance/admittance, radius (re) and offsets (ae and be) of the circle represented by measured variables Re, Ge, Xe, Be, and parameters of a reference circle plots, as described in FIGS. 60-64, based on real time measurements of complex impedance/admittance, radius (rr) and offsets (ar, br) of the reference circle represented by reference variables Rref, Gref, Xref, Bref. These values are then compared with established values for given conditions. These conditions may be: 1) open with nothing in jaws, 2) tip bite 3) full bite and staple in jaws. The equivalent circuit of the ultrasonic transducer was modeled as follows and the frequency was swept from 55 kHz to 5 kHz:

$$Ls = L1 = 1.1068H$$

$$Rs = R1 = 311.352\Omega$$

$$Cs = C1 = 7.43265 \text{ pF and}$$

$$C0 = C0 = 3.64026 \text{ nF}$$

TABLE 6

| | Reference Circle Plot | | | |
|---|---|---|---|---|
| Reference Jaw Conditions | $R_{ref}$ ($\Omega$) | $G_{ref}$ ($\mu$S) | $X_{ref}$ ($\Omega$) | $B_{ref}$ (mS) |
| Jaw open and no loading | 1.66026 | 64.0322 | −697.309 | 1.63007 |
| Jaw clamped on dry chamois | 434.577 | 85.1712 | −758.772 | 1.49569 |
| Jaw tip clamped on moist chamois | 445.259 | 96.2179 | −750.082 | 1.50236 |
| Jaw fully clamped on moist chamois | | 137.272 | | 1.48481 |

In use, the ultrasonic generator sweeps the frequency, records the measured variables, and determines estimates Re, Ge, Xe, Be. These estimates are then compared to reference variables Rref, Gref, Xref, Bref stored in memory (e.g., stored in a look-up table) and determines the jaw conditions. The reference jaw conditions shown in TABLE 6 are examples only. Additional or fewer reference jaw conditions may be classified and stored in memory. These variables can be used to estimate the radius and offsets of the impedance/admittance circle.

Figure 65:
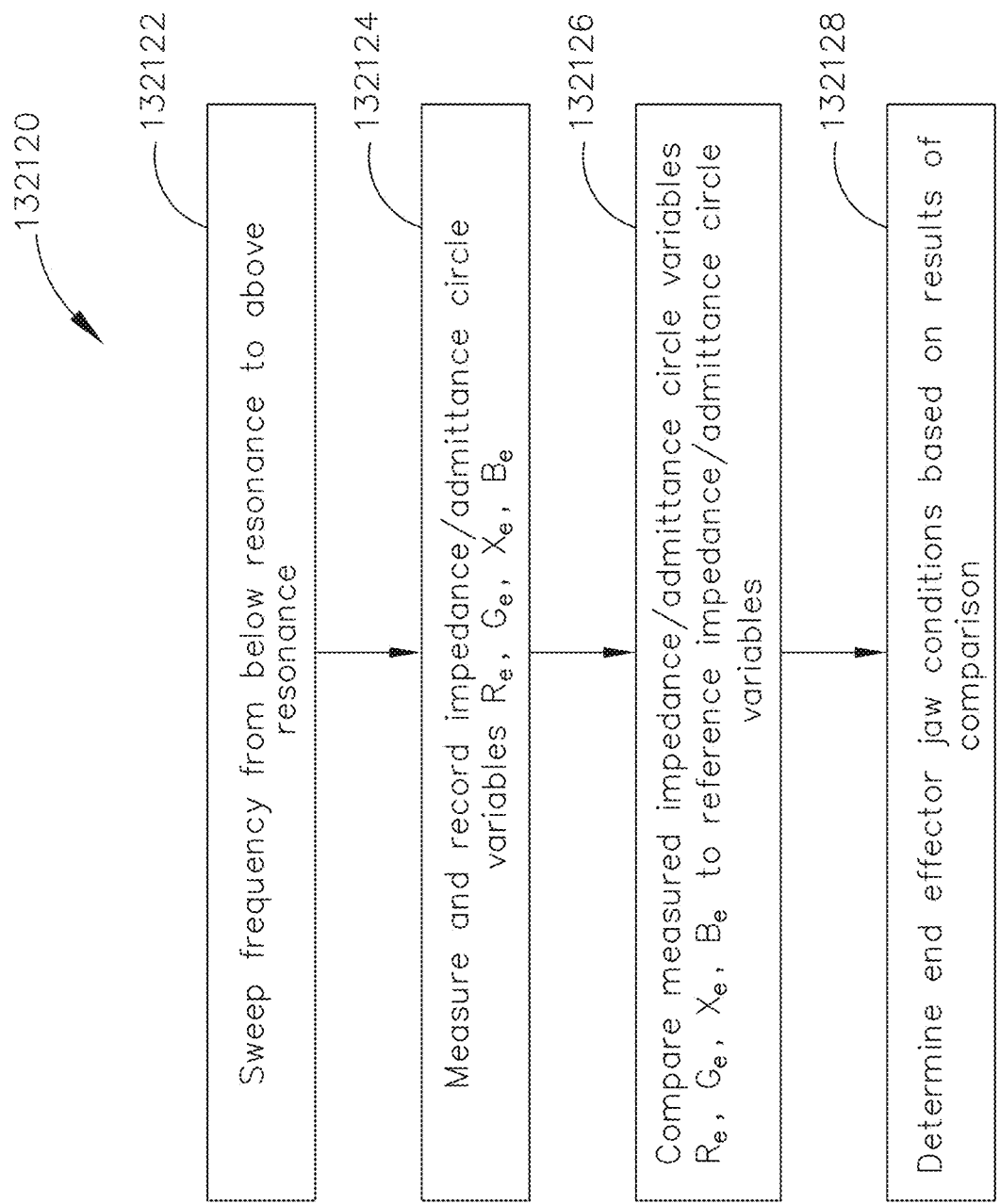
FIG. 65 is a logic flow diagram of a process depicting a control program or a logic configuration to determine jaw conditions based on estimates of the radius and offsets of an impedance/admittance circle, in accordance with at least one aspect of the present disclosure.

FIG. 65 is a logic flow diagram 132120 of a process depicting a control program or a logic configuration to determine jaw conditions based on estimates of the radius (r) and offsets (a, b) of an impedance/admittance circle, in accordance with at least one aspect of the present disclosure. Initially a data base or lookup table is populated with reference values based on reference jaw conditions as described in connection with FIGS. 60-64 and TABLE 6. A reference jaw condition is set and the frequency is swept from a value below resonance to a value above resonance. The reference values Rref, Gref, Xref, Bref that define the corresponding impedance/admittance circle plot are stored in a database or lookup table. During use, under control of a control program or logic configuration a control circuit of the generator or instrument causes the frequency to sweep 132122 from below resonance to above resonance. The control circuit measures and records 132124 (e.g., stores in memory) the variables Re, Ge, Xe, Be that define the corresponding impedance/admittance circle plot and compares 132126 them to the reference values Rref, Gref, Xref, Bref stored in the database or lookup table. The control circuit determines 132128, e.g., estimates, the end effector jaw conditions based on the results of the comparison.

Application of "Smart Blade" Technology

Current ultrasonic and/or combination ultrasonic/RF tissue treatment conditions employ advanced tissue treatment algorithms with a pre-determined current level for each step of the algorithm. Instead of using an advanced hemostasis tissue treatment algorithm with a pre-determined current level for each step of the algorithm, the proposed advanced tissue treatment technique adjusts electrical current delivered to the ultrasonic transducer to drive the ultrasonic blade to a constant temperature using a frequency-temperature control system.

FIGS. 66A-66B are graphical representations of an advanced ultrasonic transducer current controlled hemostasis algorithm. For example, the tissue treatment process may start out by driving the ultrasonic transducer current to generate a high constant temperature for a first predetermined period T1. At the end of the first predetermined period T1, the process drives the ultrasonic transducer current to generate a lower constant temperature of the ultrasonic blade for a second predetermined period T2. The lower temperature of the ultrasonic blade may be suitable to achieve a tissue seal but not a tissue transection. Finally, the process drives the ultrasonic transducer current to increase (ramps back up) the temperature of the ultrasonic blade to a higher constant temperature for a third predetermined period T3. The higher temperature is high enough to complete the transection but is lower than the melting point of the clamp arm pad. For example, the higher ultrasonic blade temperature during the third predetermined period T3 may be selected to be lower than the melting point of TEFLON, for example, which is a material commonly used for the clamp arm pad.

FIG. 66A is a graphical representation 132130 of percent of maximum current delivered into an ultrasonic transducer as a function of time, in accordance with at least one aspect of the present disclosure. The vertical axis represents percentage (%) of maximum current delivered to an ultrasonic transducer and the horizontal axis represents time (sec). The percentage of transducer current is set to a first percentage of maximum current X1% to raise the temperature of the ultrasonic blade during a first period T1. The percentage of transducer current is then lowered to a second percentage of maximum current X2% over a second period T2 to lower the blade temperature to a value that is suitable for sealing tissue but not for transecting tissue. The percentage of transducer current is then increased to a third percentage of maximum current X3% for a third period T3, to raise the blade temperature to a value that is suitable for transecting tissue but is lower than the melting point of the clamp arm pad (e.g., TEFLON). According to the process graphically depicted in FIG. 66A, the same percentage of ultrasonic transducer current profile may be used for all tissue types, loading conditions, etc.

FIG. 66B is a graphical representation 132140 of ultrasonic blade temperature as a function of time and tissue type, in accordance with at least one aspect of the present disclosure. The vertical axis represents temperature (° F.) of the ultrasonic blade and the horizontal axis represents time (sec). This technique may be combined with impedance spectroscopy to detect tissue of various thicknesses. Such as for example, thick tissue versus thin tissue, located in the jaws of the ultrasonic end effector. Once the tissue thickness is detected, the ultrasonic blade temperature may be controlled to accommodate different levels of energy delivery as may be needed across a range of tissue types and adjust the advanced hemostasis algorithm in real-time. Once the tissue type is detected or determined, the ultrasonic blade temperature is set to a nominal temperature $Temp_1$ by controlling the driving current into the ultrasonic transducer. The temperature of the ultrasonic blade is set to a first temperature $Temp_1$, which may be raised (+) or lowered (−) based on tissue type over a first period T1. The ultrasonic blade temperature is then lowered to a second temperature $Temp_2$ over a second period T2 to lower the blade temperature to a value that is suitable for sealing tissue but not for transecting tissue. The second temperature $Temp_2$, also may be raised (+) or lowered (−) based on the detected tissue type. The ultrasonic blade temperature is then increased to a third temperature $Temp_3$ over a third period T3 to a value that is suitable for transecting tissue but that is lower than the melting point temperature TMP of the clamp jaw pad material. According to the process depicted in FIG. 66B, the ultrasonic blade temperature can be varied based on tissue types, loading conditions, etc. In addition, the ultrasonic blade temperature versus time profile can be varied by varying the periods T1-T3. Finally, the ultrasonic blade temperature versus time profile can be varied by varying both the temperature of the ultrasonic blade and the time periods T1-T3.

In one example, for audible surgeon feedback, tones can be tied to achieving a certain temperature threshold. This would improve consistency in advanced hemostasis transection times and hemostasis across a range of tissue types.

FIG. 67 is a logic flow diagram 132150 of a process depicting a control program or a logic configuration to control the temperature of an ultrasonic blade based on tissue type, in accordance with at least one aspect of the present disclosure. The tissue type may be determined 132152 using the techniques described in FIGS. 54-56 under the heading ESTIMATING THE STATE OF THE JAW (PAD BURN THROUGH, STAPLES, BROKEN BLADE, BONE IN JAW, TISSUE IN JAW and/or FIGS. 57-65 under the heading STATE OF JAW CLASSIFIER BASED ON MODEL and/or techniques for estimating the temperature of the ultrasonic blade are described in related U.S. Provisional Patent Application Ser. No. 62/640,417, titled TEMPERATURE CONTROL IN ULTRASONIC DEVICE AND CONTROL SYSTEM THEREFOR, to Nott et al, which is incorporated herein by reference in its entirety. According to the process, a control circuit in the generator or instrument determines the tissue type and sets the initial temperature of the ultrasonic blade to a nominal temperature by controlling the driving current into the ultrasonic transducer. The control circuit raises (+) or lowers (−) the temperature of the ultrasonic blade based on tissue type over a first period T1. The control circuit then lowers the temperature of the ultrasonic blade to a second temperature over a second period T2 to lower the blade temperature to a value that is suitable for sealing tissue but not for transecting tissue. The control circuit raises (+) or lowers (−) the second temperature based on the detected tissue type. The control circuit increases the temperature of the ultrasonic blade to a third temperature over a third period T3, to a value that is suitable for transecting tissue but is lower than the melting point of the clamp jaw pad material (e.g., TEFLON).

Smart Blade and Power Pulsing

During surgery with an ultrasonic shears device the power delivered to the tissue is set at a predetermined level. That predetermined level is used to transect the tissue throughout the transection procedure. Certain tissues may seal better or cut better/faster if the power delivered varies throughout the transection procedure. A solution is needed to vary the power delivered to the tissue through the blade during the transection process. In various aspects, the tissue type and changes to the tissue during the transection process may be determined using the techniques described in FIGS. 54-56 under the heading ESTIMATING THE STATE OF THE JAW (PAD BURN THROUGH, STAPLES, BROKEN BLADE, BONE IN JAW, TISSUE IN JAW and/or FIGS. 57-65 under the heading STATE OF JAW CLASSIFIER BASED ON MODEL and/or techniques for estimating the temperature of the ultrasonic blade are described in related U.S. Provisional Patent Application Ser. No. 62/640,417, titled TEMPERATURE CONTROL IN ULTRASONIC DEVICE AND CONTROL SYSTEM THEREFOR, to Nott et al, which is incorporated herein by reference in its entirety.

One solution that provides better ultrasonic transection employs the impedance feedback of the ultrasonic blade. As previously discussed, the impedance of the ultrasonic blade is related to the impedance of the electromechanical ultrasonic system and may be determined by measuring the phase angle between the voltage and current signals applied to the ultrasonic transducer as described herein. This technique may be employed to measure the magnitude and phase of the impedance of the ultrasonic transducer. The impedance of the ultrasonic transducer may be employed to profile factors that may be influencing the ultrasonic blade during use (e.g., force, temperature, vibration, force over time, etc.). This information may be employed to affect the power delivered to the ultrasonic blade during the transection process.

FIG. 68 is a logic flow diagram 132170 of a process depicting a control program or a logic configuration to monitor the impedance of an ultrasonic transducer to profile an ultrasonic blade and deliver power to the ultrasonic blade on the profile according to one aspect of the resent disclosure. According to the process, a control circuit determines 132172 (e.g., measures) the impedance (Z) of the ultrasonic transducer during a tissue transection process. The control circuit analyzes and profiles 132174 the ultrasonic blade right after the tissue is fully clamped in jaw of the end effector of the ultrasonic device based on the determined 132172 impedance (Z). The control circuit adjusts 132176 a power output level based on the profile (e.g., high power for dense tissue low power for thin tissue) of the ultrasonic blade. The control circuit controls the generator to momentarily drive the ultrasonic transducer and the ultrasonic blade and then stops. The control circuit again determines 132172 the impedance (Z) of the ultrasonic blade and profiles 132174 the ultrasonic blade based on the determined 132172 impedance (Z). The control circuit controls the generator to adjust the output power level or keep it the same based on the profile of the ultrasonic blade. The control circuit again controls the generator to momentarily drive the ultrasonic transducer and the ultrasonic blade and then stops. The process repeats and determines 132172 the impedance (Z), profiles 132174 the ultrasonic blade, and adjusts 132176 the power level until the impedance profile detected is that of the clam arm pad and then adjusts the power to prevent the clamp arm pad from melting.

The process discussed in connection with FIG. 68 allows the ultrasonic transducer power level to be adjusted on the fly as the tissue changes from being heated and cut. Accordingly, if the tissue is initially tough and then weakens or if different layers of tissue are encountered during the transection process, the power level can be optimally adjusted to match the profile of the ultrasonic blade. This method could eliminate the need for the user to set the power level. The ultrasonic device would adapt and choose the right power level based on current tissue conditions and transection process.

This technique provides intelligent control for power level setting based on tissue feedback. This technique may eliminate the need for power settings on the generator and may lead to faster transection times. In one aspect, in an ultrasonic transection medical device including a jaw with an ultrasonic blade, the impedance of the ultrasonically driven blade is used to profile the ultrasonic blade characteristics (force, heat, vibration, etc.) and that profile is used to influence the power output of the transducer during the transection process. Power may be pulsed on and off so that the tissue changes can be read for feedback in between pulses to adjust the power during the transection process.

FIGS. 69A-69D is a series of graphical representations of the impedance of an ultrasonic transducer to profile an ultrasonic blade and deliver power to the ultrasonic blade based on the profile, in accordance with at least one aspect of the present disclosure. FIG. 69A is a graphical representation 132180 of ultrasonic transducer impedance versus time. The generator control circuit reads the initial impedance Z1 which is based on the contents of the jaw and applies a pulsed power P1 to the ultrasonic transducer as shown in FIG. 69B, which is a graphical depiction 132182 of pulsed power versus time. FIG. 69C is a graphical representation 132184 of a new impedance Z2 versus time. The control circuit of the generator reads the new impedance Z2 and applies pulsed power P2 to the ultrasonic transducer to meet the new tissue condition as plotted in FIG. 69D, which is a graphical representation 132186 of pulsed power P2 versus time.

Adjustment of Complex Impedance to Compensate for Lost Power in an Articulating Ultrasonic Device FIG. 70 is a system 132190 for adjusting complex impedance of the ultrasonic transducer 132192 to compensate for power lost when the ultrasonic blade 132194 is articulated, in accordance with at least one aspect of the present disclosure. The performance of an articulatable ultrasonic blade 132194 is inconsistent throughout the full articulation angle θ from A-B. For example, power is lost when the ultrasonic blade 132194 is articulated. Knowing the articulation angle θ that the ultrasonic blade 132194 is at, the generator 132196 or the surgical instrument 132199 can adjust the complex impedance (Z) to compensate for the power lost when the ultrasonic blade 132194 is articulated. Also, by analyzing the performance of the ultrasonic blade 132194 through its full articulation angle θ, the generator 132196 can execute an algorithm to adjust the complex impedance (Z) to compensate for power loss.

Adjusting complex impedance of the ultrasonic transducer 132192 to compensate for power lost when the ultrasonic blade 132194 may employ the techniques described in FIGS. 54-56 under the heading ESTIMATING THE STATE OF THE JAW (PAD BURN THROUGH, STAPLES, BROKEN BLADE, BONE IN JAW, TISSUE IN JAW and/or FIGS. 57-65 under the heading STATE OF JAW CLASSIFIER BASED ON MODEL and/or techniques for estimating the temperature of the ultrasonic blade are described in related U.S. Provisional Patent Application Ser. No. 62/640,417, titled TEMPERATURE CONTROL IN ULTRASONIC DEVICE AND CONTROL SYSTEM THEREFOR, to Nott et al, which is incorporated herein by reference in its entirety.

These techniques may be employed to determine the articulation angle θ of the ultrasonic blade 132194 by sweeping through a range of articulation angles θ from A-B at a predetermined angular increment. At each angular increment, activating the ultrasonic transducer 132192 at either a therapeutic or non-therapeutic energy level, measuring the complex impedance (Z) of the ultrasonic transducer 132192, recording a set of complex impedance (Z) measurements, generating reference complex impedance characteristic patterns or a training data sets S as a function of articulation angle θ, and storing the reference complex impedance characteristic patterns or a training data sets S in a memory or database that is accessible by the ultrasonic instrument 132199 during a surgical procedure. During a surgical procedure, the ultrasonic instrument 132199 can determine articulation angle θ by comparing real time complex impedance (Z) measurements of the ultrasonic transducer 132192 with the reference complex impedance characteristic patterns or a training data sets S.

Articulatable ultrasonic waveguides 132198 are described in U.S. Pat. No. 9,095,367 titled FLEXIBLE HARMONIC WAVEGUIDES/BLADES FOR SURGICAL INSTRUMENTS, which is incorporated herein by reference. See FIGS. 47-66B and associated description. Measurement of articulation angle is described in U.S. Pat. No. 9,808,244 titled SENSOR ARRANGEMENTS FOR ABSOLUTE POSITIONING SYSTEM FOR SURGICAL INSTRUMENTS, which is incorporated herein by reference. See FIGS. 193-196 and associated description.

FIG. 71 is a logic flow diagram 132200 of a process depicting a control program or a logic configuration to compensate output power as a function of articulation angle, in accordance with at least one aspect of the present disclosure. Accordingly, in conjunction with FIG. 70, during use, a control circuit of the generator 132196 or instrument determines 132202 the articulation angle θ of the ultrasonic blade 132194. The control circuit adjusts 132204 the complex impedance (Z) to compensate for power lost as a function of articulation angle θ. The control circuit applies 132206 the output power of the generator 132196 applied to the ultrasonic transducer 132192 based on the articulation angle θ of the ultrasonic blade 132194.

Using Spectroscopy to Determine Device Use State in Combo Instrument

FIG. 72 is a system 132210 for measuring complex impedance (Z) of an ultrasonic transducer 132212 in real time to determine action being performed by an ultrasonic blade 132214, in accordance with at least one aspect of the present disclosure. Current surgical instruments include three functions (seal+cut, seal only, and spot coagulation). These functions can be executed by activating two buttons. It would be useful if the surgeon only had to press one button and could receive either the seal only or spot coagulation algorithm based on the desired action to be performed. Ultrasonic spectroscopy can be used to measure the complex impedance (Z) of the ultrasonic blade 132214 in real time. The real time measurements can be compared to predefined data to determine which action is being performed. The different complex impedance (Z) patterns between spot coagulation and seal only enable the generator 132216 to determine which action is being performed and to execute the appropriate algorithm.

Measuring complex impedance (Z) of an ultrasonic transducer 132212 in real time to determine action being performed by an ultrasonic blade 132214 may employ the techniques described in FIGS. 54-56 under the heading ESTIMATING THE STATE OF THE JAW (PAD BURN THROUGH, STAPLES, BROKEN BLADE, BONE IN JAW, TISSUE IN JAW and/or FIGS. 57-65 under the heading STATE OF JAW CLASSIFIER BASED ON MODEL and/or techniques for estimating the temperature of the ultrasonic blade are described in related U.S. Provisional Patent Application Ser. No. 62/640,417, titled TEMPERATURE CONTROL IN ULTRASONIC DEVICE AND CONTROL SYSTEM THEREFOR, to Nott et al, which is incorporated herein by reference in its entirety.

TABLE 7 is a chart of ultrasonic blade action and corresponding complex impedance. This information is stored in a memory lookup table or database.

TABLE 7

| Ultrasonic Blade Action | Impedance (Z) |
| --- | --- |
| Seal only | Z1 |
| Spot coagulation | Z2 |

FIG. 73 is a logic flow diagram 132220 of a process depicting a control program or a logic configuration to determine action being performed by an ultrasonic blade 132214 (FIG. 72) based on the complex impedance pattern, in accordance with at least one aspect of the present disclosure. Prior to implementing the process described in FIG. 73 and in conjunction with FIG. 72, a database or memory lookup table is populated with data of ultrasonic blade 132214 actions and observed complex impedances (Z) associated with the ultrasonic blade 132214 actions. The database or lookup table can be accessed by the ultrasonic instrument 132218 or generator 132216 while executing the ultrasonic blade 132214 action. Accordingly, during a hemostasis procedure, a control circuit of the generator 132216 or instrument 13218 determines 132222 the complex impedance (Z) of the ultrasonic blade 132214. The control circuit compares 132224 the measured complex impedance (Z) to stored values of complex impedance patterns associated with ultrasonic blade 132214 functions. The control circuit controls the generator 132216 to apply 132226 an output power algorithm to the ultrasonic transducer 132212 based on the comparison.

Vessel Sensing for Adaptive Advanced Hemostasis

In various aspects, the present disclosure provides adaptive vessel sealing modes. In one aspect, the ultrasonic instrument can deliver ultrasonic energy uniquely for veins as opposed to arteries.

In another aspect, the present disclosure provides a technique for identifying the jaw contents of an ultrasonic device. Using this approach, a vessel clamped in the jaw is identified as either a vein or an artery, which can be characterized as differences in vessel wall and pressure. Knowing that a vessel is a vein or an artery can be used to activate a unique advanced hemostasis cycle for each type. A vein requires more time and lower temperature due to the thinner vessel walls, so an advanced hemostasis cycle will include lower current and longer time in the vessel sealing portion of the cycle.

FIG. 74 is a logic flow diagram 132230 depicting a control program or a logic configuration of an adaptive process for identifying a hemostasis vessel, in accordance with at least one aspect of the present disclosure. In accordance with the process, a control circuit of the generator or instrument senses 132232 the vessel located in the jaw of the ultrasonic device using any of the smart blade algorithm techniques for estimating or classifying the state of the jaw of an ultrasonic device described in connection with FIGS. 54-56 under the heading ESTIMATING THE STATE OF THE JAW (PAD BURN THROUGH, STAPLES, BROKEN BLADE, BONE IN JAW, TISSUE IN JAW and/or FIGS. 57-65 under the heading STATE OF JAW CLASSIFIER BASED ON MODEL and/or techniques for estimating the temperature of the ultrasonic blade are described in related U.S. Provisional Patent Application Ser. No. 62/640,417, titled TEMPERATURE CONTROL IN ULTRASONIC DEVICE AND CONTROL SYSTEM THEREFOR, to Nott et al, which is incorporated herein by reference in its entirety. When a vein is sensed 132234 or an artery is sensed 132236, the control circuit receives a command for sealing either a vein or an artery and activates 132238 an advanced hemostasis algorithm based on the type of vessel sensed. In one aspect, the command may be originated by a user from a button located on the instrument to activate the appropriate advanced hemostasis algorithm. In other aspects, the command may be originated automatically based on tissue characterization algorithms.

When a vein is sensed 132234, the control circuit executes 132240 a first algorithm that can seal slower at a lower power level and lower ultrasonic blade temperature. Accordingly, to treat a vein, the control circuit controls the generator to output a lower power P1 and activates the generator for a longer time T1.

When an artery is sensed 132236, the control circuit executes 132242 a second algorithm that can seal faster at a higher power level and higher ultrasonic blade temperature. Accordingly, to treat an artery, the control circuit controls the generator to output higher power P2 and activates the generator for a shorter time T2.

FIG. 75 is a graphical representation 132250 of ultrasonic transducer current profiles as a function of time for vein and artery vessel types, in accordance with at least one aspect of the present disclosure. The vertical axis is generator output current (I) delivered to the ultrasonic transducer and the horizontal axis is time (sec). With reference also to FIG. 74, the first curve 132252 represents a vein and is treated with lower power (P1 at 11) and longer period (T1) and the second curve 132254 represents an artery and is treated with higher power (P2 at 12) applied for a shorter period (T2) relative to the first curve 132252.

In another aspect, the present disclosure provides a technique for delivering ultrasonic transducer current (I) in a feedback control loop to achieve a targeted frequency which is associated with a desired ultrasonic blade temperature. When sealing a vein, for example, the feedback control loop will drive to a higher targeted frequency which corresponds to a cooler ultrasonic blade temperature that is suitable (and may be ideal) for sealing the vein. An artery would be driven to a slightly lower frequency target associated with a hotter ultrasonic blade temperature.

FIG. 76 is a logic flow diagram 132260 depicting a control program or a logic configuration of an adaptive process for identifying a hemostasis vessel, in accordance with at least one aspect of the present disclosure. In accordance with the process, a control circuit of the generator or instrument senses 132262 the vessel in the jaw using any of the smart blade algorithm techniques for estimating or classifying the state of the jaw of an ultrasonic device described in connection with FIGS. 54-56 under the heading ESTIMATING THE STATE OF THE JAW (PAD BURN THROUGH, STAPLES, BROKEN BLADE, BONE IN JAW, TISSUE IN JAW and/or FIGS. 57-65 under the heading STATE OF JAW CLASSIFIER BASED ON MODEL and/or techniques for estimating the temperature of the ultrasonic blade are described in related U.S. Provisional Patent Application Ser. No. 62/640,417, titled TEMPERATURE CONTROL IN ULTRASONIC DEVICE AND CONTROL SYSTEM THEREFOR, to Nott et al, which is incorporated herein by reference in its entirety.

When a vein is sensed 132264, the control circuit executes a first algorithm to supply 132268 current to the ultrasonic transducer to achieve a targeted seal temperature for a vein. A feedback control loop estimates the temperature of the ultrasonic blade and adjusts the current delivered to the ultrasonic transducer to control the temperature of the ultrasonic blade. When an artery is sensed 132266, the control circuit executes a second algorithm to supply 132269 current to the ultrasonic transducer to achieve a targeted seal temperature for an artery. A feedback control loop estimates the temperature of the ultrasonic blade and adjusts the current delivered to the ultrasonic transducer to control the temperature of the ultrasonic blade.

FIG. 77 is a graphical representation 132270 of ultrasonic transducer frequency profiles as a function of time for vein and artery vessel types, in accordance with at least one aspect of the present disclosure. The vertical axis represents the frequency (kHz) of the signal applied to the ultrasonic transducer and the horizontal axis represents time (sec). The first curve 132272 represents a vein. A vein requires a cooler ultrasonic blade temperature to effect a seal. The first algorithm controls the temperature of the ultrasonic blade by setting the frequency applied to the ultrasonic transducer to a higher frequency and controls current delivered to the ultrasonic transducer to maintain the set frequency. The second curve 132274 represents an artery. An artery requires a hotter ultrasonic blade temperature to effect a seal. The second algorithm controls the temperature of the ultrasonic blade by setting the frequency applied to the ultrasonic transducer to a lower frequency and controls current delivered to the ultrasonic transducer to maintain the set frequency.

Calcified Vessel Identification

In various aspects, the present disclosure provides various techniques for improving hemostasis when sealing calcified vessels and to address challenges in sealing calcified vessels. In one aspect, the ultrasonic instrument is configured to manage sealing of calcified vessels with intelligence. In one aspect, the jaw contents may be identified identification using smart blade algorithm techniques for estimating or classifying the state of the jaw of an ultrasonic device described in connection with FIGS. 54-56 under the heading ESTIMATING THE STATE OF THE JAW (PAD BURN THROUGH, STAPLES, BROKEN BLADE, BONE IN JAW, TISSUE IN JAW and/or FIGS. 57-65 under the heading STATE OF JAW CLASSIFIER BASED ON MODEL and/or techniques for estimating the temperature of the ultrasonic blade are described in related U.S. Provisional Patent Application Ser. No. 62/640,417, titled TEMPERATURE CONTROL IN ULTRASONIC DEVICE AND CONTROL SYSTEM THEREFOR, to Nott et al, which is incorporated herein by reference in its entirety. Accordingly, these techniques may be employed to identify a calcified vessel when clamped in the jaws of the ultrasonic instrument.

Three possible scenarios are disclosed. In one aspect, the user is prompted with a warning from the generator that the jaws are clamping on a calcified vessel and the instrument will not fire. In another aspect, the instruments prompts a user that they the jaws have clamped a calcified vessel and it will not allow the instrument to fire until a minimum amount of compression time (say 10-15 seconds) has elapsed. This additional time allows the calcification/plaque to migrate away from the transection side and improve hemostasis of the seal. In a third aspect, upon grasping a calcified vessel and pressing the activation button, the instrument employs an internal motor to displace the spring stack an additional amount in order to deliver slightly more clamp force and better compression of the calcified vessel.

FIG. 78 is a logic flow diagram 132280 depicting a control program or a logic configuration of a process for identifying a calcified vessel, in accordance with at least one aspect of the present disclosure. According to the process, a control circuit of the generator or instrument identifies a vessel located in the jaw of the ultrasonic device when the jaw clamps 132282 on the vessel. When the control circuit identifies 132284 a calcified vessel, the control circuit sends 132286 a warning message that can be perceived by the user. The message contains information to notify the user that a calcified vessel has been detected. The control circuit then prompts 132288 to maintain compression on the calcified vessel for a predetermined waiting period T1 (e.g., x-seconds). This will allow the calcification to migrate away from the jaws. At the expiration of the compression waiting period T1, the control circuit enables 132290 the activation of the ultrasonic generator. When the control circuit identifies 132292 a "normal (e.g., not calcified) vessel, the control circuit enables 132294 normal activation of the ultrasonic device. Accordingly, the ultrasonic device can execute one or more hemostasis algorithms as described herein.

FIG. 79 is a logic flow diagram 132300 depicting a control program or a logic configuration of a process for identifying a calcified vessel, in accordance with at least one aspect of the present disclosure. According to the process, a control circuit of the generator or instrument identifies a vessel located in the jaw of the ultrasonic device when the jaw clamps 132302 on the vessel. When the control circuit identifies 132304 a calcified vessel, the control circuit sends 132306 a warning message that can be perceived by the user that a calcified vessel was detected. The control circuit disables 132308 or alternatively does not enable activation of the ultrasonic device. When the control circuit identifies 132310 a "normal" vessel (e.g., not calcified), the control circuit enables 132312 normal activation of the ultrasonic device. Accordingly, the ultrasonic device can execute one or more hemostasis algorithms as described herein.

FIG. 80 is a logic flow diagram 132320 depicting a control program or a logic configuration of a process for identifying a calcified vessel, in accordance with at least one aspect of the present disclosure. According to the process, a control circuit of the generator or instrument identifies a vessel located in the jaw of the ultrasonic device when the jaw clamps 132322 on the vessel. When the control circuit identifies 132324 a calcified vessel, the control circuit sends 132326 a warning message that can be perceived by the user that a calcified vessel was detected. The control circuit increases 132328 the jaw clamp force with a motor in order to achieve better compression of the calcified vessel. The control circuit then enables 132330 activation of the ultrasonic energy after a clamp force adjustment. When the control circuit identifies 132332 a "normal" vessel (e.g., not calcified), the control circuit enables 132334 normal activation of the ultrasonic device. Accordingly, the ultrasonic device can execute one or more hemostasis algorithms as described herein.

Detection of Large Vessels During Parenchymal Dissection Using a Smart Blade

During liver resection procedures, surgeons risk cutting large vessels because they are buried inside the parenchyma that is being dissected, and thus cannot be seen. FIGS. 81-86 of this disclosure outlines an application for a "smart blade" (e.g., an ultrasonic blade with feedback to provide jaw content identification) that can detect the difference between parenchymal tissue, and large vessels within the parenchymal tissue by using the magnitude and phase of the impedance measurements over a swept frequency range. During a parenchymal dissection procedure, vessels may be detected using smart blade algorithm techniques for estimating or classifying the state of the jaw of an ultrasonic device described in connection with FIGS. 54-56 under the heading ESTIMATING THE STATE OF THE JAW (PAD BURN THROUGH, STAPLES, BROKEN BLADE, BONE IN JAW, TISSUE IN JAW and/or FIGS. 57-65 under the heading STATE OF JAW CLASSIFIER BASED ON MODEL and/or techniques for estimating the temperature of the ultrasonic blade are described in related U.S. Provisional Patent Application Ser. No. 62/640,417, titled TEMPERATURE CONTROL IN ULTRASONIC DEVICE AND CONTROL SYSTEM THEREFOR, to Nott et al, which is incorporated herein by reference in its entirety.

During liver resection and dissection procedures of other vascular parenchymal tissues, the surgeon cannot see vessels that are embedded within the parenchyma along the dissection plane. This can cause surgeons to cut large vessels without sealing, resulting in excessive bleeding that causes blood loss to the patient and stress for the surgeon. FIGS. 81-86 describe a solution that offers a method of detecting large vessels embedded in parenchymal tissues without the need to visualize the large vessels using a smart ultrasonic blade application.

The ultrasonic devices described herein may be employed to accomplish following vessel detection prior to initiating a liver resection and dissection procedure. A control circuit of the generator or the ultrasonic device initiates a frequency sweep from below resonance to above resonance of the electromechanical ultrasonic system to enable measurements of the magnitude and phase of the impedance. The results are plotted on a 3D curve as described in connection with FIGS. 54-56. The resulting 3D curve will have a particular form when the ultrasonic blade is in contact with parenchymal tissue and will have other forms when the ultrasonic blade contacts tissue other than parenchymal tissue, as discussed below.

A different 3D curve is generated by the frequency sweep when the ultrasonic blade is contacting a large vessel. When the ultrasonic blade contacts a vessel, the control circuit compares the test frequency sweep of the new (vessel) curve with the frequency sweep of the old (parenchyma) curve and identifies the new (vessel) curve as being different from the old (parenchyma) curve. Based on the comparison results, the control circuit enables an action to be taken by the ultrasonic device to prevent cutting into the large vessel, and to inform the surgeon that a large vessel is located on or is in contact with the ultrasonic blade.

The various actions that can be taken by the ultrasonic device include without limitation, change the therapeutic output of the device to prevent cutting of the vessel or change the tone from the generator to inform the surgeon that a vessel has been detected, or a combination thereof.

Alternatively, various aspects of this technique may be applied to detect blood if a vessel had been cut, allowing the surgeon to quickly seal the vessel, even without seeing the cut vessel.

FIG. 81 is a diagram 132340 of a liver resection 132350 with vessels 132354 (FIG. 82) embedded in parenchymal tissue, in accordance with at least one aspect of the present disclosure. An ultrasonic instrument 132342 including an ultrasonic blade 132344 and clamp arm 132346 is shown cutting into a liver 132348 to create a resection 132350. The ultrasonic instrument 132342 is coupled to a generator 132352 that controls the delivery of energy to the ultrasonic instrument 132342. Either the generator 132252 or the ultrasonic instrument 132342, or both, include a control circuit configured to execute the advanced smart blade algorithms discussed herein.

FIG. 82 is a diagram 132356 of an ultrasonic blade 132344 in the process of cutting through parenchyma without contacting a vessel 132354 embedded in the liver 132348, in accordance with at least one aspect of the present disclosure. During the resection process the control circuit monitors the impedance, magnitude, and phase of the signals driving the ultrasonic transducer to assess the state of the jaw, e.g. the state of the ultrasonic blade 132344, as depicted in FIGS. 83A and 83B. Accordingly, as the ultrasonic blade 132344 resects liver 132348 the ultrasonic transducer produces a first response and when the ultrasonic blade 132344 contacts the embedded vessel 132354 the ultrasonic transducer produces a second response, which is associated with the embedded vessel 132354 type as described herein in connection with FIGS. 54-81.

FIGS. 83A and 83B are graphical representations 132360 of ultrasonic transducer impedance magnitude/phase with the parenchyma curves 132362 shown in bold line, in accordance with at least one aspect of the present disclosure. FIG. 83A is a three-dimensional plot and FIG. 83B is a two-dimensional plot. These curves are generated in accordance with FIGS. 54-56, for example, and associated description under the heading ESTIMATING THE STATE OF THE JAW (PAD BURN THROUGH, STAPLES, BROKEN BLADE, BONE IN JAW, TISSUE IN JAW. Alternatively, techniques for estimating or classifying the state of the jaw of an ultrasonic device described in connection with FIGS. 57-65 under the heading STATE OF JAW CLASSIFIER BASED ON MODEL and/or techniques for estimating the temperature of the ultrasonic blade are described in related U.S. Provisional Patent Application Ser. No. 62/640,417, titled TEMPERATURE CONTROL IN ULTRASONIC DEVICE AND CONTROL SYSTEM THEREFOR may be employed.

FIG. 84 is a diagram 132364 of an ultrasonic blade 132344 in the process of cutting through parenchyma and contacting a vessel 132354 embedded in the liver 132348, in accordance with at least one aspect of the present disclosure. As the ultrasonic blade 132344 transects the liver 132348 parenchyma tissue, the ultrasonic blade 132344 contacts the vessel 132354 at a location 132366 and thus shifts the resonant frequency of the ultrasonic transducer as depicted in FIGS. 85A and 85B. The control circuit monitors the impedance, magnitude, and phase of the signals driving the ultrasonic transducer to assess the state of the jaw, e.g. the state of the ultrasonic blade 132344 while contacting the vessel 132354, as depicted in FIGS. 85A and 85B.

FIGS. 85A and 85B are graphical representations 132370 ultrasonic transducer impedance magnitude/phase with large vessel curves 132372 shown in bold line, in accordance with at least one aspect of the present disclosure. FIG. 85A is a three-dimensional plot and FIG. 85B is a two-dimensional plot. These curves are generated in accordance with FIGS. 54-56 and associated description under the heading ESTIMATING THE STATE OF THE JAW (PAD BURN THROUGH, STAPLES, BROKEN BLADE, BONE IN JAW, TISSUE IN JAW. Alternatively, techniques for estimating or classifying the state of the jaw of an ultrasonic device described in connection with FIGS. 57-65 under the heading STATE OF JAW CLASSIFIER BASED ON MODEL and/or techniques for estimating the temperature of the ultrasonic blade are described in related U.S. Provisional Patent Application Ser. No. 62/640,417, titled TEMPERATURE CONTROL IN ULTRASONIC DEVICE AND CONTROL SYSTEM THEREFOR may be employed.

FIG. 86 is a logic flow diagram 132380 depicting a control program or a logic configuration of a process for treating tissue in parenchyma when a vessel is detected as shown in FIGS. 84-85B, in accordance with at least one aspect of the present disclosure. According to the process, using the techniques for estimating or classifying the state of the jaw of an ultrasonic device described in connection with FIGS. 54-56 under the heading ESTIMATING THE STATE OF THE JAW (PAD BURN THROUGH, STAPLES, BROKEN BLADE, BONE IN JAW, TISSUE IN JAW and/or FIGS. 57-65 under the heading STATE OF JAW CLASSIFIER BASED ON MODEL and/or techniques for estimating the temperature of the ultrasonic blade are described in related U.S. Provisional Patent Application Ser. No. 62/640,417, titled TEMPERATURE CONTROL IN ULTRASONIC DEVICE AND CONTROL SYSTEM THEREFOR, the control circuit determines if a vessel 132354 is located is in contact with the ultrasonic blade 132344. If the control circuit detects a vessel 132382, the control circuit stops 132384 the cutting energy, switches 132386 to a lower power level, and sends 132388 a warning message or alert to the user. For example, the control circuit lowers the excitation voltage/current signal power to a level below what is required for cutting a vessel. The warning message or alert may include emitting a light, emitting a sounding, activating a buzzer, and the like. If a vessel 132354 is not detected, the resection process continues 132390.

Smart Ultrasonic Blade Application for Reusable and Disposable Devices

The smart blade algorithm uses spectroscopy to identify the status of an ultrasonic blade. This capability can be applied to reusable and disposable devices with detachable clamp arms to distinguish if the disposable portion of the device has been installed correctly. The status of the ultrasonic blade may be determined using smart blade algorithm techniques for estimating or classifying the state of the jaw of an ultrasonic device described in connection with FIGS. 54-56 under the heading ESTIMATING THE STATE OF THE JAW (PAD BURN THROUGH, STAPLES, BROKEN BLADE, BONE IN JAW, TISSUE IN JAW and/or FIGS. 57-65 under the heading STATE OF JAW CLASSIFIER BASED ON MODEL and/or techniques for estimating the temperature of the ultrasonic blade are described in related U.S. Provisional Patent Application Ser. No. 62/640,417, titled TEMPERATURE CONTROL IN ULTRASONIC DEVICE AND CONTROL SYSTEM THEREFOR, to Nott et al, which is incorporated herein by reference in its entirety.

The smart blade algorithm techniques described herein can be employed to identify the status of components of reusable and disposable devices. In one aspect, the status of the ultrasonic blade may be determined to distinguish if disposable portions of reusable and disposable devices have been installed correctly or incorrectly.

FIGS. 87 and 88 is a reusable and disposable ultrasonic device 132400 configured to identify the status of the ultrasonic blade 132402 and determine the clocked status of the clamp arm 132404 to determine whether a portion of the reusable and disposable ultrasonic device 132400 has been installed correctly, in accordance with at least one aspect of the present disclosure. FIG. 88 is an end effector 132406 portion of the reusable and disposable ultrasonic device 132400 shown in FIG. 87. Similarities and differences between the spectroscopy signatures can be used to determine whether the reusable and disposable components of the reusable and disposable ultrasonic device 132400 have been installed correctly or incorrectly.

The reusable and disposable ultrasonic device 132400 shown in FIGS. 87 and 88 includes a reusable handle 132408 and a disposable ultrasonic waveguide/blade 132402. Prior to use, a proximal end 132410 of the disposable ultrasonic waveguide/blade 132402 is inserted 132414 into a distal opening 132412 of the reusable handle 132408 and twisted or rotated clockwise 132416 to lock the disposable ultrasonic waveguide/blade 132402 into the handle 132408 as shown in FIG. 87. If the disposable ultrasonic waveguide/blade 132402 is not fully inserted 132414 and/or fully rotated clockwise 132416, the reusable and disposable ultrasonic device 132400 will not operate properly. For example, improper insertion 132414 and rotation 132416 of the disposable ultrasonic waveguide/blade 132402 will result in poor mechanical coupling of the disposable ultrasonic waveguide/blade 132402 and will produce a different spectroscopy signature. Therefore, the smart blade algorithm techniques described herein can be used to determine if the disposable portion of the reusable and disposable ultrasonic device 132400 has been inserted 132414 and rotated 132416 completely.

In another misaligned configuration, if the clamp arm 132404 shown in FIG. 88 is clocked (rotated) relative to the ultrasonic blade 132402, the orientation of the ultrasonic blade 132402 relative to the clamp arm 132404 will be out of alignment. This also will produce a different spectroscopy signature when the reusable and disposable ultrasonic device 132400 is actuated and/or clamped. Therefore, the smart blade algorithm techniques described herein can be used to determine if the disposable portion of the reusable and disposable ultrasonic device 132400 has been properly clocked (rotated) relative to the clamp arm 132404.

In another aspect, the smart blade algorithm techniques described herein can be used to determine if a disposable portion of the reusable and disposable ultrasonic device 132400 has been pushed in or inserted 132414 all the way into the reusable portion 132408. This may be applicable to the reusable and disposable ultrasonic device 132400 in FIG. 89 below where a reusable portion such as the handle 132408, for example, is 132414 inserted into a disposable portion, such as the ultrasonic blade 132402, for example, prior to operation.

FIG. 89 is a reusable and disposable ultrasonic device 132420 configured to identify the status of the ultrasonic blade 132422 and determine whether the clamp arm 132424 is not completely distal to determine whether a disposable portion 132426 of the reusable and disposable ultrasonic device 132420 has been installed correctly, in accordance with at least one aspect of the present disclosure. If the clamp arm is not installed completely distal there will be a different spectroscopy signature when the device is clamped. In another aspect, if the disposable portion 132426 is not installed completely distal on the reusable component 132428, the ultrasonic blade 132422 spectroscopy signature will be different when clamped into position. Therefore, the smart blade algorithm techniques described herein can be used to determine if the disposable portion 132426 of the reusable and disposable ultrasonic device 132420 has been fully and properly coupled to the reusable portion 132428.

FIG. 90 is a logic flow diagram 132430 depicting a control program or a logic configuration to identify the status of components of reusable and disposable ultrasonic devices, in accordance with at least one aspect of the present disclosure. According to the process depicted by the logic flow diagram 132430, a control circuit of the generator or instrument executes a smart blade algorithm technique and determines 132432 the spectroscopy signature of assembled reusable and disposable ultrasonic devices 132400, 132420 (FIGS. 88 and 89) comprising reusable and disposable components. The control circuit compares 132434 the measured spectroscopy signature to a reference spectroscopy signature, where the reference spectroscopy signature is associated with a properly assembled reusable and disposable ultrasonic device 132400, 132420 and is stored in a database or memory of the generator or instrument. When the control circuit determines 132436 that the measured spectroscopy signature differs from the reference spectroscopy signature, the control circuit disables 132438 the operation of the reusable and disposable ultrasonic device 132400, 132420 and generates 132440 a warning that can be perceived by the user. The waning may include activating a light source sound source, or vibration source. When the measured spectroscopy signature is the same or substantially similar to the reference spectroscopy signature, the control circuit enables 132442 the normal operation of the reusable and disposable ultrasonic device 132400, 132420.

Live Time Tissue Classification Using Electrical Parameters

Sealing without Cutting, RF/Ultrasonic Combination Technology, Tailored Algorithms In one aspect, the present disclosure provides an algorithm for classifying tissue into groups. The ability to classify tissue in live time will allow for tailoring algorithms to a specific tissue group. The tailored algorithms can optimize seal times and hemostasis across all tissue types. In one aspect, the present disclosure provides a sealing algorithm to provide hemostasis needed for large vessels and quickly seal smaller structures that do not need extended energy activation. The ability to classify these distinct tissue types allows for optimized algorithms for each group in live time.

In this aspect, during the first 0.75 seconds of the activation, 3 RF electrical parameters are used in a plot to classify tissue into distinct groups. These electrical parameters are: Initial RF impedance (taken at 0.15 seconds), Minimum RF impedance in first 0.75 seconds, and the amount of time the RF impedance slope is ~0 in milliseconds. A plurality of other times that these data points are taken could be implemented. All of this data is collected in a set amount of time, and then using a Support Vector Machine (SVM) or another classification algorithm the tissue can be classified into a distinct group in live time. Each tissue group would have an algorithm specific to it that would be implemented for the remainder of the activation. Types of SVM's include linear, polynomial, and radial basis function (RBF).

FIG. 91 is a three-dimensional graphical representation 132450 of epidermal growth factor (EGF) radio frequency (RF) tissue impedance classification, in accordance with at least one aspect of the present disclosure. The x-axis represents the minimum RF impedance (Zmin) of the tissue, the y-axis represents initial RF impedance (Zinit) of the tissue, and the z-axis represents the amount of time that the derivative of the RF impedance (Z) of the tissue is approximately 0. FIG. 91 shows a grouping of large vessels 132452, e.g., carotids—thick tissue, and small vessels 132454, e.g., thyros—thin tissue, when using the three RF parameters of Initial RF impedance, Minimum RF Impedance, and the amount of time the derivative (slope) of the RF impedance is approximately zero within the first 0.75 seconds of activation. A distinction of this classification method is that the tissue type can be classified in a set amount of time. The advantage to this method is a tissue specific algorithm can be chosen towards the beginning of the activation, so specialized tissue treatment can begin before the exit out of the RF bathtub. It will be appreciated that in the context of tissue impedance under the influence of RF energy a bathtub region is a curve wherein the tissue impedance drops after the initial application of RF energy and stabilizes until the tissue begins to dry out. Thereafter the tissue impedance increases. Thus, the impedance versus time curve resembles the shape of a "bathtub."

This data was used to train and test a Support Vector Machine to group thick and thin tissue, and accurately classified 94% of the time.

In one aspect, the present disclosure provides a device comprising one combo RF/Ultrasonic algorithm that is used for all tissue types and it has been identified that seal speeds for thin tissues are longer than necessary, however larger vessels and thicker structures could benefit from an extended activation. This classification scheme will enable the combo RF/ultrasonic device to seal small structures with optimal speeds and burst pressures, and to seal larger structures to ensure maximum hemostasis is achieved.

FIG. 92 is a three-dimensional graphical representation 132460 of epidermal growth factor (EGF) radio frequency (RF) tissue impedance analysis, in accordance with at least one aspect of the present disclosure. The x=axis represents the minimum RF impedance (Zmin) of the tissue, the y-axis represents the initial RF impedance (Zinit) of the tissue, and the z-axis represents the amount of time that the derivative of the RF impedance (Z) of the tissue is approximately 0. To determine if this classification model of thick tissue 132462 versus thin tissue 132464 was robust to different tissue types, data was added for various benchtop tissue types, and the tissue grouped into two distinct groups. It is possible to separate this data into a plurality of groups if it is deemed beneficial or necessary. The different thick tissue 132462 types include, for example, carotid, jejunum, mesentery, jugular, and liver tissue. The different thin tissue 132464 types include, for example, thyro and thyro vein.

Fine Dissection Mode for Tissue Classification

Tissue Classification to Enable Multiple Modes to Account for Different Surgical Techniques In one aspect, the present disclosure provides an algorithm for classifying tissue into groups and tailoring an algorithm to classify specific tissue classes in live time. This disclosure builds upon the foundation and details of another potential benefit to classifying tissue as previously discussed herein under the heading LIVE TIME TISSUE CLASSIFICATION USING ELECTRICAL PARAMETERS.

FIG. 93 is a graphical representation 132470 of carotid technique sensitivity where the time that the RF impedance (Z) derivative is approximately 0 is plotted as a function of initial RF impedance, in accordance with at least one aspect of the present disclosure. It is known that different surgical techniques exist in different regions of the world, and vary widely from surgeon to surgeon. For this reason, a technique mode may be provided on the generator to enable more efficient energy delivery based upon the user's specific surgical technique such as, for example, a tip bite of tissue versus a full bite of tissue. A tip bite refers to the end effector of a surgical device grasping tissue at the tip only. A full bite refers to the end effector of a surgical device grasping tissue within the entire end effector. The generator may be configured to detect if a user is consistently operating with a tip bite of tissue or a full bite of tissue. As shown in FIG. 93 initial RF impedance data was measured and plotted for tip bites as Group 1 132472 and full bites as Group 2 132474. As shown, Group 1 132472 tip bites of tissue register an initial RF impedance $Z_{init}$ of less than 250 Ohms and Group 2 132474 full bites of tissue register an initial impedance $Z_{init}$ between 250 Ohms and 500 Ohms, the maximum RF tissue impedance $Z_{Max}$. Upon detecting whether the user grasps a tip bite of tissue or a full bite of tissue, the algorithm can suggest a predetermined dissection mode. For example, for a tip bite of tissue the algorithm may suggest a fine dissection mode to the user or this option may be selected before a procedure. For example, for a full bite of tissue the algorithm may suggest a course dissection mode to the user or this option may be selected before a procedure. In fine dissection mode, the algorithm may be tailored to optimize energy delivery for this surgical technique by lowering the ultrasonic displacement to protect the clamp arm pad from burning through. Also it is known that tip biting has a greater amount of RF noise, causing longer seal times, and greater variation in seal performance. Fine dissection mode for tip biting cold have an algorithm tailored to having a lower RF termination impedance and/or different filtering signal to increase accuracy of energy delivery.

A technique sensitivity analysis was conducted as part of the development work for classification. The testing was conducted by transecting 3-7 mm vessels in a benchtop setting using different surgical techniques such as full bite transection with and without tension, and tip bite transection with and without tension. The initial RF impedance, and the time the slope the RF impedance=0 were all examined as significant factors in classifying the tissue into groups.

It was determined that surgical techniques could be grouped into 3 distinct groups based on the initial RF impedance $Z_{init}$. Initial RF impedance $Z_{init}$ generally ranging between 0-100 ohms indicates operating in a bloody field. Initial RF impedance $Z_{init}$ generally ranging between 100-300 ohms indicates operating under normal conditions, and initial RF impedance $Z_{init}$ greater than 300 ohms indicates abuse condition especially where tensions is present.

Controlled Thermal Management (CTM) for Pad Protection

In one aspect, the present disclosure provides a controlled thermal management (CTM) algorithm to regulate temperature with feedback control. The output of the feedback control can be used to prevent the ultrasonic end effector clamp arm pad from burning through, which is not a desirable effect for ultrasonic surgical instruments. As previously discussed, in general, pad burn through is caused by the continued application of ultrasonic energy to an ultrasonic blade in contact with the pad after tissue grasped in the end effector has been transected.

The CTM algorithm leverages the fact that the resonant frequency of an ultrasonic blade, general made of titanium, varies in proportion to temperature. As the temperature increases, the modulus of elasticity of the ultrasonic blade decreases, and so does the natural frequency of the ultrasonic blade. A factor to consider is that when the distal end of the ultrasonic blade is hot but the waveguide is cold, there is a different frequency difference (delta) to achieve a predetermined temperature than when the distal end of the ultrasonic blade and the waveguide are both hot.

In one aspect, the CTM algorithm calculates a change in frequency of the ultrasonic transducer drive signal that is required to reach a certain predetermined temperature as a function of the resonant frequency of the ultrasonic electromechanical system at the beginning of activation (at lock). The ultrasonic electromechanical system comprising an ultrasonic transducer coupled to an ultrasonic blade by an ultrasonic waveguide has a predefined resonant frequency that varies with temperature. The resonant frequency of the ultrasonic electromechanical system at lock can be employed to estimate the change in ultrasonic transducer drive frequency that is required to achieve a temperature end point to account for the initial thermal state of the ultrasonic blade. The resonant frequency of the ultrasonic electromechanical system can vary as a function of temperature of the ultrasonic transducer or ultrasonic waveguide or ultrasonic blade or a combination of these components.

FIG. 94 is a graphical representation 133300 of the relationship between initial resonant frequency (frequency at lock) and the change in frequency (delta frequency) required to achieve a temperature of approximately 340° C., in accordance with at least one aspect of the present disclosure. The change in frequency required to reach an ultrasonic blade temperature of approximately 340° C. is shown along the vertical axis and the resonant frequency of the electromechanical ultrasonic system at lock is shown along the horizontal axis. Based on measurement data points 133302 shown as scatter plot there is a linear relationship 133304 between the change in frequency required to reach an ultrasonic blade temperature of approximately 340° C. and the resonant frequency at lock.

At resonant frequency lock, the CTM algorithm employs the linear relationship 133304 between the lock frequency and the delta frequency required to achieve a temperature just below the melting point of a TEFLON pad (approximately 340° C.). Once the frequency is within a certain buffer distance from a lower bound on frequency, as shown in FIG. 95, a feedback control system 133310 comprising an ultrasonic generator 133312 regulates the electrical current (i) set point applied to the ultrasonic transducer of the ultrasonic electromechanical system 133314 to prevent the frequency (f) of the ultrasonic transducer from decreasing lower than a predetermined threshold, in accordance with at least one aspect of the present disclosure. Decreasing the electrical current set point decreases the displacement of the ultrasonic blade, which in turn decreases the temperature of the ultrasonic blade and increases the natural frequency of the ultrasonic blade. This relationship allows a change in the electrical current applied to the ultrasonic transducer to regulate the natural frequency of the ultrasonic blade and indirectly control the temperature of the ultrasonic blade or the ultrasonic electromechanical system 133314. In one aspect, the generator 133312 may be implemented as the ultrasonic generator described with reference to FIGS. 21, 26, 27A-27C, and 28A-28B, for example. The feedback control system 133310 may be implemented as the PID controller described with reference to FIGS. 44-45, for example.

FIG. 96 is a flow diagram 133320 of a process or logic configuration of a controlled thermal management (CTM) algorithm to protect the clamp arm pad in an ultrasonic end effector, in accordance with at least one aspect of the present disclosure. The process or logic configuration illustrated by way of the flow diagram 133320 may be executed by the ultrasonic generator 133312 as described herein or by control circuits located in the ultrasonic instrument or a combination thereof. As previously discussed, the generator 133312 may be implemented as the generator described with reference to FIGS. 21, 26, 27A-27C, and 28A-28B, for example.

In one aspect, initially the control circuit in the generator 133312 activates the ultrasonic instrument by applying an electrical current to the ultrasonic transducer. The resonant frequency of the ultrasonic electromechanical system is initially locked at initial conditions where the ultrasonic blade temperature is cold or close to room temperature. As the temperature of the ultrasonic blade increases due to frictional contact with tissue, for example, the control circuit monitors the change or delta in the resonant frequency of the ultrasonic electromechanical system and determines 133324 whether the delta frequency threshold for a predetermined blade temperature has been reached. If the delta frequency is below the threshold, the process continues along the NO branch and the control circuit continues to seek 133325 the new resonant frequency and monitor the delta frequency. When the delta frequency meets or exceeds the delta frequency threshold, the process continues along the YES branch and calculates 133326 a new lower frequency limit (threshold), which corresponds to the melting point of the clamp arm pad. In one non-limiting example, the clamp arm pad is made of TEFLON and the melting point is approximately 340° C.

Once a new frequency lower limit is calculated 133326, the control circuit determines 133328 if the resonant frequency is near the newly calculated lower frequency limit. For example, in the case of a TEFLON clamp arm pad, the control circuit determines 133328 if the ultrasonic blade temperature is approaching 350° C., for example, based on the current resonant frequency. If the current resonant frequency is above the lower frequency limit, the process continues along the NO branch and applies 133330 a normal level of electrical current to the ultrasonic transducer suitable for tissue transection. Alternatively, if the current resonant frequency is at or below the lower frequency limit, the process continues along the YES branch and regulates 133332 the resonant frequency by modifying the electrical current applied to the ultrasonic transducer. In ne aspect, the control circuit employs a PID controller as described with reference to FIGS. 44-45, for example. The control circuit regulates 133332 the frequency in a loop to determine 133328 when the frequency is near the lower limit until the "seal and cut" surgical procedure is terminated and the ultrasonic transducer is deactivated. Since the CTM algorithm depicted by the logic flow diagram 133320 only has an effect at or near the melting point of the clamp arm pad, the CTM algorithm is activated after the tissue is transected.

Burst pressure testing conducted on samples indicates that there is no impact on the burst pressure of the seal when the CTM process or logic configuration depicted by the logic flow diagram 133320 is employed to seal and cut vessels or other tissue. Furthermore, based on test samples, transection times were affected. Moreover, temperature measurements confirm that the ultrasonic blade temperature is bounded by the CTM algorithm compared to devices without CTM feedback algorithm control and devices that underwent 10 firings at maximum power for ten seconds against the pad with 5 seconds rest between firings showed significantly reduced pad wear whereas no device without CTM algorithm feedback control lasted more than 2 firings in this abuse test.

FIG. 97 is a graphical representation 133340 of temperature versus time comparing the desired temperature of an ultrasonic blade with a smart ultrasonic blade and a conventional ultrasonic blade, in accordance with at least one aspect of the present disclosure. Temperature (deg. C.) is shown along the vertical axis and Time (sec) is shown along the horizontal axis. In the plot, the dash-dot line is a temperature threshold 133342 that represents the desired temperature of the ultrasonic blade. The solid line is a temperature versus time curve 133344 of a smart ultrasonic blade under the control of the CTM algorithm described with reference to FIGS. 95 and 96. The dotted line is a temperature versus time curve 133346 of a regular ultrasonic blade that is not under the control of the CTM algorithm described with reference to FIGS. 95 and 96. As shown. Once the temperature of the smart ultrasonic blade under the control of the CTM algorithm exceeds the desired temperature threshold (~340° C.), the CTM algorithm takes control and regulates the temperature of the smart ultrasonic blade to match the threshold as closely as possible until the transection procedure is completed and the power to the ultrasonic transducer is deactivated or cut off.

In another aspect, the present disclosure provides a CTM algorithm for a "seal only" tissue effect by an ultrasonic device, such as ultrasonic shears, for example. Generally speaking, ultrasonic surgical instruments typically seal and cut tissue simultaneously. Creating an ultrasonic device configured to seal only without cutting has not been difficult to achieve using ultrasonic technology alone due to the uncertainty of knowing when the seal was completed before initiating the cutting. In one aspect, the CTM algorithm may be configured to protect the end effector clamp arm pad by allowing the temperature of the ultrasonic blade to exceed the temperature required for cutting (transecting) the tissue but not to exceed the melting point of the clamp arm pad. In another aspect, the CTM seal only algorithm may be tuned to exceed the sealing temperature of tissue (approximately 115° C. to approximately 180° C. based on experimentation) but not to exceed the cutting (transecting) temperature of tissue (approximately 180° C. to approximately 350° C.). In the latter configuration, the CTM seal only algorithm provides a "seal only" tissue effect that has been successfully demonstrated. In a linear fit that calculates the change in frequency with respect to the initial lock frequency, as shown in FIG. 94, for example, changing the intercept of the fit regulates the final steady state temperature of the ultrasonic blade. By adjusting the intercept parameter, the ultrasonic blade can be set to never exceed approximately 180° C. resulting in the tissue sealing but not cutting. In one aspect, increasing the clamp force may improve the sealing process without impacting clamp arm pad burn through because the temperature of the blade is controlled by the CTM seal only algorithm. As previously described, the CTM seal only algorithm may be implemented by the generator and PID controller described with reference to FIGS. 21, 26, 27A-27C, 28A-28B, and 44-45, for example. Accordingly, the flow diagram 133320 shown in FIG. 96 may be modified such that the control circuit calculates 133326 a new lower frequency limit (threshold t correspond with a "seal only" temperature such as, for example, approximately 180° C., determine 133328 when the frequency is near the lower limit, and regulate 133332 the temperature until the "seal only" surgical procedure is terminated and the ultrasonic transducer is deactivated.

In another aspect, the present disclosure provides a cool thermal monitoring (CTMo) algorithm configured to detect when atraumatic grasping is feasible. Acoustic ultrasonic energy results in an ultrasonic blade temperature of approximately 230° C. to approximately 300° C. to achieve the desired effect of cutting or transecting tissue. Because heat is retained in the metal body of the ultrasonic blade for a period of time after deactivation of the ultrasonic transducer, the residual heat stored in the ultrasonic blade can cause tissue damage if the ultrasonic end effector is used to grasp tissue before the ultrasonic blade has had an opportunity to cool down.

In one aspect, the CTMo algorithm calculates a change in the natural frequency of the ultrasonic electromechanical system from the natural frequency at a hot state to a natural frequency at a temperature where atraumatic grasping is possible without damaging the tissue grasped by the end effector. Directly or a predetermined period of time after activating the ultrasonic transducer, a non-therapeutic signal (approximately 5 mA) is applied to the ultrasonic transducer containing a bandwidth of frequencies, approximately 48,000 Hz to 52,000 Hz, for example, at which the natural frequency is expected to be found. A FFT algorithm, or other mathematically efficient algorithm of detecting the natural frequency of the ultrasonic electromechanical system, of the impedance of the ultrasonic transducer measured during the stimulation of the ultrasonic transducer with the non-therapeutic signal will indicate the natural frequency of the ultrasonic blade as being the frequency at which the impedance magnitude is at a minimum. Continually stimulating the ultrasonic transducer in this manner provides continual feedback of the natural frequency of the ultrasonic blade within a frequency resolution of the FFT or other algorithm for estimating or measuring the natural frequency. When a change in natural frequency is detected that corresponds to a temperature that is feasible for atraumatic grasping, a tone, or a LED, or an on screen display or other form of notification, or a combination thereof, is provided to indicate that the device is capable of atraumatic grasping.

In another aspect, the present disclosure provides a CTM algorithm configured to tone for seal and end of cut or transection. Providing "tissue sealed" and "end of cut" notifications is a challenge for conventional ultrasonic devices because temperature measurement cannot easily be directly mounted to the ultrasonic blade and the clamp arm pad is not explicitly detected by the blade using sensors. A CTM algorithm can indicate temperature state of the ultrasonic blade and can be employed to indicate the "end of cut" or "tissue sealed"\", or both, states because these are temperature-based events.

In one aspect, a CTM algorithm according to the present disclosure detects the "end of cut" state and activates a notification. Tissue typically cuts at approximately 210° C. to approximately 320° C. with high probability. A CTM algorithm can activate a tone at 320° C. (or similar) to indicate that further activation on the tissue is not productive as that the tissue is probably cut and the ultrasonic blade is now running against the clamp arm pad, which is acceptable when the CTM algorithm is active because it controls the temperature of the ultrasonic blade. In one aspect, the CTM algorithm is programmed to control or regulate power to the ultrasonic transducer to maintain the temperature of the ultrasonic blade to approximately 320° C. when the temperature of the ultrasonic blade is estimated to have reached 320° C. Initiating a tone at this point provides an indication that the tissue has been cut. The CTM algorithm is based on a variation in frequency with temperature. After determining an initial state temperature (based on initial frequency), the CTM algorithm can calculate a frequency change that corresponds to a temperature that implies when the tissue is cut. For example, if the starting frequency is 51,000 Hz, the CTM algorithm will calculate the change in frequency required to achieve 320° C. which might be −112 Hz. It will then initiate control to maintain that frequency set point (e.g., 50,888 Hz) thereby regulating the temperature of the ultrasonic blade. Similarly, a frequency change can be calculated based on an initial frequency that indicates when the ultrasonic blade is at a temperature which indicates that the tissue is probably cut. At this point, the CTM algorithm does not have to control power, but simply initiate a tone to indicate the state of the tissue or the CTM algorithm can control frequency at this point to maintain that temperature if desired. Either way, the "end of cut" is indicated.

In one aspect, a CTM algorithm according to the present disclosure detects the "tissue sealed" state and activates a notification. Similar to the end of cut detection, tissue seals between approximately 105° C. and approximately 200° C. The change in frequency from an initial frequency required to indicate that a temperature of the ultrasonic blade has reached 200° C., which indicates a seal only state, can be calculated at the onset of activation of the ultrasonic transducer. The CTM algorithm can activate a tone at this point and if the surgeon wishes to obtain a seal only state, the surgeon could stop activation or to achieve a seal only state the surgeon could stop activation of the ultrasonic transducer and automatically initiate a specific seal only algorithm from this point on or the surgeon could continue activation of the ultrasonic transducer to achieve a tissue cut state.

Situational Awareness

Referring now to FIG. 98, a timeline 5200 depicting situational awareness of a hub, such as the surgical hub 106 or 206, for example, is depicted. The timeline 5200 is an illustrative surgical procedure and the contextual information that the surgical hub 106, 206 can derive from the data received from the data sources at each step in the surgical procedure. The timeline 5200 depicts the typical steps that would be taken by the nurses, surgeons, and other medical personnel during the course of a lung segmentectomy procedure, beginning with setting up the operating theater and ending with transferring the patient to a post-operative recovery room.

The situationally aware surgical hub 106, 206 receives data from the data sources throughout the course of the surgical procedure, including data generated each time medical personnel utilize a modular device that is paired with the surgical hub 106, 206. The surgical hub 106, 206 can receive this data from the paired modular devices and other data sources and continually derive inferences (i.e., contextual information) about the ongoing procedure as new data is received, such as which step of the procedure is being performed at any given time. The situational awareness system of the surgical hub 106, 206 is able to, for example, record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the field of view (FOV) of the medical imaging device, or change the energy level of an ultrasonic surgical instrument or RF electrosurgical instrument), and take any other such action described above.

As the first step 5202 in this illustrative procedure, the hospital staff members retrieve the patient's EMR from the hospital's EMR database. Based on select patient data in the EMR, the surgical hub 106, 206 determines that the procedure to be performed is a thoracic procedure.

Second step 5204, the staff members scan the incoming medical supplies for the procedure. The surgical hub 106, 206 cross-references the scanned supplies with a list of supplies that are utilized in various types of procedures and confirms that the mix of supplies corresponds to a thoracic procedure. Further, the surgical hub 106, 206 is also able to determine that the procedure is not a wedge procedure (because the incoming supplies either lack certain supplies that are necessary for a thoracic wedge procedure or do not otherwise correspond to a thoracic wedge procedure).

Third step 5206, the medical personnel scan the patient band via a scanner that is communicably connected to the surgical hub 106, 206. The surgical hub 106, 206 can then confirm the patient's identity based on the scanned data.

Fourth step 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices can automatically pair with the surgical hub 106, 206 that is located within a particular vicinity of the modular devices as part of their initialization process. The surgical hub 106, 206 can then derive contextual information about the surgical procedure by detecting the types of modular devices that pair with it during this pre-operative or initialization phase. In this particular example, the surgical hub 106, 206 determines that the surgical procedure is a VATS procedure based on this particular combination of paired modular devices. Based on the combination of the data from the patient's EMR, the list of medical supplies to be used in the procedure, and the type of modular devices that connect to the hub, the surgical hub 106, 206 can generally infer the specific procedure that the surgical team will be performing. Once the surgical hub 106, 206 knows what specific procedure is being performed, the surgical hub 106, 206 can then retrieve the steps of that procedure from a memory or from the cloud and then cross-reference the data it subsequently receives from the connected data sources (e.g., modular devices and patient monitoring devices) to infer what step of the surgical procedure the surgical team is performing.

Fifth step 5210, the staff members attach the EKG electrodes and other patient monitoring devices to the patient. The EKG electrodes and other patient monitoring devices are able to pair with the surgical hub 106, 206. As the surgical hub 106, 206 begins receiving data from the patient monitoring devices, the surgical hub 106, 206 thus confirms that the patient is in the operating theater.

Sixth step 5212, the medical personnel induce anesthesia in the patient. The surgical hub 106, 206 can infer that the patient is under anesthesia based on data from the modular devices and/or patient monitoring devices, including EKG data, blood pressure data, ventilator data, or combinations thereof, for example. Upon completion of the sixth step 5212, the pre-operative portion of the lung segmentectomy procedure is completed and the operative portion begins.

Seventh step 5214, the patient's lung that is being operated on is collapsed (while ventilation is switched to the contralateral lung). The surgical hub 106, 206 can infer from the ventilator data that the patient's lung has been collapsed, for example. The surgical hub 106, 206 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth step 5216, the medical imaging device (e.g., a scope) is inserted and video from the medical imaging device is initiated. The surgical hub 106, 206 receives the medical imaging device data (i.e., video or image data) through its connection to the medical imaging device. Upon receipt of the medical imaging device data, the surgical hub 106, 206 can determine that the laparoscopic portion of the surgical procedure has commenced. Further, the surgical hub 106, 206 can determine that the particular procedure being performed is a segmentectomy, as opposed to a lobectomy (note that a wedge procedure has already been discounted by the surgical hub 106, 206 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 106, 206), and monitoring the types of visualization devices utilized. For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device, the surgical hub 106, 206 can thereby determine the specific type of surgical procedure being performed and/or the technique being used for a particular type of surgical procedure.

Ninth step 5218, the surgical team begins the dissection step of the procedure. The surgical hub 106, 206 can infer that the surgeon is in the process of dissecting to mobilize the patient's lung because it receives data from the RF or ultrasonic generator indicating that an energy instrument is being fired. The surgical hub 106, 206 can cross-reference the received data with the retrieved steps of the surgical procedure to determine that an energy instrument being fired at this point in the process (i.e., after the completion of the previously discussed steps of the procedure) corresponds to the dissection step. In certain instances, the energy instrument can be an energy tool mounted to a robotic arm of a robotic surgical system.

Tenth step 5220, the surgical team proceeds to the ligation step of the procedure. The surgical hub 106, 206 can infer that the surgeon is ligating arteries and veins because it receives data from the surgical stapling and cutting instrument indicating that the instrument is being fired. Similarly to the prior step, the surgical hub 106, 206 can derive this inference by cross-referencing the receipt of data from the surgical stapling and cutting instrument with the retrieved steps in the process. In certain instances, the surgical instrument can be a surgical tool mounted to a robotic arm of a robotic surgical system.

Eleventh step 5222, the segmentectomy portion of the procedure is performed. The surgical hub 106, 206 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 106, 206 to infer that the segmentectomy portion of the procedure is being performed.

Twelfth step 5224, the node dissection step is then performed. The surgical hub 106, 206 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 106, 206 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Moreover, in certain instances, robotic tools can be utilized for one or more steps in a surgical procedure and/or handheld surgical instruments can be utilized for one or more steps in the surgical procedure. The surgeon(s) can alternate between robotic tools and handheld surgical instruments and/or can use the devices concurrently, for example. Upon completion of the twelfth step 5224, the incisions are closed up and the post-operative portion of the procedure begins.

Thirteenth step 5226, the patient's anesthesia is reversed. The surgical hub 106, 206 can infer that the patient is emerging from the anesthesia based on the ventilator data (i.e., the patient's breathing rate begins increasing), for example.

Lastly, the fourteenth step 5228 is that the medical personnel remove the various patient monitoring devices from the patient. The surgical hub 106, 206 can thus infer that the patient is being transferred to a recovery room when the hub loses EKG, BP, and other data from the patient monitoring devices. As can be seen from the description of this illustrative procedure, the surgical hub 106, 206 can determine or infer when each step of a given surgical procedure is taking place according to data received from the various data sources that are communicably coupled to the surgical hub 106, 206.

Situational awareness is further described in U.S. Provisional Patent Application Ser. No. 62/611,341, titled INTERACTIVE SURGICAL PLATFORM, filed Dec. 28, 2017, which is herein incorporated by reference in its entirety. In certain instances, operation of a robotic surgical system, including the various robotic surgical systems disclosed herein, for example, can be controlled by the hub 106, 206 based on its situational awareness and/or feedback from the components thereof and/or based on information from the cloud 102.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

Various aspects of the subject matter described herein are set out in the following numbered examples:

Example 1. A method of estimating a state of an end effector of an ultrasonic device, the ultrasonic device including an electromechanical ultrasonic system defined by a predetermined resonant frequency, the electromechanical ultrasonic system including an ultrasonic transducer coupled to an ultrasonic blade, the method comprising: measuring, by a control circuit, a complex impedance of an ultrasonic transducer, wherein the complex impedance is defined a $$Z_g(t) = \frac{V_g(t)}{I_g(t)};$$

receiving, by the control circuit, a complex impedance measurement data point; comparing, by the control circuit, the complex impedance measurement data point to a data point in a reference complex impedance characteristic pattern; classifying, by the control circuit, the complex impedance measurement data point based on a result of the comparison analysis; and assigning, by the control circuit, a state or condition of the end effector based on the result of the comparison analysis.

Example 2. The method of Example 1, comprising: receiving, by the control circuit, the reference complex impedance characteristic pattern from a database or memory coupled to the control circuit; and generating, by the control circuit, the reference complex impedance characteristic pattern as follows: applying, by a drive circuit coupled to the control circuit, a nontherapeutic drive signal to the ultrasonic transducer starting at an initial frequency, ending at a final frequency, and at a plurality of frequencies therebetween; measuring, by the control circuit, the impedance of the ultrasonic transducer at each frequency; storing, by the control circuit, a data point corresponding to each impedance measurement; and curve fitting, by the control circuit, a plurality of data points to generate a three-dimensional curve of representative of the reference complex impedance characteristic pattern, wherein the magnitude |Z| and phase φ are plotted as a function of frequency f.

Example 3. The method of Example 2, where the curve fitting includes a polynomial curve fit, a Fourier series, and/or a parametric equation.

Example 4. The method of any one of Examples 1-3, comprising: receiving, by the control circuit, a new impedance measurement data point; and classifying, by the control circuit, the new impedance measurement data point using a Euclidean perpendicular distance from the new impedance measurement data point to a trajectory which has been fitted to the reference complex impedance characteristic pattern.

Example 5. The method of Example 4, comprising estimating, by the control circuit, a probability that the new impedance measurement data point is correctly classified.

Example 6. The method of Example 5, comprising adding, by the control circuit, the new impedance measurement data point to the reference complex impedance characteristic pattern based on the probability of the estimated correct classification of the new impedance measurement data point.

Example 7. The method of Example 4, comprising: classifying by the control circuit, data based on a set of training data S, where the set of training data S comprises a plurality of complex impedance measurement data; curve fitting, by the control circuit, the set of training data S using a parametric Fourier series; wherein S is defined by:

$$\vec{p} = \vec{a}_0 + \sum_{n=1}^{\infty}\left(\vec{a}_n \cos\frac{n\pi t}{L} + \vec{b}_n \sin\frac{n\pi t}{L}\right)$$

wherein, for a new impedance measurement data point $\vec{z}$ a perpendicular distance from $\vec{p}$ to $\vec{z}$ is found by:

$$D = \|\vec{p} - \vec{z}\|$$

when:

$$\frac{\partial D}{\partial t} = 0$$

then:

$$D = D_\perp$$

wherein the probability distribution of D is used to estimate the probability of the new impedance measurement data point z belonging to the group S.

Example 8. The method of claim 1, wherein the control circuit is located at a surgical hub in communication with the ultrasonic electromechanical system.

Example 9. A generator for estimating a state of an end effector of an ultrasonic device, the ultrasonic device including an electromechanical ultrasonic system defined by a predetermined resonant frequency, the electromechanical ultrasonic system including an ultrasonic transducer coupled to an ultrasonic blade, the generator comprising: a control circuit coupled to a memory, the control circuit configured to: measure a complex impedance of an ultrasonic transducer, wherein the complex impedance is defined as $$Z_g(t) = \frac{V_g(t)}{I_g(t)};$$

receive a complex impedance measurement data point; compare the complex impedance measurement data point to a data point in a reference complex impedance characteristic pattern; classify the complex impedance measurement data point based on a result of the comparison analysis; and assign a state or condition of the end effector based on the result of the comparison analysis.

Example 10. The generator of Example 9, further comprising: a drive circuit coupled to the control circuit, the drive circuit configured to apply a nontherapeutic drive signal to the ultrasonic transducer starting at an initial frequency, ending at a final frequency, and at a plurality of frequencies therebetween; wherein the control circuit is further configured to generate the reference complex impedance characteristic pattern; wherein the control circuit is configured to receive the reference complex impedance characteristic pattern from a database or the memory coupled to the control circuit; measure the impedance of the ultrasonic transducer at each frequency; store in the memory a data point corresponding to each impedance measurement; and curve fit a plurality of data points to generate a three-dimensional curve of representative of the reference complex impedance characteristic pattern, wherein the magnitude |Z| and phase φ are plotted as a function of frequency f.

Example 11. The generator of any one of Example 10, wherein the curve fit includes a polynomial curve fit, a Fourier series, and/or a parametric equation.

Example 12. The generator of any one of Examples 9-11, wherein the control circuit is further configured to: receive a new impedance measurement data point; and classify the new impedance measurement data point using a Euclidean perpendicular distance from the new impedance measurement data point to a trajectory which has been fitted to the reference complex impedance characteristic pattern.

Example 13. The generator of Example 11, wherein the control circuit is further configured to estimate a probability that the new impedance measurement data point is correctly classified.

Example 14. The generator of Example 13, wherein the control circuit is further configured to add the new impedance measurement data point to the reference complex impedance characteristic pattern based on the probability of the estimated correct classification of the new impedance measurement data point.

Example 15. The generator of Example 13, wherein the control circuit is further configured to: classify data based on a set of training data S, where the set of training data S comprises a plurality of complex impedance measurement data; curve fit the set of training data S using a parametric Fourier series; wherein S is defined by:

$$\vec{p} = \vec{a}_0 + \sum_{n=1}^{\infty}\left(\vec{a}_n \cos\frac{n\pi t}{L} + \vec{b}_n \sin\frac{n\pi t}{L}\right)$$

wherein, for a new impedance measurement data point $\vec{z}$, a perpendicular distance from $\vec{p}$ to $\vec{z}$ is found by:

$$D = \|\vec{p} - \vec{z}\|$$

when:

$$\frac{\partial D}{\partial t} = 0$$

then:

$$D = D_\perp$$

wherein the probability distribution of D is used to estimate the probability of the new impedance measurement data point $\vec{z}$ belonging to the group S.

Example 16. The generator of claim 9, wherein the control circuit and the memory are located at a surgical hub in communication with the ultrasonic electromechanical system.

Example 17. An ultrasonic device for estimating a state of an end effector thereof, the ultrasonic device comprising: an electromechanical ultrasonic system defined by a predetermined resonant frequency, the electromechanical ultrasonic system comprising an ultrasonic transducer coupled to an ultrasonic blade; a control circuit coupled to a memory, the control circuit configured to: measure a complex impedance of the ultrasonic transducer, wherein the complex impedance is defined as $$Z_g(t) = \frac{V_g(t)}{I_g(t)};$$

receive a complex impedance measurement data point; compare the complex impedance measurement data point to a data point in a reference complex impedance characteristic pattern; classify the complex impedance measurement data point based on a result of the comparison analysis; and assign a state or condition of the end effector based on the result of the comparison analysis.

Example 18. The ultrasonic device of Example 17, further comprising: a drive circuit coupled to the control circuit, the drive circuit configured to apply a nontherapeutic drive signal to the ultrasonic transducer starting at an initial frequency, ending at a final frequency, and at a plurality of frequencies therebetween; wherein the control circuit is further configured to generate the reference complex impedance characteristic pattern; wherein the control circuit is configured to receive the reference complex impedance characteristic pattern from a database or the memory coupled to the control circuit; measure the impedance of the ultrasonic transducer at each frequency; store in the memory a data point corresponding to each impedance measurement; and curve fit a plurality of data points to generate a three-dimensional curve of representative of the reference complex impedance characteristic pattern, wherein the magnitude |Z| and phase φ are plotted as a function of frequency f.

Example 19. The ultrasonic device of Example 18, wherein the curve fit includes a polynomial curve fit, a Fourier series, and/or a parametric equation.

Example 20. The ultrasonic device of any one of Examples 17-19, wherein the control circuit is further configured to: receive a new impedance measurement data point; and classify the new impedance measurement data point using a Euclidean perpendicular distance from the new impedance measurement data point to a trajectory which has been fitted to the reference complex impedance characteristic pattern.

Example 21. The ultrasonic device of Example 20, wherein the control circuit is further configured to estimate a probability that the new impedance measurement data point is correctly classified.

Example 22. The ultrasonic device of Example 21, wherein the control circuit is further configured to add the new impedance measurement data point to the reference complex impedance characteristic pattern based on the probability of the estimated correct classification of the new impedance measurement data point.

Example 23. The ultrasonic device of Example 21, wherein the control circuit is further configured to: classify data based on a set of training data S, where the set of training data S comprises a plurality of complex impedance measurement data; curve fit the set of training data S using a parametric Fourier series; wherein S is defined by:

$$\vec{p} = \vec{a}_0 + \sum_{n=1}^{\infty}\left(\vec{a}_n \cos\frac{n\pi t}{L} + \vec{b}_n \sin\frac{n\pi t}{L}\right)$$

wherein, for a new impedance measurement data point $\vec{z}$, a perpendicular distance from $\vec{p}$ to $\vec{z}$ is found by:

$$D = \|\vec{p} - \vec{z}\|$$

when:

$$\frac{\partial D}{\partial t} = 0$$

then:

$$D = D_\perp$$

wherein the probability distribution of D is used to estimate the probability of the new impedance measurement data point z belonging to the group S.

Example 24. The ultrasonic device of any one of Examples 17-23, wherein the control circuit and the memory are located at a surgical hub in communication with the ultrasonic electromechanical system.

Example 25. A method of estimating a state of an end effector of an ultrasonic device, the ultrasonic device including an electromechanical ultrasonic system defined by a predetermined resonant frequency, the electromechanical ultrasonic system including an ultrasonic transducer coupled to an ultrasonic blade, the method comprising: applying, by a drive circuit, a drive signal to an ultrasonic transducer, wherein the drive signal is a periodic signal defined by a magnitude and frequency; sweeping, by a processor or control circuit, the frequency of the drive signal from below resonance to above resonance of the electromagnetic ultrasonic system; measuring and recording, by the processor or control circuit, impedance/admittance circle variables $R_e$, $G_e$, $X_e$, $B_e$; comparing, by the processor or control circuit, measured impedance/admittance circle variables $R_e$, $G_e$, $X_e$, $B_e$ to reference impedance/admittance circle variables $R_{ref}$, $G_{ref}$, $X_{ref}$, $B_{ref}$; and determining, by the processor or control circuit, a state or condition of the end effector based on the result of the comparison analysis.

The invention claimed is:

1. A surgical system comprising:
   an ultrasonic device comprising a jaw clamp and an electromechanical ultrasonic system defined by a predetermined resonant frequency,
   wherein the electromechanical ultrasonic system comprises an ultrasonic transducer coupled to an ultrasonic blade via an ultrasonic waveguide;
   a surgical hub system comprising a communication circuit, wherein the surgical hub system is in communication with the ultrasonic device;
   a generator configured to supply power to the ultrasonic transducer, wherein the generator comprises a control circuit to:
   cause a drive circuit to apply a drive signal to the ultrasonic transducer, wherein the drive signal is defined by a magnitude and a frequency;
   sweep the frequency of the drive signal from below the predetermined resonant frequency to above the predetermined resonant frequency;
   measure and record impedance circle variables $R_e$ and $X_e$, and admittance circle variables $G_e$ and $B_e$;
   compare the measured impedance circle variables $R_e$ and $X_e$ and the measured admittance circle variables Ge and Be to reference impedance circle variables $R_{ref}$ and $X_{ref}$, and reference admittance circle variables $G_{ref}$ and $B_{ref}$, respectively; and
   determine a state or condition of an end effector of the ultrasonic device based on the result of the comparison.

2. The surgical system of claim 1, wherein the reference impedance circle variables $R_{ref}$ and $X_{ref}$, and the reference admittance circle variables $G_{ref}$ and $B_{ref}$ are stored in a database of the ultrasonic device.

3. The surgical system of claim 1, wherein the reference impedance circle variables $R_{ref}$ and $X_{ref}$, and the reference admittance circle variables $G_{ref}$ and $B_{ref}$ correspond to an open and unloaded jaw clamp.

4. The surgical system of claim 1, wherein the reference impedance circle variables $R_{ref}$ and $X_{ref}$, and the reference admittance circle variables $G_{ref}$ and $B_{ref}$ correspond to the jaw clamp fully clamped on a moist chamois.

5. The surgical system of claim 1, wherein the reference impedance circle variables $R_{ref}$ and $X_{ref}$, and the reference admittance circle variables $G_{ref}$ and $B_{ref}$ are accessible to the surgical hub system from a cloud-based memory storage unit.

6. The surgical system of claim 1, wherein the drive signal is a periodic signal.

7. The surgical system of claim 1, wherein the control circuit is further configured to:
   plot real resistance values $R_e$ and imaginary impedance values $X_e$ on a two-dimensional graph; and
   fit the real resistance values $R_e$ and the imaginary impedance values $X_e$ to a circle having a radius and offset values.

8. The surgical system of claim 1, wherein the control circuit is further configured to:
   plot real conductance values $G_e$ and imaginary susceptance values $B_e$ on a second two-dimensional graph; and
   fit the real conductance values $G_e$ and the imaginary susceptance values $B_e$ to a second circle having a second radius and second offset values.

9. The surgical system of claim 1, wherein the generator is disposed within a generator module of the surgical hub system.

10. A surgical system comprising:
    a smart surgical device;
    a surgical hub system comprising a communication circuit, wherein the surgical hub system is in communication with the smart surgical device;
    a generator configured to supply power to the smart surgical device, wherein the generator comprises a control circuit to:
    cause a drive circuit to apply a drive signal to the smart surgical device, wherein the drive signal is defined by a magnitude and a frequency;
    sweep the frequency of the drive signal from below a predetermined resonant frequency of the smart surgical device to above the predetermined resonant frequency;
    measure and record impedance circle variables $R_e$ and $X_e$, and admittance circle variables $G_e$ and $B_e$;
    compare the measured impedance circle variables $R_e$ and $X_e$ and the measured admittance circle variables $G_e$ and $B_e$ to reference impedance circle variables $R_{ref}$ and $X_{ref}$, and reference admittance circle variables $G_{ref}$ and $B_{ref}$, respectively; and determine a state or condition of an end effector of the smart surgical device based on the result of the comparison.

11. The surgical system of claim 10, wherein the reference impedance circle variables $R_{ref}$ and $X_{ref}$, and the reference admittance circle variables $G_{ref}$ and $B_{ref}$ are stored in a database of the ultrasonic smart surgical device instrument.

12. The surgical system of claim 10, wherein the reference impedance circle variables $R_{ref}$ and $X_{ref}$, and the reference admittance circle variables $G_{ref}$ and $B_{ref}$ are accessible to the surgical hub system from a cloud-based memory storage unit.

13. The surgical system of claim 10, wherein the drive signal is a periodic signal.

14. The surgical system of claim 10, wherein the control circuit is further configured to:
 plot real resistance values $R_e$ and imaginary impedance values $X_e$ on a two-dimensional graph; and
 fit the real resistance values $R_e$ and the imaginary impedance values $X_e$ to a circle having a radius and offset values.

15. The surgical system of claim 10, wherein the control circuit is further configured to:
 plot real conductance values $G_e$ and imaginary susceptance values $B_e$ on a second two-dimensional graph; and
 fit the real conductance values $G_e$ and the imaginary susceptance values $B_e$ to a second circle having a second radius and second offset values.

16. The surgical system of claim 10, wherein the generator is disposed within a generator module of the surgical hub system.

17. A method of controlling a surgical system comprising:
 applying, by a control circuit, a drive signal to an ultrasonic transducer of an electromechanical ultrasonic system, wherein the drive signal is defined by a magnitude and a frequency;
 sweeping, by the control circuit, the frequency of the drive signal from below a predetermined resonant frequency of the electromechanical ultrasonic system to above the predetermined resonant frequency of the electromechanical ultrasonic system;
 measuring and recording, by the control circuit, impedance circle variables $R_e$ and $X_e$, and admittance circle variables $G_e$ and $B_e$;
 obtaining, by a surgical hub system comprising a communication circuit, reference impedance circle variables $R_{ref}$ and $X_{ref}$, and reference admittance circle variables $G_{ref}$ and $B_{ref}$, from a cloud-based memory storage unit;
 comparing, by the control circuit, the measured impedance circle variables $R_e$ and $X_e$ and the measured admittance circle variables $G_e$ and $B_e$ to the reference impedance circle variables $R_{ref}$ and $X_{ref}$, and the reference admittance circle variables $G_{ref}$ and $B_{ref}$, respectively; and
 determining, by the control circuit, a state or condition of an end effector of the electromechanical ultrasonic system based on the result of the comparison.

18. The method of controlling the surgical system of claim 17, further comprising:
 plotting, by the control circuit, real resistance values $R_e$ and imaginary impedance values $X_e$ on a two-dimensional graph; and
 fitting, by the control circuit, the real resistance values $R_e$ and the imaginary impedance values $X_e$ to a circle having a radius and offset values.

19. The method of controlling the surgical system of claim 17, further comprising:
 plotting, by the control circuit, real conductance values $G_e$ and imaginary susceptance values $B_e$ on a second two-dimensional graph; and
 fitting, by the control circuit, the real conductance values $G_e$ and the imaginary susceptance values $B_e$ to a second circle having a second radius and second offset values.

* * * * *